US008337845B2

(12) United States Patent
Park et al.

(10) Patent No.: US 8,337,845 B2
(45) Date of Patent: Dec. 25, 2012

(54) A-BETA BINDING POLYPEPTIDES

(75) Inventors: John E. Park, Warthausen (DE); Cornelia Dorner-Ciossek, Warthausen (DE); Stefan Hoerer, Biberach (DE); Lothar Kussmaul, Schemmerhofen (DE); Martin Lenter, Neu-Ulm (DE); Katharina Zimmermann, Biberach (DE); Gerald Beste, Ghent (BE); Toon Laeremans, Dworp (BE); Pascal Merchiers, Kasterlee (BE); Jo Vercammen, Sint-Pieters-Leeuw (BE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/038,471

(22) Filed: Mar. 2, 2011

(65) Prior Publication Data

US 2012/0058118 A1 Mar. 8, 2012

(30) Foreign Application Priority Data

Mar. 3, 2010 (EP) ..................................... 10155339

(51) Int. Cl.
*A61K 39/395* (2006.01)
*C07K 16/18* (2006.01)

(52) U.S. Cl. ............... 424/136.1; 424/133.1; 424/139.1; 530/387.3; 530/387.9

(58) Field of Classification Search ........................ None
See application file for complete search history.

(56) References Cited

U.S. PATENT DOCUMENTS 7,807,162 B2 * 10/2010 Silence ...................... 424/133.1
2008/0107601 A1 * 5/2008 Lauwereys et al. ............ 424/9.1
2010/0104568 A1 * 4/2010 Beirnaert et al. .......... 424/133.1
2011/0262427 A1 * 10/2011 Hermans et al. ........... 424/130.1
2012/0058118 A1 3/2012 Park et al.

FOREIGN PATENT DOCUMENTS

WO 2006040153 A2 4/2006
WO 2009149185 A2 12/2009
WO 2011107507 A1 9/2011

OTHER PUBLICATIONS

Van Bockstaele, F. et al. "The Development of nanobodies for therapeutic applications". Current Opinion in Investigational Drugs, vol. 10, No. 11, Nov. 2009, pp. 1212-1224.
Holz, J-B, "Developing nanobodies from bench to bedside". Chief Medical Officer Ablynx NV, PDA/EBE Workshop, Dublin, Jun. 24, 2008. pp. 14-18.
Conrath, K. E. et al., "Camel single-domain antibodies as modular building units in bispecific and bivalent antibody constructs". Journal of Biological Chemistry, American Societiy for Biochemistry and Molecular Biology, vol. 276, No. 10, Mar. 9, 2001, pp. 7346-7350.
International Search Report and Written Opinion for PCT/EP2011/053090 mailed Jul. 18, 2011.

* cited by examiner

*Primary Examiner* — Elizabeth C Kemmerer
*Assistant Examiner* — Kimberly A Ballard
(74) *Attorney, Agent, or Firm* — Michael P. Morris; David L. Kershner

(57) ABSTRACT

The invention relates to biparatopic A-beta binding polypeptides and, more specifically, to biparatopic A-beta binding polypeptides comprising at least two immunoglobulin single variable domains binding to different epitopes of A-beta. The invention also relates to specific sequences of such polypeptides, methods of their production, and methods of using them, including methods of treatment of diseases such as Alzheimer's Disease.

12 Claims, 2 Drawing Sheets

Biparatopic VHH construct:

A-beta peptide (Target): human: DAEFRHDSGYEVHHQKLVFFAEDVGSNKGAIIGLMVGGVV
rodent: DAEFGHDSGFEVRHQKLVFFAEDVGSNKGAIIGLMVGGVV

FIG. 2

```
SEQUENCE LISTING

<160> NUMBER OF SEQ ID NOS: 153

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Mus musculus

<400> SEQUENCE: 2

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 16
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

<210> SEQ ID NO 4
<211> LENGTH: 13
<212> TYPE: PRT
<213> ORGANISM: Homo sapiens

<400> SEQUENCE: 4

Lys Leu Val Phe Phe Ala Glu Asp Val Gly Ser Asn Lys
1               5                   10
```

<210> SEQ ID NO 5
<211> LENGTH: 15
<212> TYPE: PRT
<213> ORGANISM: Homo sapiens

<400> SEQUENCE: 5

```
Lys Gly Ala Ile Ile Gly Leu Met Val Gly Gly Val Val Ile Ala
1               5                   10                  15
```

<210> SEQ ID NO 6
<211> LENGTH: 9
<212> TYPE: PRT
<213> ORGANISM: Artificial
<220> FEATURE:
<223> OTHER INFORMATION: linker GS9, C5

<400> SEQUENCE: 6

```
Gly Gly Gly Gly Cys Gly Gly Gly Ser
1               5
```

<210> SEQ ID NO 7
<211> LENGTH: 25
<212> TYPE: PRT
<213> ORGANISM: Artificial
<220> FEATURE:
<223> OTHER INFORMATION: linker GS25, C5

<400> SEQUENCE: 7

```
Gly Gly Gly Gly Cys Gly Gly Gly Gly Ser Gly Gly Gly Gly Ser
1               5                   10                  15

Gly Gly Gly Ser Gly Gly Gly Gly Ser
            20                  25
```

<210> SEQ ID NO 8
<211> LENGTH: 27
<212> TYPE: PRT
<213> ORGANISM: Artificial
<220> FEATURE:
<223> OTHER INFORMATION: linker GS27, C14

<400> SEQUENCE: 8

```
Gly Gly Gly Ser Gly Gly Gly Gly Ser Gly Gly Gly Cys Gly Gly
1               5                   10                  15

Gly Gly Ser Gly Gly Gly Gly Ser Gly Gly Gly
            20                  25
```

<210> SEQ ID NO 9
<211> LENGTH: 35
<212> TYPE: PRT
<213> ORGANISM: Artificial
<220> FEATURE:
<223> OTHER INFORMATION: linker GS35, C15

<400> SEQUENCE: 9

```
Gly Gly Gly Gly Ser Gly Gly Gly Gly Ser Gly Gly Gly Cys Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 10
<211> LENGTH: 35
<212> TYPE: PRT

```
-continued

<213> ORGANISM: Artificial
<220> FEATURE:
<223> OTHER INFORMATION: linker GS35, C5

<400> SEQUENCE: 10

Gly Gly Gly Gly Cys Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser
        35

<210> SEQ ID NO 11
<211> LENGTH: 5
<212> TYPE: PRT
<213> ORGANISM: Artificial
<220> FEATURE:
<223> OTHER INFORMATION: CDR

<400> SEQUENCE: 11

Thr Asp Thr Met Gly
1               5

<210> SEQ ID NO 12
<211> LENGTH: 17
<212> TYPE: PRT
<213> ORGANISM: Artificial
<220> FEATURE:
<223> OTHER INFORMATION: CDR

<400> SEQUENCE: 12

Ala Val Thr Trp Asn Ser Gly Arg Thr Asn Tyr Ala Asp Ser Val Lys
1               5                   10                  15

Gly

<210> SEQ ID NO 13
<211> LENGTH: 15
<212> TYPE: PRT
<213> ORGANISM: Artificial
<220> FEATURE:
<223> OTHER INFORMATION: CDR

<400> SEQUENCE: 13

His Arg Leu Val Val Gly Gly Thr Ser Val Gly Asp Trp Arg Tyr
1               5                   10                  15

<210> SEQ ID NO 14
<211> LENGTH: 5
<212> TYPE: PRT
<213> ORGANISM: Artificial
<220> FEATURE:
<223> OTHER INFORMATION: CDR

<400> SEQUENCE: 14

Thr Asp Thr Met Gly
1               5

<210> SEQ ID NO 15
<211> LENGTH: 17
<212> TYPE: PRT
<213> ORGANISM: Artificial
<220> FEATURE:
<223> OTHER INFORMATION: CDR

<400> SEQUENCE: 15

Ala Val Thr Trp Asn Ser Gly Arg Ile Asn Tyr Ala Asp Ser Val Lys
```

-continued

```
               1               5                  10                 15
Gly

<210> SEQ ID NO 16
<211> LENGTH: 15
<212> TYPE: PRT
<213> ORGANISM: Artificial
<220> FEATURE:
<223> OTHER INFORMATION: CDR

<400> SEQUENCE: 16

His Arg Phe Val Val Gly Gly Asn Arg Val Glu Asp Trp Arg Tyr
1               5                  10                 15

<210> SEQ ID NO 17
<211> LENGTH: 5
<212> TYPE: PRT
<213> ORGANISM: Artificial
<220> FEATURE:
<223> OTHER INFORMATION: CDR

<400> SEQUENCE: 17

Asn Tyr Asn Met Gly
1               5

<210> SEQ ID NO 18
<211> LENGTH: 17
<212> TYPE: PRT
<213> ORGANISM: Artificial
<220> FEATURE:
<223> OTHER INFORMATION: CDR

<400> SEQUENCE: 18

Ala Val Ser Arg Ser Gly Val Ser Thr Tyr Tyr Ala Asp Ser Val Lys
1               5                  10                 15
Gly

<210> SEQ ID NO 19
<211> LENGTH: 15
<212> TYPE: PRT
<213> ORGANISM: Artificial
<220> FEATURE:
<223> OTHER INFORMATION: CDR

<400> SEQUENCE: 19

Ala Tyr Arg Gly Thr Ala Ile Asn Val Arg Arg Ser Tyr Ser Ser
1               5                  10                 15

<210> SEQ ID NO 20
<211> LENGTH: 29
<212> TYPE: PRT
<213> ORGANISM: Artificial
<220> FEATURE:
<223> OTHER INFORMATION: FR1/1

<400> SEQUENCE: 20

Val Gln Leu Leu Glu Ser Gly Gly Gly Leu Val Gln Pro Gly Gly Ser
1               5                  10                 15
Leu Arg Leu Ser Cys Val His Ser Gly Pro Thr Phe Arg
                20                  25

<210> SEQ ID NO 21
<211> LENGTH: 29
<212> TYPE: PRT
<213> ORGANISM: Artificial
<220> FEATURE:
```

<223> OTHER INFORMATION: FR1/2

<400> SEQUENCE: 21

Val Gln Leu Leu Glu Ser Gly Gly Gly Leu Val Gln Pro Gly Gly Ser
1               5                   10                  15

Leu Arg Leu Ser Cys Ala Ala Ser Gly Arg Thr Phe Asn
            20                  25

<210> SEQ ID NO 22
<211> LENGTH: 14
<212> TYPE: PRT
<213> ORGANISM: Artificial
<220> FEATURE:
<223> OTHER INFORMATION: FR2

<400> SEQUENCE: 22

Trp Phe Arg Gln Ala Pro Gly Lys Gly Arg Glu Phe Val Ala
1               5                   10

<210> SEQ ID NO 23
<211> LENGTH: 32
<212> TYPE: PRT
<213> ORGANISM: Artificial
<220> FEATURE:
<223> OTHER INFORMATION: FR3/1

<400> SEQUENCE: 23

Arg Phe Thr Ile Ser Arg Asp Asn Ser Lys Asn Thr Ala Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 24
<211> LENGTH: 32
<212> TYPE: PRT
<213> ORGANISM: Artificial
<220> FEATURE:
<223> OTHER INFORMATION: FR3/2

<400> SEQUENCE: 24

Arg Phe Thr Ile Ser Arg Asp Asn Ser Lys Asn Thr Val Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 25
<211> LENGTH: 11
<212> TYPE: PRT
<213> ORGANISM: Artificial
<220> FEATURE:
<223> OTHER INFORMATION: FR4

<400> SEQUENCE: 25

Trp Gly Gln Gly Thr Leu Val Thr Val Ser Ser
1               5                   10

<210> SEQ ID NO 26
<211> LENGTH: 587
<212> TYPE: PRT
<213> ORGANISM: Artificial
<220> FEATURE:
<223> OTHER INFORMATION: Fc fusion protein

<400> SEQUENCE: 26

Glu Val Gln Leu Leu Glu Ser Gly Gly Gly Leu Val Gln Pro Gly Gly
1               5                   10                  15

```
Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Leu Glu Ser Gly Gly Gly Leu
130                 135                 140

Val Gln Pro Gly Gly Ser Leu Arg Leu Ser Cys Ala Ala Ser Gly Arg
145                 150                 155                 160

Thr Phe Asn Asn Tyr Asn Met Gly Trp Phe Arg Gln Ala Pro Gly Lys
                165                 170                 175

Gly Arg Glu Phe Val Ala Ala Val Ser Arg Ser Gly Val Ser Thr Tyr
            180                 185                 190

Tyr Ala Asp Ser Val Lys Gly Arg Phe Thr Ile Ser Arg Asp Asn Ser
        195                 200                 205

Lys Asn Thr Val Tyr Leu Gln Met Asn Ser Leu Arg Pro Glu Asp Thr
210                 215                 220

Ala Val Tyr Tyr Cys Ala Ala Tyr Arg Gly Thr Ala Ile Asn Val
225                 230                 235                 240

Arg Arg Ser Tyr Ser Ser Trp Gly Gln Gly Thr Leu Val Thr Val Ser
                245                 250                 255

Ser Ala Ser Thr Lys Gly Pro Ser Val Phe Pro Leu Ala Pro Ser Ser
            260                 265                 270

Lys Ser Thr Ser Gly Gly Thr Ala Ala Leu Gly Cys Leu Val Lys Asp
        275                 280                 285

Tyr Phe Pro Glu Pro Val Thr Val Ser Trp Asn Ser Gly Ala Leu Thr
290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Gln
                325                 330                 335

Thr Tyr Ile Cys Asn Val Asn His Lys Pro Ser Asn Thr Lys Val Asp
            340                 345                 350

Lys Arg Val Glu Pro Lys Ser Cys Asp Lys Thr His Thr Cys Pro Pro
        355                 360                 365

Cys Pro Ala Pro Glu Leu Leu Gly Gly Pro Ser Val Phe Leu Phe Pro
370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
```

```
                435                 440                 445
Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Glu
                485                 490                 495

Glu Met Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
        515                 520                 525

Asn Asn Tyr Lys Thr Thr Pro Pro Val Leu Asp Ser Asp Gly Ser Phe
530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 27
<211> LENGTH: 605
<212> TYPE: PRT
<213> ORGANISM: Artificial
<220> FEATURE:
<223> OTHER INFORMATION: Fc fusion protein

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser Gly Gly Gly Ser
        115                 120                 125

Gly Gly Gly Gly Ser Gly Gly Gly Ser Gly Gly Gly Ser Gly
    130                 135                 140

Gly Gly Gly Ser Gly Gly Gly Glu Val Gln Leu Leu Glu Ser Gly Gly
145                 150                 155                 160

Gly Leu Val Gln Pro Gly Gly Ser Leu Arg Leu Ser Cys Val His Ser
                165                 170                 175

Gly Pro Thr Phe Arg Thr Asp Thr Met Gly Trp Phe Arg Gln Ala Pro
            180                 185                 190

Gly Lys Gly Arg Glu Phe Val Ala Ala Val Thr Trp Asn Ser Gly Arg
        195                 200                 205

Ile Asn Tyr Ala Asp Ser Val Lys Gly Arg Phe Thr Ile Ser Arg Asp
    210                 215                 220
```

```
Asn Ser Lys Asn Thr Ala Tyr Leu Gln Met Asn Ser Leu Arg Pro Glu
225                 230                 235                 240

Asp Thr Ala Val Tyr Tyr Cys Ala Ala His Arg Phe Val Val Gly Gly
            245                 250                 255

Asn Arg Val Glu Asp Trp Arg Tyr Trp Gly Gln Gly Thr Leu Val Thr
        260                 265                 270

Val Ser Ser Ala Ser Thr Lys Gly Pro Ser Val Phe Pro Leu Ala Pro
    275                 280                 285

Ser Ser Lys Ser Thr Ser Gly Gly Thr Ala Ala Leu Gly Cys Leu Val
    290                 295                 300

Lys Asp Tyr Phe Pro Glu Pro Val Thr Val Ser Trp Asn Ser Gly Ala
305                 310                 315                 320

Leu Thr Ser Gly Val His Thr Phe Pro Ala Val Leu Gln Ser Ser Gly
            325                 330                 335

Leu Tyr Ser Leu Ser Ser Val Val Thr Val Pro Ser Ser Ser Leu Gly
        340                 345                 350

Thr Gln Thr Tyr Ile Cys Asn Val Asn His Lys Pro Ser Asn Thr Lys
    355                 360                 365

Val Asp Lys Arg Val Glu Pro Lys Ser Cys Asp Lys Thr His Thr Cys
370                 375                 380

Pro Pro Cys Pro Ala Pro Glu Leu Leu Gly Gly Pro Ser Val Phe Leu
385                 390                 395                 400

Phe Pro Pro Lys Pro Lys Asp Thr Leu Met Ile Ser Arg Thr Pro Glu
            405                 410                 415

Val Thr Cys Val Val Val Asp Val Ser His Glu Asp Pro Glu Val Lys
        420                 425                 430

Phe Asn Trp Tyr Val Asp Gly Val Glu Val His Asn Ala Lys Thr Lys
    435                 440                 445

Pro Arg Glu Glu Gln Tyr Asn Ser Thr Tyr Arg Val Val Ser Val Leu
450                 455                 460

Thr Val Leu His Gln Asp Trp Leu Asn Gly Lys Glu Tyr Lys Cys Lys
465                 470                 475                 480

Val Ser Asn Lys Ala Leu Pro Ala Pro Ile Glu Lys Thr Ile Ser Lys
            485                 490                 495

Ala Lys Gly Gln Pro Arg Glu Pro Gln Val Tyr Thr Leu Pro Pro Ser
        500                 505                 510

Arg Glu Glu Met Thr Lys Asn Gln Val Ser Leu Thr Cys Leu Val Lys
    515                 520                 525

Gly Phe Tyr Pro Ser Asp Ile Ala Val Glu Trp Glu Ser Asn Gly Gln
    530                 535                 540

Pro Glu Asn Asn Tyr Lys Thr Thr Pro Val Leu Asp Ser Asp Gly
545                 550                 555                 560

Ser Phe Phe Leu Tyr Ser Lys Leu Thr Val Asp Lys Ser Arg Trp Gln
            565                 570                 575

Gln Gly Asn Val Phe Ser Cys Ser Val Met His Glu Ala Leu His Asn
        580                 585                 590

His Tyr Thr Gln Lys Ser Leu Ser Leu Ser Pro Gly Lys
    595                 600                 605
```

<210> SEQ ID NO 28
<211> LENGTH: 330
<212> TYPE: PRT
<213> ORGANISM: Artificial
<220> FEATURE:
<223> OTHER INFORMATION: Fc fusion protein

```
<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 330
<212> TYPE: PRT
<213> ORGANISM: Artificial
<220> FEATURE:
<223> OTHER INFORMATION: Fc fusion protein

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                20              25              30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 30
<211> LENGTH: 605
<212> TYPE: PRT
<213> ORGANISM: Artificial
<220> FEATURE:
<223> OTHER INFORMATION: Fc fusion protein

<400> SEQUENCE: 30

Glu Val Gln Leu Leu Glu Ser Gly Gly Gly Leu Val Gln Pro Gly Gly
1               5                   10                  15
Ser Leu Arg Leu Ser Cys Ala Ala Ser Gly Arg Thr Phe Asn Asn Tyr
            20                  25                  30
Asn Met Gly Trp Phe Arg Gln Ala Pro Gly Lys Gly Arg Glu Phe Val
        35                  40                  45
Ala Ala Val Ser Arg Ser Gly Val Ser Thr Tyr Tyr Ala Asp Ser Val
    50                  55                  60
```

-continued

```
Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Ala Tyr Arg Gly Thr Ala Ile Asn Val Arg Arg Ser Tyr Ser
        100                 105                 110

Ser Trp Gly Gln Gly Thr Leu Val Thr Val Ser Ser Gly Gly Gly Ser
        115                 120                 125

Gly Gly Gly Gly Ser Gly Gly Gly Ser Gly Gly Gly Ser Gly
    130                 135                 140

Gly Gly Gly Ser Gly Gly Gly Glu Val Gln Leu Leu Glu Ser Gly Gly
145                 150                 155                 160

Gly Leu Val Gln Pro Gly Gly Ser Leu Arg Leu Ser Cys Val His Ser
                165                 170                 175

Gly Pro Thr Phe Arg Thr Asp Thr Met Gly Trp Phe Arg Gln Ala Pro
            180                 185                 190

Gly Lys Gly Arg Glu Phe Val Ala Ala Val Thr Trp Asn Ser Gly Arg
        195                 200                 205

Ile Asn Tyr Ala Asp Ser Val Lys Gly Arg Phe Thr Ile Ser Arg Asp
        210                 215                 220

Asn Ser Lys Asn Thr Ala Tyr Leu Gln Met Asn Ser Leu Arg Pro Glu
225                 230                 235                 240

Asp Thr Ala Val Tyr Tyr Cys Ala Ala His Arg Phe Val Val Gly Gly
            245                 250                 255

Asn Arg Val Glu Asp Trp Arg Tyr Trp Gly Gln Gly Thr Leu Val Thr
        260                 265                 270

Val Ser Ser Ala Ser Thr Lys Gly Pro Ser Val Phe Pro Leu Ala Pro
        275                 280                 285

Ser Ser Lys Ser Thr Ser Gly Gly Thr Ala Ala Leu Gly Cys Leu Val
        290                 295                 300

Lys Asp Tyr Phe Pro Glu Pro Val Thr Val Ser Trp Asn Ser Gly Ala
305                 310                 315                 320

Leu Thr Ser Gly Val His Thr Phe Pro Ala Val Leu Gln Ser Ser Gly
            325                 330                 335

Leu Tyr Ser Leu Ser Ser Val Val Thr Val Pro Ser Ser Ser Leu Gly
        340                 345                 350

Thr Gln Thr Tyr Ile Cys Asn Val Asn His Lys Pro Ser Asn Thr Lys
        355                 360                 365

Val Asp Lys Arg Val Glu Pro Lys Ser Cys Asp Lys Thr His Thr Cys
370                 375                 380

Pro Pro Cys Pro Ala Pro Glu Ala Ala Gly Gly Pro Ser Val Phe Leu
385                 390                 395                 400

Phe Pro Pro Lys Pro Lys Asp Thr Leu Met Ile Ser Arg Thr Pro Glu
            405                 410                 415

Val Thr Cys Val Val Val Asp Val Ser His Glu Asp Pro Glu Val Lys
        420                 425                 430

Phe Asn Trp Tyr Val Asp Gly Val Glu Val His Asn Ala Lys Thr Lys
        435                 440                 445

Pro Arg Glu Glu Gln Tyr Asn Ser Thr Tyr Arg Val Val Ser Val Leu
        450                 455                 460

Thr Val Leu His Gln Asp Trp Leu Asn Gly Lys Glu Tyr Lys Cys Lys
465                 470                 475                 480

Val Ser Asn Lys Ala Leu Pro Ala Pro Ile Glu Lys Thr Ile Ser Lys
```

```
                    485                 490                 495
Ala Lys Gly Gln Pro Arg Glu Pro Gln Val Tyr Thr Leu Pro Pro Ser
                500                 505                 510

Arg Glu Glu Met Thr Lys Asn Gln Val Ser Leu Thr Cys Leu Val Lys
            515                 520                 525

Gly Phe Tyr Pro Ser Asp Ile Ala Val Glu Trp Glu Ser Asn Gly Gln
        530                 535                 540

Pro Glu Asn Asn Tyr Lys Thr Thr Pro Val Leu Asp Ser Asp Gly
545                 550                 555                 560

Ser Phe Phe Leu Tyr Ser Lys Leu Thr Val Asp Lys Ser Arg Trp Gln
                565                 570                 575

Gln Gly Asn Val Phe Ser Cys Ser Val Met His Glu Ala Leu His Asn
            580                 585                 590

His Tyr Thr Gln Lys Ser Leu Ser Leu Ser Pro Gly Lys
        595                 600                 605

<210> SEQ ID NO 31
<211> LENGTH: 613
<212> TYPE: PRT
<213> ORGANISM: Artificial
<220> FEATURE:
<223> OTHER INFORMATION: Fc fusion protein

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser Gly Gly Gly Gly
        115                 120                 125

Ser Gly Gly Gly Gly Ser Gly Gly Cys Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Leu Glu Ser Gly Gly Leu Val Gln Pro Gly Gly Ser
                165                 170                 175

Leu Arg Leu Ser Cys Val His Ser Gly Pro Thr Phe Arg Thr Asp Thr
            180                 185                 190

Met Gly Trp Phe Arg Gln Ala Pro Gly Lys Gly Arg Glu Phe Val Ala
        195                 200                 205

Ala Val Thr Trp Asn Ser Gly Arg Ile Asn Tyr Ala Asp Ser Val Lys
    210                 215                 220

Gly Arg Phe Thr Ile Ser Arg Asp Asn Ser Lys Asn Thr Ala Tyr Leu
225                 230                 235                 240

Gln Met Asn Ser Leu Arg Pro Glu Asp Thr Ala Val Tyr Tyr Cys Ala
                245                 250                 255
```

Ala His Arg Phe Val Gly Asn Arg Val Glu Asp Trp Arg Tyr
            260                 265                 270

Trp Gly Gln Gly Thr Leu Val Thr Val Ser Ser Ala Ser Thr Lys Gly
        275                 280                 285

Pro Ser Val Phe Pro Leu Ala Pro Ser Ser Lys Ser Thr Ser Gly Gly
290                 295                 300

Thr Ala Ala Leu Gly Cys Leu Val Lys Asp Tyr Phe Pro Glu Pro Val
305                 310                 315                 320

Thr Val Ser Trp Asn Ser Gly Ala Leu Thr Ser Gly Val His Thr Phe
                325                 330                 335

Pro Ala Val Leu Gln Ser Ser Gly Leu Tyr Ser Leu Ser Ser Val Val
                340                 345                 350

Thr Val Pro Ser Ser Ser Leu Gly Thr Gln Thr Tyr Ile Cys Asn Val
                355                 360                 365

Asn His Lys Pro Ser Asn Thr Lys Val Asp Lys Arg Val Glu Pro Lys
            370                 375                 380

Ser Cys Asp Lys Thr His Thr Cys Pro Pro Cys Pro Ala Pro Glu Ala
385                 390                 395                 400

Ala Gly Gly Pro Ser Val Phe Leu Phe Pro Pro Lys Pro Lys Asp Thr
                405                 410                 415

Leu Met Ile Ser Arg Thr Pro Glu Val Thr Cys Val Val Val Asp Val
                420                 425                 430

Ser His Glu Asp Pro Glu Val Lys Phe Asn Trp Tyr Val Asp Gly Val
            435                 440                 445

Glu Val His Asn Ala Lys Thr Lys Pro Arg Glu Glu Gln Tyr Asn Ser
    450                 455                 460

Thr Tyr Arg Val Val Ser Val Leu Thr Val Leu His Gln Asp Trp Leu
465                 470                 475                 480

Asn Gly Lys Glu Tyr Lys Cys Lys Val Ser Asn Lys Ala Leu Pro Ala
                485                 490                 495

Pro Ile Glu Lys Thr Ile Ser Lys Ala Lys Gly Gln Pro Arg Glu Pro
            500                 505                 510

Gln Val Tyr Thr Leu Pro Pro Ser Arg Glu Glu Met Thr Lys Asn Gln
            515                 520                 525

Val Ser Leu Thr Cys Leu Val Lys Gly Phe Tyr Pro Ser Asp Ile Ala
530                 535                 540

Val Glu Trp Glu Ser Asn Gly Gln Pro Glu Asn Asn Tyr Lys Thr Thr
545                 550                 555                 560

Pro Pro Val Leu Asp Ser Asp Gly Ser Phe Phe Leu Tyr Ser Lys Leu
                565                 570                 575

Thr Val Asp Lys Ser Arg Trp Gln Gln Gly Asn Val Phe Ser Cys Ser
                580                 585                 590

Val Met His Glu Ala Leu His Asn His Tyr Thr Gln Lys Ser Leu Ser
            595                 600                 605

Leu Ser Pro Gly Lys
        610

<210> SEQ ID NO 32
<211> LENGTH: 860
<212> TYPE: PRT
<213> ORGANISM: Artificial
<220> FEATURE:
<223> OTHER INFORMATION: HSA fusion protein

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser Gly Gly Gly Ser
        115                 120                 125

Gly Gly Gly Gly Ser Gly Gly Gly Ser Gly Gly Gly Gly Ser Gly
    130                 135                 140

Gly Gly Gly Ser Gly Gly Glu Val Gln Leu Leu Glu Ser Gly Gly
145                 150                 155                 160

Gly Leu Val Gln Pro Gly Gly Ser Leu Arg Leu Ser Cys Val His Ser
            165                 170                 175

Gly Pro Thr Phe Arg Thr Asp Thr Met Gly Trp Phe Arg Gln Ala Pro
            180                 185                 190

Gly Lys Gly Arg Glu Phe Val Ala Ala Val Thr Trp Asn Ser Gly Arg
            195                 200                 205

Ile Asn Tyr Ala Asp Ser Val Lys Gly Arg Phe Thr Ile Ser Arg Asp
210                 215                 220

Asn Ser Lys Asn Thr Ala Tyr Leu Gln Met Asn Ser Leu Arg Pro Glu
225                 230                 235                 240

Asp Thr Ala Val Tyr Tyr Cys Ala Ala His Arg Phe Val Val Gly Gly
            245                 250                 255

Asn Arg Val Glu Asp Trp Arg Tyr Trp Gly Gln Gly Thr Leu Val Thr
            260                 265                 270

Val Ser Ser Asp Ala His Lys Ser Glu Val Ala His Arg Phe Lys Asp
        275                 280                 285

Leu Gly Glu Glu Asn Phe Lys Ala Leu Val Leu Ile Ala Phe Ala Gln
        290                 295                 300

Tyr Leu Gln Gln Cys Pro Phe Glu Asp His Val Lys Leu Val Asn Glu
305                 310                 315                 320

Val Thr Glu Phe Ala Lys Thr Cys Val Ala Asp Glu Ser Ala Glu Asn
            325                 330                 335

Cys Asp Lys Ser Leu His Thr Leu Phe Gly Asp Lys Leu Cys Thr Val
            340                 345                 350

Ala Thr Leu Arg Glu Thr Tyr Gly Glu Met Ala Asp Cys Cys Ala Lys
            355                 360                 365

Gln Glu Pro Glu Arg Asn Glu Cys Phe Leu Gln His Lys Asp Asp Asn
        370                 375                 380

Pro Asn Leu Pro Arg Leu Val Arg Pro Glu Val Asp Val Met Cys Thr
385                 390                 395                 400

Ala Phe His Asp Asn Glu Glu Thr Phe Leu Lys Lys Tyr Leu Tyr Glu
            405                 410                 415

Ile Ala Arg Arg His Pro Tyr Phe Tyr Ala Pro Glu Leu Leu Phe Phe
            420                 425                 430
```

```
Ala Lys Arg Tyr Lys Ala Ala Phe Thr Glu Cys Cys Gln Ala Ala Asp
        435                 440                 445
Lys Ala Ala Cys Leu Leu Pro Lys Leu Asp Glu Leu Arg Asp Glu Gly
        450                 455                 460
Lys Ala Ser Ser Ala Lys Gln Arg Leu Lys Cys Ala Ser Leu Gln Lys
465                 470                 475                 480
Phe Gly Glu Arg Ala Phe Lys Ala Trp Ala Val Ala Arg Leu Ser Gln
                485                 490                 495
Arg Phe Pro Lys Ala Glu Phe Ala Glu Val Ser Lys Leu Val Thr Asp
            500                 505                 510
Leu Thr Lys Val His Thr Glu Cys Cys His Gly Asp Leu Leu Glu Cys
        515                 520                 525
Ala Asp Asp Arg Ala Asp Leu Ala Lys Tyr Ile Cys Glu Asn Gln Asp
        530                 535                 540
Ser Ile Ser Ser Lys Leu Lys Glu Cys Cys Glu Lys Pro Leu Leu Glu
545                 550                 555                 560
Lys Ser His Cys Ile Ala Glu Val Glu Asn Asp Glu Met Pro Ala Asp
                565                 570                 575
Leu Pro Ser Leu Ala Ala Asp Phe Val Glu Ser Lys Asp Val Cys Lys
            580                 585                 590
Asn Tyr Ala Glu Ala Lys Asp Val Phe Leu Gly Met Phe Leu Tyr Glu
        595                 600                 605
Tyr Ala Arg Arg His Pro Asp Tyr Ser Val Val Leu Leu Leu Arg Leu
        610                 615                 620
Ala Lys Thr Tyr Glu Thr Thr Leu Glu Lys Cys Cys Ala Ala Ala Asp
625                 630                 635                 640
Pro His Glu Cys Tyr Ala Lys Val Phe Asp Glu Phe Lys Pro Leu Val
                645                 650                 655
Glu Glu Pro Gln Asn Leu Ile Lys Gln Asn Cys Glu Leu Phe Glu Gln
            660                 665                 670
Leu Gly Glu Tyr Lys Phe Gln Asn Ala Leu Leu Val Arg Tyr Thr Lys
        675                 680                 685
Lys Val Pro Gln Val Ser Thr Pro Thr Leu Val Glu Val Ser Arg Asn
        690                 695                 700
Leu Gly Lys Val Gly Ser Lys Cys Cys Lys His Pro Glu Ala Lys Arg
705                 710                 715                 720
Met Pro Cys Ala Glu Asp Tyr Leu Ser Val Val Leu Asn Gln Leu Cys
                725                 730                 735
Val Leu His Glu Lys Thr Pro Val Ser Asp Arg Val Thr Lys Cys Cys
            740                 745                 750
Thr Glu Ser Leu Val Asn Arg Arg Pro Cys Phe Ser Ala Leu Glu Val
        755                 760                 765
Asp Glu Thr Tyr Val Pro Lys Glu Phe Asn Ala Glu Thr Phe Thr Phe
        770                 775                 780
His Ala Asp Ile Cys Thr Leu Ser Glu Lys Glu Arg Gln Ile Lys Lys
785                 790                 795                 800
Gln Thr Ala Leu Val Glu Leu Val Lys His Lys Pro Lys Ala Thr Lys
                805                 810                 815
Glu Gln Leu Lys Ala Val Met Asp Asp Phe Ala Ala Phe Val Glu Lys
            820                 825                 830
Cys Cys Lys Ala Asp Asp Lys Glu Thr Cys Phe Ala Glu Glu Gly Lys
        835                 840                 845
Lys Leu Val Ala Ala Ser Gln Ala Ala Leu Gly Leu
```

<210> SEQ ID NO 33
<211> LENGTH: 115
<212> TYPE: PRT
<213> ORGANISM: Artificial
<220> FEATURE:
<223> OTHER INFORMATION: albumin binding protein

<400> SEQUENCE: 33

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser
        115
```

<210> SEQ ID NO 34
<211> LENGTH: 381
<212> TYPE: PRT
<213> ORGANISM: Artificial
<220> FEATURE:
<223> OTHER INFORMATION: ABII316

<400> SEQUENCE: 34

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Arg Thr Phe Asn Asn Tyr
            20                  25                  30
Asn Met Gly Trp Phe Arg Gln Ala Pro Gly Lys Gly Arg Glu Phe Val
        35                  40                  45
Ala Ala Val Ser Arg Ser Gly Val Ser Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Val Tyr Tyr Cys
                85                  90                  95
Ala Ala Ala Tyr Arg Gly Thr Ala Ile Asn Val Arg Arg Ser Tyr Ser
            100                 105                 110
Ser Trp Gly Gln Gly Thr Leu Val Thr Val Ser Ser Gly Gly Gly Gly
        115                 120                 125
Ser Gly Gly Gly Ser Glu Val Gln Leu Val Glu Ser Gly Gly Gly Leu
    130                 135                 140
Val Gln Pro Gly Asn Ser Leu Arg Leu Ser Cys Ala Ala Ser Gly Phe
145                 150                 155                 160
Thr Phe Ser Ser Phe Gly Met Ser Trp Val Arg Gln Ala Pro Gly Lys
                165                 170                 175
Gly Leu Glu Trp Val Ser Ser Ile Ser Gly Ser Gly Ser Asp Thr Leu
```

-continued

```
                180                 185                 190
Tyr Ala Asp Ser Val Lys Gly Arg Phe Thr Ile Ser Arg Asp Asn Ala
            195                 200                 205
Lys Thr Thr Leu Tyr Leu Gln Met Asn Ser Leu Arg Pro Glu Asp Thr
        210                 215                 220
Ala Val Tyr Tyr Cys Thr Ile Gly Gly Ser Leu Ser Arg Ser Ser Gln
225                 230                 235                 240
Gly Thr Leu Val Thr Val Ser Ser Gly Gly Gly Gly Ser Gly Gly Gly
                245                 250                 255
Ser Glu Val Gln Leu Leu Glu Ser Gly Gly Gly Leu Val Gln Pro Gly
            260                 265                 270
Gly Ser Leu Arg Leu Ser Cys Val His Ser Gly Pro Thr Phe Arg Thr
        275                 280                 285
Asp Thr Met Gly Trp Phe Arg Gln Ala Pro Gly Lys Gly Arg Glu Phe
    290                 295                 300
Val Ala Ala Val Thr Trp Asn Ser Gly Arg Ile Asn Tyr Ala Asp Ser
305                 310                 315                 320
Val Lys Gly Arg Phe Thr Ile Ser Arg Asp Asn Ser Lys Asn Thr Ala
                325                 330                 335
Tyr Leu Gln Met Asn Ser Leu Arg Pro Glu Asp Thr Ala Val Tyr Tyr
            340                 345                 350
Cys Ala Ala His Arg Phe Val Val Gly Gly Asn Arg Val Glu Asp Trp
        355                 360                 365
Arg Tyr Trp Gly Gln Gly Thr Leu Val Thr Val Ser Ser
    370                 375                 380

<210> SEQ ID NO 35
<211> LENGTH: 407
<212> TYPE: PRT
<213> ORGANISM: Artificial
<220> FEATURE:
<223> OTHER INFORMATION: ABII317

<400> SEQUENCE: 35

Glu Val Gln Leu Leu Glu Ser Gly Gly Gly Leu Val Gln Pro Gly Gly
1               5                   10                  15
Ser Leu Arg Leu Ser Cys Ala Ala Ser Gly Arg Thr Phe Asn Asn Tyr
            20                  25                  30
Asn Met Gly Trp Phe Arg Gln Ala Pro Gly Lys Gly Arg Glu Phe Val
        35                  40                  45
Ala Ala Val Ser Arg Ser Gly Val Ser Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Val Tyr Tyr Cys
                85                  90                  95
Ala Ala Ala Tyr Arg Gly Thr Ala Ile Asn Val Arg Arg Ser Tyr Ser
            100                 105                 110
Ser Trp Gly Gln Gly Thr Leu Val Thr Val Ser Ser Gly Gly Gly Gly
        115                 120                 125
Ser Gly Gly Gly Gly Ser Gly Gly Gly Gly Ser Gly Gly Gly Gly Ser
    130                 135                 140
Gly Gly Gly Gly Ser Gly Gly Gly Ser Gly Gly Gly Ser Gly Gly Glu
145                 150                 155                 160
Val Gln Leu Leu Glu Ser Gly Gly Gly Leu Val Gln Pro Gly Gly Ser
                165                 170                 175
```

```
Leu Arg Leu Ser Cys Val His Ser Gly Pro Thr Phe Arg Thr Asp Thr
            180                 185                 190

Met Gly Trp Phe Arg Gln Ala Pro Gly Lys Gly Arg Glu Phe Val Ala
        195                 200                 205

Ala Val Thr Trp Asn Ser Arg Ile Asn Tyr Ala Asp Ser Val Lys
    210                 215                 220

Gly Arg Phe Thr Ile Ser Arg Asp Asn Ser Lys Asn Thr Ala Tyr Leu
225                 230                 235                 240

Gln Met Asn Ser Leu Arg Pro Glu Asp Thr Ala Val Tyr Tyr Cys Ala
                245                 250                 255

Ala His Arg Phe Val Val Gly Asn Arg Val Glu Asp Trp Arg Tyr
            260                 265                 270

Trp Gly Gln Gly Thr Leu Val Thr Val Ser Ser Gly Gly Gly Ser
        275                 280                 285

Gly Gly Gly Ser Glu Val Gln Leu Val Glu Ser Gly Gly Leu Val
    290                 295                 300

Gln Pro Gly Asn Ser Leu Arg Leu Ser Cys Ala Ala Ser Gly Phe Thr
305                 310                 315                 320

Phe Ser Ser Phe Gly Met Ser Trp Val Arg Gln Ala Pro Gly Lys Gly
                325                 330                 335

Leu Glu Trp Val Ser Ser Ile Ser Gly Ser Gly Ser Asp Thr Leu Tyr
            340                 345                 350

Ala Asp Ser Val Lys Gly Arg Phe Thr Ile Ser Arg Asp Asn Ala Lys
            355                 360                 365

Thr Thr Leu Tyr Leu Gln Met Asn Ser Leu Arg Pro Glu Asp Thr Ala
370                 375                 380

Val Tyr Tyr Cys Thr Ile Gly Gly Ser Leu Ser Arg Ser Ser Gln Gly
385                 390                 395                 400

Thr Leu Val Thr Val Ser Ser
                405

<210> SEQ ID NO 36
<211> LENGTH: 381
<212> TYPE: PRT
<213> ORGANISM: Artificial
<220> FEATURE:
<223> OTHER INFORMATION: ABII318

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser Gly Gly Gly Gly
        115                 120                 125
```

-continued

```
Ser Gly Gly Gly Ser Glu Val Gln Leu Leu Glu Ser Gly Gly Leu
130                 135                 140

Val Gln Pro Gly Gly Ser Leu Arg Leu Ser Cys Val His Ser Gly Pro
145                 150                 155                 160

Thr Phe Arg Thr Asp Thr Met Gly Trp Phe Arg Gln Ala Pro Gly Lys
                165                 170                 175

Gly Arg Glu Phe Val Ala Ala Val Thr Trp Asn Ser Gly Arg Ile Asn
            180                 185                 190

Tyr Ala Asp Ser Val Lys Gly Arg Phe Thr Ile Ser Arg Asp Asn Ser
        195                 200                 205

Lys Asn Thr Ala Tyr Leu Gln Met Asn Ser Leu Arg Pro Glu Asp Thr
210                 215                 220

Ala Val Tyr Tyr Cys Ala Ala His Arg Phe Val Val Gly Gly Asn Arg
225                 230                 235                 240

Val Glu Asp Trp Arg Tyr Trp Gly Gln Gly Thr Leu Val Thr Val Ser
                245                 250                 255

Ser Gly Gly Gly Gly Ser Gly Gly Gly Ser Glu Val Gln Leu Val Glu
            260                 265                 270

Ser Gly Gly Gly Leu Val Gln Pro Gly Asn Ser Leu Arg Leu Ser Cys
        275                 280                 285

Ala Ala Ser Gly Phe Thr Phe Ser Ser Phe Gly Met Ser Trp Val Arg
290                 295                 300

Gln Ala Pro Gly Lys Gly Leu Glu Trp Val Ser Ser Ile Ser Gly Ser
305                 310                 315                 320

Gly Ser Asp Thr Leu Tyr Ala Asp Ser Val Lys Gly Arg Phe Thr Ile
                325                 330                 335

Ser Arg Asp Asn Ala Lys Thr Thr Leu Tyr Leu Gln Met Asn Ser Leu
            340                 345                 350

Arg Pro Glu Asp Thr Ala Val Tyr Tyr Cys Thr Ile Gly Gly Ser Leu
        355                 360                 365

Ser Arg Ser Ser Gln Gly Thr Leu Val Thr Val Ser Ser
370                 375                 380

<210> SEQ ID NO 37
<211> LENGTH: 407
<212> TYPE: PRT
<213> ORGANISM: Artificial
<220> FEATURE:
<223> OTHER INFORMATION: ABII319

<400> SEQUENCE: 37

Glu Val Gln Leu Leu Glu Ser Gly Gly Leu Val Gln Pro Gly Gly
1                   5                   10                  15

Ser Leu Arg Leu Ser Cys Val His Ser Gly Pro Thr Phe Arg Thr Asp
                20                  25                  30

Thr Met Gly Trp Phe Arg Gln Ala Pro Gly Lys Gly Arg Glu Phe Val
            35                  40                  45

Ala Ala Val Thr Trp Asn Ser Gly Arg Ile Asn Tyr Ala Asp Ser Val
        50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
```

```
            115                 120                 125
Ser Gly Gly Gly Ser Gly Gly Gly Ser Gly Gly Gly Ser
130                 135                 140
Gly Gly Gly Gly Ser Gly Gly Gly Ser Gly Gly Gly Ser Glu
145                 150                 155                 160
Val Gln Leu Leu Glu Ser Gly Gly Leu Val Gln Pro Gly Gly Ser
                165                 170                 175
Leu Arg Leu Ser Cys Ala Ala Ser Gly Arg Thr Phe Asn Asn Tyr Asn
            180                 185                 190
Met Gly Trp Phe Arg Gln Ala Pro Gly Lys Gly Arg Glu Phe Val Ala
        195                 200                 205
Ala Val Ser Arg Ser Gly Val Ser Thr Tyr Tyr Ala Asp Ser Val Lys
    210                 215                 220
Gly Arg Phe Thr Ile Ser Arg Asp Asn Ser Lys Asn Thr Val Tyr Leu
225                 230                 235                 240
Gln Met Asn Ser Leu Arg Pro Glu Asp Thr Ala Val Tyr Tyr Cys Ala
                245                 250                 255
Ala Ala Tyr Arg Gly Thr Ala Ile Asn Val Arg Arg Ser Tyr Ser Ser
            260                 265                 270
Trp Gly Gln Gly Thr Leu Val Thr Val Ser Gly Gly Gly Gly Ser
        275                 280                 285
Gly Gly Gly Ser Glu Val Gln Leu Val Glu Ser Gly Gly Leu Val
    290                 295                 300
Gln Pro Gly Asn Ser Leu Arg Leu Ser Cys Ala Ala Ser Gly Phe Thr
305                 310                 315                 320
Phe Ser Ser Phe Gly Met Ser Trp Val Arg Gln Ala Pro Gly Lys Gly
                325                 330                 335
Leu Glu Trp Val Ser Ser Ile Ser Gly Ser Gly Ser Asp Thr Leu Tyr
            340                 345                 350
Ala Asp Ser Val Lys Gly Arg Phe Thr Ile Ser Arg Asp Asn Ala Lys
        355                 360                 365
Thr Thr Leu Tyr Leu Gln Met Asn Ser Leu Arg Pro Glu Asp Thr Ala
    370                 375                 380
Val Tyr Tyr Cys Thr Ile Gly Gly Ser Leu Ser Arg Ser Ser Gln Gly
385                 390                 395                 400
Thr Leu Val Thr Val Ser Ser
                405

<210> SEQ ID NO 38
<211> LENGTH: 381
<212> TYPE: PRT
<213> ORGANISM: Artificial
<220> FEATURE:
<223> OTHER INFORMATION: ABII320

<400> SEQUENCE: 38

Glu Val Gln Leu Leu Glu Ser Gly Gly Gly Leu Val Gln Pro Gly Gly
1               5                   10                  15
Ser Leu Arg Leu Ser Cys Val His Ser Gly Pro Thr Phe Arg Thr Asp
                20                  25                  30
Thr Met Gly Trp Phe Arg Gln Ala Pro Gly Lys Gly Arg Glu Phe Val
            35                  40                  45
Ala Ala Val Thr Trp Asn Ser Gly Arg Ile Asn Tyr Ala Asp Ser Val
        50                  55                  60
Lys Gly Arg Phe Thr Ile Ser Arg Asp Asn Ser Lys Asn Thr Ala Tyr
65                  70                  75                  80
```

```
Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Gly Gly Gly Gly Ser Gly Gly Gly
                245                 250                 255

Ser Glu Val Gln Leu Leu Glu Ser Gly Gly Gly Leu Val Gln Pro Gly
            260                 265                 270

Gly Ser Leu Arg Leu Ser Cys Ala Ala Ser Gly Arg Thr Phe Asn Asn
        275                 280                 285

Tyr Asn Met Gly Trp Phe Arg Gln Ala Pro Gly Lys Gly Arg Glu Phe
        290                 295                 300

Val Ala Ala Val Ser Arg Ser Gly Val Ser Thr Tyr Tyr Ala Asp Ser
305                 310                 315                 320

Val Lys Gly Arg Phe Thr Ile Ser Arg Asp Asn Ser Lys Asn Thr Val
                325                 330                 335

Tyr Leu Gln Met Asn Ser Leu Arg Pro Glu Asp Thr Ala Val Tyr Tyr
            340                 345                 350

Cys Ala Ala Tyr Arg Gly Thr Ala Ile Asn Val Arg Arg Ser Tyr
        355                 360                 365

Ser Ser Trp Gly Gln Gly Thr Leu Val Thr Val Ser Ser
370                 375                 380

<210> SEQ ID NO 39
<211> LENGTH: 380
<212> TYPE: PRT
<213> ORGANISM: Artificial
<220> FEATURE:
<223> OTHER INFORMATION: ABII321

<400> SEQUENCE: 39

Val Gln Leu Leu Glu Ser Gly Gly Gly Leu Val Gln Pro Gly Gly Ser
1               5                   10                  15

Leu Arg Leu Ser Cys Val His Ser Gly Pro Thr Phe Arg Thr Asp Thr
            20                  25                  30

Met Gly Trp Phe Arg Gln Ala Pro Gly Lys Gly Arg Glu Phe Val Ala
        35                  40                  45

Ala Val Thr Trp Asn Ser Gly Arg Ile Asn Tyr Ala Asp Ser Val Lys
50                  55                  60
```

Gly Arg Phe Thr Ile Ser Arg Asp Asn Ser Lys Asn Thr Ala Tyr Leu
65                  70                  75                  80

Gln Met Asn Ser Leu Arg Pro Glu Asp Thr Ala Val Tyr Tyr Cys Ala
            85                  90                  95

Ala His Arg Phe Val Val Gly Gly Asn Arg Val Glu Asp Trp Arg Tyr
        100                 105                 110

Trp Gly Gln Gly Thr Leu Val Thr Val Ser Gly Gly Gly Gly Ser
        115                 120             125

Gly Gly Gly Ser Glu Val Gln Leu Val Glu Ser Gly Gly Gly Leu Val
    130                 135                 140

Gln Pro Gly Asn Ser Leu Arg Leu Ser Cys Ala Ala Ser Gly Phe Thr
145                 150                 155                 160

Phe Ser Ser Phe Gly Met Ser Trp Val Arg Gln Ala Pro Gly Lys Gly
            165                 170                 175

Leu Glu Trp Val Ser Ser Ile Ser Gly Ser Gly Ser Asp Thr Leu Tyr
            180                 185                 190

Ala Asp Ser Val Lys Gly Arg Phe Thr Ile Ser Arg Asp Asn Ala Lys
        195                 200                 205

Thr Thr Leu Tyr Leu Gln Met Asn Ser Leu Arg Pro Glu Asp Thr Ala
    210                 215                 220

Val Tyr Tyr Cys Thr Ile Gly Gly Ser Leu Ser Arg Ser Ser Gln Gly
225                 230                 235                 240

Thr Leu Val Thr Val Ser Ser Gly Gly Gly Ser Gly Gly Gly Ser
            245                 250                 255

Glu Val Gln Leu Leu Glu Ser Gly Gly Gly Leu Val Gln Pro Gly Gly
            260                 265                 270

Ser Leu Arg Leu Ser Cys Ala Ala Ser Gly Arg Thr Phe Asn Asn Tyr
    275                 280                 285

Asn Met Gly Trp Phe Arg Gln Ala Pro Gly Lys Gly Arg Glu Phe Val
290                 295                 300

Ala Ala Val Ser Arg Ser Gly Val Ser Thr Tyr Tyr Ala Asp Ser Val
305                 310                 315                 320

Lys Gly Arg Phe Thr Ile Ser Arg Asp Asn Ser Lys Asn Thr Val Tyr
            325                 330                 335

Leu Gln Met Asn Ser Leu Arg Pro Glu Asp Thr Ala Val Tyr Tyr Cys
        340                 345                 350

Ala Ala Ala Tyr Arg Gly Thr Ala Ile Asn Val Arg Arg Ser Tyr Ser
            355                 360                 365

Ser Trp Gly Gln Gly Thr Leu Val Thr Val Ser Ser
    370                 375                 380

<210> SEQ ID NO 40
<211> LENGTH: 274
<212> TYPE: PRT
<213> ORGANISM: Artificial
<220> FEATURE:
<223> OTHER INFORMATION: ABII322; PEGylated at Cys 137

<400> SEQUENCE: 40

Val Gln Leu Leu Glu Ser Gly Gly Gly Leu Val Gln Pro Gly Gly Ser
1               5                   10                  15

Leu Arg Leu Ser Cys Ala Ala Ser Gly Arg Thr Phe Asn Asn Tyr Asn
            20                  25                  30

Met Gly Trp Phe Arg Gln Ala Pro Gly Lys Gly Arg Glu Phe Val Ala
        35                  40                  45

Ala Val Ser Arg Ser Gly Val Ser Thr Tyr Tyr Ala Asp Ser Val Lys

```
                50                  55                  60
Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95

Ala Ala Tyr Arg Gly Thr Ala Ile Asn Val Arg Arg Ser Tyr Ser Ser
                100                 105                 110

Trp Gly Gln Gly Thr Leu Val Thr Val Ser Ser Gly Gly Gly Ser Gly
                115                 120                 125

Gly Gly Gly Ser Gly Gly Gly Cys Gly Gly Gly Ser Gly Gly
                130                 135                 140

Gly Gly Ser Gly Gly Gly Glu Val Gln Leu Leu Glu Ser Gly Gly Gly
145                 150                 155                 160

Leu Val Gln Pro Gly Gly Ser Leu Arg Leu Ser Cys Val His Ser Gly
                165                 170                 175

Pro Thr Phe Arg Thr Asp Thr Met Gly Trp Phe Arg Gln Ala Pro Gly
                180                 185                 190

Lys Gly Arg Glu Phe Val Ala Ala Val Thr Trp Asn Ser Gly Arg Ile
                195                 200                 205

Asn Tyr Ala Asp Ser Val Lys Gly Arg Phe Thr Ile Ser Arg Asp Asn
                210                 215                 220

Ser Lys Asn Thr Ala Tyr Leu Gln Met Asn Ser Leu Arg Pro Glu Asp
225                 230                 235                 240

Thr Ala Val Tyr Tyr Cys Ala Ala His Arg Phe Val Val Gly Gly Asn
                245                 250                 255

Arg Val Glu Asp Trp Arg Tyr Trp Gly Gln Gly Thr Leu Val Thr Val
                260                 265                 270

Ser Ser

<210> SEQ ID NO 41
<211> LENGTH: 282
<212> TYPE: PRT
<213> ORGANISM: Artificial
<220> FEATURE:
<223> OTHER INFORMATION: ABII323; PEGylated at Cys 138

<400> SEQUENCE: 41

Val Gln Leu Leu Glu Ser Gly Gly Gly Leu Val Gln Pro Gly Gly Ser
  1               5                  10                  15

Leu Arg Leu Ser Cys Ala Ala Ser Gly Arg Thr Phe Asn Asn Tyr Asn
                 20                  25                  30

Met Gly Trp Phe Arg Gln Ala Pro Gly Lys Gly Arg Glu Phe Val Ala
                 35                  40                  45

Ala Val Ser Arg Ser Gly Val Ser Thr Tyr Tyr Ala Asp Ser Val Lys
                 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95

Ala Ala Tyr Arg Gly Thr Ala Ile Asn Val Arg Arg Ser Tyr Ser Ser
                100                 105                 110

Trp Gly Gln Gly Thr Leu Val Thr Val Ser Ser Gly Gly Gly Gly Ser
                115                 120                 125

Gly Gly Gly Gly Ser Gly Gly Gly Cys Gly Gly Gly Ser Gly
                130                 135                 140
```

```
Gly Gly Gly Ser Gly Gly Gly Ser Gly Gly Gly Ser Glu Val
145                 150                 155                 160

Gln Leu Leu Glu Ser Gly Gly Leu Val Gln Pro Gly Gly Ser Leu
            165                 170                 175

Arg Leu Ser Cys Val His Ser Gly Pro Thr Phe Arg Thr Asp Thr Met
            180                 185                 190

Gly Trp Phe Arg Gln Ala Pro Gly Lys Gly Arg Glu Phe Val Ala Ala
            195                 200                 205

Val Thr Trp Asn Ser Gly Arg Ile Asn Tyr Ala Asp Ser Val Lys Gly
            210                 215                 220

Arg Phe Thr Ile Ser Arg Asp Asn Ser Lys Asn Thr Ala Tyr Leu Gln
225                 230                 235                 240

Met Asn Ser Leu Arg Pro Glu Asp Thr Ala Val Tyr Tyr Cys Ala Ala
            245                 250                 255

His Arg Phe Val Val Gly Gly Asn Arg Val Glu Asp Trp Arg Tyr Trp
            260                 265                 270

Gly Gln Gly Thr Leu Val Thr Val Ser Ser
            275                 280

<210> SEQ ID NO 42
<211> LENGTH: 283
<212> TYPE: PRT
<213> ORGANISM: Artificial
<220> FEATURE:
<223> OTHER INFORMATION: ABII305; PEGylated at Cys 129

<400> SEQUENCE: 42

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Glu Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Ile Tyr Tyr Cys
            85                  90                  95

Gly Ala Ala Tyr Arg Gly Thr Ala Ile Asn Val Arg Arg Ser Tyr Asp
            100                 105                 110

Ser Trp Gly Gln Gly Thr Gln Val Thr Val Ser Ser Gly Gly Gly Gly
        115                 120                 125

Cys Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Leu Ala Gly Gly Ser
            165                 170                 175

Leu Arg Leu Ser Cys Val His Ser Gly Pro Thr Phe Arg Thr Asp Thr
            180                 185                 190

Met Gly Trp Phe Arg Gln Ala Pro Gly Lys Glu Arg Glu Phe Val Ala
        195                 200                 205

Ala Val Thr Trp Asn Ser Gly Arg Ile Asn Tyr Ala Asp Ser Val Lys
    210                 215                 220

Gly Arg Phe Thr Val Ser Arg Asp Asn Thr Arg Asn Ala Ala Tyr Leu
```

```
                    225                 230                 235                 240
Gln Met Ser Gly Leu Lys Asp Glu Asp Thr Ala Val Tyr Tyr Cys Thr
                245                 250                 255

Ala His Arg Phe Val Val Gly Gly Asn Arg Val Glu Asp Trp Arg Tyr
            260                 265                 270

Trp Gly Gln Gly Thr Gln Val Thr Val Ser Ser
            275                 280

<210> SEQ ID NO 43
<211> LENGTH: 257
<212> TYPE: PRT
<213> ORGANISM: Artificial
<220> FEATURE:
<223> OTHER INFORMATION: ABII306; PEGylated at Cys 129

<400> SEQUENCE: 43

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Glu Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Ile Tyr Tyr Cys
                85                  90                  95

Gly Ala Ala Tyr Arg Gly Thr Ala Ile Asn Val Arg Arg Ser Tyr Asp
            100                 105                 110

Ser Trp Gly Gln Gly Thr Gln Val Thr Val Ser Ser Gly Gly Gly Gly
        115                 120                 125

Cys Gly Gly Gly Ser Glu Val Gln Leu Val Glu Ser Gly Gly Gly Leu
    130                 135                 140

Val Leu Ala Gly Gly Ser Leu Arg Leu Ser Cys Val His Ser Gly Pro
145                 150                 155                 160

Thr Phe Arg Thr Asp Thr Met Gly Trp Phe Arg Gln Ala Pro Gly Lys
                165                 170                 175

Glu Arg Glu Phe Val Ala Ala Val Thr Trp Asn Ser Gly Arg Ile Asn
            180                 185                 190

Tyr Ala Asp Ser Val Lys Gly Arg Phe Thr Val Ser Arg Asp Asn Thr
        195                 200                 205

Arg Asn Ala Ala Tyr Leu Gln Met Ser Gly Leu Lys Asp Glu Asp Thr
    210                 215                 220

Ala Val Tyr Tyr Cys Thr Ala His Arg Phe Val Val Gly Gly Asn Arg
225                 230                 235                 240

Val Glu Asp Trp Arg Tyr Trp Gly Gln Gly Thr Gln Val Thr Val Ser
                245                 250                 255

Ser

<210> SEQ ID NO 44
<211> LENGTH: 124
<212> TYPE: PRT
<213> ORGANISM: Artificial
<220> FEATURE:
<223> OTHER INFORMATION: ABII035

<400> SEQUENCE: 44
```

Glu Val Gln Leu Leu Glu Ser Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
            115                 120

<210> SEQ ID NO 45
<211> LENGTH: 124
<212> TYPE: PRT
<213> ORGANISM: Artificial
<220> FEATURE:
<223> OTHER INFORMATION: ABII059

<400> SEQUENCE: 45

Glu Val Gln Leu Leu Glu Ser Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser
            115                 120

<210> SEQ ID NO 46
<211> LENGTH: 17
<212> TYPE: PRT
<213> ORGANISM: Artificial
<220> FEATURE:
<223> OTHER INFORMATION: myc tag

<400> SEQUENCE: 46

Ala Ala Ala Glu Gln Lys Leu Ile Ser Glu Glu Asp Leu Asn Gly Ala
1               5                   10                  15

Ala

<210> SEQ ID NO 47
<211> LENGTH: 124
<212> TYPE: PRT
<213> ORGANISM: Artificial
<220> FEATURE:

<223> OTHER INFORMATION: ABIIPMP42D4

<400> SEQUENCE: 47

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Ser Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Thr Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Leu Val Val Gly Gly Thr Ser Val Gly Asp Trp Arg
            100                 105                 110

Tyr Trp Gly Gln Gly Thr Gln Val Thr Val Ser Ser
        115                 120

<210> SEQ ID NO 48
<211> LENGTH: 124
<212> TYPE: PRT
<213> ORGANISM: Artificial
<220> FEATURE:
<223> OTHER INFORMATION: ABIIPMP111B4

<400> SEQUENCE: 48

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Trp Thr Asp
            20                  25                  30

Thr Met Gly Trp Phe Arg Gln Ala Pro Gly Lys Glu Arg Glu Phe Val
        35                  40                  45

Ala Ala Val Thr Trp Ser Ser Gly Arg Ala Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Gly Val Val Gly Gly Trp Val Val Asp Trp Arg
            100                 105                 110

Tyr Trp Gly Gln Gly Thr Gln Val Thr Val Ser Ser
        115                 120

<210> SEQ ID NO 49
<211> LENGTH: 124
<212> TYPE: PRT
<213> ORGANISM: Artificial
<220> FEATURE:
<223> OTHER INFORMATION: ABII111E5c11

<400> SEQUENCE: 49

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Leu Thr Asp
            20                  25                  30

Thr Met Gly Trp Phe Arg Gln Ala Pro Gly Lys Glu Arg Glu Phe Val
        35                  40                  45

```
Ala Ala Val Thr Trp Asn Ser Gly Arg Ile Asn Tyr Ala Asp Ser Val
    50                  55                  60
Lys Gly Arg Phe Thr Val Ser Arg Asp Asn Thr Arg Asn Ala Ala Tyr
65                  70                  75                  80
Leu Gln Met Ser Gly Leu Lys Asp Glu Asp Thr Ala Val Tyr Tyr Cys
                85                  90                  95
Thr Ala His Arg Phe Val Val Gly Gly Arg Glu Val Gln Asp Trp Arg
                100                 105                 110
Tyr Trp Gly Gln Gly Thr Gln Val Thr Val Ser Ser
        115                 120
```

<210> SEQ ID NO 50
<211> LENGTH: 124
<212> TYPE: PRT
<213> ORGANISM: Artificial
<220> FEATURE:
<223> OTHER INFORMATION: ABIIPMP111C6

<400> SEQUENCE: 50

```
Glu Val Gln Leu Val Glu Ser Gly Gly Gly Leu Val Leu Ala Gly Gly
1               5                   10                  15
Ser Leu Arg Leu Ser Cys Val His Ser Gly Pro Thr Phe Trp Thr Asp
                20                  25                  30
Thr Met Gly Trp Phe Arg Gln Ala Pro Gly Lys Glu Arg Glu Phe Val
            35                  40                  45
Ala Ala Val Thr Trp Asn Ser Gly Arg Leu Asn Tyr Ala Asp Ser Val
    50                  55                  60
Lys Gly Arg Phe Thr Val Ser Arg Asp Asn Thr Arg Asn Ala Ala Tyr
65                  70                  75                  80
Leu Gln Met Ser Gly Leu Lys Asp Glu Asp Thr Ala Val Tyr Tyr Cys
                85                  90                  95
Thr Ala His Arg Gln Val Gly Gly Val Gln Val Leu Asp Trp Arg
                100                 105                 110
Tyr Trp Gly Gln Gly Thr Gln Val Thr Val Ser Ser
        115                 120
```

<210> SEQ ID NO 51
<211> LENGTH: 124
<212> TYPE: PRT
<213> ORGANISM: Artificial
<220> FEATURE:
<223> OTHER INFORMATION: ABIIPMP111F2

<400> SEQUENCE: 51

```
Glu Val Gln Leu Val Glu Ser Gly Gly Gly Leu Val Leu Ala Gly Gly
1               5                   10                  15
Ser Leu Arg Leu Ser Cys Val His Ser Gly Pro Thr Phe Ser Thr Asp
                20                  25                  30
Thr Met Gly Trp Phe Arg Gln Ala Pro Gly Lys Glu Arg Glu Phe Val
            35                  40                  45
Ala Ala Val Thr Trp Asn Ser Gly Arg Thr Asn Tyr Ala Asp Ser Val
    50                  55                  60
Lys Gly Arg Phe Thr Val Ser Arg Asp Asn Thr Arg Asn Ala Ala Tyr
65                  70                  75                  80
Leu Gln Met Ser Gly Leu Lys Asp Glu Asp Thr Ala Val Tyr Tyr Cys
                85                  90                  95
Thr Ala Asn Arg His Ser Val Gly Arg Leu Ser Val Gly Asp Trp Arg
                100                 105                 110
```

```
Tyr Trp Gly Gln Gly Ser Gln Val Thr Val Ser Ser
        115                 120

<210> SEQ ID NO 52
<211> LENGTH: 124
<212> TYPE: PRT
<213> ORGANISM: Artificial
<220> FEATURE:
<223> OTHER INFORMATION: ABIIPMP111E4

<400> SEQUENCE: 52

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Ser Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Thr Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala Ala Arg Leu Thr Val Gly Ser Leu Ser Val Gly Asp Trp Arg
            100                 105                 110

Tyr Trp Gly Gln Gly Thr Gln Val Thr Val Ser Ser
        115                 120

<210> SEQ ID NO 53
<211> LENGTH: 124
<212> TYPE: PRT
<213> ORGANISM: Artificial
<220> FEATURE:
<223> OTHER INFORMATION: ABIIPMP111C4

<400> SEQUENCE: 53

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Leu Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ala Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Ser Val Val Gly Val Gly Val Trp Asp Trp Arg
            100                 105                 110

Tyr Trp Ser Gln Gly Thr Gln Val Thr Val Ser Ser
        115                 120

<210> SEQ ID NO 54
<211> LENGTH: 124
<212> TYPE: PRT
<213> ORGANISM: Artificial
<220> FEATURE:
<223> OTHER INFORMATION: ABIIPMP111B5
```

-continued

<400> SEQUENCE: 54

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Asn Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Leu Val Val Gly Gly Gly Val Arg Asp Trp Arg
            100                 105                 110

Tyr Trp Gly Gln Gly Thr Gln Val Thr Val Ser Ser
        115                 120

<210> SEQ ID NO 55
<211> LENGTH: 124
<212> TYPE: PRT
<213> ORGANISM: Artificial
<220> FEATURE:
<223> OTHER INFORMATION: ABIIPMP111B9

<400> SEQUENCE: 55

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Gly Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ala Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Gly Cys Val Lys Asp Trp Arg
            100                 105                 110

Tyr Trp Gly Gln Gly Thr Gln Val Thr Val Ser Ser
        115                 120

<210> SEQ ID NO 56
<211> LENGTH: 124
<212> TYPE: PRT
<213> ORGANISM: Artificial
<220> FEATURE:
<223> OTHER INFORMATION: ABII111B5_R30K

<400> SEQUENCE: 56

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Lys Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val

```
                    50                  55                  60
Lys Gly Arg Phe Thr Val Ser Arg Asp Asn Thr Arg Asn Ala Ala Tyr
 65                  70                  75                  80

Leu Gln Met Ser Gly Leu Lys Asp Glu Asp Thr Ala Val Tyr Tyr Cys
                 85                  90                  95

Thr Ala His Arg Phe Val Val Gly Gly Asn Met Val Glu Asp Trp Arg
            100                 105                 110

Tyr Trp Gly Gln Gly Thr Gln Val Thr Val Ser Ser
        115                 120

<210> SEQ ID NO 57
<211> LENGTH: 124
<212> TYPE: PRT
<213> ORGANISM: Artificial
<220> FEATURE:
<223> OTHER INFORMATION: ABII111B5_R30W

<400> SEQUENCE: 57

Glu Val Gln Leu Val Glu Ser Gly Gly Gly Leu Val Leu Ala Gly Gly
 1               5                  10                  15

Ser Leu Arg Leu Ser Cys Val His Ser Gly Pro Thr Phe Trp Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
 50                  55                  60

Lys Gly Arg Phe Thr Val Ser Arg Asp Asn Thr Arg Asn Ala Ala Tyr
 65                  70                  75                  80

Leu Gln Met Ser Gly Leu Lys Asp Glu Asp Thr Ala Val Tyr Tyr Cys
                 85                  90                  95

Thr Ala His Arg Phe Val Val Gly Gly Asn Met Val Glu Asp Trp Arg
            100                 105                 110

Tyr Trp Gly Gln Gly Thr Gln Val Thr Val Ser Ser
        115                 120

<210> SEQ ID NO 58
<211> LENGTH: 124
<212> TYPE: PRT
<213> ORGANISM: Artificial
<220> FEATURE:
<223> OTHER INFORMATION: ABII111B5_N106T

<400> SEQUENCE: 58

Glu Val Gln Leu Val Glu Ser Gly Gly Gly Leu Val Leu Ala Gly Gly
 1               5                  10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
 50                  55                  60

Lys Gly Arg Phe Thr Val Ser Arg Asp Asn Thr Arg Asn Ala Ala Tyr
 65                  70                  75                  80

Leu Gln Met Ser Gly Leu Lys Asp Glu Asp Thr Ala Val Tyr Tyr Cys
                 85                  90                  95

Thr Ala His Arg Phe Val Val Gly Gly Thr Met Val Glu Asp Trp Arg
            100                 105                 110

Tyr Trp Gly Gln Gly Thr Gln Val Thr Val Ser Ser
```

115             120

<210> SEQ ID NO 59
<211> LENGTH: 124
<212> TYPE: PRT
<213> ORGANISM: Artificial
<220> FEATURE:
<223> OTHER INFORMATION: ABII111B5_N106V

<400> SEQUENCE: 59

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Val Met Val Glu Asp Trp Arg
            100                 105                 110

Tyr Trp Gly Gln Gly Thr Gln Val Thr Val Ser Ser
        115                 120

<210> SEQ ID NO 60
<211> LENGTH: 124
<212> TYPE: PRT
<213> ORGANISM: Artificial
<220> FEATURE:
<223> OTHER INFORMATION: ABII111B5_F101W

<400> SEQUENCE: 60

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Trp Val Val Gly Gly Asn Met Val Glu Asp Trp Arg
            100                 105                 110

Tyr Trp Gly Gln Gly Thr Gln Val Thr Val Ser Ser
        115                 120

<210> SEQ ID NO 61
<211> LENGTH: 124
<212> TYPE: PRT
<213> ORGANISM: Artificial
<220> FEATURE:
<223> OTHER INFORMATION: ABII111B5_M107E

<400> SEQUENCE: 61

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Glu Val Glu Asp Trp Arg
            100                 105                 110

Tyr Trp Gly Gln Gly Thr Gln Val Thr Val Ser Ser
            115                 120

<210> SEQ ID NO 62
<211> LENGTH: 124
<212> TYPE: PRT
<213> ORGANISM: Artificial
<220> FEATURE:
<223> OTHER INFORMATION: ABII111B5_M107R = ABII002

<400> SEQUENCE: 62

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Gln Val Thr Val Ser Ser
            115                 120

<210> SEQ ID NO 63
<211> LENGTH: 124
<212> TYPE: PRT
<213> ORGANISM: Artificial
<220> FEATURE:
<223> OTHER INFORMATION: ABII111B5_E109W

<400> SEQUENCE: 63

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Glu Arg Glu Phe Val
        35                  40                  45

Ala Ala Val Thr Trp Asn Ser Gly Arg Ile Asn Tyr Ala Asp Ser Val
50                  55                  60

```
Lys Gly Arg Phe Thr Val Ser Arg Asp Asn Thr Arg Asn Ala Ala Tyr
 65                  70                  75                  80

Leu Gln Met Ser Gly Leu Lys Asp Glu Asp Thr Ala Val Tyr Tyr Cys
             85                  90                  95

Thr Ala His Arg Phe Val Val Gly Gly Asn Met Val Trp Asp Trp Arg
            100                 105                 110

Tyr Trp Gly Gln Gly Thr Gln Val Thr Val Ser Ser
        115                 120

<210> SEQ ID NO 64
<211> LENGTH: 124
<212> TYPE: PRT
<213> ORGANISM: Artificial
<220> FEATURE:
<223> OTHER INFORMATION: ABII111B5_E109Q

<400> SEQUENCE: 64

Glu Val Gln Leu Val Glu Ser Gly Gly Gly Leu Val Leu Ala Gly Gly
 1               5                  10                  15

Ser Leu Arg Leu Ser Cys Val His Ser Gly Pro Thr Phe Arg Thr Asp
             20                  25                  30

Thr Met Gly Trp Phe Arg Gln Ala Pro Gly Lys Glu Arg Glu Phe Val
         35                  40                  45

Ala Ala Val Thr Trp Asn Ser Gly Arg Ile Asn Tyr Ala Asp Ser Val
     50                  55                  60

Lys Gly Arg Phe Thr Val Ser Arg Asp Asn Thr Arg Asn Ala Ala Tyr
 65                  70                  75                  80

Leu Gln Met Ser Gly Leu Lys Asp Glu Asp Thr Ala Val Tyr Tyr Cys
             85                  90                  95

Thr Ala His Arg Phe Val Val Gly Gly Asn Met Val Gln Asp Trp Arg
            100                 105                 110

Tyr Trp Gly Gln Gly Thr Gln Val Thr Val Ser Ser
        115                 120

<210> SEQ ID NO 65
<211> LENGTH: 124
<212> TYPE: PRT
<213> ORGANISM: Artificial
<220> FEATURE:
<223> OTHER INFORMATION: ABII003

<400> SEQUENCE: 65

Glu Val Gln Leu Leu Glu Ser Gly Gly Gly Leu Val Leu Pro Gly Gly
 1               5                  10                  15

Ser Leu Arg Leu Ser Cys Val His Ser Gly Pro Thr Phe Arg Thr Asp
             20                  25                  30

Thr Met Gly Trp Phe Arg Gln Ala Pro Gly Lys Gly Arg Glu Phe Val
         35                  40                  45

Ala Ala Val Thr Trp Asn Ser Gly Arg Ile Asn Tyr Ala Asp Ser Val
     50                  55                  60

Lys Gly Arg Phe Thr Val Ser Arg Asp Asn Thr Arg Asn Ala Ala Tyr
 65                  70                  75                  80

Leu Gln Met Ser Gly Leu Lys Asp Glu Asp Thr Ala Val Tyr Tyr Cys
             85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120
```

<210> SEQ ID NO 66
<211> LENGTH: 124
<212> TYPE: PRT
<213> ORGANISM: Artificial
<220> FEATURE:
<223> OTHER INFORMATION: ABII004

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120
```

<210> SEQ ID NO 67
<211> LENGTH: 124
<212> TYPE: PRT
<213> ORGANISM: Artificial
<220> FEATURE:
<223> OTHER INFORMATION: ABII005

<400> SEQUENCE: 67

```
Glu Val Gln Leu Leu Glu Ser Gly Gly Gly Leu Val Leu Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120
```

<210> SEQ ID NO 68
<211> LENGTH: 124
<212> TYPE: PRT
<213> ORGANISM: Artificial
<220> FEATURE:
<223> OTHER INFORMATION: ABII006

<400> SEQUENCE: 68

```
Glu Val Gln Leu Leu Glu Ser Gly Gly Gly Leu Val Leu Pro Gly Gly
1               5                   10                  15
```

```
Ser Leu Arg Leu Ser Cys Val Ala Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
                100                 105                 110

Tyr Trp Gly Gln Gly Thr Leu Val Thr Val Ser Ser
                115                 120
```

<210> SEQ ID NO 69
<211> LENGTH: 124
<212> TYPE: PRT
<213> ORGANISM: Artificial
<220> FEATURE:
<223> OTHER INFORMATION: ABII007

<400> SEQUENCE: 69

```
Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
                100                 105                 110

Tyr Trp Gly Gln Gly Thr Leu Val Thr Val Ser Ser
                115                 120
```

<210> SEQ ID NO 70
<211> LENGTH: 124
<212> TYPE: PRT
<213> ORGANISM: Artificial
<220> FEATURE:
<223> OTHER INFORMATION: ABII008

<400> SEQUENCE: 70

```
Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Ser Arg Asn Ala Ala Tyr
65                  70                  75                  80
```

-continued

```
Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 71
<211> LENGTH: 124
<212> TYPE: PRT
<213> ORGANISM: Artificial
<220> FEATURE:
<223> OTHER INFORMATION: ABII009

<400> SEQUENCE: 71

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Lys Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 72
<211> LENGTH: 124
<212> TYPE: PRT
<213> ORGANISM: Artificial
<220> FEATURE:
<223> OTHER INFORMATION: ABII010

<400> SEQUENCE: 72

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Thr Ala Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 73
```

<211> LENGTH: 124
<212> TYPE: PRT
<213> ORGANISM: Artificial
<220> FEATURE:
<223> OTHER INFORMATION: ABII011

<400> SEQUENCE: 73

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Leu Tyr
65                  70                  75                  80

Leu Gln Met Ser Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 74
<211> LENGTH: 124
<212> TYPE: PRT
<213> ORGANISM: Artificial
<220> FEATURE:
<223> OTHER INFORMATION: ABII012

<400> SEQUENCE: 74

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Asn Gly Leu Lys Asp Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 75
<211> LENGTH: 124
<212> TYPE: PRT
<213> ORGANISM: Artificial
<220> FEATURE:
<223> OTHER INFORMATION: ABII013

<400> SEQUENCE: 75

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
            20                  25                  30

```
                    20                  25                  30
Thr Met Gly Trp Phe Arg Gln Ala Pro Gly Lys Gly Arg Glu Phe Val
        35                  40                  45
Ala Ala Val Thr Trp Asn Ser Gly Arg Ile Asn Tyr Ala Asp Ser Val
    50                  55                  60
Lys Gly Arg Phe Thr Val Ser Arg Asp Asn Thr Arg Asn Ala Ala Tyr
65                  70                  75                  80
Leu Gln Met Ser Ser Leu Lys Asp Glu Asp Thr Ala Val Tyr Tyr Cys
                85                  90                  95
Thr Ala His Arg Phe Val Val Gly Gly Asn Arg Val Glu Asp Trp Arg
            100                 105                 110
Tyr Trp Gly Gln Gly Thr Leu Val Thr Val Ser Ser
        115                 120

<210> SEQ ID NO 76
<211> LENGTH: 124
<212> TYPE: PRT
<213> ORGANISM: Artificial
<220> FEATURE:
<223> OTHER INFORMATION: ABII014

<400> SEQUENCE: 76

Glu Val Gln Leu Leu Glu Ser Gly Gly Gly Leu Val Leu Pro Gly Gly
1               5                   10                  15
Ser Leu Arg Leu Ser Cys Val His Ser Gly Pro Thr Phe Arg Thr Asp
            20                  25                  30
Thr Met Gly Trp Phe Arg Gln Ala Pro Gly Lys Gly Arg Glu Phe Val
        35                  40                  45
Ala Ala Val Thr Trp Asn Ser Gly Arg Ile Asn Tyr Ala Asp Ser Val
    50                  55                  60
Lys Gly Arg Phe Thr Val Ser Arg Asp Asn Thr Arg Asn Ala Ala Tyr
65                  70                  75                  80
Leu Gln Met Ser Gly Leu Arg Asp Glu Asp Thr Ala Val Tyr Tyr Cys
                85                  90                  95
Thr Ala His Arg Phe Val Val Gly Gly Asn Arg Val Glu Asp Trp Arg
            100                 105                 110
Tyr Trp Gly Gln Gly Thr Leu Val Thr Val Ser Ser
        115                 120

<210> SEQ ID NO 77
<211> LENGTH: 124
<212> TYPE: PRT
<213> ORGANISM: Artificial
<220> FEATURE:
<223> OTHER INFORMATION: ABII015

<400> SEQUENCE: 77

Glu Val Gln Leu Leu Glu Ser Gly Gly Gly Leu Val Leu Pro Gly Gly
1               5                   10                  15
Ser Leu Arg Leu Ser Cys Val His Ser Gly Pro Thr Phe Arg Thr Asp
            20                  25                  30
Thr Met Gly Trp Phe Arg Gln Ala Pro Gly Lys Gly Arg Glu Phe Val
        35                  40                  45
Ala Ala Val Thr Trp Asn Ser Gly Arg Ile Asn Tyr Ala Asp Ser Val
    50                  55                  60
Lys Gly Arg Phe Thr Val Ser Arg Asp Asn Thr Arg Asn Ala Ala Tyr
65                  70                  75                  80
Leu Gln Met Ser Gly Leu Lys Ala Glu Asp Thr Ala Val Tyr Tyr Cys
```

```
                        85                  90                  95

Thr Ala His Arg Phe Val Val Gly Gly Asn Arg Val Glu Asp Trp Arg
                100                 105                 110

Tyr Trp Gly Gln Gly Thr Leu Val Thr Val Ser Ser
        115                 120

<210> SEQ ID NO 78
<211> LENGTH: 124
<212> TYPE: PRT
<213> ORGANISM: Artificial
<220> FEATURE:
<223> OTHER INFORMATION: ABII016

<400> SEQUENCE: 78

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
                20                  25                  30

Thr Met Gly Trp Phe Arg Gln Ala Pro Gly Lys Gly Arg Glu Phe Val
            35                  40                  45

Ala Ala Val Thr Trp Asn Ser Gly Arg Ile Asn Tyr Ala Asp Ser Val
        50                  55                  60

Lys Gly Arg Phe Thr Val Ser Arg Asp Asn Thr Arg Asn Ala Ala Tyr
65                  70                  75                  80

Leu Gln Met Ser Gly Leu Lys Pro Glu Asp Thr Ala Val Tyr Tyr Cys
                85                  90                  95

Thr Ala His Arg Phe Val Val Gly Gly Asn Arg Val Glu Asp Trp Arg
                100                 105                 110

Tyr Trp Gly Gln Gly Thr Leu Val Thr Val Ser Ser
        115                 120

<210> SEQ ID NO 79
<211> LENGTH: 124
<212> TYPE: PRT
<213> ORGANISM: Artificial
<220> FEATURE:
<223> OTHER INFORMATION: ABII017

<400> SEQUENCE: 79

Glu Val Gln Leu Leu Glu Ser Gly Gly Gly Leu Val Leu Pro Gly Gly
1               5                   10                  15

Ser Leu Arg Leu Ser Cys Val His Ser Gly Pro Thr Phe Arg Thr Asp
                20                  25                  30

Thr Met Gly Trp Phe Arg Gln Ala Pro Gly Lys Gly Arg Glu Phe Val
            35                  40                  45

Ala Ala Val Thr Trp Asn Ser Gly Arg Ile Asn Tyr Ala Asp Ser Val
        50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Ala Ala His Arg Phe Val Val Gly Gly Asn Arg Val Glu Asp Trp Arg
                100                 105                 110

Tyr Trp Gly Gln Gly Thr Leu Val Thr Val Ser Ser
        115                 120

<210> SEQ ID NO 80
<211> LENGTH: 124
<212> TYPE: PRT
```

```
<213> ORGANISM: Artificial
<220> FEATURE:
<223> OTHER INFORMATION: ABII018

<400> SEQUENCE: 80
```

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Val Ser Arg Asp Asn Thr Arg Asn Ala Ala Tyr
65                  70                  75                  80

Leu Gln Met Ser Gly Leu Lys Pro Glu Asp Thr Ala Val Tyr Tyr Cys
                85                  90                  95

Thr Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

```
<210> SEQ ID NO 81
<211> LENGTH: 124
<212> TYPE: PRT
<213> ORGANISM: Artificial
<220> FEATURE:
<223> OTHER INFORMATION: ABII019

<400> SEQUENCE: 81
```

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

```
<210> SEQ ID NO 82
<211> LENGTH: 124
<212> TYPE: PRT
<213> ORGANISM: Artificial
<220> FEATURE:
<223> OTHER INFORMATION: ABII020

<400> SEQUENCE: 82
```

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
            35                  40                  45

Ala Ala Val Thr Trp Asn Ser Gly Arg Ile Asn Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
            115                 120

<210> SEQ ID NO 83
<211> LENGTH: 124
<212> TYPE: PRT
<213> ORGANISM: Artificial
<220> FEATURE:
<223> OTHER INFORMATION: ABII021

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
            35                  40                  45

Ala Ala Val Thr Trp Asn Ser Gly Arg Ile Asn Tyr Ala Asp Ser Val
        50                  55                  60

Lys Gly Arg Phe Thr Ile Ser Arg Asp Asn Ser Lys Asn Ala Val Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
            115                 120

<210> SEQ ID NO 84
<211> LENGTH: 124
<212> TYPE: PRT
<213> ORGANISM: Artificial
<220> FEATURE:
<223> OTHER INFORMATION: ABII022

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
            35                  40                  45

Ala Ala Val Thr Trp Asn Ser Gly Arg Ile Asn Tyr Ala Asp Ser Val
        50                  55                  60

Lys Gly Arg Phe Thr Ile Ser Arg Asp Asn Ser Lys Asn Ala Val Tyr
65                  70                  75                  80

Leu Gln Met Ser Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 85
<211> LENGTH: 124
<212> TYPE: PRT
<213> ORGANISM: Artificial
<220> FEATURE:
<223> OTHER INFORMATION: ABII023

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Ala Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 86
<211> LENGTH: 124
<212> TYPE: PRT
<213> ORGANISM: Artificial
<220> FEATURE:
<223> OTHER INFORMATION: ABII024

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Ala Ala Tyr
65                  70                  75                  80

Leu Gln Met Ser Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 87
<211> LENGTH: 124
<212> TYPE: PRT
<213> ORGANISM: Artificial
<220> FEATURE:

-continued

<223> OTHER INFORMATION: ABII025

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Ser Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 88
<211> LENGTH: 124
<212> TYPE: PRT
<213> ORGANISM: Artificial
<220> FEATURE:
<223> OTHER INFORMATION: ABII026

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 89
<211> LENGTH: 124
<212> TYPE: PRT
<213> ORGANISM: Artificial
<220> FEATURE:
<223> OTHER INFORMATION: ABII027

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

```
Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Ser Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120
```

<210> SEQ ID NO 90
<211> LENGTH: 124
<212> TYPE: PRT
<213> ORGANISM: Artificial
<220> FEATURE:
<223> OTHER INFORMATION: ABII028

<400> SEQUENCE: 90

```
Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120
```

<210> SEQ ID NO 91
<211> LENGTH: 124
<212> TYPE: PRT
<213> ORGANISM: Artificial
<220> FEATURE:
<223> OTHER INFORMATION: ABII029

<400> SEQUENCE: 91

```
Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110
```

```
Tyr Trp Gly Gln Gly Thr Leu Val Thr Val Ser Ser
        115                 120

<210> SEQ ID NO 92
<211> LENGTH: 124
<212> TYPE: PRT
<213> ORGANISM: Artificial
<220> FEATURE:
<223> OTHER INFORMATION: ABII030

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Ala Val Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 93
<211> LENGTH: 124
<212> TYPE: PRT
<213> ORGANISM: Artificial
<220> FEATURE:
<223> OTHER INFORMATION: ABII031

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Ala Val Tyr
65                  70                  75                  80

Leu Gln Met Ser Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 94
<211> LENGTH: 124
<212> TYPE: PRT
<213> ORGANISM: Artificial
<220> FEATURE:
<223> OTHER INFORMATION: ABII032
```

```
<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Ala Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 95
<211> LENGTH: 124
<212> TYPE: PRT
<213> ORGANISM: Artificial
<220> FEATURE:
<223> OTHER INFORMATION: ABII033

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Ala Ala Tyr
65                  70                  75                  80

Leu Gln Met Ser Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 96
<211> LENGTH: 124
<212> TYPE: PRT
<213> ORGANISM: Artificial
<220> FEATURE:
<223> OTHER INFORMATION: ABII034

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
```

```
                    50                  55                  60

Lys Gly Arg Phe Thr Ile Ser Arg Asp Asn Ser Lys Asn Thr Val Tyr
 65                  70                  75                  80

Leu Gln Met Ser Ser Leu Arg Pro Glu Asp Thr Ala Val Tyr Tyr Cys
                 85                  90                  95

Ala Ala His Arg Phe Val Val Gly Gly Asn Arg Val Glu Asp Trp Arg
                100                 105                 110

Tyr Trp Gly Gln Gly Thr Leu Val Thr Val Ser Ser
            115                 120

<210> SEQ ID NO 97
<211> LENGTH: 124
<212> TYPE: PRT
<213> ORGANISM: Artificial
<220> FEATURE:
<223> OTHER INFORMATION: ABII035

<400> SEQUENCE: 97

Glu Val Gln Leu Leu Glu Ser Gly Gly Gly Leu Val Gln Pro Gly Gly
  1               5                  10                  15

Ser Leu Arg Leu Ser Cys Val His Ser Gly Pro Thr Phe Arg Thr Asp
                 20                  25                  30

Thr Met Gly Trp Phe Arg Gln Ala Pro Gly Lys Gly Arg Glu Phe Val
             35                  40                  45

Ala Ala Val Thr Trp Asn Ser Gly Arg Ile Asn Tyr Ala Asp Ser Val
         50                  55                  60

Lys Gly Arg Phe Thr Ile Ser Arg Asp Asn Ser Lys Asn Thr Ala Tyr
 65                  70                  75                  80

Leu Gln Met Asn Ser Leu Arg Pro Glu Asp Thr Ala Val Tyr Tyr Cys
                 85                  90                  95

Ala Ala His Arg Phe Val Val Gly Gly Asn Arg Val Glu Asp Trp Arg
                100                 105                 110

Tyr Trp Gly Gln Gly Thr Leu Val Thr Val Ser Ser
            115                 120

<210> SEQ ID NO 98
<211> LENGTH: 124
<212> TYPE: PRT
<213> ORGANISM: Artificial
<220> FEATURE:
<223> OTHER INFORMATION: ABII036

<400> SEQUENCE: 98

Glu Val Gln Leu Leu Glu Ser Gly Gly Gly Leu Val Gln Pro Gly Gly
  1               5                  10                  15

Ser Leu Arg Leu Ser Cys Val His Ser Gly Pro Thr Phe Arg Thr Asp
                 20                  25                  30

Thr Met Gly Trp Phe Arg Gln Ala Pro Gly Lys Gly Arg Glu Phe Val
             35                  40                  45

Ala Ala Val Thr Trp Asn Ser Gly Arg Ile Asn Tyr Ala Asp Ser Val
         50                  55                  60

Lys Gly Arg Phe Thr Ile Ser Arg Asp Asn Ser Lys Asn Thr Ala Tyr
 65                  70                  75                  80

Leu Gln Met Ser Ser Leu Arg Pro Glu Asp Thr Ala Val Tyr Tyr Cys
                 85                  90                  95

Ala Ala His Arg Phe Val Val Gly Gly Asn Arg Val Glu Asp Trp Arg
                100                 105                 110

Tyr Trp Gly Gln Gly Thr Leu Val Thr Val Ser Ser
            115                 120
```

<210> SEQ ID NO 99
<211> LENGTH: 124
<212> TYPE: PRT
<213> ORGANISM: Artificial
<220> FEATURE:
<223> OTHER INFORMATION: ABII037

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser
        115                 120

<210> SEQ ID NO 100
<211> LENGTH: 124
<212> TYPE: PRT
<213> ORGANISM: Artificial
<220> FEATURE:
<223> OTHER INFORMATION: ABII60A10 = ABII050

<400> SEQUENCE: 100

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Glu Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Ile Tyr Tyr Cys
                85                  90                  95

Gly Ala Ala Tyr Arg Gly Thr Ala Ile Asn Val Arg Arg Ser Tyr Asp
            100                 105                 110

Ser Trp Gly Gln Gly Thr Gln Val Thr Val Ser Ser
        115                 120

<210> SEQ ID NO 101
<211> LENGTH: 124
<212> TYPE: PRT
<213> ORGANISM: Artificial
<220> FEATURE:
<223> OTHER INFORMATION: ABII051

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Arg Pro Glu Asp Thr Ala Ile Tyr Tyr Cys
                85                  90                  95

Gly Ala Ala Tyr Arg Gly Thr Ala Ile Asn Val Arg Arg Ser Tyr Asp
            100                 105                 110

Ser Trp Gly Gln Gly Thr Leu Val Thr Val Ser Ser
        115                 120

<210> SEQ ID NO 102
<211> LENGTH: 124
<212> TYPE: PRT
<213> ORGANISM: Artificial
<220> FEATURE:
<223> OTHER INFORMATION: ABII052

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Ala Val Tyr
65                  70                  75                  80

Leu Gln Met Asn Ser Leu Arg Pro Glu Asp Thr Ala Ile Tyr Tyr Cys
                85                  90                  95

Gly Ala Ala Tyr Arg Gly Thr Ala Ile Asn Val Arg Arg Ser Tyr Asp
            100                 105                 110

Ser Trp Gly Gln Gly Thr Leu Val Thr Val Ser Ser
        115                 120

<210> SEQ ID NO 103
<211> LENGTH: 124
<212> TYPE: PRT
<213> ORGANISM: Artificial
<220> FEATURE:
<223> OTHER INFORMATION: ABII053

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

```
Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Ile Tyr Tyr Cys
                 85                  90                  95

Gly Ala Ala Tyr Arg Gly Thr Ala Ile Asn Val Arg Arg Ser Tyr Asp
                100                 105                 110

Ser Trp Gly Gln Gly Thr Leu Val Thr Val Ser Ser
        115                 120

<210> SEQ ID NO 104
<211> LENGTH: 124
<212> TYPE: PRT
<213> ORGANISM: Artificial
<220> FEATURE:
<223> OTHER INFORMATION: ABII054

<400> SEQUENCE: 104

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Arg Thr Phe Asn Asn Tyr
                 20                  25                  30

Asn Met Gly Trp Phe Arg Gln Ala Pro Gly Lys Gly Arg Glu Phe Val
             35                  40                  45

Ala Ala Val Ser Arg Ser Gly Val Ser Thr Tyr Tyr Ala Asp Ser Val
         50                  55                  60

Lys Gly Arg Phe Thr Ile Ser Arg Asp Asn Ala Lys Asn Ala Leu Tyr
 65                  70                  75                  80

Leu Gln Met Asn Ser Leu Arg Pro Glu Asp Thr Ala Ile Tyr Tyr Cys
                 85                  90                  95

Gly Ala Ala Tyr Arg Gly Thr Ala Ile Asn Val Arg Arg Ser Tyr Asp
                100                 105                 110

Ser Trp Gly Gln Gly Thr Leu Val Thr Val Ser Ser
        115                 120

<210> SEQ ID NO 105
<211> LENGTH: 124
<212> TYPE: PRT
<213> ORGANISM: Artificial
<220> FEATURE:
<223> OTHER INFORMATION: ABII055

<400> SEQUENCE: 105

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Arg Thr Phe Asn Asn Tyr
                 20                  25                  30

Asn Met Gly Trp Phe Arg Gln Ala Pro Gly Lys Gly Arg Glu Phe Val
             35                  40                  45

Ala Ala Val Ser Arg Ser Gly Val Ser Thr Tyr Tyr Ala Asp Ser Val
         50                  55                  60

Lys Gly Arg Phe Thr Ile Ser Arg Asp Asn Ala Lys Asn Ala Val Tyr
 65                  70                  75                  80

Leu Gln Met Asn Ser Leu Arg Pro Glu Asp Thr Ala Val Tyr Tyr Cys
                 85                  90                  95

Gly Ala Ala Tyr Arg Gly Thr Ala Ile Asn Val Arg Arg Ser Tyr Asp
                100                 105                 110

Ser Trp Gly Gln Gly Thr Leu Val Thr Val Ser Ser
        115                 120
```

<210> SEQ ID NO 106
<211> LENGTH: 124
<212> TYPE: PRT
<213> ORGANISM: Artificial
<220> FEATURE:
<223> OTHER INFORMATION: ABII056

<400> SEQUENCE: 106

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Arg Pro Glu Asp Thr Ala Ile Tyr Tyr Cys
                85                  90                  95

Ala Ala Ala Tyr Arg Gly Thr Ala Ile Asn Val Arg Arg Ser Tyr Asp
            100                 105                 110

Ser Trp Gly Gln Gly Thr Leu Val Thr Val Ser Ser
        115                 120
```

<210> SEQ ID NO 107
<211> LENGTH: 124
<212> TYPE: PRT
<213> ORGANISM: Artificial
<220> FEATURE:
<223> OTHER INFORMATION: ABII057

<400> SEQUENCE: 107

```
Glu Val Gln Leu Leu Glu Ser Gly Gly Gly Leu Val Gln Pro Gly Gly
1               5                  10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Asp
            100                 105                 110

Ser Trp Gly Gln Gly Thr Leu Val Thr Val Ser Ser
        115                 120
```

<210> SEQ ID NO 108
<211> LENGTH: 124
<212> TYPE: PRT
<213> ORGANISM: Artificial
<220> FEATURE:
<223> OTHER INFORMATION: ABII058

<400> SEQUENCE: 108

```
Glu Val Gln Leu Leu Glu Ser Gly Gly Gly Leu Val Gln Pro Gly Gly
1               5                  10                  15
```

```
Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Ala Ala Ala Tyr Arg Gly Thr Ala Ile Asn Val Arg Arg Ser Tyr Asp
                100                 105                 110

Ser Trp Gly Gln Gly Thr Leu Val Thr Val Ser Ser
            115                 120

<210> SEQ ID NO 109
<211> LENGTH: 124
<212> TYPE: PRT
<213> ORGANISM: Artificial
<220> FEATURE:
<223> OTHER INFORMATION: ABII059

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Ala Tyr Arg Gly Thr Ala Ile Asn Val Arg Arg Ser Tyr Ser
                100                 105                 110

Ser Trp Gly Gln Gly Thr Leu Val Thr Val Ser Ser
            115                 120

<210> SEQ ID NO 110
<211> LENGTH: 124
<212> TYPE: PRT
<213> ORGANISM: Artificial
<220> FEATURE:
<223> OTHER INFORMATION: ABII060

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Pro Glu Asp Thr Ala Val Tyr Tyr Cys
                85                  90                  95

Ala Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser
        115                 120

<210> SEQ ID NO 111
<211> LENGTH: 124
<212> TYPE: PRT
<213> ORGANISM: Artificial
<220> FEATURE:
<223> OTHER INFORMATION: ABII061

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
    50                  55                  60

Lys Gly Arg Phe Thr Ile Ser Arg Asp Asn Lys Asn Thr Val Tyr
65                  70                  75                  80

Leu Gln Met Asn Ser Leu Arg Pro Glu Asp Thr Ala Val Tyr Tyr Cys
                85                  90                  95

Gly Ala Ala Tyr Arg Gly Thr Ala Ile Asn Val Arg Arg Ser Tyr Ser
            100                 105                 110

Ser Trp Gly Gln Gly Thr Leu Val Thr Val Ser Ser
        115                 120

<210> SEQ ID NO 112
<211> LENGTH: 123
<212> TYPE: PRT
<213> ORGANISM: Artificial
<220> FEATURE:
<223> OTHER INFORMATION: ABII1E11

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Asp Tyr
            20                  25                  30

Asn Met Gly Trp Phe His Gln Ala Pro Gly Lys Glu Arg Glu Ile Val
        35                  40                  45

Ala Ala Ile Ser Arg Ser Gly Arg Ser Thr Tyr Tyr Thr Val Ser Val
    50                  55                  60

Glu Gly Arg Phe Thr Ile Ser Arg Asp Asn Ala Lys Asn Thr Val Asp
65                  70                  75                  80

Leu Glu Met Asn Ser Leu Lys Pro Glu Asp Thr Gly Ile Tyr Tyr Cys
                85                  90                  95

Ala Ala Asn Ser Ala Gly Arg Ala Ile Asn Leu Pro Leu Tyr Lys Tyr
            100                 105                 110

Trp Gly Gln Gly Thr Gln Val Thr Val Ser Ser
        115                 120

<210> SEQ ID NO 113

```
<211> LENGTH: 124
<212> TYPE: PRT
<213> ORGANISM: Artificial
<220> FEATURE:
<223> OTHER INFORMATION: ABII14D4

<400> SEQUENCE: 113

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Asn Met Ala Trp Phe Arg His Ala Pro Gly Lys Glu Arg Glu Phe Val
        35                  40                  45

Ala Ala Ile Ser Arg Ser Gly Gly Ser Thr Tyr Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Ala Pro Arg Gly Arg Ser Ile Val Thr Thr Ala Thr Tyr Asp
            100                 105                 110

Tyr Trp Gly Gln Gly Thr Gln Val Thr Val Ser Ser
        115                 120

<210> SEQ ID NO 114
<211> LENGTH: 123
<212> TYPE: PRT
<213> ORGANISM: Artificial
<220> FEATURE:
<223> OTHER INFORMATION: ABII5D2

<400> SEQUENCE: 114

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Val Arg Gln Ala Pro Gly Lys Glu Arg Glu Leu Val
        35                  40                  45

Ala Thr Ile Ser Gln Ser Gly Gly Leu Arg Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Thr Pro Gly Asp Thr Ala Val Tyr Tyr Cys
                85                  90                  95

Ala Ala Gln Ala Arg Ala Thr Ala Trp Ser Pro Gln Arg Val Asp Tyr
            100                 105                 110

Trp Gly Gln Gly Thr Gln Val Thr Val Ser Ser
        115                 120

<210> SEQ ID NO 115
<211> LENGTH: 124
<212> TYPE: PRT
<213> ORGANISM: Artificial
<220> FEATURE:
<223> OTHER INFORMATION: ABII35C7

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ile Tyr
```

```
                    20                  25                  30
Asn Met Gly Trp Phe Arg Gln Ala Pro Gly Lys Glu Arg Glu Phe Val
            35                  40                  45
Ala Ala Ile Ser Arg Ser Gly Ser Thr Tyr Tyr Gly Asp Ser Val
    50                  55                  60
Lys Gly Arg Phe Thr Ile Ser Arg Asp Asn Ala Lys Lys Thr Val Tyr
65                  70                  75                  80
Leu Gln Met Asn Ser Leu Lys Pro Glu Asp Thr Ala Val Tyr His Cys
                85                  90                  95
Ala Ala Ala Arg Phe Gly Thr Pro Ile Asn Thr Arg Gly Ser Tyr Asp
            100                 105                 110
Tyr Trp Gly Gln Gly Thr Gln Val Thr Val Ser Ser
        115                 120
```

<210> SEQ ID NO 116
<211> LENGTH: 124
<212> TYPE: PRT
<213> ORGANISM: Artificial
<220> FEATURE:
<223> OTHER INFORMATION: ABII35D2

<400> SEQUENCE: 116

```
Glu Val Gln Leu Val Glu Ser Gly Gly Gly Leu Val Gln Ala Gly Gly
1               5                   10                  15
Ser Leu Arg Leu Ser Cys Val Ala Ser Gly Leu Thr Phe Ser Ser Tyr
            20                  25                  30
Asn Met Gly Trp Phe Arg Gln Ala Pro Gly Lys Glu Arg Glu Phe Val
        35                  40                  45
Ala Ala Ile Ser Arg Ser Gly Ser Thr Tyr Tyr Thr Asp Ser Val
    50                  55                  60
Lys Gly Arg Phe Thr Ile Ser Arg Asp Ser Ser Lys Asn Thr Val Tyr
65                  70                  75                  80
Leu Gln Met Asn Ser Leu Lys Pro Glu Asp Thr Ala Asp Tyr Tyr Cys
                85                  90                  95
Ala Ala Ala Leu Phe Gly Ser Ala Ile Asn Leu Leu Ser Glu Tyr Arg
            100                 105                 110
Tyr Trp Gly Gln Gly Thr Gln Val Thr Val Ser Ser
        115                 120
```

<210> SEQ ID NO 117
<211> LENGTH: 124
<212> TYPE: PRT
<213> ORGANISM: Artificial
<220> FEATURE:
<223> OTHER INFORMATION: ABII35G2

<400> SEQUENCE: 117

```
Glu Val Gln Leu Val Glu Ser Gly Gly Gly Leu Val Gln Ala Gly Gly
1               5                   10                  15
Ser Leu Arg Leu Ser Cys Val Ala Ser Gly Arg Thr Phe Ser Asn Tyr
            20                  25                  30
Gly Met Gly Trp Phe Arg Gln Ala Pro Gly Lys Asp Arg Glu Phe Val
        35                  40                  45
Ala Ala Ile Ser Arg Ser Gly Thr Thr Tyr Tyr Glu Asp Asp Val
    50                  55                  60
Lys Gly Arg Phe Thr Ile Ser Arg Asp Asn Ala Lys Asn Ser Val Tyr
65                  70                  75                  80
Leu Gln Met Asn Ser Leu Lys Pro Glu Asp Thr Ala Val Tyr Tyr Cys
```

```
                    85                  90                  95
Ala Ala Arg Pro Ser Tyr Val Ala Val Asn Ile Ala Ser Tyr Asn
                100                 105                 110

Asn Trp Gly Gln Gly Thr Gln Val Thr Val Ser Ser
        115                 120

<210> SEQ ID NO 118
<211> LENGTH: 124
<212> TYPE: PRT
<213> ORGANISM: Artificial
<220> FEATURE:
<223> OTHER INFORMATION: ABII42D4

<400> SEQUENCE: 118

Glu Val Gln Leu Val Glu Ser Gly Gly Gly Leu Val Leu Ala Gly Gly
1               5                   10                  15

Ser Leu Arg Leu Ser Cys Val His Ser Gly Pro Thr Phe Ser Thr Asp
                20                  25                  30

Thr Met Gly Trp Phe Arg Gln Ala Pro Gly Lys Glu Arg Glu Phe Val
            35                  40                  45

Ala Ala Val Thr Trp Asn Ser Gly Arg Thr Asn Tyr Ala Asp Ser Val
        50                  55                  60

Lys Gly Arg Phe Thr Val Ser Arg Asp Asn Thr Arg Asn Ala Ala Tyr
65                  70                  75                  80

Leu Gln Met Ser Gly Leu Lys Asp Glu Asp Thr Ala Val Tyr Tyr Cys
                85                  90                  95

Thr Ala His Arg Leu Val Val Gly Thr Ser Val Gly Asp Trp Arg
                100                 105                 110

Tyr Trp Gly Gln Gly Thr Gln Val Thr Val Ser Ser
        115                 120

<210> SEQ ID NO 119
<211> LENGTH: 124
<212> TYPE: PRT
<213> ORGANISM: Artificial
<220> FEATURE:
<223> OTHER INFORMATION: ABII42B10

<400> SEQUENCE: 119

Glu Val Gln Leu Val Glu Ser Gly Gly Gly Leu Val Gln Arg Gly Gly
1               5                   10                  15

Ser Leu Arg Leu Ser Cys Ala Ala Ser Gly Arg Thr Phe Ser Asn Leu
                20                  25                  30

Asn Met Gly Trp Phe Arg Gln Ala Pro Gly Lys Glu Arg Glu Phe Gln
            35                  40                  45

Ala Ala Ile Ser Arg Ser Gly Thr Thr Tyr Tyr Ala Asp Ser Val
        50                  55                  60

Lys Gly Arg Phe Thr Ile Ser Arg Asp Asn Ala Lys Ser Thr Val Phe
65                  70                  75                  80

Leu Gln Met Asn Ser Leu Lys Pro Glu Asp Thr Ala Val Tyr Tyr Cys
                85                  90                  95

Ala Ala Ala Ser Pro Gly Gly Pro Ile Asn Tyr Gly Arg Ala Tyr Asp
        100                 105                 110

Ser Trp Gly Gln Gly Thr Gln Val Thr Val Ser Ser
        115                 120

<210> SEQ ID NO 120
<211> LENGTH: 124
<212> TYPE: PRT
```

<213> ORGANISM: Artificial
<220> FEATURE:
<223> OTHER INFORMATION: ABII42F5

<400> SEQUENCE: 120

```
Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Thr Asp Tyr
            20                  25                  30

Asn Ile Gly Trp Phe Cys Gln Ala Pro Gly Lys Glu Arg Glu Phe Val
        35                  40                  45

Ala Ala Ile Ser Gly Ser Gly Ser Thr Tyr Tyr Ala Asp Ser Ala
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ala Cys
                85                  90                  95

Ala Ala Ala Gln Arg Arg Leu Ala Val Asn Val Asp Thr Ser Tyr Asn
                100                 105                 110

Val Trp Gly Gln Gly Thr Gln Val Thr Val Ser Ser
            115                 120
```

<210> SEQ ID NO 121
<211> LENGTH: 124
<212> TYPE: PRT
<213> ORGANISM: Artificial
<220> FEATURE:
<223> OTHER INFORMATION: ABII42E10

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Thr Leu Tyr
            20                  25                  30

Thr Met Gly Trp Phe Arg Gln Ala Pro Gly Lys Glu Arg Glu Phe Val
        35                  40                  45

Ala Ala Ile Ser Ala Ser Gly Gly Thr Thr Tyr Tyr Ala Asp Ser Val
    50                  55                  60

Lys Gly Arg Phe Ala Leu Ser Arg Asp Asn Ala Lys Asn Thr Val Phe
65                  70                  75                  80

Leu Gln Met Asn Thr Leu Lys Pro Glu Asp Thr Ala Glu Tyr Leu Cys
                85                  90                  95

Ala Ala Ala Phe Arg Gly Phe Ala Ile Asn Thr Pro Thr Ser Tyr Asn
                100                 105                 110

Tyr Trp Gly Gln Gly Thr Gln Val Thr Val Ser Ser
            115                 120
```

<210> SEQ ID NO 122
<211> LENGTH: 121
<212> TYPE: PRT
<213> ORGANISM: Artificial
<220> FEATURE:
<223> OTHER INFORMATION: ABII42G10

<400> SEQUENCE: 122

```
Glu Val Gln Leu Val Glu Ser Gly Gly Gly Leu Val Gln Ala Gly Gly
1               5                   10                  15

Ser Leu Arg Leu Ser Cys Leu Phe Ser Gly Arg Thr Phe Ser Thr Asn
            20                  25                  30
```

Gly Val Gly Trp Phe Arg Gln Val Pro Gly Lys Glu Arg Glu Phe Val
    35                  40                  45

Ser Ala Ile Asn Trp Ser Gly Ser Lys Thr Asn Tyr Ala Glu Pro Val
50                  55                  60

Lys Gly Arg Phe Thr Ile Ser Arg Asp Asn Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Tyr Arg Thr Ser Ile Ser Arg Tyr Glu Tyr Ala Tyr Trp Gly
            100                 105                 110

Gln Gly Thr Gln Val Thr Val Ser Ser
            115                 120

<210> SEQ ID NO 123
<211> LENGTH: 124
<212> TYPE: PRT
<213> ORGANISM: Artificial
<220> FEATURE:
<223> OTHER INFORMATION: ABII60A10

<400> SEQUENCE: 123

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Glu Arg Glu Phe Val
            35                  40                  45

Ala Ala Val Ser Arg Ser Gly Val Ser Thr Tyr Tyr Ala Asp Ser Val
50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Ile Tyr Tyr Cys
                85                  90                  95

Gly Ala Ala Tyr Arg Gly Thr Ala Ile Asn Val Arg Arg Ser Tyr Asp
            100                 105                 110

Ser Trp Gly Gln Gly Thr Gln Val Thr Val Ser Ser
            115                 120

<210> SEQ ID NO 124
<211> LENGTH: 125
<212> TYPE: PRT
<213> ORGANISM: Artificial
<220> FEATURE:
<223> OTHER INFORMATION: ABII60G11

<400> SEQUENCE: 124

Glu Val Gln Leu Val Glu Ser Gly Gly Gly Ser Glu Gln Ala Gly Gly
1               5                   10                  15

Ser Leu Arg Leu Ser Cys Ala Thr Ser Gly Arg Ala Phe Ser Val Tyr
            20                  25                  30

Ala Trp Phe Arg Gln Ala Pro Gly Lys Glu Arg Thr Phe Val Ala Ala
            35                  40                  45

Val Ala Trp Val Gly Gly Ser Thr Tyr Ser Asp Ser Val Lys Gly
50                  55                  60

Arg Phe Thr Ile Ser Arg Asp Asn Ala Lys Asn Thr Val Phe Leu His
65                  70                  75                  80

Met Asn Ser Leu Lys Pro Glu Asp Thr Ala Ala Tyr Tyr Cys Ala Ala
                85                  90                  95

```
Arg Leu Tyr Gly Gly Arg Trp Tyr Asn Ser Pro Arg Val Asp Asp Phe
            100                 105                 110

Glu Tyr Trp Gly Gln Gly Thr Gln Val Thr Val Ser Ser
        115                 120                 125
```

<210> SEQ ID NO 125
<211> LENGTH: 117
<212> TYPE: PRT
<213> ORGANISM: Artificial
<220> FEATURE:
<223> OTHER INFORMATION: ABII60D2

<400> SEQUENCE: 125

```
Glu Val Gln Leu Val Glu Ser Gly Gly Gly Ser Val Gln Ala Gly Gly
1               5                   10                  15

Ser Leu Arg Leu Ser Cys Ala Tyr Ser Gly Ser Ile Phe Ser Ile Lys
            20                  25                  30

Thr Met Gly Trp Tyr Arg Gln Ala Pro Gly Lys Gln Arg Glu Leu Val
        35                  40                  45

Gly Arg Ile Thr Ser Gly Asp Ser Thr Asn Tyr Ala Asp Ser Val Lys
    50                  55                  60

Gly Arg Phe Thr Ile Ser Arg Asp Lys Ala Lys Thr Thr Val Tyr Leu
65                  70                  75                  80

Gln Met Asn Asn Leu Lys Pro Glu Asp Thr Ala Val Tyr Tyr Cys Ala
                85                  90                  95

Ala Arg Arg Pro Trp Pro Arg Ser Asp Val Trp Gly Gln Gly Thr Gln
            100                 105                 110

Val Thr Val Ser Ser
        115
```

<210> SEQ ID NO 126
<211> LENGTH: 119
<212> TYPE: PRT
<213> ORGANISM: Artificial
<220> FEATURE:
<223> OTHER INFORMATION: ABII60H5

<400> SEQUENCE: 126

```
Glu Val Gln Leu Val Glu Ser Gly Gly Gly Leu Val Gln Val Gly Gly
1               5                   10                  15

Ser Leu Arg Leu Ser Cys Ala Ala Ser Gly Asn Ile Gly Ser Ile Asn
            20                  25                  30

Ala Met Gly Trp Tyr Arg Gln Ala Pro Gly Lys Glu Arg Glu Trp Val
        35                  40                  45

Ala Ile Ile Thr Asn Ser Gly Ser Val Asn Tyr Gly Pro Asp Ser Val
    50                  55                  60

Lys Gly Arg Phe Thr Ile Ser Gly Asp Asn Ala Lys Asn Arg Val Tyr
65                  70                  75                  80

Leu Gln Met Asp Ser Leu Lys Pro Glu Asp Thr Ala Val Tyr Tyr Cys
                85                  90                  95

Ala Ala Glu Ser Trp Gly Arg Ser Pro Leu Lys Tyr Leu Gly Gln Gly
            100                 105                 110

Thr Gln Val Thr Val Ser Ser
        115
```

<210> SEQ ID NO 127
<211> LENGTH: 119
<212> TYPE: PRT
<213> ORGANISM: Artificial
<220> FEATURE:

<223> OTHER INFORMATION: ABII61F6

<400> SEQUENCE: 127

Glu Val Gln Leu Val Glu Ser Gly Gly Gly Leu Val Gln Thr Gly Gly
1               5                   10                  15

Ser Leu Arg Leu Ser Cys Ala Ala Ser Gly Ser Thr Val Asn Ile Asn
            20                  25                  30

Ala Met Gly Trp Tyr Arg Gln Ala Pro Gly Lys Gln Arg Glu Leu Val
        35                  40                  45

Ala Ile Ile Asn Lys Arg Gly Val Thr Asn Tyr Ala Asp Ser Thr Glu
    50                  55                  60

Gly Arg Phe Thr Ile Ser Arg Asp Asn Ser Lys Arg Thr Leu Tyr Leu
65                  70                  75                  80

Gln Met Asn Ser Leu Lys Pro Glu Asp Thr Ala Val Tyr Tyr Cys Asn
                85                  90                  95

Ala Val Val Gly Arg Tyr Gly Arg Thr Tyr Gly Tyr Trp Gly Gln Gly
            100                 105                 110

Thr Gln Val Thr Val Ser Ser
        115

<210> SEQ ID NO 128
<211> LENGTH: 112
<212> TYPE: PRT
<213> ORGANISM: Artificial
<220> FEATURE:
<223> OTHER INFORMATION: 3D6 VL

<400> SEQUENCE: 128

Tyr Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Ile Glu Ala Glu Asp Leu Gly Leu Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 129
<211> LENGTH: 119
<212> TYPE: PRT
<213> ORGANISM: Artificial
<220> FEATURE:
<223> OTHER INFORMATION: 3D6 VH

<400> SEQUENCE: 129

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Asn Ser Asp Lys Arg Leu Glu Trp Val
        35                  40                  45

Ala Ser Ile Arg Ser Gly Gly Gly Arg Thr Tyr Tyr Ser Asp Asn Val
    50                  55                  60

```
Lys Gly Arg Phe Thr Ile Ser Arg Glu Asn Ala Lys Asn Thr Leu Tyr
 65                  70                  75                  80

Leu Gln Met Ser Ser Leu Lys Ser Glu Asp Thr Ala Leu Tyr Tyr Cys
                 85                  90                  95

Val Arg Tyr Asp His Tyr Ser Gly Ser Ser Asp Tyr Trp Gly Gln Gly
            100                 105                 110

Thr Thr Val Thr Val Ser Ser
            115

<210> SEQ ID NO 130
<211> LENGTH: 112
<212> TYPE: PRT
<213> ORGANISM: Artificial
<220> FEATURE:
<223> OTHER INFORMATION: m266 VL

<400> SEQUENCE: 130

Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Ile Tyr Ser
                 20                  25                  30

Asp Gly Asn Ala Tyr Leu His Trp Phe Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Thr Glu Asp Leu Gly Val Tyr Phe Cys Ser Gln Ser
                 85                  90                  95

Thr His Val Pro Trp Thr Phe Gly Gly Thr Lys Leu Glu Ile Lys
            100                 105                 110

<210> SEQ ID NO 131
<211> LENGTH: 112
<212> TYPE: PRT
<213> ORGANISM: Artificial
<220> FEATURE:
<223> OTHER INFORMATION: m266 VH

<400> SEQUENCE: 131

Glu Val Lys Leu Val Glu Ser Gly Gly Gly Leu Val Gln Pro Gly Gly
  1               5                  10                  15

Ser Leu Lys Leu Ser Cys Ala Val Ser Gly Phe Thr Phe Ser Arg Tyr
                 20                  25                  30

Ser Met Ser Trp Val Arg Gln Thr Pro Glu Lys Arg Leu Glu Leu Val
             35                  40                  45

Ala Gln Ile Asn Ser Val Gly Asn Ser Thr Tyr Tyr Pro Asp Thr Val
 50                  55                  60

Lys Gly Arg Phe Thr Ile Ser Arg Asp Asn Ala Glu Tyr Thr Leu Ser
 65                  70                  75                  80

Leu Gln Met Ser Gly Leu Arg Ser Asp Asp Thr Ala Thr Tyr Tyr Cys
                 85                  90                  95

Ala Ser Gly Asp Tyr Trp Gly Gln Gly Thr Thr Leu Thr Val Ser Ser
            100                 105                 110

<210> SEQ ID NO 132
<211> LENGTH: 124
<212> TYPE: PRT
<213> ORGANISM: Artificial
```

```
<220> FEATURE:
<223> OTHER INFORMATION: 2D2

<400> SEQUENCE: 132

Ala Val Gln Leu Val Asp Ser Gly Gly Leu Val Gln Ala Gly Gly
1               5                   10                  15

Ser Leu Arg Leu Ser Cys Ala Val Ser Gly Thr Phe Ser Ser Ile
            20                  25                  30

Gly Met Gly Trp Phe Arg Gln Ala Pro Gly Lys Glu Arg Glu Phe Val
        35                  40                  45

Gly Ala Ile Ser Arg Ser Gly Asp Ser Thr Tyr Tyr Ala Asp Ser Val
    50                  55                  60

Lys Gly Arg Phe Thr Ile Ser Arg Asp Gly Ala Lys Asn Thr Val Tyr
65                  70                  75                  80

Leu Gln Met Asn Ser Leu Lys Asp Glu Asp Thr Ala Val Tyr Tyr Cys
                85                  90                  95

Ala Gly Arg Pro Ala Gly Thr Ala Ile Asn Ile Arg Arg Ser Tyr Asn
            100                 105                 110

Tyr Trp Gly Gln Gly Thr Gln Val Thr Val Ser Ser
        115                 120

<210> SEQ ID NO 133
<211> LENGTH: 124
<212> TYPE: PRT
<213> ORGANISM: Artificial
<220> FEATURE:
<223> OTHER INFORMATION: 2G6

<400> SEQUENCE: 133

Gln Val Lys Leu Glu Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Thr Ile Ser Pro Arg Ala Ala Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Glu Pro Asp Asp Thr Ala Leu Tyr Tyr Cys
                85                  90                  95

Ala Lys Ser Leu Arg Tyr Arg Asp Arg Pro Gln Ser Ser Asp Phe Leu
            100                 105                 110

Phe Trp Arg Gln Gly Thr Gln Val Thr Val Ser Ser
        115                 120

<210> SEQ ID NO 134
<211> LENGTH: 124
<212> TYPE: PRT
<213> ORGANISM: Artificial
<220> FEATURE:
<223> OTHER INFORMATION: 3A

<400> SEQUENCE: 134

Ala Val Gln Leu Val Glu Ser Gly Gly Leu Val Arg Asp Gly Asp
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
```

-continued

```
                35                  40                  45
Ala Ala Ile Gly Trp Ser Gly Gly Ser Thr Ala Tyr Ala Asp Ser Val
         50                  55                  60
Lys Gly Arg Phe Thr Ile Ser Arg Asp Asn Ala Arg Asn Thr Val Tyr
 65                  70                  75                  80
Leu Gln Met Asn Ser Leu Lys Pro Glu Asp Thr Ala Val Tyr Tyr Cys
                 85                  90                  95
Ala Ser Ala Pro Thr Arg Trp Val Pro Arg Asp Ser Arg Phe Tyr Asp
                100                 105                 110
Arg Trp Gly Gln Gly Thr Arg Val Thr Val Ser Ser
            115                 120

<210> SEQ ID NO 135
<211> LENGTH: 124
<212> TYPE: PRT
<213> ORGANISM: Artificial
<220> FEATURE:
<223> OTHER INFORMATION: 1B

<400> SEQUENCE: 135

Gln Val Gln Leu Gln Glu Ser Gly Gly Gly Leu Val Gln Pro Gly Gly
 1               5                  10                  15
Ser Leu Arg Leu Ser Cys Ala Ala Ser Glu Phe Thr Leu Asp Tyr Tyr
                20                  25                  30
Ser Ile Ala Trp Phe Arg Gln Ala Pro Gly Lys Glu Arg Glu Gly Val
                35                  40                  45
Ser Cys Ile Ser Ser Tyr Asp Gly Ser Thr Ser Tyr Ala Asp Ser Val
         50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Ile Tyr Tyr Cys
                 85                  90                  95
Ala Ala Gly Ile Arg Asp Trp Ala Thr Leu Arg Glu Tyr Glu Tyr Asp
                100                 105                 110
Asp Trp Gly Gln Gly Thr Gln Val Thr Val Ser Ser
            115                 120

<210> SEQ ID NO 136
<211> LENGTH: 121
<212> TYPE: PRT
<213> ORGANISM: Artificial
<220> FEATURE:
<223> OTHER INFORMATION: 11G

<400> SEQUENCE: 136

Gln Val Gln Leu Gln Glu Ser Gly Gly Gly Leu Val Gln Pro Gly Gly
 1               5                  10                  15
Ser Leu Arg Leu Ser Cys Ala Ala Ser Gly Ser Ile Phe Ser Ile Asn
                20                  25                  30
Thr Met Ala Trp Tyr Arg Gln Ala Pro Gly Lys Glu Arg Asp Leu Val
                35                  40                  45
Ala Ala Ile Ile Ser Ser Gly Ser Thr Asn Tyr Ala Asp Ser Val Lys
         50                  55                  60
Gly Arg Phe Thr Ile Ser Arg Asp Asn Thr Lys Asn Thr Val Tyr Leu
 65                  70                  75                  80
Gln Met Asn Ser Leu Lys Leu Glu Asp Thr Ala Val Tyr Tyr Cys Asn
                 85                  90                  95
Ala Ala Ile Arg Arg Ser Val Ile Asp Ala Trp Gly Ala Tyr Trp Gly
```

```
                      100                 105                  110

Gln Gly Thr Gln Val Thr Val Ser Ser
        115                 120

<210> SEQ ID NO 137
<211> LENGTH: 120
<212> TYPE: PRT
<213> ORGANISM: Artificial
<220> FEATURE:
<223> OTHER INFORMATION: 4D

<400> SEQUENCE: 137

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Thr Ile Arg Trp Asn Gly Asp Tyr Ala Asp Ser Val Arg Asp Arg
    50                  55                  60

Phe Thr Ile Ser Arg Asp Asp Ala Lys Asn Thr Val Phe Leu Gln Met
65                  70                  75                  80

Asn Ser Leu Lys Pro Glu Asp Thr Ala Ile Tyr Tyr Cys Ala Ala Arg
                85                  90                  95

Leu Gly Pro Arg Thr Ser Gln Ala Ala Leu Tyr Arg Tyr Trp Gly Gln
            100                 105                 110

Gly Thr Gln Val Thr Val Ser Ser
        115                 120

<210> SEQ ID NO 138
<211> LENGTH: 124
<212> TYPE: PRT
<213> ORGANISM: Artificial
<220> FEATURE:
<223> OTHER INFORMATION: 8B

<400> SEQUENCE: 138

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Ala Ala Ile Gly Trp Ser Gly Gly Ser Thr Ala Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ser Ala Pro Thr Arg Trp Val Pro Arg Asp Ser Arg Phe Tyr Asp
            100                 105                 110

Arg Trp Gly Gln Gly Thr Arg Val Thr Val Ser Ser
        115                 120

<210> SEQ ID NO 139
<211> LENGTH: 123
<212> TYPE: PRT
<213> ORGANISM: Artificial
<220> FEATURE:
<223> OTHER INFORMATION: 31-1
```

-continued

<400> SEQUENCE: 139

Ala Glu Val Gln Leu Gln Ala Ser Gly Gly Ser Val Gln Pro Gly
1               5                   10                  15

Gly Ser Leu Arg Leu Ser Cys Ala Ala Ser Gly Phe Ile Phe Gly Trp
            20                  25                  30

Ser Thr Met Ser Trp Val Arg Gln Ala Pro Gly Lys Gly Leu Glu Trp
        35                  40                  45

Val Ser Thr Ile Ser Gly Gly Ser Ala Thr Thr Tyr Thr Asp Ser
    50                  55                  60

Val Lys Gly Arg Phe Thr Ile Ser Arg Asp Arg Ala Lys Asn Thr Leu
65                  70                  75                  80

Tyr Leu Gln Met Asn Ser Leu Lys Pro Glu Asp Thr Ala Ile Tyr Tyr
                85                  90                  95

Cys Asn Ala Asp Val Ser Thr Gly Phe Arg Tyr Gln Arg Lys Asp Tyr
            100                 105                 110

Trp Gly Arg Gly Thr Gln Val Thr Val Ser Ser
            115                 120

<210> SEQ ID NO 140
<211> LENGTH: 98
<212> TYPE: PRT
<213> ORGANISM: Artificial
<220> FEATURE:
<223> OTHER INFORMATION: VH3-23 (DP-47)

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 141
<211> LENGTH: 9
<212> TYPE: PRT
<213> ORGANISM: Artificial
<220> FEATURE:
<223> OTHER INFORMATION: 9GS

<400> SEQUENCE: 141

Gly Gly Gly Gly Ser Gly Gly Gly Gly
1               5

<210> SEQ ID NO 142
<211> LENGTH: 283
<212> TYPE: PRT
<213> ORGANISM: Artificial
<220> FEATURE:
<223> OTHER INFORMATION: ABII314, PEGylated at Cys 129

<400> SEQUENCE: 142

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Ala Tyr Arg Gly Thr Ala Ile Asn Val Arg Arg Ser Tyr Ser
        100                 105                 110

Ser Trp Gly Gln Gly Thr Leu Val Thr Val Ser Ser Gly Gly Gly Gly
        115                 120                 125

Cys Gly Gly Gly Ser Gly Gly Gly Ser Gly Gly Gly Gly Gly Gly Ser
        130                 135                 140

Gly Gly Gly Gly Ser Gly Gly Gly Ser Gly Gly Gly Ser Glu
145                 150                 155                 160

Val Gln Leu Leu Glu Ser Gly Gly Leu Val Gln Pro Gly Gly Ser
            165                 170                 175

Leu Arg Leu Ser Cys Val His Ser Gly Pro Thr Phe Arg Thr Asp Thr
        180                 185                 190

Met Gly Trp Phe Arg Gln Ala Pro Gly Lys Gly Arg Glu Phe Val Ala
        195                 200                 205

Ala Val Thr Trp Asn Ser Gly Arg Ile Asn Tyr Ala Asp Ser Val Lys
210                 215                 220

Gly Arg Phe Thr Ile Ser Arg Asp Asn Ser Lys Asn Thr Ala Tyr Leu
225                 230                 235                 240

Gln Met Asn Ser Leu Arg Pro Glu Asp Thr Ala Val Tyr Tyr Cys Ala
            245                 250                 255

Ala His Arg Phe Val Val Gly Asn Arg Val Glu Asp Trp Arg Tyr
        260                 265                 270

Trp Gly Gln Gly Thr Leu Val Thr Val Ser Ser
        275                 280

<210> SEQ ID NO 143
<211> LENGTH: 257
<212> TYPE: PRT
<213> ORGANISM: Artificial
<220> FEATURE:
<223> OTHER INFORMATION: ABII315, PEGylated at Cys 129

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Asn Asn Tyr
            20                  25                  30

Asn Met Gly Trp Phe Arg Gln Ala Pro Gly Lys Gly Arg Glu Phe Val
        35                  40                  45

Ala Ala Val Ser Arg Ser Gly Val Ser Thr Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
```

```
                        85                   90                   95
Ala Ala Ala Tyr Arg Gly Thr Ala Ile Asn Val Arg Arg Ser Tyr Ser
                    100                 105                 110

Ser Trp Gly Gln Gly Thr Leu Val Thr Val Ser Ser Gly Gly Gly Gly
                115                 120                 125

Cys Gly Gly Gly Ser Glu Val Gln Leu Leu Glu Ser Gly Gly Gly Leu
            130                 135                 140

Val Gln Pro Gly Gly Ser Leu Arg Leu Ser Cys Val His Ser Gly Pro
145                 150                 155                 160

Thr Phe Arg Thr Asp Thr Met Gly Trp Phe Arg Gln Ala Pro Gly Lys
                165                 170                 175

Gly Arg Glu Phe Val Ala Ala Val Thr Trp Asn Ser Gly Arg Ile Asn
            180                 185                 190

Tyr Ala Asp Ser Val Lys Gly Arg Phe Thr Ile Ser Arg Asp Asn Ser
                195                 200                 205

Lys Asn Thr Ala Tyr Leu Gln Met Asn Ser Leu Arg Pro Glu Asp Thr
            210                 215                 220

Ala Val Tyr Tyr Cys Ala Ala His Arg Phe Val Val Gly Gly Asn Arg
225                 230                 235                 240

Val Glu Asp Trp Arg Tyr Trp Gly Gln Gly Thr Leu Val Thr Val Ser
                245                 250                 255

Ser

<210> SEQ ID NO 144
<211> LENGTH: 403
<212> TYPE: PRT
<213> ORGANISM: Artificial
<220> FEATURE:
<223> OTHER INFORMATION: His.Xa.Abeta1-28.GS

<400> SEQUENCE: 144

Met His His His His His Ile Glu Gly Arg Asp Ala Glu Phe Arg
1               5                   10                  15

His Asp Ser Gly Tyr Glu Val His His Gln Lys Leu Val Phe Phe Ala
                20                  25                  30

Glu Asp Val Gly Ser Asn Lys Gly Gly Ser Gly Gly Ser Gln Glu Arg
            35                  40                  45

Pro Thr Phe Tyr Arg Gln Glu Leu Asn Lys Thr Ile Trp Glu Val Pro
        50                  55                  60

Glu Arg Tyr Gln Asn Leu Ser Pro Val Gly Ser Gly Ala Tyr Gly Ser
65                  70                  75                  80

Val Cys Ala Ala Phe Asp Thr Lys Thr Gly His Arg Val Ala Val Lys
                85                  90                  95

Lys Leu Ser Arg Pro Phe Gln Ser Ile Ile His Ala Lys Arg Thr Tyr
            100                 105                 110

Arg Glu Leu Arg Leu Leu Lys His Met Lys His Glu Asn Val Ile Gly
        115                 120                 125

Leu Leu Asp Val Phe Thr Pro Ala Arg Ser Leu Glu Glu Phe Asn Asp
130                 135                 140

Val Tyr Leu Val Thr His Leu Met Gly Ala Asp Leu Asn Asn Ile Val
145                 150                 155                 160

Lys Cys Gln Lys Leu Thr Asp Asp His Val Gln Phe Leu Ile Tyr Gln
                165                 170                 175

Ile Leu Arg Gly Leu Lys Tyr Ile His Ser Ala Asp Ile Ile His Arg
            180                 185                 190
```

```
Asp Leu Lys Pro Ser Asn Leu Ala Val Asn Glu Asp Cys Glu Leu Lys
        195                 200                 205

Ile Leu Asp Phe Gly Leu Ala Arg His Thr Asp Asp Glu Met Thr Gly
210                 215                 220

Tyr Val Ala Thr Arg Trp Tyr Arg Ala Pro Glu Ile Met Leu Asn Trp
225                 230                 235                 240

Met His Tyr Asn Gln Thr Val Asp Ile Trp Ser Val Gly Cys Ile Met
                245                 250                 255

Ala Glu Leu Leu Thr Gly Arg Thr Leu Phe Pro Gly Thr Asp His Ile
            260                 265                 270

Asp Gln Leu Lys Leu Ile Leu Arg Leu Val Gly Thr Pro Gly Ala Glu
        275                 280                 285

Leu Leu Lys Lys Ile Ser Ser Glu Ser Ala Arg Asn Tyr Ile Gln Ser
    290                 295                 300

Leu Ala Gln Met Pro Lys Met Asn Phe Ala Asn Val Phe Ile Gly Ala
305                 310                 315                 320

Asn Pro Leu Ala Val Asp Leu Leu Glu Lys Met Leu Val Leu Asp Ser
                325                 330                 335

Asp Lys Arg Ile Thr Ala Ala Gln Ala Leu Ala His Ala Tyr Phe Ala
            340                 345                 350

Gln Tyr His Asp Pro Asp Asp Glu Pro Val Ala Asp Pro Tyr Asp Gln
        355                 360                 365

Ser Phe Glu Ser Arg Asp Leu Leu Ile Asp Glu Trp Lys Ser Leu Thr
    370                 375                 380

Tyr Asp Glu Val Ile Ser Phe Val Pro Pro Leu Asp Gln Glu Glu
385                 390                 395                 400

Met Glu Ser

<210> SEQ ID NO 145
<211> LENGTH: 512
<212> TYPE: PRT
<213> ORGANISM: Artificial
<220> FEATURE:
<223> OTHER INFORMATION: ABII400

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Gln Ala Ser Gly Gly Gly Leu
    130                 135                 140

Val Gln Ala Gly Gly Ser Leu Arg Leu Ser Cys Ala Ala Ser Gly Phe
145                 150                 155                 160
```

```
Lys Ile Thr His Tyr Thr Met Gly Trp Phe Arg Gln Ala Pro Gly Lys
            165                 170                 175

Glu Arg Glu Phe Val Ser Arg Ile Thr Trp Gly Gly Asp Asn Thr Phe
        180                 185                 190

Tyr Ser Asn Ser Val Lys Gly Arg Phe Thr Ile Ser Arg Asp Asn Ala
        195                 200                 205

Lys Asn Thr Val Tyr Leu Gln Met Asn Ser Leu Lys Pro Glu Asp Thr
210                 215                 220

Ala Asp Tyr Tyr Cys Ala Ala Gly Ser Thr Ser Thr Ala Thr Pro Leu
225                 230                 235                 240

Arg Val Asp Tyr Trp Gly Lys Gly Thr Gln Val Thr Val Ser Ser Gly
                245                 250                 255

Gly Gly Gly Ser Gly Gly Ser Glu Val Gln Leu Val Glu Ser Gly
            260                 265                 270

Gly Gly Leu Val Gln Pro Gly Asn Ser Leu Arg Leu Ser Cys Ala Ala
        275                 280                 285

Ser Gly Phe Thr Phe Ser Ser Phe Gly Met Ser Trp Val Arg Gln Ala
        290                 295                 300

Pro Gly Lys Gly Leu Glu Trp Val Ser Ser Ile Ser Gly Ser Gly Ser
305                 310                 315                 320

Asp Thr Leu Tyr Ala Asp Ser Val Lys Gly Arg Phe Thr Ile Ser Arg
                325                 330                 335

Asp Asn Ala Lys Thr Thr Leu Tyr Leu Gln Met Asn Ser Leu Arg Pro
            340                 345                 350

Glu Asp Thr Ala Val Tyr Tyr Cys Thr Ile Gly Gly Ser Leu Ser Arg
        355                 360                 365

Ser Ser Gln Gly Thr Leu Val Thr Val Ser Ser Gly Gly Gly Gly Ser
        370                 375                 380

Gly Gly Gly Ser Glu Val Gln Leu Leu Glu Ser Gly Gly Gly Leu Val
385                 390                 395                 400

Gln Pro Gly Gly Ser Leu Arg Leu Ser Cys Ala Ala Ser Gly Arg Thr
                405                 410                 415

Phe Asn Asn Tyr Asn Met Gly Trp Phe Arg Gln Ala Pro Gly Lys Gly
            420                 425                 430

Arg Glu Phe Val Ala Ala Val Ser Arg Ser Gly Val Ser Thr Tyr Tyr
        435                 440                 445

Ala Asp Ser Val Lys Gly Arg Phe Thr Ile Ser Arg Asp Asn Ser Lys
450                 455                 460

Asn Thr Val Tyr Leu Gln Met Asn Ser Leu Arg Pro Glu Asp Thr Ala
465                 470                 475                 480

Val Tyr Tyr Cys Ala Ala Ala Tyr Arg Gly Thr Ala Ile Asn Val Arg
                485                 490                 495

Arg Ser Tyr Ser Ser Trp Gly Gln Gly Thr Leu Val Thr Val Ser Ser
            500                 505                 510

<210> SEQ ID NO 146
<211> LENGTH: 515
<212> TYPE: PRT
<213> ORGANISM: Artificial
<220> FEATURE:
<223> OTHER INFORMATION: ABII401

<400> SEQUENCE: 146

Glu Val Gln Leu Leu Glu Ser Gly Gly Gly Leu Val Gln Pro Gly Gly
1               5                   10                  15
```

-continued

```
Ser Leu Arg Leu Ser Cys Val His Ser Gly Pro Thr Phe Arg Thr Asp
            20              25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
 50                  55                  60

Lys Gly Arg Phe Thr Ile Ser Arg Asp Asn Ser Lys Asn Thr Ala Tyr
 65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Gly Gly Gly Ser Gly Gly Gly
                245                 250                 255

Ser Glu Val Gln Leu Gln Ala Ser Gly Gly Gly Leu Val Gln Ala Gly
            260                 265                 270

Gly Ser Leu Arg Leu Ser Cys Ser Ala Ser Val Arg Thr Phe Ser Ile
        275                 280                 285

Tyr Ala Met Gly Trp Phe Arg Gln Ala Pro Gly Lys Glu Arg Glu Phe
    290                 295                 300

Val Ala Gly Ile Asn Arg Ser Gly Asp Val Thr Lys Tyr Ala Asp Phe
305                 310                 315                 320

Val Lys Gly Arg Phe Ser Ile Ser Arg Asp Asn Ala Lys Asn Met Val
                325                 330                 335

Tyr Leu Gln Met Asn Ser Leu Lys Pro Glu Asp Thr Ala Leu Tyr Tyr
            340                 345                 350

Cys Ala Ala Thr Trp Ala Tyr Asp Thr Val Gly Ala Leu Thr Ser Gly
        355                 360                 365

Tyr Asn Phe Trp Gly Gln Gly Thr Gln Val Thr Val Ser Ser Gly Gly
    370                 375                 380

Gly Gly Ser Gly Gly Gly Ser Glu Val Gln Leu Leu Glu Ser Gly Gly
385                 390                 395                 400

Gly Leu Val Gln Pro Gly Gly Ser Leu Arg Leu Ser Cys Ala Ala Ser
                405                 410                 415

Gly Arg Thr Phe Asn Asn Tyr Asn Met Gly Trp Phe Arg Gln Ala Pro
            420                 425                 430

Gly Lys Gly Arg Glu Phe Val Ala Ala Val Ser Arg Ser Gly Val Ser
        435                 440                 445
```

```
Thr Tyr Tyr Ala Asp Ser Val Lys Gly Arg Phe Thr Ile Ser Arg Asp
    450                 455                 460

Asn Ser Lys Asn Thr Val Tyr Leu Gln Met Asn Ser Leu Arg Pro Glu
465                 470                 475                 480

Asp Thr Ala Val Tyr Tyr Cys Ala Ala Ala Tyr Arg Gly Thr Ala Ile
                485                 490                 495

Asn Val Arg Arg Ser Tyr Ser Ser Trp Gly Gln Gly Thr Leu Val Thr
            500                 505                 510

Val Ser Ser
        515

<210> SEQ ID NO 147
<211> LENGTH: 512
<212> TYPE: PRT
<213> ORGANISM: Artificial
<220> FEATURE:
<223> OTHER INFORMATION: ABII402

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Gly Gly Gly Gly Ser Gly Gly Gly
                245                 250                 255

Ser Glu Val Gln Leu Leu Glu Ser Gly Gly Gly Leu Val Gln Pro Gly
            260                 265                 270

Gly Ser Leu Arg Leu Ser Cys Ala Ala Ser Gly Arg Thr Phe Asn Asn
        275                 280                 285
```

```
Tyr Asn Met Gly Trp Phe Arg Gln Ala Pro Gly Lys Gly Arg Glu Phe
        290                 295                 300

Val Ala Ala Val Ser Arg Ser Gly Val Ser Thr Tyr Tyr Ala Asp Ser
305                 310                 315                 320

Val Lys Gly Arg Phe Thr Ile Ser Arg Asp Asn Ser Lys Asn Thr Val
                325                 330                 335

Tyr Leu Gln Met Asn Ser Leu Arg Pro Glu Asp Thr Ala Val Tyr Tyr
                    340                 345                 350

Cys Ala Ala Ala Tyr Arg Gly Thr Ala Ile Asn Val Arg Arg Ser Tyr
                355                 360                 365

Ser Ser Trp Gly Gln Gly Thr Leu Val Thr Val Ser Ser Gly Gly Gly
    370                 375                 380

Gly Ser Gly Gly Gly Ser Glu Val Gln Leu Gln Ala Ser Gly Gly Gly
385                 390                 395                 400

Leu Val Gln Ala Gly Gly Ser Leu Arg Leu Ser Cys Ala Ala Ser Gly
                405                 410                 415

Phe Lys Ile Thr His Tyr Thr Met Gly Trp Phe Arg Gln Ala Pro Gly
                    420                 425                 430

Lys Glu Arg Glu Phe Val Ser Arg Ile Thr Trp Gly Gly Asp Asn Thr
                435                 440                 445

Phe Tyr Ser Asn Ser Val Lys Gly Arg Phe Thr Ile Ser Arg Asp Asn
    450                 455                 460

Ala Lys Asn Thr Val Tyr Leu Gln Met Asn Ser Leu Lys Pro Glu Asp
465                 470                 475                 480

Thr Ala Asp Tyr Tyr Cys Ala Ala Gly Ser Thr Ser Thr Ala Thr Pro
                    485                 490                 495

Leu Arg Val Asp Tyr Trp Gly Lys Gly Thr Gln Val Thr Val Ser Ser
                500                 505                 510
```

<210> SEQ ID NO 148
<211> LENGTH: 515
<212> TYPE: PRT
<213> ORGANISM: Artificial
<220> FEATURE:
<223> OTHER INFORMATION: ABII403

<400> SEQUENCE: 148

```
Glu Val Gln Leu Gln Ala Ser Gly Gly Gly Leu Val Gln Ala Gly Gly
1               5                   10                  15

Ser Leu Arg Leu Ser Cys Ser Ala Ser Val Arg Thr Phe Ser Ile Tyr
                20                  25                  30

Ala Met Gly Trp Phe Arg Gln Ala Pro Gly Lys Glu Arg Glu Phe Val
            35                  40                  45

Ala Gly Ile Asn Arg Ser Gly Asp Val Thr Lys Tyr Ala Asp Phe Val
        50                  55                  60

Lys Gly Arg Phe Ser Ile Ser Arg Asp Asn Ala Lys Asn Met Val Tyr
65                  70                  75                  80

Leu Gln Met Asn Ser Leu Lys Pro Glu Asp Thr Ala Leu Tyr Tyr Cys
                85                  90                  95

Ala Ala Thr Trp Ala Tyr Asp Thr Val Gly Ala Leu Thr Ser Gly Tyr
            100                 105                 110

Asn Phe Trp Gly Gln Gly Thr Gln Val Thr Val Ser Ser Gly Gly Gly
        115                 120                 125

Gly Ser Gly Gly Gly Ser Glu Val Gln Leu Leu Glu Ser Gly Gly Gly
130                 135                 140

Leu Val Gln Pro Gly Gly Ser Leu Arg Leu Ser Cys Val His Ser Gly
```

```
            145                 150                 155                 160
Pro Thr Phe Arg Thr Asp Thr Met Gly Trp Phe Arg Gln Ala Pro Gly
                165                 170                 175

Lys Gly Arg Glu Phe Val Ala Ala Val Thr Trp Asn Ser Gly Arg Ile
            180                 185                 190

Asn Tyr Ala Asp Ser Val Lys Gly Arg Phe Thr Ile Ser Arg Asp Asn
        195                 200                 205

Ser Lys Asn Thr Ala Tyr Leu Gln Met Asn Ser Leu Arg Pro Glu Asp
    210                 215                 220

Thr Ala Val Tyr Tyr Cys Ala Ala His Arg Phe Val Val Gly Asn
225                 230                 235                 240

Arg Val Glu Asp Trp Arg Tyr Trp Gly Gln Gly Thr Leu Val Thr Val
                245                 250                 255

Ser Ser Gly Gly Gly Gly Ser Gly Gly Gly Ser Glu Val Gln Leu Val
            260                 265                 270

Glu Ser Gly Gly Gly Leu Val Gln Pro Gly Asn Ser Leu Arg Leu Ser
        275                 280                 285

Cys Ala Ala Ser Gly Phe Thr Phe Ser Ser Phe Gly Met Ser Trp Val
    290                 295                 300

Arg Gln Ala Pro Gly Lys Gly Leu Glu Trp Val Ser Ser Ile Ser Gly
305                 310                 315                 320

Ser Gly Ser Asp Thr Leu Tyr Ala Asp Ser Val Lys Gly Arg Phe Thr
                325                 330                 335

Ile Ser Arg Asp Asn Ala Lys Thr Thr Leu Tyr Leu Gln Met Asn Ser
            340                 345                 350

Leu Arg Pro Glu Asp Thr Ala Val Tyr Tyr Cys Thr Ile Gly Gly Ser
        355                 360                 365

Leu Ser Arg Ser Ser Gln Gly Thr Leu Val Thr Val Ser Ser Gly Gly
    370                 375                 380

Gly Gly Ser Gly Gly Gly Ser Glu Val Gln Leu Leu Glu Ser Gly Gly
385                 390                 395                 400

Gly Leu Val Gln Pro Gly Gly Ser Leu Arg Leu Ser Cys Ala Ala Ser
                405                 410                 415

Gly Arg Thr Phe Asn Asn Tyr Asn Met Gly Trp Phe Arg Gln Ala Pro
            420                 425                 430

Gly Lys Gly Arg Glu Phe Val Ala Ala Val Ser Arg Ser Gly Val Ser
        435                 440                 445

Thr Tyr Tyr Ala Asp Ser Val Lys Gly Arg Phe Thr Ile Ser Arg Asp
    450                 455                 460

Asn Ser Lys Asn Thr Val Tyr Leu Gln Met Asn Ser Leu Arg Pro Glu
465                 470                 475                 480

Asp Thr Ala Val Tyr Tyr Cys Ala Ala Tyr Arg Gly Thr Ala Ile
                485                 490                 495

Asn Val Arg Ser Tyr Ser Ser Trp Gly Gln Gly Thr Leu Val Thr
            500                 505                 510

Val Ser Ser
        515

<210> SEQ ID NO 149
<211> LENGTH: 541
<212> TYPE: PRT
<213> ORGANISM: Artificial
<220> FEATURE:
<223> OTHER INFORMATION: ABII404

<400> SEQUENCE: 149
```

```
Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65              70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Ser Gly Gly Gly Gly Ser
            130                 135                 140

Gly Gly Gly Gly Ser Gly Gly Gly Ser Gly Gly Gly Gly Ser Glu
145                 150                 155                 160

Val Gln Leu Leu Glu Ser Gly Gly Leu Val Gln Pro Gly Gly Ser
                165                 170                 175

Leu Arg Leu Ser Cys Ala Ala Ser Gly Arg Thr Phe Asn Asn Tyr Asn
            180                 185                 190

Met Gly Trp Phe Arg Gln Ala Pro Gly Lys Gly Arg Glu Phe Val Ala
        195                 200                 205

Ala Val Ser Arg Ser Gly Val Ser Thr Tyr Tyr Ala Asp Ser Val Lys
    210                 215                 220

Gly Arg Phe Thr Ile Ser Arg Asp Asn Ser Lys Asn Thr Val Tyr Leu
225                 230                 235                 240

Gln Met Asn Ser Leu Arg Pro Glu Asp Thr Ala Val Tyr Tyr Cys Ala
                245                 250                 255

Ala Ala Tyr Arg Gly Thr Ala Ile Asn Val Arg Arg Ser Tyr Ser Ser
            260                 265                 270

Trp Gly Gln Gly Thr Leu Val Thr Val Ser Ser Gly Gly Gly Gly Ser
        275                 280                 285

Gly Gly Gly Ser Glu Val Gln Leu Val Glu Ser Gly Gly Gly Leu Val
        290                 295                 300

Gln Pro Gly Asn Ser Leu Arg Leu Ser Cys Ala Ala Ser Gly Phe Thr
305                 310                 315                 320

Phe Ser Ser Phe Gly Met Ser Trp Val Arg Gln Ala Pro Gly Lys Gly
            325                 330                 335

Leu Glu Trp Val Ser Ser Ile Ser Gly Ser Gly Ser Asp Thr Leu Tyr
            340                 345                 350

Ala Asp Ser Val Lys Gly Arg Phe Thr Ile Ser Arg Asp Asn Ala Lys
            355                 360                 365

Thr Thr Leu Tyr Leu Gln Met Asn Ser Leu Arg Pro Glu Asp Thr Ala
        370                 375                 380

Val Tyr Tyr Cys Thr Ile Gly Gly Ser Leu Ser Arg Ser Ser Gln Gly
385                 390                 395                 400

Thr Leu Val Thr Val Ser Ser Gly Gly Gly Gly Ser Gly Gly Gly Ser
            405                 410                 415

Glu Val Gln Leu Gln Ala Ser Gly Gly Gly Leu Val Gln Ala Gly Gly
```

-continued

```
                420                 425                 430
Ser Leu Arg Leu Ser Cys Ser Ala Ser Val Arg Thr Phe Ser Ile Tyr
            435                 440                 445
Ala Met Gly Trp Phe Arg Gln Ala Pro Gly Lys Glu Arg Glu Phe Val
        450                 455                 460
Ala Gly Ile Asn Arg Ser Gly Asp Val Thr Lys Tyr Ala Asp Phe Val
465                 470                 475                 480
Lys Gly Arg Phe Ser Ile Ser Arg Asp Asn Ala Lys Asn Met Val Tyr
                485                 490                 495
Leu Gln Met Asn Ser Leu Lys Pro Glu Asp Thr Ala Leu Tyr Tyr Cys
            500                 505                 510
Ala Ala Thr Trp Ala Tyr Asp Thr Val Gly Ala Leu Thr Ser Gly Tyr
        515                 520                 525
Asn Phe Trp Gly Gln Gly Thr Gln Val Thr Val Ser Ser
530                 535                 540

<210> SEQ ID NO 150
<211> LENGTH: 515
<212> TYPE: PRT
<213> ORGANISM: Artificial
<220> FEATURE:
<223> OTHER INFORMATION: ABII405

<400> SEQUENCE: 150

Glu Val Gln Leu Leu Glu Ser Gly Gly Gly Leu Val Gln Pro Gly Gly
1               5                   10                  15
Ser Leu Arg Leu Ser Cys Val His Ser Gly Pro Thr Phe Arg Thr Asp
            20                  25                  30
Thr Met Gly Trp Phe Arg Gln Ala Pro Gly Lys Gly Arg Glu Phe Val
        35                  40                  45
Ala Ala Val Thr Trp Asn Ser Gly Arg Ile Asn Tyr Ala Asp Ser Val
    50                  55                  60
Lys Gly Arg Phe Thr Ile Ser Arg Asp Asn Ser Lys Asn Thr Ala Tyr
65                  70                  75                  80
Leu Gln Met Asn Ser Leu Arg Pro Glu Asp Thr Ala Val Tyr Tyr Cys
                85                  90                  95
Ala Ala His Arg Phe Val Val Gly Gly Asn Arg Val Glu Asp Trp Arg
            100                 105                 110
Tyr Trp Gly Gln Gly Thr Leu Val Thr Val Ser Ser Gly Gly Gly Gly
        115                 120                 125
Ser Gly Gly Gly Ser Glu Val Gln Leu Gln Ala Ser Gly Gly Gly Leu
    130                 135                 140
Val Gln Ala Gly Gly Ser Leu Arg Leu Ser Cys Ser Ala Ser Val Arg
145                 150                 155                 160
Thr Phe Ser Ile Tyr Ala Met Gly Trp Phe Arg Gln Ala Pro Gly Lys
                165                 170                 175
Glu Arg Glu Phe Val Ala Gly Ile Asn Arg Ser Gly Asp Val Thr Lys
            180                 185                 190
Tyr Ala Asp Phe Val Lys Gly Arg Phe Ser Ile Ser Arg Asp Asn Ala
        195                 200                 205
Lys Asn Met Val Tyr Leu Gln Met Asn Ser Leu Lys Pro Glu Asp Thr
    210                 215                 220
Ala Leu Tyr Tyr Cys Ala Ala Thr Trp Ala Tyr Asp Thr Val Gly Ala
225                 230                 235                 240
Leu Thr Ser Gly Tyr Asn Phe Trp Gly Gln Gly Thr Gln Val Thr Val
                245                 250                 255
```

```
Ser Ser Gly Gly Gly Ser Gly Gly Ser Glu Val Gln Leu Leu
            260                 265                 270

Glu Ser Gly Gly Gly Leu Val Gln Pro Gly Ser Leu Arg Leu Ser
            275                 280                 285

Cys Ala Ala Ser Gly Arg Thr Phe Asn Asn Tyr Asn Met Gly Trp Phe
290                 295                 300

Arg Gln Ala Pro Gly Lys Gly Arg Glu Phe Val Ala Ala Val Ser Arg
305                 310                 315                 320

Ser Gly Val Ser Thr Tyr Tyr Ala Asp Ser Val Lys Gly Arg Phe Thr
            325                 330                 335

Ile Ser Arg Asp Asn Ser Lys Asn Thr Val Tyr Leu Gln Met Asn Ser
            340                 345                 350

Leu Arg Pro Glu Asp Thr Ala Val Tyr Tyr Cys Ala Ala Tyr Arg
            355                 360                 365

Gly Thr Ala Ile Asn Val Arg Arg Ser Tyr Ser Ser Trp Gly Gln Gly
    370                 375                 380

Thr Leu Val Thr Val Ser Ser Gly Gly Gly Ser Gly Gly Gly Ser
385                 390                 395                 400

Glu Val Gln Leu Val Glu Ser Gly Gly Gly Leu Val Gln Pro Gly Asn
            405                 410                 415

Ser Leu Arg Leu Ser Cys Ala Ala Ser Gly Phe Thr Phe Ser Ser Phe
            420                 425                 430

Gly Met Ser Trp Val Arg Gln Ala Pro Gly Lys Gly Leu Glu Trp Val
    435                 440                 445

Ser Ser Ile Ser Gly Ser Gly Ser Asp Thr Leu Tyr Ala Asp Ser Val
            450                 455                 460

Lys Gly Arg Phe Thr Ile Ser Arg Asp Asn Ala Lys Thr Thr Leu Tyr
465                 470                 475                 480

Leu Gln Met Asn Ser Leu Arg Pro Glu Asp Thr Ala Val Tyr Tyr Cys
            485                 490                 495

Thr Ile Gly Gly Ser Leu Ser Arg Ser Ser Gln Gly Thr Leu Val Thr
            500                 505                 510

Val Ser Ser
        515

<210> SEQ ID NO 151
<211> LENGTH: 512
<212> TYPE: PRT
<213> ORGANISM: Artificial
<220> FEATURE:
<223> OTHER INFORMATION: ABII406

<400> SEQUENCE: 151

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
            85                  90                  95
```

```
Ala Ala Gly Ser Thr Ser Thr Ala Thr Pro Leu Arg Val Asp Tyr Trp
                100                 105                 110
Gly Lys Gly Thr Gln Val Thr Val Ser Ser Gly Gly Gly Ser Gly
        115                 120                 125
Gly Gly Ser Glu Val Gln Leu Leu Glu Ser Gly Gly Gly Leu Val Gln
130                 135                 140
Pro Gly Gly Ser Leu Arg Leu Ser Cys Val His Ser Gly Pro Thr Phe
145                 150                 155                 160
Arg Thr Asp Thr Met Gly Trp Phe Arg Gln Ala Pro Gly Lys Gly Arg
                165                 170                 175
Glu Phe Val Ala Ala Val Thr Trp Asn Ser Gly Arg Ile Asn Tyr Ala
                180                 185                 190
Asp Ser Val Lys Gly Arg Phe Thr Ile Ser Arg Asp Asn Ser Lys Asn
                195                 200                 205
Thr Ala Tyr Leu Gln Met Asn Ser Leu Arg Pro Glu Asp Thr Ala Val
                210                 215                 220
Tyr Tyr Cys Ala Ala His Arg Phe Val Val Gly Asn Arg Val Glu
225                 230                 235                 240
Asp Trp Arg Tyr Trp Gly Gln Gly Thr Leu Val Thr Val Ser Ser Gly
                245                 250                 255
Gly Gly Ser Gly Gly Gly Ser Glu Val Gln Leu Leu Glu Ser Gly
                260                 265                 270
Gly Gly Leu Val Gln Pro Gly Gly Ser Leu Arg Leu Ser Cys Ala Ala
        275                 280                 285
Ser Gly Arg Thr Phe Asn Asn Tyr Asn Met Gly Trp Phe Arg Gln Ala
        290                 295                 300
Pro Gly Lys Gly Arg Glu Phe Val Ala Ala Val Ser Arg Ser Gly Val
305                 310                 315                 320
Ser Thr Tyr Tyr Ala Asp Ser Val Lys Gly Arg Phe Thr Ile Ser Arg
                325                 330                 335
Asp Asn Ser Lys Asn Thr Val Tyr Leu Gln Met Asn Ser Leu Arg Pro
                340                 345                 350
Glu Asp Thr Ala Val Tyr Tyr Cys Ala Ala Ala Tyr Arg Gly Thr Ala
                355                 360                 365
Ile Asn Val Arg Arg Ser Tyr Ser Ser Trp Gly Gln Gly Thr Leu Val
        370                 375                 380
Thr Val Ser Ser Gly Gly Gly Ser Gly Gly Gly Ser Glu Val Gln
385                 390                 395                 400
Leu Val Glu Ser Gly Gly Gly Leu Val Gln Pro Gly Asn Ser Leu Arg
                405                 410                 415
Leu Ser Cys Ala Ala Ser Gly Phe Thr Phe Ser Ser Phe Gly Met Ser
                420                 425                 430
Trp Val Arg Gln Ala Pro Gly Lys Gly Leu Glu Trp Val Ser Ser Ile
                435                 440                 445
Ser Gly Ser Gly Ser Asp Thr Leu Tyr Ala Asp Ser Val Lys Gly Arg
                450                 455                 460
Phe Thr Ile Ser Arg Asp Asn Ala Lys Thr Thr Leu Tyr Leu Gln Met
465                 470                 475                 480
Asn Ser Leu Arg Pro Glu Asp Thr Ala Val Tyr Tyr Cys Thr Ile Gly
                485                 490                 495
Gly Ser Leu Ser Arg Ser Ser Gln Gly Thr Leu Val Thr Val Ser Ser
                500                 505                 510

<210> SEQ ID NO 152
```

<211> LENGTH: 538
<212> TYPE: PRT
<213> ORGANISM: Artificial
<220> FEATURE:
<223> OTHER INFORMATION: ABII407

<400> SEQUENCE: 152

```
Glu Val Gln Leu Leu Glu Ser Gly Gly Gly Leu Val Gln Pro Gly Gly
1               5                   10                  15

Ser Leu Arg Leu Ser Cys Val His Ser Gly Pro Thr Phe Arg Thr Asp
            20                  25                  30

Thr Met Gly Trp Phe Arg Gln Ala Pro Gly Lys Gly Arg Glu Phe Val
        35                  40                  45

Ala Ala Val Thr Trp Asn Ser Gly Arg Ile Asn Tyr Ala Asp Ser Val
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Pro Glu Asp Thr Ala Val Tyr Tyr Cys
                85                  90                  95

Ala Ala His Arg Phe Val Val Gly Gly Asn Arg Val Glu Asp Trp Arg
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Leu Glu Ser Gly Gly Gly Leu Val Gln Pro Gly Gly Ser
                165                 170                 175

Leu Arg Leu Ser Cys Ala Ala Ser Gly Arg Thr Phe Asn Asn Tyr Asn
            180                 185                 190

Met Gly Trp Phe Arg Gln Ala Pro Gly Lys Gly Arg Glu Phe Val Ala
        195                 200                 205

Ala Val Ser Arg Ser Gly Val Ser Thr Tyr Tyr Ala Asp Ser Val Lys
    210                 215                 220

Gly Arg Phe Thr Ile Ser Arg Asp Asn Ser Lys Asn Thr Val Tyr Leu
225                 230                 235                 240

Gln Met Asn Ser Leu Arg Pro Glu Asp Thr Ala Val Tyr Tyr Cys Ala
                245                 250                 255

Ala Tyr Arg Gly Thr Ala Ile Asn Val Arg Arg Ser Tyr Ser Ser
            260                 265                 270

Trp Gly Gln Gly Thr Leu Val Thr Val Ser Ser Gly Gly Gly Gly Ser
        275                 280                 285

Gly Gly Gly Ser Glu Val Gln Leu Gln Ala Ser Gly Gly Gly Leu Val
    290                 295                 300

Gln Ala Gly Gly Ser Leu Arg Leu Ser Cys Ala Ala Ser Gly Phe Lys
305                 310                 315                 320

Ile Thr His Tyr Thr Met Gly Trp Phe Arg Gln Ala Pro Gly Lys Glu
                325                 330                 335

Arg Glu Phe Val Ser Arg Ile Thr Trp Gly Gly Asp Asn Thr Phe Tyr
            340                 345                 350

Ser Asn Ser Val Lys Gly Arg Phe Thr Ile Ser Arg Asp Asn Ala Lys
        355                 360                 365

Asn Thr Val Tyr Leu Gln Met Asn Ser Leu Lys Pro Glu Asp Thr Ala
    370                 375                 380
```

```
Asp Tyr Tyr Cys Ala Ala Gly Ser Thr Ser Thr Ala Thr Pro Leu Arg
385                 390                 395                 400

Val Asp Tyr Trp Gly Lys Gly Thr Gln Val Thr Val Ser Ser Gly Gly
                405                 410                 415

Gly Gly Ser Gly Gly Gly Ser Glu Val Gln Leu Val Glu Ser Gly Gly
            420                 425                 430

Gly Leu Val Gln Pro Gly Asn Ser Leu Arg Leu Ser Cys Ala Ala Ser
            435                 440                 445

Gly Phe Thr Phe Ser Ser Phe Gly Met Ser Trp Val Arg Gln Ala Pro
        450                 455                 460

Gly Lys Gly Leu Glu Trp Val Ser Ser Ile Ser Gly Ser Gly Ser Asp
465                 470                 475                 480

Thr Leu Tyr Ala Asp Ser Val Lys Gly Arg Phe Thr Ile Ser Arg Asp
                485                 490                 495

Asn Ala Lys Thr Thr Leu Tyr Leu Gln Met Asn Ser Leu Arg Pro Glu
                500                 505                 510

Asp Thr Ala Val Tyr Tyr Cys Thr Ile Gly Gly Ser Leu Ser Arg Ser
            515                 520                 525

Ser Gln Gly Thr Leu Val Thr Val Ser Ser
        530                 535

<210> SEQ ID NO 153
<211> LENGTH: 16
<212> TYPE: PRT
<213> ORGANISM: Artificial
<220> FEATURE:
<223> OTHER INFORMATION: JH5

<400> SEQUENCE: 153

Asn Trp Phe Asp Ser Trp Gly Gln Gly Thr Leu Val Thr Val Ser Ser
1               5                   10                  15
```

A-BETA BINDING POLYPEPTIDES

FIELD OF THE INVENTION

The present invention relates to novel beta-amyloid peptide (in the following: "A-beta") binding polypeptides, the polypeptides comprising specific immunoglobulin domains. The invention also relates to nucleic acids encoding such polypeptides; to methods for preparing such polypeptides; to host cells expressing or capable of expressing such polypeptides; to compositions comprising such polypeptides; and to uses of such polypeptides or such compositions, in particular for prophylactic, therapeutic and diagnostic purposes.

BACKGROUND OF THE INVENTION

Several degenerative neural diseases are caused by the improper folding or processing of proteins or by prions, both of which result in invasive neural depositions known as amyloid plaques. The most widely known degenerative neural disease is probably Alzheimer's Disease (AD).

The incidence of AD warrants an urgent and unmet medical need: between 10 and 40% of all people aged 65 to 85 develop AD. Moreover, this segment of the population continues to grow exponentially. Therefore, from a humane, as well as from a social and economical point of view, it is imperative to find ways to efficiently diagnose and treat this devastating disorder. Concerning treatment, drugs are needed not only to slow or stop the disease progression, but also to restore brain damage that has already occurred during the initial stages of AD (before diagnosis). At this moment, neither early-diagnosis nor therapy treatment are efficient.

AD is defined as a dementia that coincides with the presence in the brain of extracellular amyloid plaques, composed mainly of amyloid peptides, and by intracellular neurofibrillary tangles (NFT) composed mainly of protein tau.

A primary component of amyloid plaques characteristic of AD is beta amyloid peptide (A-beta), a highly insoluble peptide 39-43 amino acids (aa) in length that has a strong propensity to adopt beta sheet structures, oligomerize and form protein aggregates. A-beta is produced from the A-beta precursor protein (APP) by two proteolytic events. A beta-secretase activity cleaves APP at the N-terminus of A-beta ("beta-site") between amino acids Met-671 and Asp-672 (using the numbering of the 770 aa isoform of APP). Cleavage at the beta-site yields a membrane-associated APP fragment of 99 aa (C99). A second site within the transmembrane domain of C99 ("gamma site") can then be cleaved by a gamma-secretase to release A-beta. APP can alternatively be cleaved within its A-beta region, predominantly at the alpha-secretase cleavage site of APP, to produce a C-terminal APP fragment of 83 aa (C83), which can also be further cleaved by gamma-secretase to produce a small soluble secreted peptide, p3. This pathway reduces the potential accumulation of A-beta.

The intra- and extracellular A-beta adopts a beta-sheet conformation and forms intermediates named ADDL (amyloid derived diffusible ligands) and protofibrils, finally precipitates in the form of amyloid fibrils which assemble into amyloid plaques. In these processes, the more hydrophobic A-beta(1-42) peptide (cf. below) is presumed to serve as a nucleating agent around which the plaques steadily grow.

A number of missense mutations in APP have been implicated in forms of early-onset familial AD. All of these are at or near one of the canonical cleavage sites of APP. Thus, the Swedish double mutation (K670N/M671L) is immediately adjacent to the beta-secretase cleavage site and increases the efficiency of beta-secretase activity, resulting in production of more total A-beta. Any of three mutations at APP residue 717, near the gamma-secretase cleavage site, increases the proportion of a more amyloidogenic 42 aa form of A-beta, also named A-beta(1-42), relative to the more common 40 aa form, A-beta(1-40). Two additional mutations of APP have been described which are close but not adjacent to the alpha-site. A mutation (A692G, A-beta residue 21) in a Flemish family and a mutation (E693Q, A-beta residue 22) in a Dutch family each have been implicated in distinct forms of familial AD. The Flemish mutation, in particular, presents as a syndrome of repetitive intracerebral hemorrhages or as an AD-type dementia. The neuropathological findings include senile plaques in the cortex and hippocampus, and usually multiple amyloid deposits in the walls of cerebral microvessels.

Several years ago, the membrane-associated aspartyl protease, BACE (also called memapsin or Asp2) has been shown to exhibit properties expected of a beta-secretase. This enzyme cleaves APP at its beta-site and between Tyr-10 and Glu-11 of the A-beta region with comparable efficiency. A-beta fragments cleaved at this latter site have been observed in amyloid plaques in AD and in media of APP-transfected HEK293 human embryonic kidney cells. Several groups also observed the presence in the database of an additional aspartyl protease, BACE2 (also called Asp1), a close homologue of BACE (now also referred to as BACE1). BACE2 cleaves APP at its beta-site and more efficiently at sites within the A-beta region of APP, after Phe-19 and Phe-20 of A-beta. These internal A-beta-sites are adjacent to the Flemish APP mutation at residue 21, and this mutation markedly increases the proportion of beta-site cleavage product generated by BACE2. Conservative beta-site mutations of APP that either increase (the Swedish mutation) or inhibit (M671V) beta-secretase activity affect BACE1 and BACE2 activity similarly. BACE2, like BACE1, proteolyzes APP maximally at acidic pH.

Mutations in the APP gene or in the presenilin 1 (PS1) gene (carrying "gamma-secretase" activity) cause early-onset familial AD. Examples of APP mutations are the above-mentioned 'Swedish' and 'London' (717) mutations located respectively near the beta- and gamma-secretase cleavage sites. These mutations increase the formation of A-beta peptides and especially of A-beta(1-42), and thereby increase the formation of amyloid aggregates and plaques. Whereas initially plaques were believed to be a major trigger for the development of AD, current studies emphasize the role of protofibrils and ADDL as the major toxic components. It is even conceivable that plaques are a mechanism whereby the neurotoxic peptides are actually rendered biologically inactive.

Further information on neurodegenerative diseases and on the role of A-beta therein can be taken from Wisniewski & Konietzko (2008), Lancet Neurol. 7(9), 805-811, Spires-Jones et al. (2009), Neurobiology of Disease, 213-220, and Lichlen & Mohajeri (2008), Journal of Neurochem. 104, 859-874.

Most current treatments of AD target the acetylcholine deficiency using acetylcholinesterase inhibitors such as donepezil (Aricept®), galantamine (Reminyl®), and rivastigmine (Exelon®) which are registered for the treatment of mild to moderate AD. Donepezil is also approved for severe Dementia Alzheimer's type (DAT) in the U.S.A. and Canada. The acetylcholine deficit reflects the degeneration of cholinergic neurons of the basal forebrain and appears to correlate well with the neuropsychiatric manifestations of the disease. Treatment with acetylcholinesterase inhibitors has some beneficial effects (consistent and significant but modest efficacy on clinical measures of cognition and global function), but cannot cure or stop the progression of the disease, as the etiology of the neurodegeneration is left untreated.

Memantine (Axura®, Namenda®, Ebixa®; Merz Pharmaceuticals) is an NMDA receptor antagonist that showed better outcome in comparison to placebo in the clinical domains cognition, activities of daily living and overall clinical response in AD patients with moderate to severe Alzheimer's disease. Memantine remains a symptomatic therapy that is approved for moderate to severe Alzheimer's disease only. It neither cures nor stops the progression of the disease. A combination of memantine and acetylcholinesterase inhibitors has been shown to have superior efficacy in moderately severe to severe DAT but not in the mild to moderate disease stage.

Some current experimental therapeutic strategies focus on A-beta as a target. There are three major research lines:

a) The development of small molecules (often peptidomimetics) named beta-sheet breakers, which are designed to interfere with the beta-sheet structure of amyloid peptide aggregates. It has been demonstrated that a stable "beta-sheet breaker", when administered to a transgenic mouse model of AD, is able to penetrate the blood brain barrier and reduce the number of plaques (Permanne et al. (2002), FASEB J. 16, 860-862). It remains to be demonstrated whether this approach results in cognitive protection and/or restoration.

b) The development of small molecules which inhibit the proteolytic processing of APP into amyloid peptides. Inhibitors of the beta- or gamma-secretase should efficiently block the formation of A-beta and hence protect the brain from neurotoxic effects of amyloid. Effects on already existing brain A-beta burden, such as amyloid plaques which have accumulated over years, are not expected.

c) Passive and active vaccination against A-beta. This research line started with the observation by Schenk et al. (1999), Nature 400, 173-177, that vaccination of transgenic AD mice with A-beta(1-42) prevented the formation of amyloid plaques. In a first experiment, monthly vaccination of young adult mice (age 6 weeks) essentially prevented plaque formation and the concomitant inflammatory reaction in the brain, i.e. absence of amyloid plaques, of astrocytosis and microgliosis. Vaccination starting at a later age, when amyloid plaques were already established, resulted in a partial clearance. Subsequently, it was demonstrated that vaccination with A-beta improved the behavioral and memory deficits as measured in the water maze memory tests. Given the side-effects of vaccination with the entire A-beta, alternative shorter peptides have been designed and used to vaccinate transgenic mice. Clinical trials suggested that the active immunization with A-beta is therapeutically active, as demonstrated by eliciting plaque clearance, attenuating plaque-related pathology, decreasing tau levels and slowing patients' cognitive decline. However, a significant number of patients developed autoimmune meningoencephalitis, caused primarily by the infiltration of autoreactive T lymphocytes into the brain in response to active immunization (Ferrer et al. (2004), Brain Pathol. 14, 11-20; Nicoll et al. (2003), Nat. Med. 9, 448-452; Masliah et al. (2005), Neurology 64, 1553-1562).

As an alternative to active immunization approaches, antibodies directed against A-beta may be administered to a patient. Such passive immunization approach was shown to be successful in reducing brain A-beta burden in transgenic AD mice (DeMattos et al. (2001), Proc. Natl. Acad. Sci. USA 98, 8850-8855). The underlying mechanisms remain open for speculation since it was thought unlikely that antibodies could cross the blood-brain barrier and target the plaques present in brain. The authors therefore suggested that the antibody created an 'A-beta sink' in the plasma which titrated A-beta out of the brain. Subsequently, using gelsolin and ganglioside 1, it was demonstrated that any A-beta-binding ligand has the potential to reduce amyloid burden in transgenic AD mice without crossing the blood-brain barrier (Matsuoka et al. (2003) J. Neuroscience 23, 29-33). Short-term (24 hours) passive immunization appeared to restore cognitive deficits of transgenic AD mice even without affecting the total brain amyloid load (Dodart et al. (2002) Nature Neuroscience 5, 452-457). The result would suggest that smaller, still soluble aggregates of A-beta are targeted first by some antibodies, and also that these are the most toxic forms of A-beta. Hence, clearance of proto-fibrillar A-beta could restore memory, at least in transgenic APP-mice.

The humanized anti-A-beta monoclonal antibody bapineuzumab (an analogue of the anti-A-beta mouse antibody known as "3D6") has meanwhile entered clinical trials. However, the first data reported from Phase II trial showed mixed results: Statistically significant effects on several efficacy endpoints were observed in ApoE4 non-carriers only. Furthermore, bapineuzumab was well tolerated and safe in ApoE4 non-carriers, while in ApoE4 carriers, serious adverse events were more frequently observed in bapineuzumab-treated patients than in the placebo arm. Moreover, vasogenic edema events have been observed. The induction of cerebral microhemorrhages has also been described pre-clinically in transgenic APP mice.

Conventional antibodies (containing an Fc part) used in anti-A-beta passive immunizations are suspected to account for the induction of vasogenic edema or microhemorrhages observed in humans and animal models, which are associated with a targeting of cerebral vascular A-beta deposits (Cerebral amyloid angiopathy) leading to microbleedings via ADCC and/or CDC (Wilcock, D M, Colton, C A, CNS Neurol. Disord. Drug Targets (2009) Vol. 8(1):50-64). Finally, the binding affinity of about 2.5 nM of this antibody, as measured by Biacore, is assumed to be too low to induce an effective "peripheral sink effect".

Another anti-A-beta antibody, solanezumab (humanized antibody m266; LY-2062430), has also entered clinical testings. The maximal plaque load reduction that could be achieved was published to be about 60%. In addition, specificity of this antibody is limited to soluble A-beta, so that binding of aggregates or plaques cannot be expected.

A third anti-A-beta antibody, ponezumab (PF4360365), only binds to A-beta(x-40) molecules, and not to A-beta(x-42) molecules, the latter being assumed to be the (more) pathogenic A-beta species. Its affinity is even lower than the affinity of bapineuzumab, and the risk of cerebral microhemorrhages can not yet be ruled out, due to its ability to bind to A-beta plaques in blood vessels, combined with a remaining ADCC/CDC activity of its Fc portion.

In summary, the above demonstrates that even if A-beta binding and clearance by (classical) antibodies appears to be an attractive mode-of-action for the development of therapeutical agents for the treatment of e.g. AD, other characteristics and effects of such immunoglobulins which have not yet been fully elucidated, such as the pharmacological implications of their property to bind to certain forms of A-beta, make it far more difficult than one might have initially assumed to find and develop safe and efficient therapeutical antibodies.

Antibody fragments, such as immunoglobulin single variable domain antibodies or VHH domains (as defined below), having specificity for A-beta have also been described in the art: WO2004/44204; WO2006/40153; WO2007/35092; WO2008/122441; and WO2009/04494. Binding characteristics of VHHs synthesized by the present inventors in accordance with the above WO publications were unsatisfactory, for which reason they are not supposed to enter clinical development.

WO09/149,185 discloses so-called DVD constructs, and, inter alia, DVD constructs having A-beta binding specificity. Upon combination of two different anti-A-bata variable domains in such DVD constructs, binding of the parental antibodies was maintained, but no increase in affinity was observed by this combination. Moreover, the disclosed DVD constructs contain an Fc part which is present in "classical" antibodies, so that side effects caused by Fc effector functions, such as complement-dependent cytotoxicity (CDC) or antibody-dependent cellular cytotoxicity (ADCC), cannot be avoided (cf. above).

Definitive diagnosis of AD still requires post-mortem pathological examination of the brain to demonstrate the presence of amyloid plaques, neurofibrillary tangles, synaptic loss and neuronal degeneration. This is essentially the same procedure as defined by Alois Alzheimer in 1906. In 1984 the National Institute of Neurological and Communicative Disorders and Stroke and the Alzheimer's Disease and Related Disorders Association (NINCDS-ADRDA) established formal criteria for the diagnosis of AD (reviewed in Petrella et al. (2003), Radiology 226, 315-336). Patients meeting all of the following criteria are diagnosed probable AD: dementia evidenced by examination and testing (e.g. Mini-Mental Test, Blessed Dementia Scale, or similar tests), impairment of memory and at least one other cognitive function, normal consciousness, onset between 40 and 90 years of age, absence of signs of other diseases that cause dementia (exclusion criterion). A gradual progressive, cognitive impairment without an identifiable cause will be diagnosed as possible AD. Probable AD is further defined as mild (early), moderate (middle) or severe (late) dementia. Laboratory analysis is used to objectively define or exclude alternative causes of dementia. ELISA assays of A-beta(1-42) and phospho-tau in cerebrospinal fluid (CSF), combined with genotyping for ApoE4 (a predisposing genetic factor) appear to be sensitive and specific. The methods are, however, not widely applicable because of the invasive CSF puncture, preventing this to become routine screening. ELISA for the neural thread protein (AD7C-NTP) (developed by Nymox) demonstrated higher levels in urine from AD patients than from non-AD dementia patients or healthy controls. However, the mean levels were significantly lower in early AD cases, suggesting the test is not reliable for testing for early onset of AD.

No biochemical method is as yet suited for the firm diagnosis of early stages of AD, rather they merely help to confirm the clinical diagnosis of advanced cases. Clearly, more advanced techniques are needed to allow early diagnosis before onset of clinical symptoms that signal irreversible brain damage.

Finally, not only for diagnostic purposes but also in e.g. pre-clinical research and development, A-beta binding molecules are useful as research tools. Widely used are the antibodies already mentioned above, i.e. antibody 3D6 and antibody m266. Antibody 3D6 binds to A-beta with a relatively low affinity and may therefore not be suitable for all purposes. Antibody m266 cross-reacts with N-terminally truncated versions of A-beta, such as p3, which does not allow to distinguish between disease-relevant A-beta species, such as A-beta(1-40) and A-beta(1-42), and other molecules such as p3.

In view of the above, it is an object of the invention to provide pharmacologically active agents, as well as compositions comprising the same, that can be used in the prevention, treatment, alleviation and/or diagnosis of diseases, disorders or conditions associated with A-beta and/or mediated by A-beta, such as AD, and to provide methods for the prevention, treatment, alleviation and/or diagnosis of such diseases, disorders or conditions, involving the use and/or administration of such agents and compositions. Such agents may also be useful for doing research into the field of AD in general and, specifically, into the elucidation of AD disease mechanisms and potential therapeutic and/or prophylactic mechanisms.

In particular, it is an object of the invention to provide such pharmacologically active agents, compositions and/or methods that provide certain advantages compared to the agents, compositions and/or methods currently used and/or known in the art. These advantages include improved therapeutic and/or pharmacological properties and/or other advantageous properties (such as, for example, improved ease of preparation and/or reduced costs of goods), especially as compared to conventional antibodies against A-beta or fragments thereof as those described in the above section. Further advantages will become clear from the further description below.

More in particular, it is an object of the invention to provide novel A-beta binding molecules and, specifically, polypeptides binding to mammalian and, especially, human A-beta, wherein such molecules or polypeptides are suitable for the above diagnostic, therapeutic and research purposes.

BRIEF SUMMARY OF THE INVENTION

According to a first aspect of the invention, there are provided polypeptides which comprise a first immunoglobulin single variable domain which specifically binds to a first epitope of A-beta, and a second immunoglobulin single variable domain which specifically binds to a second epitope of A-beta, wherein said first and said second epitopes of A-beta are not identical epitopes, i.e. are different epitopes, such as e.g. the N-terminal epitope (SEQ ID NO:3) on the one hand and the central epitope (SEQ ID NO:4) on the other hand.

Preferably, said first and said second immunoglobulin single variable domains each essentially consist of four framework regions (FR1 to FR4, respectively) and three complementarity determining regions (CDR1 to CDR3, respectively), wherein said first and said second immunoglobulin single variable domains are covalently linked by a linker peptide, wherein said linker peptide optionally comprises or consists of a third immunoglobulin domain, such as e.g. a third immunoglobulin single variable domain.

Furthermore, said first and said second immunoglobulin single variable domains are preferably antibody domains, more preferably VHH domains, and even more preferably humanized VHH domains.

The immunoglobulin single variable domains comprised in such polypeptide of the invention will typically have the structure
FR(1)1-CDR(1)1-FR(1)2-CDR(1)2-FR(1)3-CDR(1)3-FR(1)4, and
FR(2)1-CDR(2)1-FR(2)2-CDR(2)2-FR(2)3-CDR(2)3-FR(2)4, respectively.

Preferably, CDR(1)3 is selected from the group consisting of:
the amino acid sequences according to SEQ ID NO:13 and SEQ ID NO:16; and
amino acid sequences which have up to three, preferably up to two, and more preferably one amino acid difference as compared to said amino acid sequences according to SEQ ID NO:13 or SEQ ID NO:16, respectively; and CDR(2)3 is selected from the group consisting of:
  the amino acid sequence according to SEQ ID NO:19; and
  amino acid sequences which have up to three, preferably up to two, and more preferably one amino acid difference as compared to said amino acid sequence according to SEQ ID NO:19.

Alternatively, CDR(1)3 is selected from the group consisting of:
  the amino acid sequence according to SEQ ID NO:19; and
  amino acid sequences which have up to three, preferably up to two, and more preferably one amino acid difference as compared to said amino acid sequence according to SEQ ID NO:19; and CDR(2)3 is selected from the group consisting of:
  the amino acid sequences according to SEQ ID NO:13 and SEQ ID NO:16; and
  amino acid sequences which have up to three, preferably up to two, and more preferably one amino acid difference as compared to said amino acid sequences according to SEQ ID NO:13 or SEQ ID NO:16, respectively.

Especially useful polypeptides of the invention will include the following CDR sequences (numbering as indicated in the paragraph above):
  CDR(1)1: SEQ ID NO:11
  CDR(1)2: SEQ ID NO:12
  CDR(1)3: SEQ ID NO:13
  CDR(2)1: SEQ ID NO:17
  CDR(2)2: SEQ ID NO:18
  CDR(2)3: SEQ ID NO:19
or:
  CDR(1)1: SEQ ID NO:14
  CDR(1)2: SEQ ID NO:15
  CDR(1)3: SEQ ID NO:16
  CDR(2)1: SEQ ID NO:17
  CDR(2)2: SEQ ID NO:18
  CDR(2)3: SEQ ID NO:19
or:
  CDR(1)1: SEQ ID NO:17
  CDR(1)2: SEQ ID NO:18
  CDR(1)3: SEQ ID NO:19
  CDR(2)1: SEQ ID NO:11
  CDR(2)2: SEQ ID NO:12
  CDR(2)3: SEQ ID NO:13
or:
  CDR(1)1: SEQ ID NO:17
  CDR(1)2: SEQ ID NO:18
  CDR(1)3: SEQ ID NO:19
  CDR(2)1: SEQ ID NO:14
  CDR(2)2: SEQ ID NO:15
  CDR(2)3: SEQ ID NO:16.

According to a specific embodiment of the invention, the polypeptides of the invention comprise, as a first immunoglobulin single variable domain, the VHH domain ABII035 (SEQ ID NO:44), and as the second immunoglobulin single variable domain the VHH domain ABII059 (SEQ ID NO:45), or vice versa.

In an especially preferred embodiment, such polypeptide of the invention additionally comprises a half-life extending moiety, preferably covalently linked to said polypeptide, such as an albumin binding moiety (e.g. an anti-albumin immunoglobulin domain), a transferrin binding moiety (e.g. an anti-transferrin immunoglobulin domain), a polyethylene glycol molecule, a recombinant polyethylene glycol molecule, human serum albumin, a fragment of human serum albumin, and an albumin binding peptide.

Very specific embodiments of the invention are the polypeptides having an amino acid sequence as shown in SEQ ID NOs:26 to 31 (Fc fusion polypeptides); SEQ ID NO:32 (HSA fusion polypeptide); SEQ ID NOs:34 to 39 and 145 to 152 (albumin binding immunoglobulin single variable domain fusion polypeptides); and SEQ ID NOs:40 to 43, 142 and 143 (PEGylated polypeptides).

The polypeptides of the invention preferably bind, with one of its immunoglobulin single variable domains, to the A-beta epitope defined by SEQ ID NO:3 (N-terminal epitope), and with another immunoglobulin single variable domain to the A-beta epitope defined by SEQ ID NO:4 (central epitope). Even more preferably, such polypeptides of the invention form contacts to at least amino acids 1 (aspartate), 3 (glutamate), 19 (phenylalanine), 20 (phenylalanine), and 23 (aspartate) of the human A-beta peptide (SEQ ID NO:1). The IC50 values as measured in a TR-FRET binding assay (using ABII002=SEQ ID NO:62 and ABII050=SEQ ID NO:100 as competitors; cf. Example 9.3) are preferably in the range of $10^{-9}$ moles/litre or less, and more preferably in the range of from $5 \times 10^{-10}$ moles/litre to $10^{-12}$ moles/litre.

According to another aspect, the invention relates to polypeptides comprising or consisting of an immunoglobulin single variable domain essentially consisting of four framework regions (FR1 to FR4 respectively) and three complementarity determining regions (CDR1 to CDR3 respectively), wherein said CDR sequences are defined as follows:
  CDR1: SEQ ID NO:11
  CDR2: SEQ ID NO:12
  CDR3: SEQ ID NO:13
or
  CDR1: SEQ ID NO:14
  CDR2: SEQ ID NO:15
  CDR3: SEQ ID NO:16
or
  CDR1: SEQ ID NO:17
  CDR2: SEQ ID NO:18
  CDR3: SEQ ID NO:19,
and to polypeptides comprising or consisting of a VHH domain having an amino acid sequence selected from the group consisting of SEQ ID NOs: 47 to 111.

These polypeptides are useful building blocks or intermediates for the construction of biparatopic A-beta binding polypeptides in accordance with the first aspect of the invention.

According to further aspects, the invention relates to nucleic acid molecules, expression vectors, host cells, and methods of manufacturing used in the production of a polypeptide of the invention. Nucleic acid molecules encoding the polypeptides of the invention can be used, in an isolated form, for constructing respective expression vectors, which then may be transfected into host cells used for biopharmaceutical production of the polypeptides of the invention. Such method of manufacturing typically comprises the steps of culturing the host cell under conditions that allow expression of the polypeptide, recovering the polypeptide and purifying it according to methods known in the art.

The polypeptides of the present invention are specifically useful in methods of diagnosis, prevention, treatment and/or alleviation of the diseases, disorders and conditions as set out in detail below, and, especially, for the treatment of Alzheimer's disease (AD). Thus, according to this aspect, the polypeptides of the invention will be used in the form of a pharmaceutical composition, i.e. as a medicament for the treatment, alleviation or prevention of a disease, disorder or condition, preferably in a human being, such disease, disorder or condition being selected from the group consisting of neurodegenerative diseases or disorders, Alzheimer's disease, dementia of the Alzheimer type, cerebral amyloid angiopathy (CAA), trisomy 21 (Down's Syndrome), adult Down syndrome, hereditary cerebral hemorrhage with amyloidosis of the Dutch-type (HCHWA-D), dementia with Lewy Bodies, frontotemporal lobar degeneration, glaucoma, amyotrophic lateral sclerosis, sporadic inclusion body myositis, and anxiety disorder in an elderly human subject, or will be used for the diagnosis of such disease, disorder or condition.

In addition to the above, the polypeptides of the present invention are specifically useful for the treatment of dry AMD (age-related macular degeneration) and glaucoma. The "dry" form of AMD, also known as "central geographic atrophy", results from atrophy to the retinal pigment epithelial layer below the neurosensory retina, which causes vision loss through loss of photoreceptors (rods and cones) in the central part of the eye. No medical or surgical treatment is currently available for this condition. Treatments available so far (e.g. suggested by the National Eye Institute) include the use of vitamin supplements with high doses of antioxidants, lutein and zeaxanthin, which may slow the progression of dry macular degeneration. Glaucoma is a disease where fluid pressure inside the eye increases, causing irreversible damage to the optic nerve and loss of vision. A-beta colocalizes with apoptotic retinal ganglion cells in experimental glaucoma and induces significant retinal ganglion cell apoptosis in a dose- and time-dependent manner.

For therapeutic purposes, the polypeptides of the invention or pharmaceutical compositions comprising such polypeptides may be administered to a human being in need thereof by e.g. parenteral (esp. intravenous or subcutaneous) or intravitreal (esp. for the treatment of dry AMD or glaucoma) injection.

Further aspects, embodiments and applications of the invention will become clear from the further description and the appended claims hereinbelow.

Unexpectedly, although intensive research into A-beta binding monoclonal antibodies has already been carried out and although highly specific antibodies with high affinity to A-beta are already available, the inventors succeeded to provide a group of A-beta binding molecules which have improved characteristics, e.g. are having still even better IC50 values than e.g. antibodies 3D6 and m266 (cf. e.g. Table XVI), the humanized counterparts of which are currently tested for therapeutical use in humans.

In addition, although it could be demonstrated that anti-A-beta antibodies known in the art are indeed able to reduce amyloid plaque load in transgenic mice overproducing A-beta (maximal plaque load reduction achieved by administration of monoclonal antibody m266 or its humanized counterpart having been published to be about 60%), e.g. antibody m266 lacks amyloid plaque binding. Thus, such conventional antibody may be expected to have less potential in situations where a direct binding of the anti-A-beta molecule to A-beta present in amyloid aggregates brings about additional benefit. In contrast thereto, the inventors were able to generate A-beta binding molecules which bind to amyloid plaques and are therefore expected to reduce or remove vascular amyloid by promoting physical dissociation, without increasing the risk or inducing microhemorrhages. As vascular amyloid is associated with the severity of AD, this advantage of the polypeptides of the invention may prove to be particularly useful in the treatment of later-stage or severe AD, i.e. they can be expected to be particularly useful for the treatment of patients which have a high brain amyloid plaque load, accumulated over many years.

Thus, in summary, the higher affinity of the A-beta binding polypeptides of the invention and their unique plaque binding capabilities provide an unexpected superiority as compared to conventional anti-A-beta antibodies described in the art.

Another antibody currently in clinical trials, Ponezumab, has a specificity for A-beta(x-40) and does not bind to A-beta (x-42), the major pathogenic species in AD, and is therefore expected to shift the A-beta(x-40):A-beta(x-42) balance towards the toxic A-beta(x-42) species. In contrast thereto, the present inventors succeeded to provide A-beta binding molecules which, by binding to at least two different epitopes, are able to capture the A-beta(x-40) and the A-beta(x-42) in order to neutralize toxic effects of both species.

When compared to conventional antibodies in general, the polypeptides of the invention can be manufactured much easier, quicker and cheaper, have a higher stability and low antigenicity, and may be suitable for more convenient administration routes than injection or infusion, due to their small size and structure. More specifically, production of the polypeptides of the invention through fermentation in convenient recombinant host organisms such as $E.\ coli$ and yeast is cost-effective, as compared to the manufacture of conventional antibodies which require expensive mammalian cell culture facilities. Furthermore, achievable levels of expression are high and yields of the polypeptides of the invention are in the range of 1 to 10 g/l ($E.\ coli$) and up to 10 g/l (yeast) and more. The polypeptides of the invention are more soluble, meaning they may be stored and/or administered in higher concentrations compared to conventional antibodies. They are stable at room temperature, meaning they may be prepared, stored and/or transported without the use of refrigeration equipment, conveying cost, time and environmental savings. The polypeptides of the present invention also exhibit a prolonged stability at extremes of pH, meaning they would be suitable for delivery by oral administration.

Furthermore, the polypeptides of the invention do not need to comprise an Fc part which is present in "classical" antibodies, so that side effects caused by Fc effector functions, such as complement-dependent cytotoxicity (CDC) or antibody-dependent cellular cytotoxicity (ADCC), can be avoided. When used in anti-A-beta passive immunizations, conventional antibodies (having an Fc part) are suspected to account for the induction of microhemorrhages observed in humans and animal models, which are associated with a targeting of cerebral vascular A-beta deposits (Cerebral amyloid angiopathy) leading to microbleedings via ADCC and/or CDC (Wilcock, D M, Colton, C A, CNS Neurol. Disord. Drug Targets (2009) Vol. 8(1):50-64).

Thus, in summary, the polypeptides of the invention combine the advantageous characteristics of conventional antibodies, such as high specificity and high selectivity, with the advantages as outlined above, and have surprisingly improved characteristics with regard to affinity and specificity as compared to conventional A-beta binding antibodies.

When compared to A-beta binding VHH domains already known in the art, such as the VHHs described in WO2006/040153, WO2007/35092 and WO2004/44204, the polypeptides of the invention show significantly improved binding characteristics, with respect to the binding to monomeric A-beta as well as with respect to binding to aggregated A-beta (cf. e.g. Examples 3.2 and 6 below). Moreover, the polypeptides according to the invention do bind to both monomeric A-beta as well as amyloid plaques, in contrast to VHH domains as described e.g. in WO2008/122441 or in Habicht et al. (2007), Proc. Natl. Acad. Sci. USA; 104(49):19232-19237, which only bind to aggregated amyloid plaques.

Even more, the VHH domains of A-beta binding polypeptides of the invention bind equally potent to human and rodent A-beta, as shown e.g. in Example 7 and FIG. 2. Binding of the biparatopic polypeptide of the invention even increases the affinity to human as well as rodent A-beta by a factor of at least 103, as compared to the single VHH domains. Thus, the polypeptides of the invention are ideal detection tools across species for the disease-relevant A-beta forms, such as A-beta (1-40) and A-beta(1-42), allowing the use of esp. rodent animal models for preclinical and scientific research. They provide superiority over antibody 3D6 which binds to A-beta with a significantly lower affinity and which is only weakly cross-reactive to rodent A-beta. There is also superiority as compared to antibody m266 which recognizes rodent and human A-beta equally well, but cross-reacts with N-terminally truncated versions of A-beta, such as p3 so that this antibody is not useful for certain tests or assays relying on the specific detection of disease-relevant A-beta species, such as A-beta(1-40) and A-beta(1-42).

Finally, biparatopic anti-A-beta VHH constructs according to the invention gain affinity by a factor of >1000 fold when two VHH detecting two different A-beta epitopes were combined, which is in clear contrast to those constructs disclosed in WO09/149,185.

Of course, the polypeptides of the invention are also useful for diagnostic purposes, based on their affinity (sensitivity), specificity (with regard to epitopes as well as to species), and other characteristics thereof as outlined above, as compared to other A-beta binding molecules known in the art.

BRIEF DESCRIPTION OF THE DRAWINGS

FIG. 2 shows the binding of a biparatopic anti-A-beta VHH construct, including VHH domains ABII035 and ABII059, to human and rodent (mouse) A-beta

DETAILED DESCRIPTION OF THE INVENTION

Definitions

Figure 1:
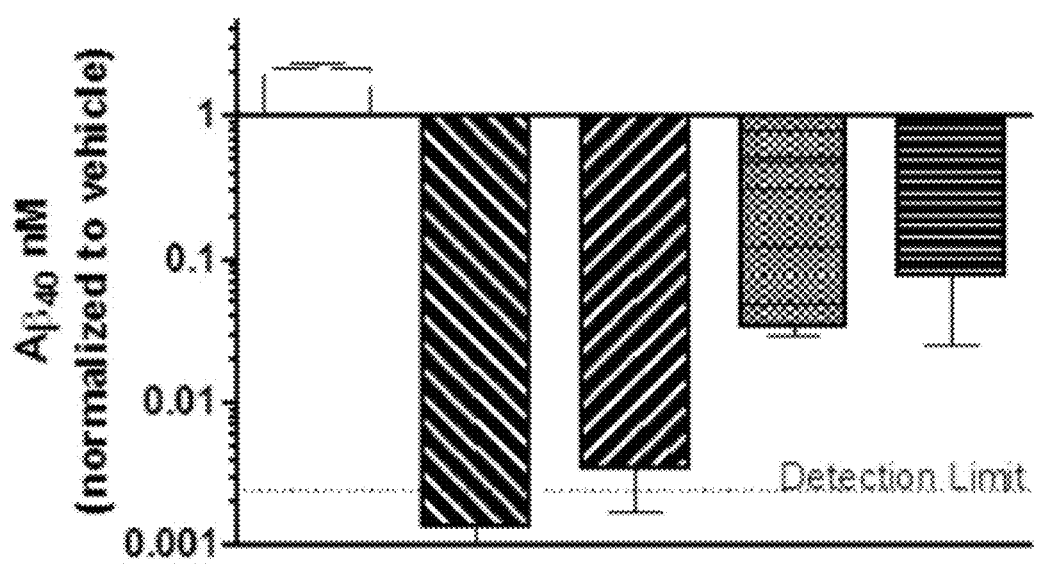
FIG. 1 shows the decrease of free/unbound A-beta(1-40) in plasma after i.p. administration of ABII320, ABII322, 3D6-IgG and m266-IgG, as detected 2 hrs after injection, in APP transgenic mice (n=3). Depicted in the first column (unfilled box): vehicle (PBS); second column: ABII320 (132 nmol/kg); third column: ABII322 (132 nmol/kg); fourth column: IgG 3D6 (132 nmol/kg); fifth column: IgG m266 (66.6 nmol/kg); concentrations for IgGs are calculated per binding site (2 binding sites per IgG molecule).

The above and other aspects and embodiments of the invention will become clear from the further description herein, in which:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, New York (1989), as well as to the general background art cited herein; Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein;

b) Unless indicated otherwise, the terms "immunoglobulin" and "immunoglobulin sequence"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation;

c) The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

d) The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

e) The term "immunoglobulin variable domain" as Used herein means an immunoglobulin domain essentially consisting of four "framework regions" which are referred to in the art and hereinbelow as "framework region 1" or "FR1"; as "framework region 2" or"FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

f) The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the present invention are "domain antibodies", such as the immunoglobulin single variable domains VH and VL (VH domains and VL domains). Another example of immunoglobulin single variable domains are "VHH domains" (or simply "VHHs") from camelids, as defined hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

f1) "VHH domains", also known as VHHs, $V_HH$ domains, VHH antibody fragments, and VHH antibodies, have originally been described as the antigen binding immunoglobulin (variable) domain of "heavy chain antibodies" (i.e. of "antibodies devoid of light chains"; Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, $V_HH$ domain, VHH antibody fragment, VHH antibody, as well as "Nanobody®" and "Nanobody® domain" ("Nanobody" being a trademark of the company Ablynx N.V.; Ghent; Belgium) are used interchangeably and are representatives of immunoglobulin single variable domains (having the structure: FR1-CDR1-FR2-CDR2-FR3-CDR3-FR4 and specifically binding to an epitope without requiring the presence of a second immunoglobulin variable domain), and which are distinguished from VH domains by the so-called "hallmark residues", as defined in e.g. WO2009/109635, FIG. 1.

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, J. Immunol. Methods 231, 25-38 (1999). According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of $V_H$ domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Further structural characteristics and functional properties of VHH domains and polypeptides containing the same can be summarized as follows:

VHH domains (which have been "designed" by nature to functionally bind to an antigen without the presence of, and without any interaction with, a light chain variable domain) can function as a single, relatively small, functional antigen-binding structural unit, domain or polypeptide. This distinguishes the VHH domains from the VH and VL domains of conventional 4-chain antibodies, which by themselves are generally not suited for practical application as single antigen-binding proteins or immunoglobulin single variable domains, but need to be combined in some form or another to provide a functional antigen-binding unit (as in for example conventional antibody fragments such as Fab fragments; in scFv's, which consist of a VH domain covalently linked to a VL domain).

Because of these unique properties, the use of VHH domains—either alone or as part of a larger polypeptide—offers a number of significant advantages over the use of conventional VH and VL domains, scFv's or conventional antibody fragments (such as Fab- or F(ab')2-fragments):

only a single domain is required to bind an antigen with high affinity and with high selectivity, so that there is no need to have two separate domains present, nor to assure that these two domains are present in the right spacial conformation and configuration (i.e. through the use of especially designed linkers, as with scFv's);

VHH domains can be expressed from a single gene and require no post-translational folding or modifications;

VHH domains can easily be engineered into multivalent and multispecific formats (as further discussed herein);

VHH domains are highly soluble and do not have a tendency to aggregate (as with the mouse-derived antigen-binding domains described by Ward et al., Nature 341: 544-546 (1989));

VHH domains are highly stable to heat, pH, proteases and other denaturing agents or conditions and, thus, may be prepared, stored or transported without the use of refrigeration equipments, conveying a cost, time and environmental savings;

VHH domains are easy and relatively cheap to prepare, even on a scale required for production. For example, VHH domains and polypeptides containing the same can be produced using microbial fermentation (e.g. as further described below) and do not require the use of mammalian expression systems, as with for example conventional antibody fragments;

VHH domains are relatively small (approximately 15 kDa, or 10 times smaller than a conventional IgG) compared to conventional 4-chain antibodies and antigen-binding fragments thereof, and therefore show high(er) penetration into tissues and can be administered in higher doses than such conventional 4-chain antibodies and antigen-binding fragments thereof;

VHH domains can show so-called cavity-binding properties (inter alia due to their extended CDR3 loop, compared to conventional VH domains) and can therefore also access targets and epitopes not accessible to conventional 4-chain antibodies and antigen-binding fragments thereof.

Methods of obtaining VHH domains binding to a specific antigen or epitope have been described earlier, e.g. in WO2006/040153 and WO2006/122786. As also described therein in detail, VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more fully human framework region sequences, and, in an even more specific embodiment, can contain human framework region sequences derived from DP-29, DP-47, DP-51, or parts thereof, optionally combined with JH sequences, such as JH5.

f2) "Domain antibodies", also known as "Dab"s, "Domain Antibodies", and "dAbs" (the terms "Domain Antibodies" and "dAbs" being used as trademarks by the GlaxoSmithKline group of companies) have been described in e.g. Ward, E. S., et al.: "Binding activities of a repertoire of single immunoglobulin variable domains secreted from *Escherichia coli*"; Nature 341: 544-546 (1989); Holt, L. J. et al.: "Domain antibodies: proteins for therapy"; TRENDS in Biotechnology 21(11): 484-490 (2003); and WO2003/002609.

Domain antibodies essentially correspond to the VH or VL domains of non-camelid mammalians, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans. As in the case of VHH domains, they are well expressed also in prokaryotic expression systems, providing a significant reduction in overall manufacturing cost.

Domain antibodies, as well as VHH domains, can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al., 1992, Biotechnology 10:779-783, or Barbas, et al., 1994, Proc. Nat. Acad. Sci, USA 91: 3809-3813.; Shier et al., 1995, Gene 169:147-155; Yelton et al., 1995, Immunol. 155: 1994-2004; Jackson et al., 1995, J. Immunol. 154(7):3310-9; and Hawkins et al., 1992, J. Mol. Biol. 226(3): 889 896; KS Johnson and R E Hawkins, "Affinity maturation of antibodies using phage display", Oxford University Press 1996.

f3) Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting are known in the art.

g) The terms "epitope" and "antigenic determinant", which can be used interchangeably, refer to the part of a macromolecule, such as a polypeptide, that is recognized by antigen-binding molecules, such as conventional antibodies or the polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as a conventional antibody or a polypeptide of the invention) that recognizes the epitope is called a paratope.

h) The term "biparatopic" (antigen-)binding molecule or "biparatopic" polypeptide as used herein shall mean a polypeptide comprising a first immunoglobulin single variable domain and a second immunoglobulin single variable domain as herein defined, wherein these two variable domains are capable of binding to two different epitopes of one antigen, which epitopes are not normally bound at the same time by one monospecific immunoglobulin, such as e.g. a conventional antibody or one immunoglobulin single variable domain. The biparatopic polypeptides according to the invention are composed of variable domains which have different epitope specificities, and do not contain mutually complementary variable domain pairs which bind to the same epitope. They do therefore not compete with each other for binding to A-beta.

i) A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein.

k) Generally, the term "specificity" refers to the number of different types of antigens or epitopes to which a particular antigen-binding molecule or antigen-binding protein (such as an immunoglobulin, an antibody, an immunoglobulin single variable domain, or a polypeptide of the invention) can bind. The specificity of an antigen-binding protein can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an immunoglobulin single variable domain, or a polypeptide of the invention) and the pertinent antigen. Avidity is related to both the affinity between an epitope and its antigen binding site on the antigen-binding molecule and the number of pertinent binding sites present on the antigen-binding molecule.

Typically, antigen-binding proteins (such as the polypeptides of the invention) will bind with a dissociation constant ($K_D$) of 10E-5 to 10E-14 moles/liter (M) or less, and preferably 10E-7 to 10E-14 moles/liter (M) or less, more preferably 10E-8 to 10E-14 moles/liter, and even more preferably 10E-11 to 10E-13 (as measured e.g. in a Kinexa assay as described in Example 9.7), and/or with an association constant ($K_A$) of at least 10E7 ME-1, preferably at least 10E8 ME-1, more preferably at least 10E9 ME-1, such as at least 10E11 ME-1. Any $K_D$ value greater than 10E-4 M is generally considered to indicate non-specific binding. Preferably, a polypeptide of the invention will bind to the desired antigen with a $K_D$ less than 500 nM, preferably less than 200 nM, more preferably less than 10 nM, such as less than 500 pM. Specific binding of an antigen-binding protein to an antigen or epitope can be determined in any suitable manner known per se, including, for example, the assays described herein, Scatchard analysis and/or competitive binding assays, such as radioimmunoassays (RIA), enzyme immunoassays (EIA) and sandwich competition assays, and the different variants thereof known per se in the art.

l) Amino acid residues will be indicated according to the standard three-letter or one-letter amino acid code, as, generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO 98/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows:
Ala into Gly or into Ser;
Arg into Lys;
Asn into Gln or into His;
Asp into Glu;
Cys into Ser;
Gln into Asn;
Glu into Asp;
Gly into Ala or into Pro;
His into Asn or into Gln;
Ile into Leu or into Val;
Leu into Ile or into Val;
Lys into Arg, into Gln or into Glu;
Met into Leu, into Tyr or into Ile;
Phe into Met, into Leu or into Tyr;
Ser into Thr;
Thr into Ser;
Trp into Tyr;
Tyr into Trp or into Phe;
Val into Ile or into Leu.

m) A nucleic acid or polypeptide molecule is considered to be "(in) essentially isolated (form)"—for example, when compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or polypeptide molecule is considered "essentially isolated" when it has been purified at least 2-fold, in particular at least 10-fold, more in particular at least 100-fold, and up to 1000-fold or more. A nucleic acid or polypeptide molecule that is "in essentially isolated form" is preferably essentially homogeneous, as determined using a suitable technique, such as a suitable chromatographical technique, such as polyacrylamide-gelelectrophoresis;

n) "Sequence identity" between e.g. two immunoglobulin single variable domain sequences indicates the percentage of amino acids that are identical between these two sequences. It may be calculated or determined as described in paragraph f) on pages 49 and 50 of WO08/020,079. "Sequence similarity" indicates the percentage of amino acids that either are identical or that represent conservative amino acid substitutions.

Target Specificity

The polypeptides of the invention have specificity for A-beta in that they comprise immunoglobulin single variable domains specifically binding to one or more A-beta molecules, and, more precisely, to epitopes within the A-beta molecule(s). A-beta may adopt and may occur e.g. in the human body in different forms, such as in monomeric form, in oligo- and multimeric forms, in aggregated soluble and insoluble forms, in fibrillar form, in proto-fibrillar form, in the form of amyloid plaques and deposits that are present in the central nervous system, skeletal muscle, platelets, vascular system, pancreas, kidney, spleen, heart, liver, testis, aorta, lung, intestine, skin, adrenal, salivary, and thyroid glands (Roher et al. Alzheimer's & Dementia 5 (2009) p. 18-29). It is within the scope of the invention that the polypeptides of the invention bind to any of the forms in which A-beta may occur, and especially to the forms that are most relevant from a biological and/or therapeutic point of view.

The polypeptides of the invention may bind to A-beta peptide molecules of different length, such as A-beta(1-42) which consists of the amino acid sequence shown as SEQ ID NO:1, A-beta(1-40) which consists of the amino acids 1 to 40 of the amino acid sequence shown as SEQ ID NO:1, A-beta (1-39) (amino acids 1 to 39), A-beta(1-38) (amino acids 1 to 38), A-beta(1-37) (amino acids 1 to 37), and the like. Binding of the polypeptide of the invention may occur at the N-terminal end, the C-terminal end, or somewhere in between.

Also, the invention is not limited with regard to the species form of A-beta. Thus, the polypeptides of the invention may preferably bind to human A-beta (SEQ ID NO:1), if intended for therapeutic purposes. However, polypeptides binding to e.g. other warm-blooded animal or, preferably, mammalian forms of A-beta are within the scope of the invention as well. A polypeptide of the invention binding to one species form of A-beta may cross-react with A-beta from one or more other species. For example, polypeptides of the invention binding to human A-beta may or may not show cross-reactivity with A-beta from one or more other species of primates and/or with A-beta from one or more species of animals that are often used in animal models for diseases (for example mouse—cf. SEQ ID NO:2, rat, rabbit, pig or dog), and in particular in animal models for diseases and disorders associated with A-beta (such as the species and animal models mentioned herein). Polypeptides of the invention that show such cross-reactivity may have advantages from a research and/or drug development point of view, since it allows the polypeptides of the invention binding to human A-beta to be tested in important disease models such as mice or rats.

Also, the invention is not limited to or defined by a specific antigenic determinant, epitope, part, domain, subunit or confirmation (where applicable) of A-beta against which the polypeptides of the invention are directed. Some of the preferred epitopes of A-beta against which the polypeptides of the present invention may be directed are the epitopes used for immunotherapy, and in particular for passive immunotherapy of AD. For example, as mentioned in Weksler M., Immunity and Ageing 1, 2 (2004) and in the background art referred to therein, it is known that there are three major epitopes on A-beta, i.e. an N-terminal epitope (amino acids 1-16 of A-beta: DAEFRHDSGYEVHHQK; SEQ ID NO:3), a central epitope (amino acids 16-28: KLVFFAEDVGSNK; SEQ ID NO:4) and a C-terminal epitope (amino acids 28-42; KGAI-IGLMVGGVVIA; SEQ ID NO:5). The polypeptides of the invention may be directed against either of these epitopes. Specifically preferred are polypeptides of the invention comprising at least two immunoglobulin single variable domains, wherein one immunoglobulin single variable domain binds to the N-terminal epitope and a second immunoglobulin single variable domain binds to the central epitope.

Polypeptides of the Invention

In its broadest sense, the invention provides novel pharmaceutically active agents for the prevention, treatment, alleviation and/or diagnosis of A-beta associated diseases, disorders or conditions and, specifically, AD. The agents according to the invention belong to a novel class of A-beta binding molecules, namely biparatopic polypeptides comprising two or more immunoglobulin single variable domains binding to the antigen A-beta at different epitopes. More specifically, such polypeptide of the invention essentially consists of or comprises (i) a first immunoglobulin single variable domain specifically binding to a first epitope of A-beta and (ii) a second immunoglobulin single variable domain specifically binding to a second epitope of A-beta, wherein the first epitope of A-beta and the second epitope of A-beta are not identical epitopes. In other words, such polypeptide of the invention comprises or essentially consist of two or more immunoglobulin single variable domains that are directed against at least two different epitopes present in A-beta, wherein said immunoglobulin single variable domains are linked to each other in such a way that they are capable of simultaneously binding A-beta. In this sense, the polypeptide of the invention can also be regarded as a "multivalent" immunoglobulin construct, and especially as a "multivalent immunoglobulin single variable domain construct", in that the whole polypeptide includes at least two binding sites for A-beta.

A polypeptide of the invention includes (at least) two anti-A-beta immunoglobulin single variable domains, wherein (the) two immunoglobulin single variable domains are directed against different epitopes within the A-beta molecule. Thus, these two immunoglobulin single variable domains will have a different epitope specificity and therefore different CDR sequences. For this reason, polypeptides of the invention will herein also be named "biparatopic polypeptides", or "biparatopic domain antibody constructs" (if the immunoglobulin single variable domains consist or essentially consist of domain antibodies), or "biparatopic Nanobody constructs" or "biparatopic VHH domain constructs", or "biparatopic VHH constructs" (if the immunoglobulin single variable domains consist or essentially consist of Nanobodies or VHH domains), respectively, as the two immunoglobulin single variable domains will include two different paratopes.

According to a specific embodiment of the invention, in case that the polypeptide of the invention includes more than two anti-A-beta immunoglobulin single variable domains, i.e. three, four or even more anti-A-beta immunoglobulin single variable domains, at least two of the anti-A-beta immunoglobulin single variable domains are directed against different epitopes within the A-beta molecule, wherein any further immunoglobulin single variable domain may bind to any of these two different epitopes and/or a further epitope present in the A-beta molecule.

According to another specific embodiment of the invention, the polypeptide of the invention can, in addition to the two anti-A-beta immunoglobulin single variable domains described above, include any other additional moiety, such as a linker (as described in more detail below) and/or additional protein domains, such as e.g. a further immunoglobulin single variable domain (as described in more detail below), as long as its binding to A-beta will not be prevented by such additional moiety. The polypeptide of the invention can additionally contain modifications such as glycosyl residues, modified amino acid side chains, and the like.

As set out before, two immunoglobulin single variable domains within one polypeptide of the invention will bind to different epitopes of A-beta. This can be achieved in one of the following manners: Either, the two immunoglobulin single variable domains will bind the two epitopes within one and the same A-beta molecule (intramolecular binding). Alternatively, they may bind epitopes located within two distinct A-beta molecules, i.e. one immunoglobulin single variable domain will bind to one epitope on one A-beta molecule, whereas the other immunoglobulin single variable domain will bind to the other epitope on another A-beta molecule, thereby cross-linking two A-beta molecules (intermolecular binding).

According to a preferred embodiment, the polypeptide of the invention will bind the two epitopes within one and the same A-beta molecule, so that no cross-linking will occur, and the polypeptide-of-the-invention—A-beta complexes will form in a stoichiometry of 1:1. Thus, (predominantly) intramolecular binding is preferred as compared to (predominantly) intermolecular binding, it being understood that a minor fraction of intermolecular binding may nevertheless occur. A distinction between intra- and intermolecular binding can be made using Biacore or size exclusion chromatorgraphy assays (as described by Santora et al., Anal. Biochem., 299: 119-129)—cf. Example 8.2 hereinbelow. However, it should be noted that polypeptides that operate via intermolecular binding of separate A-beta molecules are also within the scope of this invention.

In another preferred embodiment of the invention, the first and the second anti-A-beta immunoglobulin single variable domains comprised in a polypeptide of the invention each essentially consists of 4 framework regions (FR1 to FR4 respectively) and 3 complementarity determining regions (CDR1 to CDR3 respectively). Within the polypeptide of the invention, said first and second immunoglobulin single variable domains are covalently linked, optionally by a linker peptide as described below, wherein such linker sterically allows for optimal binding of the at least two immunoglobulin single variable domains to the respective A-beta epitopes.

It will be clear to the skilled person that for pharmaceutical uses in humans, the polypeptides of the invention are preferably directed against human A-beta, whereas for veterinary purposes, the polypeptides of the invention are preferably directed against A-beta from the species to be treated.

It will also be clear to the skilled person that when used as a therapeutic agent in humans, the immunoglobulin single variable domains comprised in the polypeptides according to the invention are preferably humanized immunoglobulin single variable domains.

According to the invention, the two or more immunoglobulin single variable domains can be, independently of each other: Domain antibodies, i.e. VL or VH antibody domains as described above, and/or VHH domains as described above, and/or any other sort of immunoglobulin single variable domains, provided that these immunoglobulin single variable domains will bind the antigen, i.e. A-beta, not by forming mutually complementary variable domain pairs jointly binding to the same epitope (as in the case of e.g. a VL-VH domain pair of a conventional antibody), but by independently binding to different epitopes (i.e. as a "biparatopic" antigen binding molecule as defined above).

According to a preferred embodiment of the invention, the first and the second immunoglobulin single variable domains essentially consist of either domain antibody sequences or VHH domain sequences as described above. According to a particularly preferred embodiment, the first and the second immunoglobulin single variable domains essentially consist of VHH domain sequences. Accordingly, the invention will herein and, especially, in the experimental part, be described in more detail with reference to biparatopic polypeptides comprising two (optionally humanized) anti-A-beta VHH domain sequences (VHHs) binding to two different epitopes of A-beta, i.e. biparatopic VHH domain constructs. However, it will be clear to the skilled person that the teaching herein may be applied analogously to polypeptides including other anti-A-beta immunoglobulin single variable domains, such as domain antibodies.

The polypeptides of the invention not only possess the advantageous characteristics of conventional antibodies, such as low toxicity and high selectivity, but they also exhibit additional properties. They are more soluble, meaning they may be stored and/or administered in higher concentrations compared to conventional antibodies. They are stable at room temperature, meaning they may be prepared, stored and/or transported without the use of refrigeration equipment, conveying cost, time and environmental savings. The polypeptides of the present invention also exhibit a prolonged stability at extremes of pH, meaning they would be suitable for delivery by oral administration.

Furthermore, the polypeptides of the invention do not need to comprise an Fc part which is present in "classical" antibodies, so that side effects caused by Fc effector functions, such as complement-dependent cytotoxicity (CDC) or antibody-dependent cellular cytotoxicity (ADCC), can be avoided. When used in anti-A-beta passive immunizations, conventional antibodies (having an Fc part) are suspected to account for the induction of microhemorrhages observed in humans and animal models, which are associated with a targeting of cerebral vascular A-beta deposits (Cerebral amyloid angiopathy) leading to microbleedings via ADCC and/or CDC (Wilcock, D M, Colton, C A, CNS Neurol. Disord. Drug Targets (2009) Vol. 8(1):50-64).

According to another embodiment of the invention, the at least two immunoglobulin single variable domains present in a polypeptide of the invention can be linked to each other directly (i.e. without use of a linker) or via a linker. The linker is preferably a linker peptide and will, according to the invention, be selected so as to allow binding of the at least two different immunoglobulin single variable domains to each of their at least two different epitopes of A-beta, either within one and the same A-beta molecule, or within two different molecules.

Suitable linkers will inter alia depend on the epitopes and, specifically, the distance between the epitopes on A-beta to which the immunoglobulin single variable domains bind, and will be clear to the skilled person based on the disclosure herein, optionally after some limited degree of routine experimentation.

Also, when the two or more immunoglobulin single variable domains that bind to A-beta are domain antibodies or VHH domains, they may also be linked to each other via a third domain antibody or VHH domain (in which the two or more immunoglobulin single variable domains may be linked directly to the third domain antibody or VHH domain or via suitable linkers). Such a third domain antibody or VHH domain may for example be a domain antibody or VHH domain that provides for an increased half-life, as further described herein. For example, the latter domain antibody or VHH domain may be a domain antibody or VHH domain that is capable of binding to a (human) serum protein such as (human) serum albumin or (human) transferrin, as further described herein.

Alternatively, the two or more immunoglobulin single variable domains that bind to A-beta may be linked in series (either directly or via a suitable linker) and the third (single) domain antibody or VHH domain (which may provide for increased half-life, as described above) may be connected directly or via a linker to one of these two or more aforementioned immunoglobulin sequences.

Suitable linkers are described herein in connection with specific polypeptides of the invention and may—for example and without limitation—comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides.

The linker sequence may be a naturally occurring sequence or a non-naturally occurring sequence. If used for therapeutical purposes, the linker is preferably non-immunogenic in the subject to which the anti-A-beta polypeptide of the invention is administered.

One useful group of linker sequences are linkers derived from the hinge region of heavy chain antibodies as described in WO 96/34103 and WO 94/04678.

Other examples are poly-alanine linker sequences such as Ala-Ala-Ala.

Further preferred examples of linker sequences are Gly/Ser linkers of different length such as $(gly_xser_y)_z$ linkers, including $(gly_4ser)_3$, $(gly_4ser)_4$, $(gly_4ser)$, $(gly_3ser)$, $gly_3$, and $(gly_3ser_2)_3$.

If the polypeptide of the invention is modified by the attachment of a polymer, for example of a polyethylene glycol (PEG) moiety, the linker sequence preferably includes an amino acid residue, such as a cysteine or a lysine, allowing such modification, e.g. PEGylation, in the linker region. Preferred examples of such linkers are:

```
                              ("GS9, C5", SEQ ID NO: 6)
GGGGCGGGS ("GS25, C5, SEQ ID NO: 7)
GGGGCGGGSGGGGSGGGGSGGGGS ("GS27, C14", SEQ ID NO: 8)
GGGSGGGGSGGGCGGGGSGGGGSGGG, ("GS35, C15" SEQ ID NO: 9)
GGGGSGGGGSGGGGCGGGGSGGGGSGGGGSGGGGS,
and ("GS35, C5", SEQ ID NO: 10)
GGGGCGGGGSGGGGSGGGGSGGGGSGGGGSGGGGS.
```

Some non-limiting examples of PEGylated polypeptides of the invention including such linkers are shown in SEQ ID NOs 40 to 43, 142, and 143.

Furthermore, the linker may also be a poly(ethylene glycol) moiety, as shown in e.g. WO04/081026.

In another embodiment, the at least two immunoglobulin single variable domains of the polypeptide of the invention are linked to each other via another moiety (optionally via one or two linkers), such as another polypeptide which, in a preferred but non-limiting embodiment, may be a further immunoglobulin single variable domain as already described above. Such moiety may either be essentially inactive or may have a biological effect such as improving the desired properties of the polypeptide or may confer one or more additional desired properties to the polypeptide. For example, and without limitation, the moiety may improve the half-life of the protein or polypeptide, and/or may reduce its immunogenicity or improve any other desired property.

Some non-limiting examples of such constructs are the constructs of SEQ ID NOs:34 to 39.

According to a preferred embodiment, the polypeptides of the invention comprise a first immunoglobulin single variable domain which binds to the epitope as defined by SEQ ID NO:3, and a second immunoglobulin single variable domain which binds to the epitope as defined by SEQ ID NO:4, or a first immunoglobulin single variable domain which binds to the epitope as defined by SEQ ID NO:4, and a second immunoglobulin single variable domain which binds to the epitope as defined by SEQ ID NO:3.

Even more preferred, contact between the immunoglobulin single variable domains and the A-beta molecule is made as described in Examples 8.2 and 8.3, i.e. the polypeptide of the invention forms contacts to at least amino acids 1, 3, 13, 20, and 23 of the human or mouse A-beta peptide.

Preferably, the polypeptides of the invention are having dissociation constant ($K_o$) values, measured in Kinexa assays as described in Example 9.7, in the range of $10^{-6}$ moles/litre or less, more preferably $10^{-9}$ moles/litre or less, and even more preferably in the range of from $10^{-11}$ to $10^{-13}$ moles/litre, or are having an IC50 value as measured in a TR-FRET binding assay, as set out in Example 9.3, of $10^{-9}$ moles/litre or below, and preferably in the range of from $5 \times 10^{-10}$ moles/litre to $10^{-12}$ moles/litre.

According to an even more preferred embodiment of the invention, the CDR sequences in the polypeptide of the invention are as defined below and are also such that the polypeptide of the invention binds to A-beta with a dissociation constant ($K_D$) as set out in the paragraph above or are having IC50 values as set out above.

According to a specific embodiment of the invention, the polypeptide of the invention comprises two A-beta binding immunoglobulin single variable domains having the structure (SEQ ID NOs as given in Table I below):
Immunoglobulin single variable domain 1:
FR(1)1-CDR(1)1-FR(1)2-CDR(1)2-FR(1)3-CDR(1)3-FR(1)4,
immunoglobulin single variable domain 2:
FR(2)1-CDR(2)1-FR(2)2-CDR(2)2-FR(2)3-CDR(2)3-FR(2)4,
wherein:
CDR(1)3 is selected from the group consisting of:
    the amino acid sequences according to SEQ ID NO:13 and SEQ ID NO:16; and
    amino acid sequences which have up to three, preferably up to two, and more preferably one amino acid difference as compared to said amino acid sequences according to SEQ ID NO:13 or SEQ ID NO:16, respectively;
and
CDR(2)3 is selected from the group consisting of:
    the amino acid sequence according to SEQ ID NO:19; and
    amino acid sequences which have up to three, preferably up to two, and more preferably one amino acid difference as compared to said amino acid sequence according to SEQ ID NO:19;
and
wherein the other CDR sequences and the framework region sequences are not specifically limited but will be selected by the skilled person according to the specific needs, such as humanized framework regions in case of a polypeptide intended for use in humans in order to reduce immunogenicity of the polypeptide of the invention. The order of the immunoglobulin single variable domains 1 and 2 is not particularly limited, so that, within a polypeptide of the invention, immunoglobulin single variable domain 1 may be located N-terminally and immunoglobulin single variable domain 2 may be located C-terminally, or vice versa.

Preferably, CDR(1)3 is selected from the group consisting of amino acid sequences according to SEQ ID NO:13 and SEQ ID NO:16, and CDR(2)3 is the amino acid sequence according to SEQ ID NO:19.

Even more preferably, the polypeptide of the invention comprises two A-beta binding immunoglobulin single variable domains having the structure (SEQ ID NOs as given in Table I below):
Immunoglobulin single variable domain 1:
FR(1)1-CDR(1)1-FR(1)2-CDR(1)2-FR(1)3-CDR(1)3-FR(1)4,
immunoglobulin single variable domain 2:
FR(2)1-CDR(2)1-FR(2)2-CDR(2)2-FR(2)3-CDR(2)3-FR(2)4,
wherein:
CDR(1)1 is the amino acid sequence according to SEQ ID NO:11 (which is the same as the amino acid sequence according to SEQ ID NO:14);
CDR(1)2 is selected from the group consisting of amino acid sequences according to SEQ ID NO:12 and SEQ ID NO:15;
CDR(1)3 is selected from the group consisting of amino acid sequences according to SEQ ID NO:13 and SEQ ID NO:16;
CDR(2)1 is the amino acid sequence according to SEQ ID NO:17;
CDR(2)2 is the amino acid sequence according to SEQ ID NO:18; and
CDR(2)3 is the amino acid sequence according to SEQ ID NO:19;
and
wherein the framework region sequences are not specifically limited but will be selected by the skilled person according to the specific needs, such as humanized framework regions in case of a polypeptide intended for use in humans in order to reduce immunogenicity of the polypeptide of the invention.

In the polypeptide of the invention as described above, the particular order of the immunoglobulin single variable domains 1 and 2 as set out above within the polypeptide is not critical, so that above-mentioned immunoglobulin single variable domain 1 may be located at the N-terminal end of the polypeptide, followed by above-mentioned immunoglobulin single variable domain 2; alternatively, above-mentioned immunoglobulin single variable domain 2 may be located at the N-terminal end of the polypeptide, followed by above-mentioned immunoglobulin single variable domain 1. In both cases, additional sequences and moieties may be present within the polypeptide of the invention, e.g. N-terminally, C-terminally, or located between the two immunoglobulin single variable domains, as set out in more detail herein.

The above CDR sequences and sets of 6 CDR sequences as present in the polypeptides of the invention and outlined above are summarized in the following Tables I and II, respectively:

TABLE I and TABLE II: Preferred CDR combinations in polypeptides of the invention comprising two different A-beta binding immunoglobulin single variable domains

TABLE I

CDR sequences

| SEQ ID NO: | amino acid sequence |
|---|---|
| 11 | TDTMG |
| 12 | AVTWNSGRTNYADSVKG |
| 13 | HRLVVGGTSVGDWRY |
| 14 | TDTMG |
| 15 | AVTWNSGRINYADSVKG |
| 16 | HRFVVGGNRVEDWRY |
| 17 | NYNMG |
| 18 | AVSRSGVSTYYADSVKG |
| 19 | AYRGTAINVRRSYSS |

TABLE II

Preferred sets of CDR sequences/CDR combinations (sequences defined by their SEQ ID NO: as given in above TABLE I):

|  | set 1 | set 2 | set 3 | set 4 |
|---|---|---|---|---|
| CDR(1)1 | 11 | 14 | 17 | 17 |
| CDR(1)2 | 12 | 15 | 18 | 18 |
| CDR(1)3 | 13 | 16 | 19 | 19 |
| CDR(2)1 | 17 | 17 | 11 | 14 |
| CDR(2)2 | 18 | 18 | 12 | 15 |
| CDR(2)3 | 19 | 19 | 13 | 16 |

Human immunoglobulin framework region sequences (FR) that can also be used as framework region sequences for the immunoglobulin single variable domains as described above are known in the art. Also known in the art are methods for humanizing framework regions of immunoglobulin single variable domains derived from species other than humans.

In a preferred embodiment, the polypeptides of the invention comprise the following framework region amino acid sequences 1 to 4 (FR1 to FR4; SEQ ID NOs as indicated in Table III below):

FR1 is or comprises an amino acid sequence selected from the group consisting of amino acid sequences according to SEQ ID NO:20 and SEQ ID NO:21;

FR2 is or comprises an amino acid sequence according to SEQ ID NO:22;

FR3 is or comprises an amino acid sequence selected from the group consisting of amino acid sequences according to SEQ ID NO:23 and SEQ ID NO:24; and FR4 is or comprises an amino acid sequence according to SEQ ID NO:25.

TABLE III

FR amino acid sequences

| SEQ ID NO: | amino acid sequence |
|---|---|
| 20 | VQLLESGGGLVQPGGSLRLSCVHSGPTFR |
| 21 | VQLLESGGGLVQPGGSLRLSCAASGRTFN |
| 22 | WFRQAPGKGREFVA |
| 23 | RFTISRDNSKNTAYLQMNSLRPEDTAVYYCAA |
| 24 | RFTISRDNSKNTVYLQMNSLRPEDTAVYYCAA |
| 25 | WGQGTLVTVSS |

Specific examples of immunoglobulin single variable domains having the FR and CDR sequences as shown above are:

Immunoglobulin single variable domain 1 (first amino acid, i.e. glutamate, may optionally be missing):
evqllesggglvqpggslrlscvhsgpt-frtdtmgwfrqapgkgrefyaavtwnsgrinyadsvkgrftisrdnskn taylqmnslrpedtavyycaahrfvvggnrvedwrywgqgtivtvss
(ABII035; SEQ ID NO:44)

Immunoglobulin single variable domain 2 (first amino acid, i.e. glutamate, may optionally be missing):
evqllesggglvqpggslrlscaasgrt-fnnynmgwfrqapgkgrefyaaysrsgvstyyadsvkgrftisrdnsk ntvylqmnslrpedtavyycaaayrgtainvrrsysswgqgtivtvss
(ABII059; SEQ ID NO:45)

Specific examples of polypeptides of the invention which include, in one single polypeptide chain, two immunoglobulin single variable domains as shown above and, optionally, a linker which connects the two immunoglobulin single variable domains, are given further below.

According to a preferred embodiment, the polypeptides of the invention include, especially when used as a therapeutic agent, a moiety which extends the half-life of the polypeptide of the invention in serum or other body fluids of a patient. The term "half-life" means the time taken for the serum concentration of the (modified) polypeptide to reduce by 50%, in vivo, for example due to degradation of the polypeptide and/or clearance and/or sequestration by natural mechanisms.

More specifically, such half-life extending moiety can be covalently linked or fused to said polypeptide and may be, without limitation, an Fc portion, an albumin moiety, a fragment of an albumin moiety, an albumin binding moiety, such as an anti-albumin immunoglobulin single variable domain, a transferrin binding moiety, such as an anti-transferrin immunoglobulin single variable domain, a polyoxyalkylene molecule, such as a polyethylene glycol molecule, an albumin binding peptide, or hydroxyethyl starch (HES) derivatives.

According to one embodiment, the polypeptide of the invention may be linked to one or more antibody parts, fragments or domains that confer one or more effector functions to the polypeptide of the invention and/or may confer the ability to bind to one or more Fc receptors. For example, for this purpose, and without being limited thereto, the antibody parts may be or may comprise CH2 and/or CH3 domains of an antibody, such as from a heavy chain antibody (as described hereabove) and more preferably from a conventional human 4-chain antibody; specifically, the polypeptide of the invention may be linked to an Fc region, for example from human IgG, from human IgE or from another human Ig. For example, WO 94/04678 describes heavy chain antibodies comprising a Camelid VHH domain or a humanized derivative thereof, in which the Camelidae CH2 and/or CH3 domain have been replaced by human CH2 and/or CH3 domains, so as to provide an immunoglobulin that consists of 2 heavy chains each comprising a—optionally humanized—VHH domain and human CH2 and CH3 domains (but no CH1 domain), which immunoglobulin has the effector function provided by the CH2 and CH3 domains, can function without the presence of any light chains, and has an increased half-life as compared to the corresponding VHH domains without such modification.

Specific examples of polypeptides of the invention including an Fc portion (with or without effector functions) are the polypeptides indicated hereinbelow:

(SEQ ID NO: 26)
evqllesggglvqpggslrlscvhsgptfrtdtmgwfrqapgkgrefvaavtwnsgrinyadsvkgrftisrdnskn
taylqmnslrpedtavyycaahrfvvggnrvedwrywgqgtlvtvssggggsgggsevqllesggglvqpggsl
rlscaasgrtfnnynmgwfrqapgkgrefvaavsrsgvstyyadsvkgrftisrdnskntvylqmnslrpedtavy
ycaaayrgtainvrrsysswgqgtlvtvssastkgpsvfplapsskstsggtaalgclvkdyfpepvtvswnsgalt
sgvhtfpavlqssglyslssvvtvpssslgtqtyicnvnhkpsntkvdkrvepkscdkthtcppcpapellggpsvf
lfppkpkdtlmisrtpevtcvvvdvshedpevkfnwyvdgvevhnaktkpreeqynstyrvvsvltvlhqdwlng
keykckvsnkalpapiektiskakgqprepqvytlppsreemtknqvsltclvkgfypsdiavewesngqpenn
ykttppvldsdgsfflysk1tvdksrwqqgnvfscsvmhealhnhytqkslslspgk (SEQ ID NO: 27)
evqllesggglvqpggslrlscaasgrtfnnynmgwfrqapgkgrefvaavsrsgvstyyadsvkgrftisrdnsk
ntvylqmnslrpedtavyycaaayrgtainvrrsysswgqgtlvtvssggggsggggsggggsggggsggggs
gggevqllesggglvqpggslrlscvhsgptfrtdtmgwfrqapgkgrefvaavtwnsgrinyadsvkgrftisrdn
skntaylqmnslrpedtavyycaahrfvvggnrvedwrywgqgtlvtvssastkgpsvfplapsskstsggtaal
gclvkdyfpepvtvswnsgaltsgvhtfpavlqssglyslssvvtvpssslgtqtyicnvnhkpsntkvdkrvepks
cdkthtcppcpapellggpsvflfppkpkdtlmisrtpevtcvvvdvshedpevkfnwyvdgvevhnaktkpre
eqynstyrvvsvltvlhqdwlngkeykckvsnkalpapiektiskakgqprepqvytlppsreemtknqvsltclv
kgfypsdiavewesngqpennykttppvldsdgsfflysk1tvdksrwqqgnvfscsvmhealhnhytqkslsls
pgk (SEQ ID NO: 28)
evqllesggglvqpggslrlscaasgrtfnnynmgwfrqapgkgrefvaavsrsgvstyyadsvkgrftisrdnsk
ntvylqmnslrpedtavyycaaayrgtainvrrsysswgqgtlvtvssggggsggggsggggcggggsgggg
sggggsgggsevqllesggglvqpggslrlscvhsgptfrtdtmgwfrqapgkgrefvaavtwnsgrinyads
vkgrftisrdnskntaylqmnslrpedtavyycaahrfvvggnrvedwrywgqgtlvtvssastkgpsvfplapss
kstsggtaalgclvkdyfpepvtvswnsgaltsgvhtfpavlqssglyslssvvtvpssslgtqtyicnvnhkpsntk
vdkrvepkscdkthtcppcpapellggpsvflfppkpkdtlmisrtpevtcvvvdvshedpevkfnwyvdgvev
hnaktkpreeqynstyrvvsvltvlhqdwlngkeykckvsnkalpapiektiskakgqprepqvytlppsreemt
knqvsltclvkgfypsdiavewesngqpennykttppvldsdgsfflysk1tvdksrwqqgnvfscsvmhealhn
hytqkslslspgk (SEQ ID NO: 29)
evqllesggglvqpggslrlscvhsgptfrtdtmgwfrqapgkgrefvaavtwnsgrinyadsvkgrftisrdnskn
taylqmnslrpedtavyycaahrfvvggnrvedwrywgqgtlvtvssggggsgggsevqllesggglvqpggsl
rlscaasgrtfnnynmgwfrqapgkgrefvaavsrsgvstyyadsvkgrftisrdnskntvylqmnslrpedtavy
ycaaayrgtainvrrsysswgqgtlvtvssastkgpsvfplapsskstsggtaalgclvkdyfpepvtvswnsgalt
sgvhtfpavlqssglyslssvvtvpssslgtqtyicnvnhkpsntkvdkrvepkscdkthtcppcpapeaaggps
vflfppkpkdtlmisrtpevtcvvvdvshedpevkfnwyvdgvevhnaktkpreeqynstyrvvsvltvlhqdwl
ngkeykckvsnkalpapiektiskakgqprepqvytlppsreemtknqvsltclvkgfypsdiavewesngqpe
nnykttppvldsdgsfflysk1tvdksrwqqgnvfscsvmhealhnhytqkslslspgk -continued (SEQ ID NO: 30)
evqllesggglvqpggslrlscaasgrtfnnynmgwfrqapgkgrefvaavsrsgvstyyadsvkgrftisrdnsk ntvylqmnslrpedtavyycaaayrgtainvrrsysswgqgtlvtvssgggsggggsggggsggggsggggs gggevqllesggglvqpggslrlscvhsgptfrtdtmgwfrqapgkgrefvaavtwnsgrinyadsvkgrftisrdn skntaylqmnslrpedtavyycaahrfvvggnrvedwrywgqgtlvtvssastkgpsvfplapsskstsggtaal gclvkdyfpepvtvswnsgaltsgvhtfpavlqssglyslssvvtvpssslgtqtyicnvnhkpsntkvdkrvepks cdkthtcppcpapeaaggpsvflfppkpkdtlmisrtpevtcvvvdvshedpevkfnwyvdgvevhnaktkpr eeqynstyrvvsvltvlhqdwlngkeykckvsnkalpapiektiskakgqprepqvytlppsreemtknqvsltcl vkgfypsdiavewesngqpennykttppvldsdgsfflyskltvdksrwqqgnvfscsvmhealhnhytqkslsl spgk (SEQ ID NO: 31)
evqllesggglvqpggslrlscaasgrtfnnynmgwfrqapgkgrefvaavsrsgvstyyadsvkgrftisrdnsk ntvylqmnslrpedtavyycaaayrgtainvrrsysswgqgtlvtvssgggsggggsggggcggggsgggg sggggsggggsevqllesggglvqpggslrlscvhsgptfrtdtmgwfrqapgkgrefvaavtwnsgrinyads vkgrftisrdnskntaylqmnslrpedtavyycaahrfvvggnrvedwrywgqgtlvtvssastkgpsvfplapss kstsggtaalgclvkdyfpepvtvswnsgaltsgvhtfpavlqssglyslssvvtvpssslgtqtyicnvnhkpsntk vdkrvepkscdkthtcppcpapeaaggpsvflfppkpkdtlmisrtpevtcvvvdvshedpevkfnwyvdgve vhnaktkpreeqynstyrvvsvltvlhqdwlngkeykckvsnkalpapiektiskakgqprepqvytlppsreem tknqvsltclvkgfypsdiavewesngqpennykttppvldsdgsfflyskltvdksrwqqgnvfscsvmhealh nhytqkslslspgk According to a further embodiment of the invention, the two immunoglobulin single variable domains may be fused to a serum albumin molecule, such as described e.g. in WO01/79271 and WO03/59934.

An example of a biparatopic A-beta binding polypeptide of the invention comprising a human serum albumin moiety is given in Table IV.

TABLE IV

| HSA-fusion protein | | |
|---|---|---|
| Sequence information | Description | SEQ ID NO: |
| EVQLLESGGGLVQPGGSLRLSCAASGRTFNNYNMG WFRQAPGKGREFVAAVSRSGVSTYYADSVKGRFTI SRDNSKNTVYLQMNSLRPEDTAVYYCAAAYRGTAI NVRRSYSSWGQGTLVTVSSGGGSGGGGSGGGGSGG GGSGGGGSGGGEVQLLESGGGLVQPGGSLRLSCVH SGPTFRTDTMGWFRQAPGKGREFVAAVTWNSGRIN YADSVKGRFTISRDNSKNTAYLQMNSLRPEDTAVY YCAAHRFVVGGNRVEDWRYWGQGTLVTVSSDAHKS EVAHRFKDLGEENFKALVLIAFAQYLQQCPFEDHV KLVNEVTEFAKTCVADESAENCDKSLHTLFGDKLC TVATLRETYGEMADCCAKQEPERNECFLQHKDDNP NLPRLVRPEVDVMCTAPHDNEETFLKKYLYEIARR HPYFYAPELLFFAKRYKAAFTECCQAADKAACLLP KLDELRDEGKASSAKQRLKCASLQKFGERAFKAWA VARLSQRFPKAEFAEVSKLVTDLTKVHTECCHGDL LECADDRADLAKYICENQDSISSKLKECCEKPLLE KSHCIAEVENDEMPADLPSLAADFVESKDVCKNYA EAKDVFLGMFLYEYARRHPDYSVVLLLRLAKTYET TLEKCCAAADPHECYAKVFDEFKPLVEEPQNLIKQ NCELFEQLGEYKFQNALLVRYTKKVPQVSTPTLVE VSRNLGKVGSKCCKHPEAKRMPCAEDYLSVVLNQL CVLHEKTPVSDRVTKCCTESLVNRRPCFSALEVDE TYVPKEFNAETFTFHADICTLSEKERQIKKQTALV | 059-27GS-035-HSA | 32 |

TABLE IV-continued

| HSA-fusion protein | | |
|---|---|---|
| Sequence information | Description | SEQ ID NO: |
| ELVKHKPKATKEQLKAVMDDFAAFVEKCCKADDKE TCFAEEGKKLVAASQAALGL | | |

In another preferred embodiment, the polypeptide of the invention comprises a moiety which binds to an antigen found in blood, such as serum albumin, serum immunoglobulins, thyroxine-binding protein, fibrinogen or transferrin, thereby conferring an increased half-life in vivo to the resulting polypeptide of the invention. According to a specifically preferred embodiment, such moiety is an albumin-binding immunoglobulin and, especially preferred, an albumin-binding immunoglobulin single variable domain such as an albumin-binding VHH domain.

If intended for use in humans, such albumin-binding immunoglobulin single variable domain will preferably bind to human serum albumin and will preferably be a humanized albumin-binding VHH domain.

Immunoglobulin single variable domains binding to human serum albumin are known in the art and are described in further detail in e.g. WO2006/122786. A specifically useful albumin binding VHH domain consists of or contains the amino acid sequence:
evqlvesggglvqpgnslrlscaasg-ftfssfgmswvrqapgkglewvssisgsgsdtlyadsvkgrftisrdnak ttlylqmnslrpedtavyyctiggslsrssqgtlvtvss (SEQ ID NO:33)

Specific examples of polypeptides of the invention which comprise an albumin binding VHH domain are shown in Table V:

TABLE V

Biparatopic polypeptides of the invention, comprising two anti-A-beta VHH domains and one anti-HSA VHH domain

| Clone | Sequence information | Description | SEQ ID NO: |
|---|---|---|---|
| ABII316 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINVR RSYSSWGQGTLVTVSSGGGGSGGGSEVQLVESGG GLVQPGNSLRLSCAASGFTFSSFGMSWVRQAPGKG LEWVSSISGSGSDTLYADSVKGRFTISRDNAKTTLYL QMNSLRPEDTAVYYCTIGGSLSRSSQGTLVTVSSGG GGSGGGSEVQLLESGGGLVQPGGSLRLSCVHSGPT FRTDTMGWFRQAPGKGREFVAAVTWNSGRINYADS VKGRFTISRDNSKNTAYLQMNSLRPEDTAVYYCAAHR FVVGGNRVEDWRYWGQGTLVTVSS | 059-9GS-Alb8-9GS-035 | 34 |
| ABII317 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINVR RSYSSWGQGTLVTVSSGGGGSGGGGSGGGGSGGG GSGGGGSGGGGSGGGGSEVQLLESGGGLVQPGGS LRLSCVHSGPTFRTDTMGWFRQAPGKGREFVAAVT WNSGRINYADSVKGRFTISRDNSKNTAYLQMNSLRPE DTAVYYCAAHRFVVGGNRVEDWRYWGQGTLVTVSS GGGGSGGGSEVQLVESGGGLVQPGNSLRLSCAASG FTFSSFGMSWVRQAPGKGLEWVSSISGSGSDTLYAD SVKGRFTISRDNAKTTLYLQMNSLRPEDTAVYYCTIG GSLSRSSQGTLVTVSS | 059-35GS-035-9GS-Alb8 | 35 |
| ABII318 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINVR RSYSSWGQGTLVTVSSGGGGSGGGSEVQLLESGGG LVQPGGSLRLSCVHSGPTFRTDTMGWFRQAPGKGR EFVAAVTWNSGRINYADSVKGRFTISRDNSKNTAYLQ MNSLRPEDTAVYYCAAHRFVVGGNRVEDWRYWGQ GTLVTVSSGGGGSGGGSEVQLVESGGGLVQPGNSL RLSCAASGFTFSSFGMSWVRQAPGKGLEWVSSISGS GSDTLYADSVKGRFTISRDNAKTTLYLQMNSLRPEDT AVYYCTIGGSLSRSSQGTLVTVSS | 059-9GS-035-9GS-Alb8 | 36 |
| ABII319 | EVQLLESGGGLVQPGGSLRLSCVHSGPTFRTDTMG WFRQAPGKGREFVAAVTWNSGRINYADSVKGRFTIS RDNSKNTAYLQMNSLRPEDTAVYYCAAHRFVVGGNR VEDWRYWGQGTLVTVSSGGGGSGGGGSGGGGSG GGGSGGGGSGGGGSGGGGSEVQLLESGGGLVQPG GSLRLSCAASGRTFNNYNMGWFRQAPGKGREFVAA VSRSGVSTYYADSVKGRFTISRDNSKNTVYLQMNSLR PEDTAVYYCAAAYRGTAINVRRSYSSWGQGTLVTVS SGGGGSGGGSEVQLVESGGGLVQPGNSLRLSCAAS GFTFSSFGMSWVRQAPGKGLEWVSSISGSGSDTLYA DSVKGRFTISRDNAKTTLYLQMNSLRPEDTAVYYCTIG GSLSRSSQGTLVTVSS | 035-35GS-059-9GS-Alb8 | 37 |
| ABII320 | EVQLLESGGGLVQPGGSLRLSCVHSGPTFRTDTMGW FRQAPGKGREFVAAVTWNSGRINYADSVKGRFTISRD NSKNTAYLQMNSLRPEDTAVYYCAAHRFVVGGNRVE DWRYWGQGTLVTVSSGGGGSGGGSEVQLVESGGG LVQPGNSLRLSCAASGFTFSSFGMSWVRQAPGKGLE WVSSISGSGSDTLYADSVKGRFTISRDNAKTTLYLQM NSLRPEDTAVYYCTIGGSLSRSSQGTLVTVSSGGGGS GGGSEVQLLESGGGLVQPGGSLRLSCAASGRTFNNY NMGWFRQAPGKGREFVAAVSRSGVSTYYADSVKGR FTISRDNSKNTVYLQMNSLRPEDTAVYYCAAAYRGTAI NVRRSYSSWGQGTLVTVSS | 035-9GS-Alb8-9GS-059 | 38 |
| ABII321 | VQLLESGGGLVQPGGSLRLSCVHSGPTFRTDTMGWF RQAPGKGREFVAAVTWNSGRINYADSVKGRFTISRDN SKNTAYLQMNSLRPEDTAVYYCAAHRFVVGGNRVED WRYWGQGTLVTVSSGGGGSGGGSEVQLVESGGGLV QPGNSLRLSCAASGFTFSSFGMSWVRQAPGKGLEW VSSISGSGSDTLYADSVKGRFTISRDNAKTTLYLQMNS LRPEDTAVYYCTIGGSLSRSSQGTLVTVSSGGGGSGG GSEVQLLESGGGLVQPGGSLRLSCAASGRTFNNYNM | 035-9GS-Alb8-9GS-059 (first E deleted) | 39 |

TABLE V-continued

Biparatopic polypeptides of the invention, comprising two anti-A-beta VHH domains and one anti-HSA VHH domain

| Clone | Sequence information | SEQ ID Description NO: |
|---|---|---|
| | GWFRQAPGKGREFVAAVSRSGVSTYYADSVKGRFTI SRDNSKNTVYLQMNSLRPEDTAVYYCAAAYRGTAINV RRSYSSWGQGTLVTVSS | |

In still another preferred embodiment, the polypeptide of the invention comprises a moiety which binds to serum albumin, wherein such moiety is an albumin binding peptide, as described e.g. in international patent publications WO2008/068280 and WO2009/127691.

According to still another embodiment, a half-life extending modification of a polypeptide of the invention (such modification also reducing immunogenicity of the polypeptide) comprises attachment of a suitable pharmacologically acceptable polymer, such as straight or branched chain poly(ethylene glycol) (PEG) or derivatives thereof (such as methoxypoly(ethylene glycol) or mPEG). Generally, any suitable form of PEGylation can be used, such as the PEGylation used in the art for antibodies and antibody fragments (including but not limited to domain antibodies and scFv's); reference is made, for example, to: Chapman, Nat. Biotechnol., 54, 531-545 (2002); Veronese and Harris, Adv. Drug Deliv. Rev. 54, 453-456 (2003); Harris and Chess, Nat. Rev. Drug. Discov. 2 (2003); WO 04/060965; and U.S. Pat. No. 6,875,841.

Various reagents for PEGylation of polypeptides are also commercially available, for example from Nektar Therapeutics, USA, or NOF Corporation, Japan, such as the Sunbright® EA Series, SH Series, MA Series, CA Series, and ME Series, such as Sunbright® ME-100MA, Sunbright® ME-200MA, and Sunbright® ME-400MA.

Preferably, site-directed PEGylation is used, in particular via a cysteine-residue (see for example Yang et al., Protein Engineering 16, 761-770 (2003)). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus and/or of a linker region that bridges two or more functional domains of a polypeptide of the invention, all using techniques of protein engineering known per se to the skilled person.

Preferably, for the polypeptides of the invention, a PEG is used with a molecular weight of more than 5 kDa, such as more than 10 kDa and less than 200 kDa, such as less than 100 kDa; for example in the range of 20 kDa to 80 kDa.

With regard to PEGylation, it should be noted that generally, the invention also encompasses any polypeptide of the invention that has been PEGylated at one or more amino acid positions, preferably in such a way that said PEGylation either (1) increases the half-life in vivo; (2) reduces immunogenicity; (3) provides one or more further beneficial properties known per se for PEGylation; (4) does not essentially affect the affinity of the polypeptide for A-beta (e.g. does not reduce said affinity by more than 50%, and more preferably not by more than 10%, as determined by a suitable assay, such as those described in the Examples below); and/or (4) does not affect any of the other desired properties of the polypeptides of the invention. Suitable PEG-groups and methods for attaching them, either specifically or non-specifically, will be clear to the skilled person.

According to a specifically preferred embodiment of the invention, a PEGylated polypeptide of the invention includes one PEG moiety of linear PEG having a molecular weight of 40 kDa or 60 kDa, wherein the PEG moiety is attached to the polypeptide in a linker region and, specifically, at a Cys residue at position 5 of a GS9-linker peptide as shown in SEQ ID NO:6, at position 14 of a GS27-linker peptide as shown in SEQ ID NO:8, or at position 15 of a GS35-linker peptide as shown in SEQ ID NO:9, or at position 5 of a 35GS-linker peptide as shown in SEQ ID NO:10.

Preferred examples of polypeptides of the invention, PEGylated preferably with one of the PEG reagents as mentioned above, such as "Sunbright® ME-400MA" as shown in the following chemical formula:

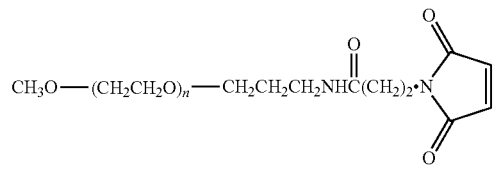

which has an average molecular weight of 40 kDa, are given in Table VI below:

TABLE VI

PEGylated polypeptides of the invention;

| Clone | Sequence information | Description | SEQ ID NO: |
|---|---|---|---|
| ABII322 | VQLLESGGGLVQPGGSLRLSCAASGRTFNNYNMGWFR QAPGKGREFVAAVSRSGVSTYYADSVKGRFTISRDNSK NTVYLQMNSLRPEDTAVYYCAAAYRGTAINVRRSYSSW GQGTLVTVSSGGGSGGGGSGGGGC*GGGGSGGGGS | ABII059-27GS linker with C at | 40 |

TABLE VI-continued

PEGylated polypeptides of the invention;

| Clone | Sequence information | Description | SEQ ID NO: |
|---|---|---|---|
|  | GGGEVQLLESGGGLVQPGGSLRLSCVHSGPTFRTDTM GWFRQAPGKGREFVAAVTWNSGRINYADSVKGRFTISR DNSKNTAYLQMNSLRPEDTAVYYCAAHRFVVGGNRVE DWRYWGQGTLVTVSS | position 14- ABII035 |  |
| ABII323 | VQLLESGGGLVQPGGSLRLSCAASGRTFNNYNMGWFR QAPGKGREFVAAVSRSGVSTYYADSVKGRFTISRDNSK NTVYLQMNSLRPEDTAVYYCAAAYRGTAINVRRSYSSW GQGTLVTVSSGGGGSGGGGSGGGGC*GGGGSGGGG SGGGGSGGGGSEVQLLESGGGLVQPGGSLRLSCVHS GPTFRTDTMGWFRQAPGKGREFVAAVTWNSGRINYAD SVKGRFTISRDNSKNTAYLQMNSLRPEDTAVYYCAAHR FVVGGNRVEDWRYWGQGTLVTVSS | ABII059-35GS linker with C at position 15- ABII035 | 41 |
| ABII305 | EVQLVESGGGLVQAGGSLRLSCAASGRTFNNYNMGWF RQAPGKEREFVAAVSRSGVSTYYADSVKGRFTISRDNA KNAVYLQMNSLKPEDTAIYYCGAAYRGTAINVRRSYDS WGQGTQVTVSSGGGGC*GGGGSGGGGSGGGGSGGG GSGGGGSGGGGSEVQLVESGGGLVLAGGSLRLSCVH SGPTFRTDTMGWFRQAPGKEREFVAAVTWNSGRINYA DSVKGRFTVSRDNTRNAAYLQMSGLKDEDTAVYYCTA HRFVVGGNRVEDWRYWGQGTQVTVSS | ABII050-35GS linker with C at position 5- ABII002 | 42 |
| ABII306 | EVQLVESGGGLVQAGGSLRLSCAASGRTFNNYNMGWF RQAPGKEREFVAAVSRSGVSTYYADSVKGRFTISRDNA KNAVYLQMNSLKPEDTAIYYCGAAYRGTAINVRRSYDS WGQGTQVTVSSGGGGC*GGGSEVQLVESGGGLVLAG GSLRLSCVHSGPTFRTDTMGWFRQAPGKEREFVAAVT WNSGRINYADSVKGRFTVSRDNTRNAAYLQMSGLKDE DTAVYYCTAHRFVVGGNRVEDWRYWGQGTQVTVSS | ABII050-9GS linker with C at position 5- ABII002 | 43 |
| ABII314 | EVQLLESGGGLVQPGGSLRLSCAASGRTFNNYNMGWF RQAPGKGREFVAAVSRSGVSTYYADSVKGRFTISRDNS KNTVYLQMNSLRPEDTAVYYCAAAYRGTAINVRRSYSS WGQGTLVTVSSGGGGC*GGGGSGGGGSGGGGSGGG GSGGGGSGGGGSEVQLLESGGGLVQPGGSLRLSCVHS GPTFRTDTMGWFRQAPGKGREFVAAVTWNSGRINYAD SVKGRFTISRDNSKNTAYLQMNSLRPEDTAVYYCAAHR FVVGGNRVEDWRYWGQGTLVTVSS | ABII059-35GS linker with C at position 5- ABII035 | 142 |
| ABII315 | EVQLLESGGGLVQPGGSLRLSCAASGRTFNNYNMGWF RQAPGKGREFVAAVSRSGVSTYYADSVKGRFTISRDNS KNTVYLQMNSLRPEDTAVYYCAAAYRGTAINVRRSYSS WGQGTLVTVSSGGGGC*GGGSEVQLLESGGGLVQPGG SLRLSCVHSGPTFRTDTMGWFRQAPGKGREFVAAVTW NSGRINYADSVKGRFTISRDNSKNTAYLQMNSLRPEDTA VYYCAAHRFVVGGNRVEDWRYWGQGTLVTVSS | ABII059-9GS linker with C at position 5- ABII035 | 143 |

C* indicates the Cys residue bearing the PEG moiety

According to a further embodiment, the polypeptide of the invention additionally comprises a moiety which allows the polypeptide to cross the blood brain barrier. In particular, said moiety that allows the resulting polypeptides of the invention to cross the blood brain barrier may be one or more (such as two and preferably one) immunoglobulin single variable domains such as the brain targeting antibody fragments (VHHs) FC44 and FC5 described in WO02/057445. Examples thereof are shown in Table XIX below.

Thus, the polypeptides of the invention can also be described by the following general formula:

A-ISVD1-B-ISVD2-C, wherein

ISVD1 and ISVD2 denote an A-beta binding immunoglobulin single variable domain as described hereinbefore, binding to different epitopes of A-beta, such as e.g. the immunoglobulin single variable domains according to SEQ ID NOs 44 and 45, respectively; and A, B and C independently of each other denote:
- no additional moiety (i.e. A is the N-terminal end of ISVD1, B is a peptide bond linking ISVD1 and ISVD2, and C is the C-terminal end of ISVD2)
- one or more domains selected from the group of CH1, CH2, and CH3 domains of human IgG, IgM, IgD, IgE, and the like, and preferably C denotes CH2-CH3;
- albumin or a fragment thereof, and preferably human serum albumin or a fragment thereof;
- an albumin binding moiety, and preferably an albumin binding immunoglobulin single variable domain or an albumin binding peptide;
- a linker peptide, which is optionally PEGylated; and preferably B denotes a linker peptide having from 3 to 45 amino acids, including at least one cysteine residue which is PEGylated, preferably with a PEG40 or PEG60 moiety;
- one or more A-beta binding moieties, preferably an additional anti-A-beta immunoglobulin variable domain, identical or not identical to ISVD1 or ISVD2 a polypeptide, preferably an immunoglobulin single variable domain, conferring to the polypeptide blood-brain-barrier crossing properties, such as FC44 and FC5 described in WO02/057445;

or wherein

ISVD1, ISVD2, B and C have the meaning as above and

A denotes an N-terminal, optionally formylated, Met residue, for example as result of expression in a heterologous host organism; and/or a signal or leader sequence that directs secretion of the polypeptide of the invention from a host cell upon synthesis; and/or a pro-sequence which is optionally removed after expression of the polypeptide in a suitable host cell;

or wherein

ISVD1, ISVD2, A and B have the meaning as above and

C denotes a "tag", such as an amino acid sequence or residue that allows or facilitates the purification of the polypeptide of the invention, for example using affinity techniques directed against said sequence or residue; such tag may optionally be removabel after such purification step, e.g. by chemical or enzymatical cleavage, to provide the mature sequence of the polypeptide; for this purpose, the tag may optionally be linked to the polypeptide sequence via a cleavable linker sequence or contain a cleavable motif. Some preferred, but non-limiting examples of such residues are multiple histidine residues, glutathione residues and a myc-tag such as AAAEQKLISEEDLNGAA (SEQ ID NO:46).

Therapeutic Use

According to an important further aspect, the polypeptide of the invention is used for therapeutic purposes, such as for the prevention, treatment and/or alleviation of a disorder, disease or condition as set out below, especially in a human being, such as Alzheimer's Disease (AD), dry AMD, or glaucoma;

in a method of treatment of a patient in need of such therapy, such method comprising administering, to the subject in need thereof, a pharmaceutically active amount of at least one polypeptide of the invention or a pharmaceutical composition (as set out in detail below) comprising such polypeptide of the invention, wherein such subject in need of such therapy may be a human being suffering from any of the disorders, diseases or conditions as set out below, such as AD, dry AMD, or glaucoma;

for the preparation of a medicament for the prevention, treatment or alleviation of disorders, diseases or conditions as set out below, such as AD, dry AMD, or glaucoma in a human being;

as an active ingredient in a pharmaceutical composition or medicament used for the before-mentioned purposes.

The disorder, disease or condition (in the following: disease) as mentioned above is a disease that can be prevented and/or treated and/or alleviated by administering a polypeptide of the invention to the patient or (human) being, and, more specifically, a disease mediated by A-beta dysfunction, such as a dysfunction of A-beta production, deposition or lack of clearance, and/or a disease mediated by amyloid plaque formation, formation of A-beta oligomers, and the like. Even more specifically, the disease is a disease that can be prevented and/or treated and/or alleviated by modulating, reducing and/or reversing the (undesired) formation or build-up of A-beta and/or of amyloid plaques and/or of A-beta oligomers in a patient, such diseases comprising e.g. neurodegenerative diseases, the most prominent A-beta related neurodegenerative disease being AD.

Thus, the polypeptides of the invention can be used in a method for the prevention, treatment or alleviation of diseases such as:

Alzheimer's disease (AD; all types and stages of the disease including preclinical and prodromal stages); also known as "dementia of the Alzheimer type";

the dry form of age-related macular degeneration (dry AMD; central geographic atrophy)

glaucoma cerebral amyloid angiopathy (CAA);

trisomy 21 (Down's Syndrome), including adult Down syndrome;

hereditary cerebral hemorrhage with amyloidosis of the Dutch-type (HCHWA-D);

dementia with Lewy Bodies;

frontotemporal lobar degeneration;

glaucoma;

amyotrophic lateral sclerosis;

sporadic inclusion body myositis; and anxiety disorder in an elderly human subject (e.g. of at least 55 years old), selected from the group consisting of obsessive-compulsive disorder, panic disorder, panic attack, agoraphobia, post-traumatic stress disorder, social phobia, disruptive behaviour disorder and chronic fatigue syndrome (wherein said elderly human subject may or may not be diagnosed with a condition related to A-beta, selected from clinical or preclinical AD, chronic amyloid angiopathy and Down's syndrome);

wherein such method comprises administering, to a subject in need thereof, a pharmaceutically active amount of a polypeptide of the invention and/or of a pharmaceutical composition comprising the same.

In the context of the present invention, the term "prevention, treatment and/or alleviation" not only comprises preventing and/or treating and/or alleviating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

Specifically, in the case of AD, the polypeptides, compositions, and methods of the invention can be used for helping to prevent or delay the onset of AD in patients with identified risk factors for AD and/or proven A-beta deposits, for treating patients with mild cognitive impairment (MCI), who are at risk to convert to AD, and for preventing or delaying the onset of AD in those patients who would otherwise be expected to progress from preclinical or prodromal disease stages to dementia. Genetic risk factors for AD include specific mutations in the APP gene (in particular at positions 670 and 671 as well as position 717), in the presenilin genes PS1 and PS2, and in ApoE4. Other risk factors include a family history of AD, hypercholesterolemia, atherosclerosis, diabetes, and/or high age. Disposition for AD can be diagnosed early by analysing A-beta(1-42) and tau concentrations in CSF. Neuroimaging techniques (e.g. PET and MRI) may identify patients at risk of converting to AD. In general, the use of several biomarkers may allow to diagnose AD in a very early stage with a high sensitivity and specificity.

In the case of a predisposition for Down's syndrome, hereditary cerebral hemorrhage with amyloidosis of the Dutch type, and cerebral beta-amyloid angiopathy, the polypeptides, compositions, and methods of the invention may also be useful for preventing their potential consequences such as single and recurrent lobar hemorrhages.

The subject to be treated will be a mammal, and more in particular a human being. As will be clear to the skilled person, the subject to be treated will in particular be a person suffering from, or at risk from, the diseases, disorders or conditions mentioned herein.

It will also be clear to the skilled person that the above methods of treatment of a disease include the preparation of a medicament for the treatment of said disease. Furthermore, it is clear that the polypeptides of the invention can be used as an active ingredient in a medicament or pharmaceutical composition intended for the treatment of the above diseases. Thus, the invention also relates to the use of a polypeptide of the invention in the preparation of a pharmaceutical composition for the prevention, treatment and/or alleviation of any of the diseases, disorders or conditions mentioned hereinabove. The invention further relates to a polypeptide of the invention for therapeutic or prophylactic use and, specifically, for the prevention, treatment and/or alleviation of any of the diseases, disorders or conditions mentioned hereinabove. The invention further relates to a pharmaceutical composition for the prevention, treatment and/or alleviation of the diseases, disorders or conditions mentioned hereinabove, wherein such composition comprises at least one polypeptide of the invention.

Without wishing to be bound by a specific theory, the above therapeutic or prophylactic effect may be effected by the following mechanism: The polypeptides of the invention bind to A-beta, thereby inhibiting its interaction with one or more other A-beta molecules or the interaction of A-beta with a receptor or the interaction of A-beta with a soluble biomolecule or the interaction of A-beta with an insoluble biomolecule. The target A-beta may be a part of a plaque or suspension or solution, or one or more of these, wherein the other A-beta molecules may also be a part of a plaque, in suspension or solution or one or more of these. Clearance of different A-beta forms, such as the monomeric form, oligo- and multimeric forms, aggregated soluble and insoluble forms, fibrillar forms, proto-fibrillar forms and amyloid plaques from the brain, blood vessels or other parts in the body may be due to the binding of the polypeptide of the invention to A-beta. Reduction of A-beta levels in a body fluid, and preferably the reduction of the level of soluble A-beta in blood by inhibition of the interaction between an A-beta molecule and another molecule, such as e.g. another A-beta molecule, will alleviate the symptoms of degenerative neural diseases, slow down or stop the disease progression and/or restore brain damage, memory and cognition.

According to a further, more general aspect, the invention relates to a method for immunotherapy, and in particular for passive immunotherapy, which method comprises administering, to a subject suffering from or at risk of the diseases as mentioned herein, a pharmaceutically active amount of a polypeptide of the invention and/or of a pharmaceutical composition comprising the same.

According to still another aspect, the invention relates to a method (i) for the prevention, treatment and/or alleviation of cognitive decline, and/or (ii) for restoring cognitive function and/or of improving cognitive function, said method comprising administering, to a subject in need thereof, a pharmaceutically active amount of a polypeptide of the invention and/or of a pharmaceutical composition comprising the same.

The polypeptides of the invention and/or the compositions comprising the same can be administered to a patient in need thereof in any suitable manner, depending on the specific pharmaceutical formulation or composition to be used. Thus, the polypeptides of the invention and/or the compositions comprising the same can for example be administered intravenously, subcutaneously, intramuscularly, intraperitoneally, transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, intravitreally (esp. for the treatment of dry AMD or glaucoma), or any other suitable manner in an effective amount or dose.

The polypeptides of the invention and/or the compositions comprising the same are administered according to a regimen of treatment that is suitable for preventing, treating and/or alleviating the disease, disorder or condition to be prevented, treated or alleviated. The clinician will generally be able to determine a suitable treatment regimen, depending on factors such as the disease, disorder or condition to be prevented, treated or alleviated, the severity of the disease, the severity of the symptoms thereof, the specific polypeptide of the invention to be used, the specific route of administration and pharmaceutical formulation or composition to be used, the age, gender, weight, diet, general condition of the patient, and similar factors well known to the clinician. Generally, the treatment regimen will comprise the administration of one or more polypeptides of the invention, or of one or more compositions comprising the same, in therapeutically and/or prophylactically effective amounts or doses.

Generally, for the prevention, treatment and/or alleviation of the diseases, disorders and conditions mentioned herein and depending on the specific disease, disorder or condition to be treated, the potency of the specific polypeptide of the invention to be used, the specific route of administration and the specific pharmaceutical formulation or composition used, the polypeptides of the invention will generally be administered in an amount between 0.005 and 20.0 mg per kilogram of body weight and dose, preferably between 0.05 and 10.0 mg/kg/dose, and more preferably between 0.5 and 10 mg/kg/dose, either continuously (e.g. by infusion) or as single doses (such as e.g. daily, weekly, or monthly doses; cf. below), but can significantly vary, especially, depending on the beforementioned parameters.

For prophylactic applications, compositions containing the polypeptides of the invention may also be administered in similar or slightly lower dosages. The dosage can also be adjusted by the individual physician in the event of any complication.

Depending on the specific polypeptide of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The efficacy of the polypeptides of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below. Thus, suitable assays are, but are not limited to, ELISA binding assays measuring the binding of the anti-A-beta polypeptides to coated monomeric or aggregated A-beta peptides or to captured biotinylated A-beta, SPR (Surface Plasmon Resonance) assays measuring the binding to coated monomeric or aggregated A-beta peptides or to captured biotinylated A-beta (Malmqvist M.: Surface plasmon resonance for detection and measurement of antibody-antigen affinity and kinetics; Curr. Opin. Immunol. 5(2):282 (1993)), competition TR-FRET (Time Resolved Fluorescence Resonance Energy Transfer) assays measuring the competition with either an A-beta(1-40) peptide/N-terminal region specific binder interaction or with an A-beta(1-40)/central region specific binder interaction, in vitro A-beta aggregation assays measuring the prevention or disaggregation of the aggregation, TAPIR (Tissue Amyloid Plaque Immunoreactivity) assays measuring the binding of molecules to amyloid plaques using immunohistochemical analysis on brains from Alzheimer's disease patients or APP transgenic animals, as well as in vivo mechanistic models.

Preferably, the polypeptides of the invention are having better characteristics than conventional antibodies known in the art (such as m266 and 3D6 anti-A-beta IgG antibodies) or the Nanobodies® described in WO2006/40153 in at least one of these assays or models, and preferably in one or more of the in vivo models.

For pharmaceutical use, the polypeptides of the invention may be formulated as a pharmaceutical preparation comprising (i) at least one polypeptide of the invention and (ii) at least one pharmaceutically acceptable carrier, diluent, excipient, adjuvant, and/or stabilizer, and (iii) optionally one or more further pharmaceutically active polypeptides and/or compounds. By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, 18$^{th}$ Ed., Mack Publishing Company, USA (1990). For example, the polypeptides of the invention may be formulated and administered in any manner known per se for conventional antibodies and antibody fragments and other pharmaceutically active proteins. Thus, according to a further embodiment, the invention relates to a pharmaceutical composition or preparation that contains at least one polypeptide of the invention and at least one pharmaceutically acceptable carrier, diluent, excipient, adjuvant and/or stabilizer, and optionally one or more further pharmaceutically active substances.

By means of non-limiting examples, such a formulation may be in a form suitable for oral administration, for parenteral administration (such as by intravenous, intramuscular, subcutaneous, intrathecal, intracavernosal or intraperitoneal injection or intravenous infusion), for topical administration, for sublingual administration, for administration by inhalation, by a skin patch, by an implant, by a suppository, for transdermal, nasal, intravitreal, rectal or vaginal administration, and the like. Such suitable administration forms—which may be solid, semi-solid or liquid, depending on the manner of administration—as well as methods and carriers for use in the preparation thereof, will be clear to the skilled person.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the active compound or its salts may also contain a preservative to prevent the growth of microorganisms, such as antibacterial and antifungal agents, for example, parabens, chlorobutanol, phenol, sorbic acid, thimerosal (thiomersal), and the like. In many cases, it will be preferable to include isotonic agents, for example, sugars, buffers or sodium chloride. The proper fluidity can be maintained, for example, by the formation of liposomes, by the maintenance of the required particle size in the case of dispersions or by the use of surfactants. Other agents delaying absorption, for example, aluminum monostearate and gelatin, may also be added.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the polypeptides of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml (i.v. administration) or 100 mg/ml (s.c. administration) and an aqueous buffer such as:

phosphate buffered saline, pH 7.4,
other phosphate buffers, pH 6.2 to 8.2,
histidine buffers, pH 5.5 to 7.0,
succinate buffers, pH 3.2 to 6.6, and
citrate buffers, pH 2.1 to 6.2, and, optionally, salts (e.g. NaCl) and/or sugars or polyalcohols (such as trehalose, mannitol, or glycerol) for providing isotonicity of the solution.

Preferred buffered protein solutions are solutions including about 0.05 mg/ml of the polypeptide of the invention dissolved in 25 mM phosphate buffer, pH 6.5, adjusted to isotonicity by adding 220 mM trehalose. In addition, other agents such as a detergent, e.g. 0.02% Tween-20 or Tween-80, may be included in such solutions. Formulations for subcutaneous application may include significantly higher concentrations of the polypeptide of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure.

The polypeptides of the invention may also be administered using suitable depot, slow-release or sustained-release formulations, e.g. suitable for injection, using controlled-release devices for implantation under the skin, and/or using a dosing pump or other devices known per se for the administration of pharmaceutically active substances or principles.

In addition, the polypeptides of the invention may be formulated in the form of a gel, cream, spray, drop, patch or film which, if placed on the skin, passes through the skin.

Also, compared to conventional antibodies or antibody fragments, one major advantage of the use of the polypeptides of the invention is that they can also be easily administered via routes other than parenteral administration and can be easily formulated for such administration. For example, as described in the international application WO2004/041867, such polypeptides may be formulated for oral, intranasal, intrapulmonary and transdermal administration.

According to another embodiment of the invention there is provided a pharmaceutical combination comprising at least one anti-A-beta polypeptide of the invention as disclosed herein and at least one other therapeutic agent selected from the group consisting of: cholinesterase inhibitors such as donepezil, rivastigmine, galantamine, and tacrine; NMDA antagonists such as memantine; A-beta lowering agents such as agents capable of inhibiting one or more enzymes involved in formation of A-beta, such as beta-secretase inhibitors, gamma-secretase inhibitors and gamma-secretase modulators; agents that prevent or reduce A-beta plaque building; A-beta aggregation inhibitors; RAGE antagonists; and other agents for preventing, treating or alleviating neurodegenerative diseases and/or decline in cognitive function. Specific examples of such other therapeutic agents are: ELND-005, Caprospinol, NRM-8499, PBT-2, Posiphen, EHT-0202, CTS-21166, Semagacest, BMS-708163, BMS-299897, BMS-433796, ELND-006, ELN-475516, ELN-318463, ELN-475513, Begacestat, E-2012, CHF-5074, Dimebolin (Latrepiridin), and PF-4494700. Such pharmaceutical combination may optionally additionally comprise a diluent, excipient, adjuvant and/or stabilizer.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

Yet a further embodiment of the invention is a method for treating the diseases and disorders as set out above, comprising administering to an individual, simultaneously, separately or sequentially, an effective amount of at least one anti-A-beta polypeptide of the invention and at least one agent selected from the group consisting of: cholinesterase inhibitors such as donepezil, rivastigmine, galantamine, and tacrine; NMDA antagonists such as memantine; A-beta lowering agents such as agents capable of inhibiting one or more enzymes involved in formation of A-beta, such as beta-secretase inhibitors, gamma-secretase inhibitors and gamma-secretase modulators; agents that prevent or reduce A-beta plaque building; A-beta aggregation inhibitors; RAGE antagonists; and other agents for preventing, treating or alleviating neurodegenerative diseases and/or decline in cognitive function, including the specific examples as set out above.

According to a further aspect of the invention, the A-beta binding polypeptide of the invention is prepared to be administered in combination with other drugs used for the treatment of the diseases and disorders set out above, such other drugs being selected from the group consisting of: cholinesterase inhibitors such as donepezil, rivastigmine, galantamine, and tacrine; NMDA antagonists such as memantine; A-beta lowering agents such as agents capable of inhibiting one or more enzymes involved in formation of A-beta, such as beta-secretase inhibitors, gamma-secretase inhibitors and gamma-secretase modulators; agents that prevent or reduce A-beta plaque building; A-beta aggregation inhibitors; RAGE antagonists; and other agents for preventing, treating or alleviating neurodegenerative diseases and/or decline in cognitive function, including the specific examples as set out above.

According to still another aspect of the invention, drugs used for the treatment of the diseases and disorders set out above, such drugs being selected from the group consisting of: cholinesterase inhibitors such as donepezil, rivastigmine, galantamine, and tacrine; NMDA antagonists such as memantine; A-beta lowering agents such as agents capable of inhibiting one or more enzymes involved in formation of A-beta, such as beta-secretase inhibitors, gamma-secretase inhibitors and gamma-secretase modulators; agents that prevent or reduce A-beta plaque building; A-beta aggregation inhibitors; RAGE antagonists; and other agents for preventing, treating or alleviating neurodegenerative diseases and/or decline in cognitive function (including the specific examples as set out above) are prepared to be administered in combination with the A-beta binding polypeptide of the invention.

According to a further aspect of the invention, the A-beta binding polypeptide of the invention is used in combination with a device useful for the administration of the polypeptide, such as a syringe, injector pen, or other device.

According to still another embodiment of the invention, there is provided a method of diagnosing a disease, disorder or condition mediated by A-beta dysfunction and/or amyloid plaque formation comprising the steps of:
  a) obtaining a sample from a subject, and
  b) contacting, in vitro, the sample with a polypeptide of the invention as defined above, and
  c) detecting the binding of said polypeptide to said sample, and
  d) comparing the binding detected in step (c) with a standard, wherein a difference in binding relative to said sample is diagnostic of a disease, disorder or condition characterised by A-beta dysfunction and/or amyloid plaque formation.

According to another embodiment of the invention, there is provided a method of diagnosing a disease, disorder or condition mediated by A-beta dysfunction and/or amyloid plaque formation comprising the steps of:
a) obtaining a sample from a subject, and
b) contacting the sample with a polypeptide of the invention as defined above;
c) determining the amount of A-beta in the sample; and
d) comparing the amount determined in step (c) with a standard, wherein a difference in amount relative to said sample is diagnostic of a disease, disorder or condition characterised by A-beta dysfunction and/or amyloid plaque formation.

The sample may e.g. be a body fluid of the subject, such as blood or cerebrospinal fluid (CSF). The step of detecting binding of a polypeptide of the invention to A-beta or the step of determining the amount of A-beta in the sample will generally involve measuring the formation of a complex between the polypeptide and A-beta. According to different embodiments of this method, complex formation will occur in solution or after immobilization of one component on a substrate and will be followed by detection of such complexes. For this purpose, it may be useful to further modify the polypeptide of the invention, such as by introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin.

The above diagnostic methods can also be used for monitoring the effectiveness of a therapeutic treatment of a subject.

According to another embodiment of the invention, there is provided a kit for diagnosing a disease, disorder or condition mediated by A-beta dysfunction, and especially amyloid plaque formation and/or AD, for use in a method as defined above, such kit comprising at least one polypeptide of the invention and, optionally, one or more media, detection means and/or in vitro or in vivo imaging agents, and, further optionally, instructions of use. Suitable in vivo imaging agents include 99mTc, 111Indium, 123Iodine, and, for magnetic resonance imaging, paramagnetic compounds. The combination of SPECT, PET or MRI with labeled anti-A-beta polypeptides of the invention will allow 'A-beta brain scans' and individual risk assessment for each patient.

According to still another embodiment of the invention, certain A-beta binding polypeptides of the invention can be used as a research tool for the specific detection of human as well as mouse A-beta, or A-beta from other animal species, and for tests and assays relying on such detection. This may be particularly useful for tests and assays making use of animal models.

The invention further provides a kit comprising at least one A-beta binding polypeptide of the invention and, additionally, one or more other components selected from the group consisting of other drugs used for the treatment of the diseases and disorders as described above, and devices as described above.

The invention further provides methods of manufacturing an A-beta binding polypeptide of the invention, such methods generally comprising the steps of:
- culturing host cells comprising a nucleic acid capable of encoding a polypeptide of the invention (hereinafter: "nucleic acid of the invention") under conditions that allow expression of the polypeptide of the invention; and,
- recovering or isolating the polypeptide expressed by the host cells from the culture; and
- optionally further purifying and/or modifying and/or formulating the polypeptide of the invention.

A nucleic acid of the invention can be genomic DNA, cDNA or synthetic DNA (such as DNA with a codon usage that has been specifically adapted for expression in the intended host cell or host organism). According to one embodiment of the invention, the nucleic acid of the invention is in essentially isolated form, as defined hereabove.

The nucleic acid of the invention may also be in the form of, be present in and/or be part of a vector, such as for example a plasmid, cosmid or YAC, which again may be in essentially isolated form. The vector may especially be an expression vector, i.e. a vector that can provide for expression of the polypeptide in vitro and/or in vivo (e.g. in a suitable host cell, host organism and/or expression system). Such expression vector generally comprises at least one nucleic acid of the invention that is operably linked to one or more suitable regulatory element(s), such as promoter(s), enhancer(s), terminator(s), and the like. Specific examples of such regulatory elements and other elements, such as integration factor(s), selection marker(s), signal or leader sequence(s), reporter gene(s), and the like, useful or necessary for expressing polypeptides of the invention, are disclosed e.g. on pp. 131 to 133 of WO2006/040153.

The nucleic acids of the invention can be prepared or obtained in a manner known per se (e.g. by automated DNA synthesis and/or recombinant DNA technology), based on the information on the amino acid sequences for the polypeptides of the invention given herein, and/or can be isolated from a suitable natural source.

According to another embodiment, the invention relates to a host or host cell that expresses or is capable of expressing a polypeptide of the invention; and/or that contains a nucleic acid encoding a polypeptide of the invention. According to a particularly preferred embodiment, said host cells are bacterial cells, yeast cells, fungal cells or mammalian cells.

Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (for example *Saccharomyces cerevisiae*), *Schizosaccharomyces* (for example *Schizosaccharomyces pombe*), *Pichia* (for example *Pichia pastoris* and *Pichia methanolica*), and *Hansenula*.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

For production on industrial scale, preferred heterologous hosts for the (industrial) production of immunoglobulin single variable domain polypeptides and protein therapeutics containing them include strains of *E. coli, Pichia pastoris*, and *S. cerevisiae* that are suitable for large scale expression, production and fermentation, and in particular for large scale (bio-)pharmaceutical expression, production and fermentation.

The choice of the specific expression system would depend in part on the requirement for certain post-translational modifications, more specifically glycosylation. The production of a polypeptide of the invention for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression.

Polypeptides of the invention produced in a cell as set out above can be produced either intracellullarly (e.g. in the cytosol, in the periplasma or in inclusion bodies) and then isolated from the host cells and optionally further purified; or they can be produced extracellularly (secreted into the medium in which the host cells are cultured) and then isolated from the culture medium and optionally further purified.

Further methods and reagents used for the recombinant production of polypeptides, such as suitable expression vectors, transformation or transfection methods, selection markers, methods of induction of protein expression, culture conditions, and the like, are known in the art. Similarly, protein isolation and purification techniques useful in a method of manufacture of a polypeptide of the invention are well known to the skilled person.

Production of the polypeptides of the invention through fermentation in convenient recombinant host organisms such as E. coli and yeast is cost-effective, as compared to conventional antibodies which also require expensive mammalian cell culture facilities. Furthermore, achievable levels of expression are high and yields of the polypeptides of the invention are in the range of 1 to 10 g/l (E. coli) and up to 10 g/l (yeast) and more.

According to still another aspect of the invention, there are provided the immunoglobulin single variable domains as listed in Table VII below, which are useful for building up or constructing A-beta binding polypeptides of the invention. Thus, if any of the immunoglobulin single variable domains as listed in Table VII (optionally after having been humanized) will be combined (preferably in the form of one continuous polypeptide chain) with one or more other A-beta binding immunoglobulin single variable domain(s), wherein such other immunoglobulin single variable domain(s) bind(s) to a different epitope of A-beta, this will result in biparatopic A-beta binding molecules according to the invention, having useful binding characteristics, as set out in detail e.g. in Examples 9 to 11 below.

TABLE VII

A-beta binding immunoglobulin single variable domains

| Clone | IC50 in TR-FRET (M) | melting temperature in ° C. | amino acid sequence | SEQ ID NO: |
|---|---|---|---|---|
| ABIIPMP42D4 | 4.40E-08 | n.d. | EVQLVESGGGLVLAGGSLRLSCVHSGPTFSTDTM GWFRQAPGKEREFVAAVTWNSGRTNYADSVKGR FTVSRDNTRNAAYLQMSGLKDEDTAVYYCTAHRL VVGGTSVGDWRYWGQGTQVTVSS | 47 |
| ABIIPMP111B4 | 5.1E-09 | n.d. | EVQLVESGGGLVLAGGSLRLSCVHSGPTFWTDTM GWFRQAPGKEREFVAAVTWSSGRANYADSVKGR FTVSRDNTRNAAYLQMSGLKDEDTAVYYCTAHRG VVGGWVVVDWRYWGQGTQVTVSS | 48 |
| ABII111E5cl1 | 8.80E-09 | n.d. | EVQLVESGGGLVLAGGSLRLSCVHSGPTFLTDTM GWFRQAPGKEREFVAAVTWNSGRINYADSVKGRF TVSRDNTRNAAYLQMSGLKDEDTAVYYCTAHRFV VGGREVQDWRYWGQGTQVTVSS | 49 |
| ABIIPMP111C6 | 6.00E-09 | n.d. | EVQLVESGGGLVLAGGSLRLSCVHSGPTFWTDTM GWFRQAPGKEREFVAAVTWNSGRLNYADSVKGR FTVSRDNTRNAAYLQMSGLKDEDTAVYYCTAHRQ VVGGVQVLDWRYWGQGTQVTVSS | 50 |
| ABIIPMP111F2 | 3.40E-09 | n.d. | EVQLVESGGGLVLAGGSLRLSCVHSGPTFSTDTM GWFRQAPGKEREFVAAVTWNSGRTNYADSVKGR FTVSRDNTRNAAYLQMSGLKDEDTAVYYCTANRH SVGRLSVGDWRYWGQGSQVTVSS | 51 |
| ABIIPMP111E4 | 6.10E-09 | n.d. | EVQLVESGGGLVLAGGSLRLSCVHSGPTFSTDTM GWFRQAPGKEREFVAAVTWNSGRTNYADSVKGR FTVSRDNTRNAAYLQMSGLKDEDTAVYYCTAARLT VGSLSVGDWRYWGQGTQVTVSS | 52 |
| ABIIPMP111C4 | 8.60E-09 | n.d. | EVQLVESGGGLVLAGGSLRLSCVHSGPTFLTDTM GWFRQAPGKEREFVAAVTWNSGRANYADSVKGR FTVSRDNTRNAAYLQMSGLKDEDTAVYYCTAHRS VVGGVGVWDWRYWSQGTQVTVSS | 53 |
| ABIIPMP111B5 | 4.40E-09 | n.d. | EVQLVESGGGLVLAGGSLRLSCVHSGPTFRTDTM GWFRQAPGKEREFVAAVTWNSGRNNYADSVKGR FTVSRDNTRNAAYLQMSGLKDEDTAVYYCTAHRL VVGGGVRDWRYWGQGTQVTVSS | 54 |
| ABIIPMP111B9 | 1.90E-08 | n.d. | EVQLVESGGGLVLAGGSLRLSCVHSGPTFGTDTM GWFRQAPGKEREFVAAVTWNSGRANYADSVKGR FTVSRDNTRNAAYLQMSGLKDEDTAVYYCTAHRF VVGGGCVKDWRYWGQGTQVTVSS | 55 |
| ABII111B5_R30K | 5.30E-09 | n.d. | EVQLVESGGGLVLAGGSLRLSCVHSGPTFKTDTM GWFRQAPGKEREFVAAVTWNSGRINYADSVKGRF TVSRDNTRNAAYLQMSGLKDEDTAVYYCTAHRFV VGGNMVEDWRYWGQGTQVTVSS | 56 |

TABLE VII-continued

A-beta binding immunoglobulin single variable domains

| Clone | IC50 in TR-FRET (M) | melting temperature in ° C. | amino acid sequence | SEQ ID NO: |
|---|---|---|---|---|
| ABII111B5_R30W | 5.00E-09 | n.d. | EVQLVESGGGLVLAGGSLRLSCVHSGPTFWTDTM GWFRQAPGKEREFVAAVTWNSGRINYADSVKGRF TVSRDNTRNAAYLQMSGLKDEDTAVYYCTAHRFV VGGNMVEDWRYWGQGTQVTVSS | 57 |
| ABII111B5_N106T | 9.20E-09 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRFV VGGTMVEDWRYWGQGTQVTVSS | 58 |
| ABII111B5_N106V | 1.00E-08 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRFV VGGVMVEDWRYWGQGTQVTVSS | 59 |
| ABII111B5_F101W | 7.30E-09 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRWV VGGNMVEDWRYWGQGTQVTVSS | 60 |
| ABII111B5_M107E | 4.30E-09 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRFV VGGNEVEDWRYWGQGTQVTVSS | 61 |
| ABII111B5_M107R = ABII002 | 2.90E-09 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRFV VGGNRVEDWRYWGQGTQVTVSS | 62 |
| ABII111B5_E109W | 4.70E-09 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRFV VGGNMVWDWRYWGQGTQVTVSS | 63 |
| ABII111B5_E109Q | 3.70E-09 | n.d. | EVQLVESGGGLVLAGGSLRLSCVHSGPTFRTDTM GWFRQAPGKEREFVAAVTWNSGRINYADSVKGRF TVSRDNTRNAAYLQMSGLKDEDTAVYYCTAHRFV VGGNMVQDWRYWGQGTQVTVSS | 64 |
| ABI1003 | 2.10E-09 | 51.1 | EVQLLESGGGLVLPGGSLRLSCVHSGPTFRTDTM GWFRQAPGKGREFVAAVTWNSGRINYADSVKGR FTVSRDNTRNAAYLQMSGLKDEDTAVYYCTAHRF VVGGNRVEDWRYWGQGTLVTVSS | 65 |
| ABII004 | 2.10E-09 | 56 | EVQLLESGGGLVQPGGSLRLSCVHSGPTFRTDTM GWFRQAPGKGREFVAAVTWNSGRINYADSVKGR FTVSRDNTRNAAYLQMSGLKDEDTAVYYCTAHRF VVGGNRVEDWRYWGQGTLVTVSS | 66 |
| ABII005 | 3.30E-09 | 48.2 | EVQLLESGGGLVLPGGSLRLSCAHSGPTFRTDTM GWFRQAPGKGREFVAAVTWNSGRINYADSVKGR FTVSRDNTRNAAYLQMSGLKDEDTAVYYCTAHRF VVGGNRVEDWRYWGQGTLVTVSS | 67 |
| ABII006 | 8.00E-08 | 51.7 | EVQLLESGGGLVLPGGSLRLSCVASGPTFRTDTM GWFRQAPGKGREFVAAVTWNSGRINYADSVKGR FTVSRDNTRNAAYLQMSGLKDEDTAVYYCTAHRF VVGGNRVEDWRYWGQGTLVTVSS | 68 |
| ABII007 | 1.60E-09 | 53.2 | EVQLLESGGGLVLPGGSLRLSCVHSGPTFRTDTM GWFRQAPGKGREFVAAVTWNSGRINYADSVKGR FTISRDNTRNAAYLQMSGLKDEDTAVYYCTAHRFV VGGNRVEDWRYWGQGTLVTVSS | 69 |
| ABII008 | 1.90E-09 | 51.9 | EVQLLESGGGLVLPGGSLRLSCVHSGPTFRTDTM GWFRQAPGKGREFVAAVTWNSGRINYADSVKGR FTVSRDNSRNAAYLQMSGLKDEDTAVYYCTAHRF VVGGNRVEDWRYWGQGTLVTVSS | 70 |
| ABII009 | 1.70E-09 | 52.2 | EVQLLESGGGLVLPGGSLRLSCVHSGPTFRTDTM GWFRQAPGKGREFVAAVTWNSGRINYADSVKGR FTVSRDNTKNAAYLQMSGLKDEDTAVYYCTAHRF VVGGNRVEDWRYWGQGTLVTVSS | 71 |

TABLE VII-continued

A-beta binding immunoglobulin single variable domains

| Clone | IC50 in TR-FRET (M) | melting temperature in ° C. | amino acid sequence | SEQ ID NO: |
|---|---|---|---|---|
| ABII010 | 1.90E-09 | 54.8 | EVQLLESGGGLVLPGGSLRLSCVHSGPTFRTDTM GWFRQAPGKGREFVAAVTWNSGRINYADSVKGR FTVSRDNTRNTAYLQMSGLKDEDTAVYYCTAHRF VVGGNRVEDWRYWGQGTLVTVSS | 72 |
| ABII011 | 2.40E-08 | 54.6 | EVQLLESGGGLVLPGGSLRLSCVHSGPTFRTDTM GWFRQAPGKGREFVAAVTWNSGRINYADSVKGR FTVSRDNTRNALYLQMSGLKDEDTAVYYCTAHRF VVGGNRVEDWRYWGQGTLVTVSS | 73 |
| ABII012 | 1.50E-09 | 53.5 | EVQLLESGGGLVLPGGSLRLSCVHSGPTFRTDTM GWFRQAPGKGREFVAAVTWNSGRINYADSVKGR FTVSRDNTRNAAYLQMNGLKDEDTAVYYCTAHRF VVGGNRVEDWRYWGQGTLVTVSS | 74 |
| ABII013 | 1.60E-09 | 52.2 | EVQLLESGGGLVLPGGSLRLSCVHSGPTFRTDTM GWFRQAPGKGREFVAAVTWNSGRINYADSVKGR FTVSRDNTRNAAYLQMSSLKDEDTAVYYCTAHRF VVGGNRVEDWRYWGQGTLVTVSS | 75 |
| ABII014 | 1.30E-09 | 52.3 | EVQLLESGGGLVLPGGSLRLSCVHSGPTFRTDTM GWFRQAPGKGREFVAAVTWNSGRINYADSVKGR FTVSRDNTRNAAYLQMSGLRDEDTAVYYCTAHRF VVGGNRVEDWRYWGQGTLVTVSS | 76 |
| ABII015 | 1.80E-09 | 55.5 | EVQLLESGGGLVLPGGSLRLSCVHSGPTFRTDTM GWFRQAPGKGREFVAAVTWNSGRINYADSVKGR FTVSRDNTRNAAYLQMSGLKAEDTAVYYCTAHRF VVGGNRVEDWRYWGQGTLVTVSS | 77 |
| ABII016 | 2.40E-09 | 57.9 | EVQLLESGGGLVLPGGSLRLSCVHSGPTFRTDTM GWFRQAPGKGREFVAAVTWNSGRINYADSVKGR FTVSRDNTRNAAYLQMSGLKPEDTAVYYCTAHRF VVGGNRVEDWRYWGQGTLVTVSS | 78 |
| ABII017 | 2.40E-09 | 59.4 | EVQLLESGGGLVLPGGSLRLSCVHSGPTFRTDTM GWFRQAPGKGREFVAAVTWNSGRINYADSVKGR FTVSRDNTRNAAYLQMSGLKDEDTAVYYCAAHRF VVGGNRVEDWRYWGQGTLVTVSS | 79 |
| ABII018 | 3.20E-09 | 60.1 | EVQLLESGGGLVQPGGSLRLSCVHSGPTFRTDTM GWFRQAPGKGREFVAAVTWNSGRINYADSVKGR FTVSRDNTRNAAYLQMSGLKPEDTAVYYCTAHRF VVGGNRVEDWRYWGQGTLVTVSS | 80 |
| ABII019 | 1.40E-08 | 71.6 | EVQLLESGGGLVQPGGSLRLSCAHSGPTFRTDTM GWFRQAPGKGREFVAAVTWNSGRINYADSVKGR FTISRDNSKNTVYLQMNSLRPEDTAVYYCAAHRFV VGGNRVEDWRYWGQGTLVTVSS | 81 |
| ABII020 | 1.10E-07 | 69.8 | EVQLLESGGGLVQPGGSLRLSCAHSGPTFRTDTM GWFRQAPGKGREFVAAVTWNSGRINYADSVKGR FTISRDNSKNTLYLQMNSLRPEDTAVYYCAAHRFV VGGNRVEDWRYWGQGTLVTVSS | 82 |
| ABII021 | 2.40E-08 | 69.9 | EVQLLESGGGLVQPGGSLRLSCAHSGPTFRTDTM GWFRQAPGKGREFVAAVTWNSGRINYADSVKGR FTISRDNSKNAVYLQMNSLRPEDTAVYYCAAHRFV VGGNRVEDWRYWGQGTLVTVSS | 83 |
| ABII022 | 1.60E-08 | 68.6 | EVQLLESGGGLVQPGGSLRLSCAHSGPTFRTDTM GWFRQAPGKGREFVAAVTWNSGRINYADSVKGR FTISRDNSKNAVYLQMSSLRPEDTAVYYCAAHRFV VGGNRVEDWRYWGQGTLVTVSS | 84 |
| ABII023 | 5.80E-09 | 64.7 | EVQLLESGGGLVQPGGSLRLSCAHSGPTFRTDTM GWFRQAPGKGREFVAAVTWNSGRINYADSVKGR FTISRDNSKNAAYLQMNSLRPEDTAVYYCAAHRFV VGGNRVEDWRYWGQGTLVTVSS | 85 |

TABLE VII-continued

A-beta binding immunoglobulin single variable domains

| Clone | IC50 in TR-FRET (M) | melting temperature in ° C. | amino acid sequence | SEQ ID NO: |
|---|---|---|---|---|
| ABII024 | 6.00E-09 | 63.6 | EVQLLESGGGLVQPGGSLRLSCAHSGPTFRTDTM GWFRQAPGKGREFVAAVTWNSGRINYADSVKGR FTISRDNSKNAAYLQMSSLRPEDTAVYYCAAHRFV VGGNRVEDWRYWGQGTLVTVSS | 86 |
| ABII025 | 1.80E-08 | 70.3 | EVQLLESGGGLVQPGGSLRLSCAHSGPTFRTDTM GWFRQAPGKGREFVAAVTWNSGRINYADSVKGR FTISRDNSKNTVYLQMSSLRPEDTAVYYCAAHRFV VGGNRVEDWRYWGQGTLVTVSS | 87 |
| ABII026 | 5.10E-09 | 66.8 | EVQLLESGGGLVQPGGSLRLSCAHSGPTFRTDTM GWFRQAPGKGREFVAAVTWNSGRINYADSVKGR FTISRDNSKNTAYLQMNSLRPEDTAVYYCAAHRFV VGGNRVEDWRYWGQGTLVTVSS | 88 |
| ABII027 | 4.40E-09 | 65.3 | EVQLLESGGGLVQPGGSLRLSCAHSGPTFRTDTM GWFRQAPGKGREFVAAVTWNSGRINYADSVKGR FTISRDNSKNTAYLQMSSLRPEDTAVYYCAAHRFV VGGNRVEDWRYWGQGTLVTVSS | 89 |
| ABII028 | 1.10E-08 | 73.8 | EVQLLESGGGLVQPGGSLRLSCVHSGPTFRTDTM GWFRQAPGKGREFVAAVTWNSGRINYADSVKGR FTISRDNSKNTVYLQMNSLRPEDTAVYYCAAHRFV VGGNRVEDWRYWGQGTLVTVSS | 90 |
| ABII029 | 8.90E-08 | 74.3 | EVQLLESGGGLVQPGGSLRLSCVHSGPTFRTDTM GWFRQAPGKGREFVAAVTWNSGRINYADSVKGR FTISRDNSKNTLYLQMNSLRPEDTAVYYCAAHRFV VGGNRVEDWRYWGQGTLVTVSS | 91 |
| ABII030 | 1.20E-08 | 73.7 | EVQLLESGGGLVQPGGSLRLSCVHSGPTFRTDTM GWFRQAPGKGREFVAAVTWNSGRINYADSVKGR FTISRDNSKNAVYLQMNSLRPEDTAVYYCAAHRFV VGGNRVEDWRYWGQGTLVTVSS | 92 |
| ABII031 | 1.30E-08 | 72.1 | EVQLLESGGGLVQPGGSLRLSCVHSGPTFRTDTM GWFRQAPGKGREFVAAVTWNSGRINYADSVKGR FTISRDNSKNAVYLQMSSLRPEDTAVYYCAAHRFV VGGNRVEDWRYWGQGTLVTVSS | 93 |
| ABII032 | 4.90E-09 | 68.3 | EVQLLESGGGLVQPGGSLRLSCVHSGPTFRTDTM GWFRQAPGKGREFVAAVTWNSGRINYADSVKGR FTISRDNSKNAAYLQMNSLRPEDTAVYYCAAHRFV VGGNRVEDWRYWGQGTLVTVSS | 94 |
| ABII033 | 4.00E-09 | 66.2 | EVQLLESGGGLVQPGGSLRLSCVHSGPTFRTDTM GWFRQAPGKGREFVAAVTWNSGRINYADSVKGR FTISRDNSKNAAYLQMSSLRPEDTAVYYCAAHRFV VGGNRVEDWRYWGQGTLVTVSS | 95 |
| ABII034 | 1.00E-08 | 72.5 | EVQLLESGGGLVQPGGSLRLSCVHSGPTFRTDTM GWFRQAPGKGREFVAAVTWNSGRINYADSVKGR FTISRDNSKNTVYLQMSSLRPEDTAVYYCAAHRFV VGGNRVEDWRYWGQGTLVTVSS | 96 |
| ABII035 | 4.00E-09 | 68.7 | EVQLLESGGGLVQPGGSLRLSCVHSGPTFRTDTM GWFRQAPGKGREFVAAVTWNSGRINYADSVKGR FTISRDNSKNTAYLQMNSLRPEDTAVYYCAAHRFV VGGNRVEDWRYWGQGTLVTVSS | 97 |
| ABII036 | 3.50E-09 | 67.5 | EVQLLESGGGLVQPGGSLRLSCVHSGPTFRTDTM GWFRQAPGKGREFVAAVTWNSGRINYADSVKGR FTISRDNSKNTAYLQMSSLRPEDTAVYYCAAHRFV VGGNRVEDWRYWGQGTLVTVSS | 98 |
| ABII037 | 3.10E-09 | 66.3 | EVQLLESGGGLVQPGGSLRLSCVHSGPTFRTDTM GWFRQAPGKGREFVAAVTWNSGRINYADSVKGR FTISRDNSKNTAYLQMNSLRAEDTAVYYCAAHRFV VGGNRVEDWRYWGQGTLVTVSS | 99 |

TABLE VII-continued

A-beta binding immunoglobulin single variable domains

| Clone | IC50 in TR-FRET (M) | melting temperature in ° C. | amino acid sequence | SEQ ID NO: |
|---|---|---|---|---|
| ABII60A10 = ABII050 | 1.90E-08 | 68.5 | EVQLVESGGGLVQAGGSLRLSCAASGRTFNNYNMGWFRQAPGKEREFVAAVSRSGVSTYYADSVKGRFTISRDNAKNAVYLQMNSLKPEDTAIYYCGAAYRGTAINVRRSYDSWGQGTQVTVSS | 100 |
| ABII051 | 1.80E-08 | 66.2 | EVQLLESGGGLVQPGGSLRLSCAASGRTFNNYNMGWFRQAPGKGREFVAAVSRSGVSTYYADSVKGRFTISRDNAKNAVYLQMNSLRPEDTAIYYCGAAYRGTAINVRRSYDSWGQGTLVTVSS | 101 |
| ABII052 | 1.90E-08 | 66.1 | EVQLLESGGGLVQPGGSLRLSCAASGRTFNNYNMGWFRQAPGKGREFVAAVSRSGVSTYYADSVKGRFTISRDNSKNAVYLQMNSLRPEDTAIYYCGAAYRGTAINVRRSYDSWGQGTLVTVSS | 102 |
| ABII053 | 2.00E-08 | 67.3 | EVQLLESGGGLVQPGGSLRLSCAASGRTFNNYNMGWFRQAPGKGREFVAAVSRSGVSTYYADSVKGRFTISRDNAKNTVYLQMNSLRPEDTAIYYCGAAYRGTAINVRRSYDSWGQGTLVTVSS | 103 |
| ABII054 | 5.10E-08 | 62 | EVQLLESGGGLVQPGGSLRLSCAASGRTFNNYNMGWFRQAPGKGREFVAAVSRSGVSTYYADSVKGRFTISRDNAKNALYLQMNSLRPEDTAIYYCGAAYRGTAINVRRSYDSWGQGTLVTVSS | 104 |
| ABII055 | 2.20E-08 | 66.2 | EVQLLESGGGLVQPGGSLRLSCAASGRTFNNYNMGWFRQAPGKGREFVAAVSRSGVSTYYADSVKGRFTISRDNAKNAVYLQMNSLRPEDTAVYYCGAAYRGTAINVRRSYDSWGQGTLVTVSS | 105 |
| ABII056 | 2.90E-08 | 69.8 | EVQLLESGGGLVQPGGSLRLSCAASGRTFNNYNMGWFRQAPGKGREFVAAVSRSGVSTYYADSVKGRFTISRDNAKNAVYLQMNSLRPEDTAIYYCAAAYRGTAINVRRSYDSWGQGTLVTVSS | 106 |
| ABII057 | 4.60E-08 | 71.5 | EVQLLESGGGLVQPGGSLRLSCAASGRTFNNYNMGWFRQAPGKGREFVAAVSRSGVSTYYADSVKGRFTISRDNSKNTVYLQMNSLRPEDTAVYYCAAAYRGTAINVRRSYDSWGQGTLVTVSS | 107 |
| ABII058 | 7.30E-08 | 68.9 | EVQLLESGGGLVQPGGSLRLSCAASGRTFNNYNMGWFRQAPGKGREFVAAVSRSGVSTYYADSVKGRFTISRDNSKNTLYLQMNSLRPEDTAVYYCAAAYRGTAINVRRSYDSWGQGTLVTVSS | 108 |
| ABII059 | 3.30E-08 | 72.7 | EVQLLESGGGLVQPGGSLRLSCAASGRTFNNYNMGWFRQAPGKGREFVAAVSRSGVSTYYADSVKGRFTISRDNSKNTVYLQMNSLRPEDTAVYYCAAAYRGTAINVRRSYSSWGQGTLVTVSS | 109 |
| ABII060 | 5.00E-08 | 69.2 | EVQLLESGGGLVQPGGSLRLSCAASGRTFNNYNMGWFRQAPGKGREFVAAVSRSGVSTYYADSVKGRFTISRDNSKNTLYLQMNSLRPEDTAVYYCAAAYRGTAINVRRSYSSWGQGTLVTVSS | 110 |
| ABII061 | 2.40E-09 | 69.3 | EVQLLESGGGLVQPGGSLRLSCAASGRTFNNYNMGWFRQAPGKGREFVAAVSRSGVSTYYADSVKGRFTISRDNSKNTVYLQMNSLRPEDTAVYYCGAAYRGTAINVRRSYSSWGQGTLVTVSS | 111 |

EXAMPLES

Example 1

Immunization of Llamas with A-Beta for the Induction of Humoral Immune Responses Generation of Monomeric A-Beta Peptide (BAM):

Monomeric A-beta peptide (BAM) is prepared via trifluoroacetic acid (TFA; Sigma)/1,1,1,3,3,3-hexafluor-2-propanol (HFIP; Fluka) treatment. The lyophilized A-beta peptide is dissolved in its original vial in 100% TFA to a final concentration of 1 mg/ml. The solution is then evaporated in a speedvac at room temperature. After this and all subsequent evaporation steps the remaining pellet is placed on ice. The pellet is resuspended in HFIP and again evaporated in a speedvac at room temperature followed by another HFIP solubilization after which the solution is divided into aliquots of appropriate volumes. The aliquots are evaporated in a speedvac at room temperature and the pellets are stored at −80° C. Immediately before use, the TFA/HFIP treated A-beta peptide aliquot is dissolved in 100% DMSO via repeated up and down pipetting. The A-beta peptide solution is centrifuged at 14000 rpm for 10 minutes to remove possible aggregates and the supernatant is used in the different assays.

Immunization of Llamas:

Llamas are immunized with aggregated A-beta peptides (BAA) and oligomeric A-beta peptides (BAO) by injecting the immunogens intramuscularly in the neck area applying decreasing doses over time. BAA consist of a mixture of synthetic A-beta(1-40) and A-beta(1-42) peptides which are prepared essentially as described by Schenk et al., 1999, Nature 400: 173-177. BAO are prepared essentially as described by Kayed et al. (2003), Science 300:486-489. The first two antigen injections consist each time of 100 4 of antigen per llama, while for all following administrations, the dose is reduced to 50 μg per llama. Llamas 144 and 145 are vaccinated with freshly prepared BAA. In total, nine BAA antigen doses are injected as an emulsion using Freund's Complete Adjuvant (first injection) or Stimune (all following immunogen boosts) in intervals of maximally 16 days. Llamas 129, 130, 177 and 178 are vaccinated with BAO. In total, six to nine BAO antigen doses are injected, as an emulsion using Freund's Complete (first injection) and Freund's Incomplete Adjuvant or Stimune (all following antigen boosts) in intervals of maximally 18 days. Llamas are also immunized with A-beta peptide fragment 1-16 conjugated to bovine serum albuming (BSA; llamas 181 and 186) or A-beta peptide fragment 1-30 conjugated to BSA (llamas 185 and 187). Four antigen injections are administered in 14-day intervals, using Freund's Complete or Freund's Incomplete adjuvant with antigen doses decreasing from 100 μg (first two injections) to 50 μg (two following injections) per llama. Immediately before the start of each immunization scheme a pre-immune serum sample and at regular time points during the immunization experiment multiple immune serum samples are collected to evaluate the A-beta peptide specific humoral response of the distinct animals.

To monitor the A-beta peptide specific serum titers via ELISA, 2 μg/ml A-beta(1-40), biotinylated at the C-terminus (Anaspec), is immobilised for two hours at room temperature on a Neutravidin-coated (0.2-0.5 μg per well) 96-well Maxisorp plate (Nunc). Wells are blocked with a casein solution (1% in PBS). After addition of a dilution series of pre-immune and immune serum samples, specifically bound llama immunoglobulins are detected using a goat anti-llama horseradish peroxidase conjugate (Bethyl Lab. Inc.), allowing to detect the humoral response mediated by both the conventional and heavy-chain only antibodies. In certain cases, a consecutive ELISA is performed to evaluate specifically the heavy-chain antibody mediated response via detection with mouse mAbs specifically recognizing the heavy-chain only llama IgG2 and IgG3 antibodies (Daley et al., 2005, Clin. Diagn. Lab. Imm. 12:380-386), followed by a rabbit anti-mouse-HRP conjugate (DAKO). ELISAs are developed using TMB (Promega) as the chromogenic substrate and absorbance is measured at 450 nm. For all four immunogen formats (BAA, BAO, A-beta(1-16)-BSA and A-beta(1-30)-BSA) both conventional and heavy-chain antibody mediated immune responses specific to (biotinylated) monomeric A-beta(1-40) are detected. Serum samples that are positive against monomeric A-beta(1-40) are also positive when tested against BAA directly coated onto a Maxisorp plate, suggesting the presence of at least partially common epitopes in the monomeric A-beta and BAA preparations used.

Example 2

Isolation of A-Beta Binding VHH Domains (VHHs) from Immunized Llamas

Cloning of the Heavy-Chain Only Antibody Fragment Repertoires:

Following the final immunogen injection, immune tissues as the source of the B-cells producing the heavy-chain antibodies are collected from the immunized llamas. Typically, two 150-ml blood samples, are collected 4 and 8 days after the last antigen injection and one lymph node biopsy, collected 4 days after the last antigen injection are collected per animal. From the blood samples, peripheral blood mononuclear cells (PBMCs) are prepared using Ficoll-Hypaque according to the manufacturer's instructions (Amersham Biosciences). From the PBMCs and the lymph node biopsy, total RNA is extracted, which are used as starting material for RT-PCR to amplify the VHH encoding gene segments (formerly described in WO2005/044858). For each immunized llama, a library is constructed by pooling the total RNA isolated from all collected immune tissues of that animal. In short, the PCR-amplified VHH repertoire is cloned via specific restriction sites into a vector designed to facilitate phage display of the VHH library. The vector is derived from pUC119 and contained the LacZ promoter, a M13 phage gIII protein coding sequence, a resistance gene for ampicillin or carbenicillin, a multiple cloning site and a hybrid gIII-pelB leader sequence (pAX050). In frame with the VHH coding sequence, the vector encodes for a C-terminal c-myc tag and a $(His)_6$ tag. Phage are prepared according to standard protocols and are stored after filter sterilization at 4° C. for further use.

Selection of A-Beta Specific VHHs Via Phage Display:

VHH repertoires obtained from all llamas and cloned as phage library are used in different selection strategies applying a multiplicity of selection conditions. Variables include:
i) the A-beta peptide format (A-beta(1-40) C- or N-terminally biotinylated, A-beta(1-16) C-terminally biotinylated, A-beta (1-30) N-terminally biotinylated and glutathione-S-transferase (GST) fusions such as A-beta(1-42)-GST, A-beta(1-10)-GST or GST-A-beta(1-42)),
ii) the A-beta peptide aggregation status (monomeric A-beta, BAO or BAA),
iii) the antigen presentation method (solid phase: directly coated or via a biotin-tag onto Neutravidin-coated plates; solution phase: incubation in solution followed by capturing on Neutravidin-coated plates),
iv) the antigen concentration and
v) different elution methods (trypsin or TEA).

Selections are performed as follows: antigen preparations for solid and solution phase selection formats are presented as described above at multiple concentrations. After 2 h incubation with the phage libraries followed by extensive washing, bound phage are eluted with trypsin (1 mg/ml) or TEA for 15 minutes. In case trypsin is used for phage elution, the protease activity is immediately neutralized applying 0.8 mM protease inhibitor ABSF. As control, selections w/o antigen are performed in parallel. Phage outputs that show enrichment over background (non-antigen control) are used to infect E. coli. Infected E. coli cells are either used to prepare phage for the next selection round (phage rescue) or are plated on agar plates (LB+Amp+2% glucose) for analysis of individual VHH clones. In order to screen a selection output for specific binders, single colonies are picked from the agar plates and grown in 1-ml 96-deep-well plates. The placZ controlled VHH expression is induced by adding IPTG (0.1-1 mM final)

in absence of glucose. Periplasmic extracts (in a volume of ~80 μl) are prepared according to standard methods.

Screening of Periplasmic Extracts for Binding to A-Beta:

2 μg/ml A-beta(1-40), biotinylated at the C-terminus (Anaspec), is captured for two hours at room temperature on a Neutravidin-coated (0.2-0.5 μg per well) 96-well Maxisorp plate (Nunc). Wells are blocked with a casein solution (1% in PBS). After addition of typically a 10-fold dilution of the periplasmic extracts, VHH binding is detected using a mouse anti-myc and an anti-mouse-HRP conjugate (DAKO). Clones that give an ELISA signal of minimally two-fold above background are retained for sequence analysis. VHHs that are able to bind (biotinylated) monomeric A-beta(1-40) can be allocated to 16 different B-cell lineages. Clones derived from the same B-cell lineage share a highly similar CDR3 sequence and are thus likely to recognize the same epitope. Table VIII summarizes the selection parameters that leads to the identification of a representative VHH of each of the 16 B-cell lineages. In Table IX, the amino acid sequences of the VHHs listed in Table VIII are shown.

TABLE VIII

Selection parameters are used for the identification of A-beta specific VHH B-cell lineages

| VHH ID | Library | Selection format (immobilized or captured A-beta peptide concentration) | Phage elution | Rounds of selection |
|---|---|---|---|---|
| ABII1E11 | 130 | BAA (200 ng) | trypsin | 2 |
| ABII5D2 | 145 | BAA (200 ng) | trypsin | 1 |
| ABII14D4 | 130 | BAA (200-40 ng) | trypsin | 2 |
| ABII35C7 | Pool of 144, 145, 129, 130 | A-beta(1-42)GST and GST-A-beta(1-42) (10 μg/well) | TEA | 2 |
| ABII35D2 | Pool of 144, 145, 129, 130 | A-beta(1-42)-GST and GST-A-beta(1-42) (10 μg/well) | TEA | 2 |
| ABII35G2 | Pool of 144, 145, 129, 130 | A-beta(1-42)GST and GST-A-beta(1-42) (10 μg/well) | TEA | 2 |
| ABII42D4 | 178 | biotinylated A-beta(1-40) (100 nM) | trypsin | 2 |
| ABII42B10 | 178 | biotinylated A-beta(1-40) (10 nM) | trypsin | 2 |
| ABII42F5 | 178 | biotinylated A-beta(1-40) (100 nM) | trypsin | 2 |
| ABII42E10 | 178 | biotinylated A-beta(1-40) (10 nM) | trypsin | 2 |
| ABII42G10 | 178 | biotinylated A-beta(1-40) (10 nM) | trypsin | 2 |
| ABII60A10 | 185 | Round I: BAA (200 ng) Round II: biotinylated A-beta(1-40) (1 nM) | trypsin | 2 |
| ABII60D2 | 181 | Round I: BAA (200 ng) Round II: biotinylated A-beta(1-40) (10 nM) | trypsin | 2 |
| ABII60G11 | 185 | Round I: BAA (200 ng) Round II: biotinylated A-beta(1-40) (1 nM) | trypsin | 2 |
| ABII60H5 | 181 | Round I: BAA (200 ng) Round II: biotinylated A-beta(1-40) (1 nM) | trypsin | 2 |
| ABII61F6 | 187 | Round I: BAA (200 ng) Round II: biotinylated A-beta(1-40) (10 nM) | trypsin | 2 |

TABLE IX

Amino acid sequencs of resulting representative VHHs:

| VHH ID | Wild type monovalent A-beta binding VHHs | SEQ ID NO: |
|---|---|---|
| ABII1E11 | EVQLVESGGGLVQPGGSLRLSCAASGRTFSDYNMGWFHQAPGKEREIVA AISRSGRSTYYTVSVEGRFTISRDNAKNTVDLEMNSLKPEDTGIYYCAANS AGRAINLPLYKYWGQGTQVTVSS | 112 |
| ABII14D4 | EVQLVESGGGLVQAGGSLRLSCAASGRTFSTYNMAWFRHAPGKEREFVA AISRSGGSTYYVDSVKGRFTISRDNAKNTVYLQMNSLKPEDTAIYYCAAAP RGRSIVTTATYDYWGQGTQVTVSS | 113 |
| ABII5D2 | EVQLVESGGGLVQAGGSLRLSCAASGRTFSSYAMGWVRQAPGKERELVA TISQSGGLRSYADSVKGRFTISRDNAKNTVYLQMNSLTPGDTAVYYCAAQA RATAWSPQRVDYWGQGTQVTVSS | 114 |
| ABII35C7 | EVQLVESGGGLVQPGGSLRLSCAASGRTFSIYNMGWFRQAPGKEREFVA AISRSGSSTYYGDSVKGRFTISRDNAKKTVYLQMNSLKPEDTAVYHCAAAR FGTPINTRGSYDYWGQGTQVTVSS | 115 |
| ABII35D2 | EVQLVESGGGLVQAGGSLRLSCVASGLTFSSYNMGWFRQAPGKEREFVA AISRSGGSTYYTDSVKGRFTISRDSSKNTVYLQMNSLKPEDTADYYCAAAL FGSAINLLSEYRYWGQGTQVTVSS | 116 |
| ABII35G2 | EVQLVESGGGLVQAGGSLRLSCVASGRTFSNYGMGWFRQAPGKDREFV AAISRSGGTTYYEDDVKGRFTISRDNAKNSVYLQMNSLKPEDTAVYYCAAR PSYVAVNIAASYNNWGQGTQVTVSS | 117 |
| ABII42D4 | EVQLVESGGGLVLAGGSLRLSCVHSGPTFSTDTMGWFRQAPGKEREFVA AVTWNSGRTNYADSVKGRFTVSRDNTRNAAYLQMSGLKDEDTAVYYCTA HRLVVGGTSVGDWRYWGQGTQVTVSS | 118 |

TABLE IX-continued

Amino acid sequencs of resulting representative VHHs:

| VHH ID | Wild type monovalent A-beta binding VHHs | SEQ ID NO: |
|---|---|---|
| ABII42B10 | EVQLVESGGGLVQRGGSLRLSCAASGRTFSNLNMGWFRQAPGKEREFQ AAISRSGGTTYYADSVKGRFTISRDNAKSTVFLQMNSLKPEDTAVYYCAAA SPGGPINYGRAYDSWGQGTQVTVSS | 119 |
| ABII42F5 | EVQLVESGGGLVQAGDSLRLSCTASGRTFTDYNIGWFCQAPGKEREFVAA ISGSGGSTYYADSAKGRFTISRDNAKNTVYLQMNSLKPEDTAVYACAAAQ RRLAVNVDTSYNVWGQGTQVTVSS | 120 |
| ABII42E10 | EVQLVESGGGLVQPGGSLRLSCAASGLTFTLYTMGWFRQAPGKEREFVA AISASGGTTYYADSVKGRFALSRDNAKNTVFLQMNTLKPEDTAEYLCAAAF RGFAINTPTSYNYWGQGTQVTVSS | 121 |
| ABII42G10 | EVQLVESGGGLVQAGGSLRLSCLFSGRTFSTNGVGWFRQVPGKEREFVS AINWSGSKTNYAEPVKGRFTISRDNAKNTAYLQMNSLKPEDTAVYYCAAY RTSISRYEYAYWGQGTQVTVSS | 122 |
| ABII60A10 | EVQLVESGGGLVQAGGSLRLSCAASGRTFNNYNMGWFRQAPGKEREFV AAVSRSGVSTYYADSVKGRFTISRDNAKNAVYLQMNSLKPEDTAIYYCGAA YRGTAINVRRSYDSWGQGTQVTVSS | 123 |
| ABII60G11 | EVQLVESGGGSEQAGGSLRLSCATSGRAFSVYAWFRQAPGKERTFVAAV AWVGGSTFYSDSVKGRFTISRDNAKNTVFLHMNSLKPEDTAAYYCAARLY GGRWYNSPRVDDFEYWGQGTQVTVSS | 124 |
| ABII60D2 | EVQLVESGGGSVQAGGSLRLSCAYSGSIFSIKTMGWYRQAPGKQRELVG RITSGDSTNYADSVKGRFTISRDKAKTTVYLQMNNLKPEDTAVYYCAARRP WPRSDVWGQGTQVTVSS | 125 |
| ABII60H5 | EVQLVESGGGLVQVGGSLRLSCAASGNIGSINAMGWYRQAPGKEREWVA IITNSGSVNYGPDSVKGRFTISGDNAKNRVYLQMDSLKPEDTAVYYCAAES WGRSPLKYLGQGTQVTVSS | 126 |
| ABII61F6 | EVQLVESGGGLVQTGGSLRLSCAASGSTVNINAMGWYRQAPGKQRELVAI INKRGVTNYADSTEGRFTISRDNSKRTLYLQMNSLKPEDTAVYYCNAVVGR YGRTYGYWGQGTQVTVSS | 127 |

The total number of variants (minimally 1 amino acid difference) found for each B-cell lineage is 1 (ABII5D2), 195 (ABII42D4), 1 (ABII42G10), 1 (ABII60D2), 1 (ABII60H5), 23 (ABII1E11), 3 (ABII14D4), 3 (ABII35C7), 6 (ABII35G2), 1 (ABII35D2), 7 (ABII42B10), 2 (ABII42F5), 3 (ABII42E10), 2 (ABII60A10), 2 (ABII60G11) and 15 (ABII61F6).

To identify the B-cell lineage variant with the best binding properties, periplasmic extracts of all VHH variants were used to determine the off-rate (Biacore T100, GE Healthcare). Monomeric A-beta(1-40) (biotinylated at the C-terminus; Anaspec), monomeric-A-beta(1-16) (biotinylated at the C-terminus; Bachem) and monomeric A-beta(12-28) (biotinylated at the N-terminus; Bachem), is prepared as described in Example 1, are irreversibly captured via streptavidin on three different channels of the same SA sensor chip (GE Healthcare). Surfaces are first washed via 3×1-minute injections of surface wash buffer (1 M NaCl in 50 mM NaOH) followed by injecting biotinylated A-beta at 50 nM up to a target level of 100 RU. After capturing, surfaces are blocked by injecting an excess (200 µg/ml) of d-biotin for 180 s at 5 µl/min. A reference surface is washed and blocked with d-biotin. HBS-EP+buffer is used as the running buffer and experiments are performed at 25° C. For off-rate screening, periplasmic extracts of VHHs are injected at a 10-fold dilution for 2 min at 45 µl/min and are allowed to dissociate for 10 min. Purified reference binders (VHHs at 100 nM, 3D6 Fab at 10 nM) are injected as positive control samples and evaluated at least at the beginning and at the end of each experiment. Between different VHH samples, the surfaces are regenerated with regeneration buffer (50 mM NaOH) for 25 s at 45 µl/min followed by 10 s 6M GuHCl at 45 µl/min if regeneration is incomplete. Off-rates are calculated from the sensorgrams obtained from the channel with captured biotinylated A-beta (1-40). The variants of only two VHH B-cell lineages, ABII42D4 and ABII60G11, showed a monophasic binding pattern and allowed the calculation of off-rates via a 1:1 interaction model: 6.1E-3 s$^{-1}$ and 2.7E-2 s$^{-1}$, respectively. For all other VHH B-cell lineages, 2 different sections of the dissociation curve are fitted separately, rendering a $k_{d1}$ (calculated from the dissociation frame between 125 and 160 s) and a $k_{d2}$ (400 s-700 s). Data are double referenced by subtraction of the curves on the reference channel and of a blank running buffer injection. Sensorgrams are evaluated by fitting a 1:1 dissociation model using the Biacore T100 Evaluation software v1.1.1. Although binding of VHHs ABII60D2 and ABII60H5 to A-beta is observed in the screening ELISA, these VHHs show poor binding to the sensor chip.

For studying binding characteristics of monovalent non-VHH binders, Fab fragments of monoclonal antibodies m266 and 3D6 are used. Monoclonal antibody 3D6 is described in Johnson-Wood et al., 1997, Proc. Natl. Acad. Sci. 94:1550-1555 and in Bard et al., 2000, Nature Medicine 6:916-919 and specifically binds to amino acid residues 1 to 5 of A-beta (N-terminal epitope). Monoclonal antibody m266 is described in Seubert et al., 1992, Nature 359:325-327 and specifically binds to amino acid residues 16 to 24 of A-beta (central epitope of A-beta). Fab fragments, comprising the variable light chain ($V_L$), variable heavy chain ($V_H$), constant light chain ($C_L$) and constant domain 1 of the heavy chain (CH$_1$) of the respective antibody (sequences as given below) and, additionally, a C-terminal c-myc tag and a hexa-histidine ((His)$_6$ tag) are cloned, expressed and purified according to conventional techniques, using *E. coli* as the host organism and immobilized metal affinity chromatography (IMAC) and size exclusion chromatography (SEC) for purification. Purified Fab fragments of m266 and 3D6 show, in the above-described binding experiment, off-rates of 4.0E-5 s$^1$ and 4.7E-4 s$^{-1}$, respectively.

VL- and VH-sequences of Fab fragment of 3D6:

VL:
(SEQ ID NO: 128)
YVVMTQTPLTLSVTIGQPASISCKSSQSLLDSDGKTYLNWLLQRPGQSPK

RLIYLVSKLDSGVPDRFTGSGSGTDFTLKISRIEAEDLGLYYCWQGTHFP

RTFGGGTKLEIK

VH:
(SEQ ID NO: 129)
EVKLVESGGGLVKPGASLKLSCAASGFTFSNYGMSWVRQNSDKRLEWVAS

IRSGGGRTYYSDNVKGRFTISRENAKNTLYLQMSSLKSEDTALYYCVRYD

HYSGSSDYWGQGTTVTVSS

VL- and VH-sequences of Fab fragment of m266:

VL:
(SEQ ID NO: 130)
DVVMTQTPLSLPVSLGDQASISCRSSQSLIYSDGNAYLHWFLQKPGQSPK

LLIYKVSNRFSGVPDRFSGSGSGTDFTLKISRVETEDLGVYFCSQSTHVP

WTFGGGTKLEIK

VH:
(SEQ ID NO: 131)
EVKLVESGGGLVQPGGSLKLSCAVSGFTFSRYSMSWVRQTPEKRLELVAQ

INSVGNSTYYPDTVKGRFTISRDNAEYTLSLQMSGLRSDDTATYYCASGD

YWGQGTTLTVSS

Example 3

Characterization of Purified VHHs

The VHH variants with the slowest dissociation rates for each B-cell lineage are recloned into an expression vector derived from pUC119, which contains the LacZ promoter, a resistance gene for either ampicillin or kanamycin, a multiple cloning site and a hybrid gIII-pelB leader sequence. In frame with the VHH coding sequence, the vector encodes for a C-terminal c-myc tag and a (His)$_6$ tag. VHHs are produced in *E. coli* TG1 and are purified via immobilized metal affinity chromatography (IMAC) and size exclusion chromatography (SEC) resulting in 95% purity as assessed via SDS-PAGE.

3.1 VHH Binding to Immobilized A-Beta (ELISA):

To quantify the binding of the VHHs to monomeric A-beta peptide (BAM), VHHs are applied as dilution series in an ELISA using the same setup as described in Example 2. Except for VHHs ABII60D2 and ABII60H5, EC50 values can be calculated and are summarized in Table X. The most potent VHHs interacting with the N-terminal epitope of A-beta (amino acids 1 to 16) or the central epitope of A-beta (amino acids 12 to 28) are determined to be ABII42D4 (EC50 of 14.2 nM) and ABII60A10 (EC50 of 4.9 nM), respectively.

VHHs that give detectable signals against BAM are tested for binding to A-beta peptide aggregates (BAA) in ELISA, applying a similar set-up as described in Example 2. Antigen is prepared and immobilized as described in Bohrmann et al., 1999, J Biol Chem 274: 15990-15995. In short, 100 μl of 10 μg/ml of A-beta(1-40) diluted in TBS buffer (50 mM Tris, 150 mM NaCl pH 7.4 and 0.05% Na-azide) from a DMSO stock solution of 2 mg/ml synthetic A-beta(1-40) (Bachem) is allowed to aggregate for 60 h at 37° C. All VHHs that recognize BAM also recognize BAA and the respective EC50 values are summarized in Table X.

TABLE X

EC50 values for purified VHHs in BAM and BAA ELISA

| VHH B-cell lineage | Epitope | BAM ELISA EC50 in nM | BAA ELISA EC50 in nM | TR-FRET IC50 in nM |
|---|---|---|---|---|
| ABII1E11 | 12-28 | 27.3 | 19.2 | 844* |
| ABII5D2 | 1-16 | 54.1 | 11.7 | >1000 |
| ABII14D4 | 12-28 | 124 | 6.8 | 744 |
| ABII35C7 | 12-28 | 1.9 | 1.3 | 206* |
| ABII35G2 | 12-28 | 10.7 | 5.4 | 645* |
| ABII35D2 | 12-28 | 37.5 | 12.8 | 773* |
| ABII42D4 | 1-16 | 14.2 | 0.9 | 46.8 |
| ABII42B10 | 12-28 | 10.8 | 2.1 | 85.6 |
| ABII42F5 | 12-28 | 41.1 | 20.0 | 228* |
| ABII42E10 | 12-28 | 17.5 | 2.6 | 205* |
| ABII42G10 | 1-16 | 87.0 | 49.5 | >1000 |
| ABII60A10 | 12-28 | 4.9 | 0.8 | 11.1 |
| ABII60G11 | 12-28 | 187 | 6.0 | 34.4 |
| ABII60D2 | 1-16 | >1 μM | ND | ND |
| ABII60H5 | 1-16 | >1 μM | ND | ND |
| ABII61F6 | 12-28 | 469 | 14.5 | 967* |
| 2D2 | 12-28 | 15.8 | 4.7 | 404* |
| 2G6 | 1-16 | 98.6 | 7.2 | >1000 |
| Fab266 | 16-24* | 1.8 | 1.8 | 0.52 |
| Fab3D6 | 1-5* | 1.8 | 0.3 | 3.4 |

ND: not determined;
*IC50 calculated from extrapolated curves 3.2 VHH Binding to A-Beta in Solution (TR-FRET):

Interaction of anti-A-beta VHHs and A-beta peptide in solution are evaluated using a Time Resolved Fluorescence Resonance Energy Transfer (TR-FRET) competition assay. In two different setups, competition with either the A-beta(1-40) peptide—ABII42D4 interaction (N-terminal region specific) or with the A-beta(1-40)—ABII60A10 interaction (central region specific) are tested. For the assay monomeric A-beta(1-40) (biotinylated at the C-terminus; Anaspec) labeled with streptavidin-Europium chelate and VHHs ABII42D4 or ABII60A10 labeled with AlexaFluor647 are incubated for 1 h with different concentrations of a non-labeled competitor (VHH, IgG or Fab). The labeled compounds are used at concentrations of 0.2 nM (A-beta(1-40)), 50 nM (ABII42D4) and 10 nM (ABII60A10), respectively and the fluorescence signal emitted upon binding interaction is detected at 665 nm. 1050 values are determined in the ABII42D4 and ABII60A10 TR-FRET assays resulting in the following potency ranking for N-terminal region specific binders tested: monoclonal antibody 3D6 (2.5 nM)>Fab fragment 3D6 (3.4 nM)>ABII42D4 (46.8 nM)>ABII5D2=42G10 (>1000 nM). The most potent central-region specific VHH identified via this assay was ABII60A10, shows an IC50 of 11.1 nM while benchmark antibodies gave IC50 s of 0.50 nM (monoclonal antibody m266) and 0.52 nM (Fab fragment of m266).

For comparative reasons, anti-A-beta VHHs as disclosed previously (the "reference VHHs") are generated and purified as described above, using the sequence information as available from the international patent publications indicated below:

VHHs 2D2 and 2G6: WO2006/40153;
VHHs 3A, 1B, 11G, 4D, and 8B: WO2007/35092; and
VHH 31-1: WO2004/44204.

Amino acid sequences thereof are shown in Table XI.

TABLE XI

Amino acid sequences of reference VHHs

| VHH ID | A-beta binding reference VHHs | SEQ ID NO: |
|---|---|---|
| 2D2 | AVQLVDSGGGLVQAGGSLRLSCAVSGGTFSSIGMGWFRQAP GKEREFVGAISRSGDSTYYADSVKGRFTISRDGAKNTVYLQM NSLKDEDTAVYYCAGRPAGTAINIRRSYNYWGQGTQVTVSS | 132 |
| 2G6 | QVKLEESGGGLVQPGGSLRLSCAASGFTFSNYWMYWVRQAP GKGLEWVSTISPRAANTYYADSVKGRFTISRDNAKNTLYLQM NSLEPDDTALYYCAKSLRYRDRPQSSDFLFWRQGTQVTVSS | 133 |
| 3A | AVQLVESGGGLVRDGDSLRLSCAASGRTFSSYVMGWFRQAP GKEREFVAAIGWSGGSTAYADSVKGRFTISRDNARNTVYLQM NSLKPEDTAVYYCASAPTRWVPRDSRFYDRWGQGTRVTVSS | 134 |
| 1B | QVQLQESGGGLVQPGGSLRLSCAASEFTLDYYSIAWFRQAPG KEREGVSCISSYDGSTSYADSVKGRFTISRDNAKNTVYLQMN SLKPEDTAIYYCAAGIRDWATLREYEYDDWGQGTQVTVSS | 135 |
| 11G | QVQLQESGGGLVQPGGSLRLSCAASGSIFSINTMAWYRQAPG KERDLVAAIISSGSTNYADSVKGRFTISRDNTKNTVYLQMNS LKLEDTAVYYCNAAIRRSVIDAWGAYWGQGTQVTVSS | 136 |
| 4D | QVQLQESGGGLVQAGGSLRLSCAASGRTFSSYAMGWFRQAP GKEREFVATIRWNGDYADSVRDRFTISRDDAKNTVFLQMNSL KPEDTAIYYCAARLGPRTSQAALYRYWGQGTQVTVSS | 137 |
| 8B | AVQLVESGGGLVQAGGSLRLSCAASGRTFSSYVMGWFRQAP GKEREFVAAIGWSGGSTAYADSVKGRFTISRDNARNTVYLQM NSLKPEDTAVYYCASAPTRWVPRDSRFYDRWGQGTRVTVSS | 138 |
| 31-1 | AEVQLQASGGGSVQPGGSLRLSCAASGFIFGWSTMSWVRQA PGKGLEWVSTISGGGSATTYTDSVKGRFTISRDRAKNTLYLQ MNSLKPEDTAIYYCNADVSTGFRYQRKDYWGRGTQVTVSS | 139 |

Compared to the reference VHHs 2G6 (N-terminal region specific) and 2D2 (central-region specific), VHHs 42D4 and 60A10 show ≧21 fold and 36 fold improved IC50s, respectively (cf. Table X).

3.3 Determination of the Affinity of A-Beta Peptide

VHH interaction: Affinities for the A-beta peptide—VHH/Fab interaction are determined via surface plasmon resonance (Biacore) using C-terminally biotinylated A-beta(1-40) captured on a streptavidin sensor chip as described before (Example 2). Purified VHHs or Fab fragments are injected at 5 different concentrations (between 2.5 and 300 nM for ABII42D4 and ABII60A10) for 2 min and allowed to dissociate for 10 min. For ABII42D4 but not for ABII60A10 association and dissociation curves can be fitted using a 1:1 interaction model (Langmuir binding) and an accurate $K_D$ value can be determined. The affinities are found to be 16 nM for VHH ABII42D4, 5.1 nM for the Fab fragment of 3D6, and 0.3 nM for the Fab fragment of m266, respectively.

3.4 Epitope Mapping Via Surface Plasmon Resonance:

Binding specificity of the VHHs are determined via surface plasmon resonance (Biacore) using A-beta(1-16) (biotinylated at the C-terminus; Bachem) and A-beta(12-28) (biotinylated at the N-terminus; Bachem) peptides are captured on a streptavidin sensor chip as described before. Five of the VHHs listed in Table IX above are found to interact with the N-terminal region of the Abeta peptide (ABII5D2, ABII42D4, ABII42G10, ABII60D2 and ABII60H5), and 11 VHHs are found to interact with the central region (ABII1E11, ABII14D4, ABII35C7, ABII35G2, ABII35D2, ABII42B10, ABII42F5, ABII42E10, ABII60A10, ABII60G11 and ABII61F6; cf. Table X).

3.5 In Vitro A-Beta Aggregation Assay:

VHHs are tested in an in vitro A-beta aggregation assay to assess whether aggregation can be inhibited or reduced. In vitro A-beta aggregation is measured using Thioflavin T (ThT) fluorescence, which undergoes a typical red shift upon A-beta fibril formation (Levine, H. 1993. Protein Science (2): 404-410). For the assay, stock solutions of synthetic A-beta (1-40) (Bachem) in 100% DMSO and ThT in 25 mM glycine-NaOH pH8.5 is prepared and stored at −20° C. Before usage, the A-beta(1-40) stock solution is diluted to 56 µM in aggregation buffer (50 mM sodium phosphate, 100 mM NaCl pH5, 0.02% NaN3). Fab fragments and VHHs are tested as dilution series in D-PBS using concentrations between 56 and 7 µM. Equal volumes (20 µl) of the 56 µM A-beta(1-40) solution and the antibody/VHH samples or appropriate negative control are mixed (in triplicate) and mixtures are incubated in low adhesion microcentrifuge tubes for 48 hours at 37° C. in a dark environment. After transfer of 30 µl of the incubated samples into a black 96-well flat bottom polypropylene plate (Greiner Bio-One), 250 µl of 2.5 µM ThT (stock solution diluted into 25 mM glycine-NaOH) solution are added and the fluorescence signal is measured (Envision, PerkinElmer). The maximum fluorescence signal of A-beta(1-40) measured in the absence of competitor is set as 100% aggregation (or 0% inhibition). The maximum inhibition at the highest VHH concentration tested (28 µM) is calculated as an average of at least two independent experiments. While a consistent background inhibition of approximately 25% is detected for a non-related (non-A-beta specific) VHH, monovalent Fab fragments 3D6 and 266 show a reproducible dose-dependent inhibition with maximal inhibition of 79 and 85%, respectively. Out of the panel of VHHs tested, 14D4, 35C7, 35G2, 35D2, 42B10, 42F5, 42E10 and 60A10 show a consistent inhibition of 78, 82, 76, 73, 77, 79, 75 and 80% of peptide aggregation, respectively (higher than the 25% background inhibition induced by the non-specific control VHH).

Example 4

Affinity Maturation of VHHs

VHH ABII42D4 is subjected to two cycles of affinity maturation. In a first cycle, individual CDR residues are mutated to all other 19 amino acids. The following residues are targeted: CDR1: G26-G35; CDR2: V51-N58; and CDR3: H95-Y102 (numbering according to Kabat). Mutagenesis is performed in a PCR-based approach using degenerate oligonucleotides containing a NNS codon at the mutated position. PCR products are pooled for each CDR and inserted via unique restriction sites into the ABII42D4 gene template. Individual mutants are produced as recombinant protein using an expression vector derived from pUC119, which contain the LacZ promoter, a resistance gene for kanamycin, a multiple cloning site and an ompA leader sequence (pAX100). E. coli TG1 cells are transformed with the expression vector library and plated on agar plates (LB+Amp+2% glucose). Single colonies are picked from the agar plates and grown in 1-ml 96-deep-well plates. VHH expression is induced by adding IPTG (1 mM). Periplasmic extracts (in a volume of ~80 µl) are prepared according to standard methods and screened for binding to A-beta(1-40) in ELISA and in a Biacore off-rate assay as described before (Example 2). Mutations at six positions (S30, T57, L97, T100b, S100c, G100e) result in slightly (~2 fold) improved off-rates.

In a second cycle, a combinatorial library is created by simultaneously randomising the six susceptible positions identified in cycle one. For this, the full length ABII42D4 gene is synthesized by overlap PCR using oligonucleotides degenerated (NNS) at the randomisation positions and a rescue PCR is performed. The randomised ABII42D4 genes are inserted into a phage display vector (pAX50) yielding a functional library size of 6×10E7. Phages are prepared according to standard protocols. The phage library is subjected to three rounds of solution phase selection against (biotinylated) monomeric A-beta(1-40) using streptavidin-coated magnetic beads (Dynal) for the capturing step. The antigen concentration is decreased 10 fold at each round starting from an antigen concentration of 50 nM at round one. Bound phages are eluted with trypsin (1 mg/ml) for 30 minutes and phage outputs are infected into E. coli TG1 for preparation of periplasmic extracts of individual VHH clones. Screening for binding to A-beta(1-40) in ELISA and in a Biacore off-rate assay (Example 2) identifies clones with up to 10 fold improved off-rates. The best ABII42D4 variants are cloned into expression vector pAX100 in frame with a C-terminal c-myc tag and a (His)6 tag. VHHs are produced in E. coli as His6-tagged proteins and purified by immobilized metal affinity chromatography (IMAC) and size exclusion chromatography (SEC). The affinities of the purified VHHs are determined via surface Plasmon resonance (Biacore) and IC50 values are determined in the ABII42D4 TR-FRET competition assay (Example 3.2).

In an attempt to further improve the binding affinity, variant ABIIPMP111B5 is used as template and divergent mutations found in clones ABIIPMP111E4 and ABIIPMP111B4 are introduced one by one. The resulting variants are produced in E. coli and characterized as described before. ABII111B5_M107R, ABII111B5_M107E and ABII111B5_E109Q are identified as the best variants with both, IC50 and $K_D$, being more than 10 fold improved over original ABII42D4. Sequence information and biological data for the variants mentioned above are summarized in Table VII above (first line: 42D4; lines 2 to 9: useful clones resulting from first two cycles of affinity maturation; lines 10 to 18: useful clones resulting from additional targeted mutations).

Example 5

Humanization of VHHs

The amino acid sequences of the anti-A-beta VHH ABII111B5_M107R (=ABII002; SEQ ID NO: 62) and of the anti-A-beta VHH ABII60A10 (=ABII050; SEQ ID NO:100) are blasted against the human germline $V_H$ sequence database. The human germline VH3-23 sequence (DP47; SEQ ID NO: 140) in combination with JH5 showed the highest sequence identity to both VHH sequences.

Sequence DP-47/VH3-23:

(SEQ ID NO: 140)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAK

Sequence JH5:

NWFDSWGQGTLVTVSS        (SEQ ID NO: 153)

17 and 10 amino acid residues of ABII002 and ABII050, respectively, were substituted for humanization purposes creating a number of different variants of each VHH. All variants were assembled from oligonucleotides using a PCR overlap extension method, cloned into an expression vector (pAX100) and produced in E. coli. The sequence information and binding data for the obtained variants of ABII002, i.e. ABII003 to ABII037, and for the obtained variants of ABII0050, i.e. ABII051 to ABII061, are summarized in Table VII above (lines 19 to 53 and lines 55 to the last line 65, respectively). Table XII additionally lists the degree of humanization of ABII002 to ABII036 and ABII050 to ABII060.

TABLE XII

Humanized variants of ABII002 and ABII050

| Clone name | % humanization | $T_m$ (° C.) | Mean IC50 in TR-FRET (M) |
|---|---|---|---|
| ABII002 | 77.8 | 57.5 | 2.0E-09 |
| ABII003 | 81.8 | 51.1 | 2.1E-09 |
| ABII004 | 82.8 | 56.0 | 2.1E-09 |
| ABII005 | 82.8 | 48.2 | 3.3E-09 |
| ABII006 | 82.8 | 51.7 | 8.0E-08 |
| ABII007 | 82.8 | 53.2 | 1.6E-09 |
| ABII008 | 82.8 | 51.9 | 1.9E-09 |
| ABII009 | 82.8 | 52.2 | 1.7E-09 |
| ABII010 | 82.8 | 54.8 | 1.9E-09 |
| ABII011 | 82.8 | 54.6 | 2.4E-08 |
| ABII012 | 82.8 | 53.5 | 1.5E-09 |
| ABII013 | 82.8 | 52.2 | 1.6E-09 |
| ABII014 | 82.8 | 52.3 | 1.3E-09 |
| ABII015 | 82.8 | 55.5 | 1.8E-09 |
| ABII016 | 81.8 | 57.9 | 2.4E-09 |
| ABII017 | 82.8 | 59.4 | 2.4E-09 |
| ABII018 | 82.8 | 60.1 | 3.2E-09 |
| ABII019 | 91.9 | 71.6 | 1.4E-08 |
| ABII020 | 92.9 | 69.8 | 1.1E-07 |
| ABII021 | 90.9 | 69.9 | 2.4E-08 |
| ABII022 | 89.9 | 68.6 | 1.6E-08 |
| ABII023 | 90.9 | 64.7 | 5.8E-09 |
| ABII024 | 89.9 | 63.6 | 6.0E-09 |
| ABII025 | 90.9 | 70.3 | 1.8E-08 |
| ABII026 | 91.9 | 66.8 | 5.1E-09 |
| ABII027 | 90.9 | 65.3 | 4.4E-09 |
| ABII028 | 90.9 | 73.8 | 1.1E-08 |
| ABII029 | 91.9 | 74.3 | 8.9E-08 |
| ABII030 | 89.9 | 73.7 | 1.2E-08 |
| ABII031 | 88.9 | 72.1 | 1.3E-08 |
| ABII032 | 89.9 | 68.3 | 4.9E-09 |
| ABII033 | 88.9 | 66.2 | 4.0E-09 |
| ABII034 | 89.9 | 72.5 | 1.0E-08 |
| ABII035 | 90.9 | 68.7 | 4.0E-09 |
| ABII036 | 89.9 | 67.5 | 3.5E-09 |
| ABII050 | 83.8 | 68.5 | 1.9E-08 |
| ABII051 | 88.9 | 66.2 | 1.8E-08 |
| ABII052 | 89.9 | 66.1 | 1.9E-08 |
| ABII053 | 89.9 | 67.3 | 2.0E-08 |
| ABII054 | 89.9 | 62.0 | 5.1E-08 |
| ABII055 | 89.9 | 66.2 | 2.2E-08 |
| ABII056 | 89.9 | 69.8 | 2.9E-08 |
| ABII057 | 92.9 | 71.5 | 4.6E-08 |
| ABII058 | 93.9 | 68.9 | 7.3E-08 |
| ABII059 | 92.9 | 72.7 | 3.3E-08 |
| ABII060 | 93.9 | 69.2 | 5.0E-08 |

According to the biological data summarized in Tables VII and XII above, all of the VHH variants listed therein can—at least as intermediates—be used for the construction of the polypeptides of the invention. Specifically, for use in humans, humanized VHH variants ABII003 to ABII037 and ABII051 to ABII061 will be preferred. Particularly useful variants, showing a high degree of humanization but preserving their binding properties are ABII035 derived from the original clone 42D4, and ABII059 derived from original clone 60A10.

ABII035 binds to the N-terminal epitope of A-beta and comprises CDR sequences SEQ ID NOs:14 to 16. ABII059 binds to the central epitope and comprises CDR sequences SEQ ID NOs:17 to 19.

Example 6

Comparison of the Humanized VHHs to the Reference VHHs

Purified anti-A-beta reference VHHs (Example 3.2, Table XI) are tested for binding as described in Example 3 to a SA sensor chip coated with C-terminally biotinylated monomeric A-beta(1-40). While ABII035 and ABII059 showed RU levels >50 at injected concentrations of 11 and 3 nM, respectively, none of the VHHs 1B, 11G, 8B, 4D, 3A and VHH31-1 show binding (>10 RUs) to the sensor chip at a concentration of 1000 nM under the conditions tested. In the same experiment, reference VHHs 2G6 and 2D2 show RU levels >50 at injected concentrations of 1000 and 100 nM, respectively, thus being much less potent than ABII035 and ABII059. No indication of surface degradation was detected during the experiment. Subsequently, binding of this set of reference VHHs is also verified to bind monomeric A-beta in multiple ELISA setups (detection described in Example 3), using distinct presentations of peptide formats such as captured A-beta (1-40) (C- or N-terminally biotinylated), directly immobilized A-beta(1-40) and A-beta(1-42), GST-A-beta(1-42) or A-beta(1-42)-GST (capturing at concentrations of 1 µg/ml). For the reference VHHs 1B, 11G, 8B, 4D, 3A no binding to monomeric A-beta is detected. In the BAA ELISA only reference VHH 8B show binding to aggregated A-beta at VHH concentrations above 1000 nM. Compared to the 2D2 and 2G6 VHHs, the ABII035 and ABII059 VHHs show >50 fold higher EC50 values. The results are summarized in Table XIIa.

TABLE XIIa

Comparison of binding characteristics of 42D4 and 60A10 derived VHHs with binding characteristics of reference anti-A-beta VHHs

| VHH | Aggregation inhibition (% inhibition at 26 µM) | BAM ELISA EC50 in nM | BAA ELISA EC50 in nM | TR-FRET IC50 in nM |
|---|---|---|---|---|
| ABII42D4 (N-terminal epitope) | ND | 14.2 | 0.9 | 46.8 |
| ABII035 (N-terminal epitope) | 54 | | | |
| ABII60A10 (central epitope) | 80 | 4.9 | 0.8 | 11.1 |
| ABII059 (central epitope) | 80 | | | |
| 2D2 (central epitope) | 69 | 15.8 | 4.7 | 404* |
| 2G6 (N-terminal epitope) | 29 | 98.6 | 7.2 | >1000 |
| 1B | ND | No binding | No binding | No competition |
| 11G | ND | No binding | No binding | No competition |
| 8B | ND | No binding | >1000 nM* | No competition |
| 4D | ND | No binding | No binding | No competition |
| 3A | ND | No binding | No binding | No competition |
| V31-1 (C-term epitope) | ND | No binding | No binding | No binding |
| Fab266 (central epitope) | 82 | 1.8 | 1.8 | 0.52 |
| Fab3D6 (N-terminal epitope) | 82 | 1.8 | 0.3 | 3.4 |

ND: not determined;
*IC50 calculated from extrapolated curves

Example 7

Binding of Anti-Human A-Beta VHHs to Rodent A-beta (ELISA and Biacore)

Binding of VHHs as obtained above to rodent A-beta is assessed in ELISA. Mouse (Bachem) or human A-beta(1-40) (Anaspec) are coated at 2 µg/ml onto Maxisorp plates and binding of VHHs and, for comparative purposes, Fab fragments, is detected via a mouse anti-myc antibody and an anti-mouse-HRP conjugate (DAKO). EC50 values are determined for the Fab fragment of 3D6, VHH ABII002, and VHH ABII035. The results are listed in Table XIII below (average of minimally two independent experiments).

TABLE XIII

EC50 values for binding to human and mouse A-beta

| Clone | human A-beta(1-40) EC50 (nM) | rodent A-beta(1-40) EC50 (nM) |
|---|---|---|
| ABII002 | 1.8 | 3.3 |
| ABII035 | 2.5 | 5.7 |
| Fab3D6 | 4.2 | 110 |

While 3D6 Fab fragments bind mouse A-beta significantly less than human A-beta (26 fold difference), ABII002 and ABII035 bind equally well to both (1.8 and 2.2 fold difference, respectively), indicating that ABII002 and its humanized derivative ABII035 recognise an epitope that is distinct from the epitope recognized by 3D6.

Binding of the VHHs to mouse and human A-beta is further assessed on Biacore with the non-biotinylated peptide coated directly onto the chip. No difference in affinity to human and rodent A-beta peptide is detected for the VHHs before and after humanisation.

Example 8

Generation and Characterization of Biparatopic Anti-A-Beta VHH Constructs

VHHs ABII42D4 (recognizing the N-terminal region of the A-beta peptide) and VHH ABII60A10 (recognizing the central region) are fused via flexible glycine-serine linkers (e.g. 9GS: GGGGSGGGG; SEQ ID NO:141) to create bivalent VHH constructs. Four biparatopic constructs (comprising two VHH domains with different epitope specificity) differing in linker length and orientation are explored in more detail: ABII42D4-25GS-ABII60A10, ABII60A10-25GS-ABII42D4, ABII42D4-35GS-ABII60A10 and ABII60A10-35GS-ABII42D4 and compared to respective VHH dimers (comprising two identical VHH domains, such as the bivalent ABII42D4-9GS-ABII42D4 construct). The biparatopic and dimeric/bivalent VHHs are produced in *E. coli* TG1 cells and purified using affinity chromatography (IMAC or protein A) and size exclusion chromatography (Superdex75 or Sephacryl S100), resulting in 95% purity as assessed via SDS-PAGE.

8.1 TR-FRET Binding Assays:

Binding of the biparatopic VHH constructs to A-beta(1-40) is evaluated using the ABII42D4 and ABII60A10 TR-FRET assays (Example 3.2). While the bivalent ABII42D4-9GS-ABII42D4 construct show only a slightly improved IC50 (3.2 fold improved vs. monovalent ABII42D4), the biparatopic VHHs are surprisingly found to bind significantly stronger to the A-beta peptide than the monovalent building blocks and the 3D6 and m266 Fab fragments (Table XIV) as well as 3D6 and m266 IgG (3D6 and m266 full-length monoclonal antibodies). No difference in potency is found between constructs with different linker lengths and orientations.

TABLE XIV

IC50 values for biparatopic anti-A-beta VHH constructs and comparative examples in ABII42D4 and ABII60A10 TR-FRET assays

| Competitor | IC50 (nM) |
|---|---|
| 42D4 TR-FRET assay | |
| ABII42D4-25GS-ABII60A10 | 0.047 |
| ABII42D4-35GS-ABII60A10 | 0.050 |
| ABII60A10-35GS-ABII42D4 | 0.055 |
| ABII60A10-25GS-ABII42D4 | 0.043 |
| ABII42D4 | 51 |
| ABII42D4-9GS-ABII42D4 | 16 |
| ABII60A10 | >1000 |
| m266Fab | >1000 |
| 3D6Fab | 17 |
| 60A10 TR-FRET assay | |
| ABII42D4-25GS-ABII60A10 | 0.066 |
| ABII42D4-35GS-ABII60A10 | 0.084 |
| ABII60A10-35GS-ABII42D4 | 0.091 |
| ABII60A10-25GS-ABII42D4 | 0.091 |
| ABII42D4 | >1000 |
| ABII42D4-9GS-ABII42D4 | >1000 |
| ABII60A10 | 30 |
| m266Fab | 2.3 |
| 3D6Fab | >1000 |

8.2 Determination of Binding Mode:

To explore the binding mode of the biparatopic constructs, it is assessed if both VHH building blocks can bind simultaneously to the same peptide molecule. In a sandwich ELISA, tag-less ABII60A10 or his-tagged ABII42D4 are coated onto a Maxisorp plate and incubated with the A-beta(1-40) peptide. The resulting VHH-peptide complex is then incubated with the c-myc-tagged VHH recognizing the N-terminal or central A-beta peptide epitope. Detection via the c-myc is performed as described before (Example 2). Binding is seen for both setups, indicating that the two VHHs recognizing the N-terminal or central epitope can bind simultaneously to the A-beta peptide.

Determination of the Binding Mode by SPR-Based Assay:

C-terminally biotinylated A-beta(1-40) is immobilized on the sensor chip as described before (Example 2). ABII60A10 is injected at a saturating concentration of 500 nM and binding to A-beta(1-40) is observed. After 120 seconds, 200 nM of ABII42D4 and 500 nM ABII60A10 are co-injected resulting in additional binding. A control injection of 500 nM 60A10 alone does not result in any additional binding, showing that the additional binding observed is due to the ABII42D4-A-beta interaction.

Determination of the Binding Mode Using Size Exclusion Chromatography:

Size exclusion chromatography (SEC) separates molecules according to differences in size as they pass through a gel filtration medium packed in a column. The binding mode of biparatopic VHH constructs to their target can be identified by analysing the protein complex after incubating a 1:2 molar ratio of the respective VHH construct and the target protein. Therefore the mixture will be separated by SEC and the contents of the resulting peaks is analyzed by protein gel electrophoresis. An A-beta(1-28)-p38 fusion protein, having a calculated molecular weight of 46 kDa, runs as a monomer in the SEC. The biparatopic VHH fused to human serum albumin (60A10-27GS-42D4-Alb) has a calculated molecular weight of 95 kDa. In order to identify whether the biparatopic VHH binds one (=intramolecular binding) or two (=intermolecular binding) A-beta(1-28)-p38 fusion proteins, a 1:2 molar ratio of the VHH and the target protein is mixed, incubated over night at 4° C. and applied to SEC using an ÄKTAexplorer (GE Healthcare, USA) in combination with a preparative size exclusion column (HiLoad 26/60 Superdex 200 prep grade, GE Healthcare, USA) in order to separate the protein complex from the single proteins. The gel filtration produced two peaks which are further analyzed by SDS-PAGE using the automated electrophoresis station Experion (Bio-Rad, USA) and the appropriate chip (Pro260 Chip, Bio-Rad, USA). Analysis on the Experion reveals that the main peak contains the VHH and the A-beta(1-28)-p38 fusion protein whereas the smaller peak contains only the A-beta(1-28)-p38 fusion protein. The amounts of VHH and A-beta(1-28)-p38 fusion protein in the complex are determined using the Experion data analysis software. The molecular weights of the proteins measured with the Experion are 53 kDa for the A-beta-p38 fusion protein and 101 kDa for the 60A10-27GS-42D4-Alb protein. The measured concentrations and therefore calculated molarity is 0.87 µM and 0.86 µM for the A-beta(1-28)-p38 fusion protein and the 60A10-27GS-42D4-Alb protein, respectively. Therefore, the ratio of A-beta(1-28)-p38 to 60A10-27GS-42D4-Alb in the analysed protein complex is about 1:1 although it is mixed at a molar ratio of 1:2. From this result it can be concluded that one biparatopic VHH binds the two epitopes of an A-beta peptide molecule within one and the same A-beta molecule, and does therefore not (or at least not primarily) act via cross-linking of A-beta-molecules via the bivalent VHH constructs.

8.3 Crystallization Studies:

For crystallization, ABII035 and ABII059 (160 µM each) are incubated with 3-fold molar excess of human A-beta peptide (residues 1-24) for 16 hours and the complex is purified by size exclusion chromatography. The complex is concentrated by diafiltration to a concentration of 4 mg/ml. Crystallization trials are set up as sitting drop vapour diffusion experiments by mixing 200 nl of protein with 200 nl of reservoir solution against a reservoir volume of 100 µl. Crystals appear after several days under a variety of different conditions, among these the following is used to determine the structure: 100 mM MMT buffer pH 5, 25% PEG1500. Crystals are treated with cryo-protectant (85 mM MMT buffer pH 5, 35% PEG1500) and flash-frozen with liquid nitrogen. Data are collected at the beamline 6SA of the swiss light source at the Paul-Scherrer Institute in Villigen, Switzerland.

In the crystal structure one molecule of ABII035, ABII059, and a peptide derived from human A-beta peptide (residues 1-24) form a ternary complex. This complex dimerizes via an anti-parallel beta-sheet which is formed by two molecules of A-beta peptide. The asymmetric unit of the crystal is occupied by two of these structures, which totals to four molecules of each A-beta peptide, ABII035 and ABII059. Residues 1 to 9 of A-beta adopt an alpha-helical conformation, residues 10 to 20 form a beta-strand. Residues 1 to 14 of A-beta are in proximity to ABII035 and among these Asp1, Ala2, Glu3, Phe4, Asp7, and His14 directly contact ABII035. Residues 15 to 24 of A-beta are in proximity to ABII059 and among these Gln15, Lys16, Val18, Phe19, Phe20, Glu22, and Asp23 directly contact ABII059.

In addition to the above, it becomes clear from the crystal structure that ABII035 and ABII059 can bind to one and the same molecule of A-beta simultaneously, confirming the results as obtained in Example 8.2 above.

Furthermore, the mode of interaction of ABII035 with the A-beta derived peptide as evidenced by the above crystal structure data is consistent with the observation as described in Example 7 above: ABII035 shows a good species cross-reactivity with regard to rodent A-beta peptides. The only sequence differences between human and rodent A-beta are R5G, Y10F and H13R. According to the above data, none of these residues form contacts to the VHH. Therefore it is assumed that rodent A-beta can bind to ABII035 in the same conformation as human A-beta, making it particularly useful as a tool reagent (research tool) for assays involving rodent animal models (producing rodent A-beta peptide), such as mice or rats.

Example 9

Generation and Characterization of Half-Life Extended Humanized Biparatopic Anti-A-beta VHH Constructs 9.1 Generation of Constructs ABII314 to ABII323:

For in vivo validation studies with humanized biparatopic VHH constructs, different half life extension (HLE) strategies are explored: 1) genetic fusion to an albumin binding VHH (as described e.g. in WO2004/041865), 2) PEGylation of a Cys residue located in the linker between VHHs or at the C-terminus of the VHHs (WO2008/142164) and 3) genetic fusion to human or mouse serum albumin. The different HLE strategies are explored with biparatopic VHH constructs comprising the ABII035 and the ABII059 VHH domains/building blocks. Constructs ABII314 to ABII323 are generated via gene assembly using appropriate sets of overlapping oligonucleotides. Sequence IDs and amino acid sequences of ABII314 to ABII323 are listed in Table XV. In constructs ABII314, ABII315, ABII322 and ABII323, building block ABII059 is fused to ABII035 via a Gly-Ser linker of different length (as indicated in Table XV), containing a cysteine residue for conjugation with PEG (at the position as indicated in Table XV). Constructs ABII316 to ABII321 consist of genetically linked VHHs ABII035, ABII059 and ALB8 (humanized anti-human albumin VHH with mouse albumin cross reactivity), in different orientations and separated by either 9- or 35-GS linkers. The constructs shown in Table XV below may optionally additionally include a hexa-histidine tag and/or other tags for e.g. facilitating purification of the resulting polypeptides.

TABLE XV

Biparatopic VHH constructs ABII314 to ABII323

| Clone | Sequence information | Description | SEQ ID NO: |
|---|---|---|---|
| ABII314 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINVR RSYSSWGQGTLVTVSSGGGGCGGGGSGGGGSGGG GSGGGGSGGGGSGGGGSEVQLLESGGGLVQPGGS LRLSCVHSGPTFRTDTMGWFRQAPGKGREFVAAVT WNSGRINYADSVKGRFTISRDNSKNTAYLQMNSLRPE DTAVYYCAAHRFVVGGNRVEDWRYWGQGTLVTVSS | 059-35GSC with C at position 5-035 | 142 |
| ABII315 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINVR RSYSSWGQGTLVTVSSGGGGCGGGSEVQLLESGGG LVQPGGSLRLSCVHSGPTFRTDTMGWFRQAPGKGR EFVAAVTWNSGRINYADSVKGRFTISRDNSKNTAYLQ MNSLRPEDTAVYYCAAHRFVVGGNRVEDWRYWGQG TLVTVSS | 059-9GSC with C at position 5-035 | 143 |
| ABII316 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINV RRSYSSWGQGTLVTVSSGGGGSGGGSEVQLVESGG GLVQPGNSLRLSCAASGFTFSSFGMSWVRQAPGKG LEWVSSISGSGSDTLYADSVKGRFTISRDNAKTTLYL QMNSLRPEDTAVYYCTIGGSLSRSSQGTLVTVSSGG GGSGGGSEVQLLESGGGLVQPGGSLRLSCVHSGPT FRTDTMGWFRQAPGKGREFVAAVTWNSGRINYADS VKGRFTISRDNSKNTAYLQMNSLRPEDTAVYYCAAHR FVVGGNRVEDWRYWGQGTLVTVSS | 059-9GS-Alb8-9GS-035 | 34 |
| ABII317 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINV RRSYSSWGQGTLVTVSSGGGGSGGGGSGGGGSGG | 059-35GS-035-9GS- | 35 |

TABLE XV-continued

Biparatopic VHH constructs ABII314 to ABII323

| Clone | Sequence information | Description | SEQ ID NO: |
|---|---|---|---|
| | GGSGGGGSGGGGSGGGGSEVQLLESGGGLVQPGG SLRLSCVHSGPTFRTDTMGWFRQAPGKGREFVAAVT WNSGRINYADSVKGRFTISRDNSKNTAYLQMNSLRP EDTAVYYCAAHRFVVGGNRVEDWRYWGQGTLVTVS SGGGGSGGGSEVQLVESGGGLVQPGNSLRLSCAAS GFTFSSFGMSWVRQAPGKGLEWVSSISGSGSDTLYA DSVKGRFTISRDNAKTTLYLQMNSLRPEDTAVYYCTI GGSLSRSSQGTLVTVSS | Alb8 | |
| ABII318 | EVQLLESGGGLVQPGGSLRLSCAASGRTFNNYNMG WFRQAPGKGREFVAAVSRSGVSTYYADSVKGRFTIS RDNSKNTVYLQMNSLRPEDTAVYYCAAAYRGTAINV RRSYSSWGQGTLVTVSSGGGGSGGGSEVQLLESGG GLVQPGGSLRLSCVHSGPTFRTDTMGWFRQAPGKG REFVAAVTWNSGRINYADSVKGRFTISRDNSKNTAYL QMNSLRPEDTAVYYCAAHRFVVGGNRVEDWRYWG QGTLVTVSSGGGGSGGGSEVQLVESGGGLVQPGNS LRLSCAASGFTFSSFGMSWVRQAPGKGLEWVSSISG SGSDTLYADSVKGRFTISRDNAKTTLYLQMNSLRPED TAVYYCTIGGSLSRSSQGTLVTVSS | 059-9GS-035-9GS-Alb8 | 36 |
| ABII319 | EVQLLESGGGLVQPGGSLRLSCVHSGPTFRTDTMG WFRQAPGKGREFVAAVTWNSGRINYADSVKGRFTIS RDNSKNTAYLQMNSLRPEDTAVYYCAAHRFVVGGNR VEDWRYWGQGTLVTVSSGGGGSGGGGSGGGGSG GGGSGGGGSGGGGSGGGGSEVQLLESGGGLVQPG GSLRLSCAASGRTFNNYNMGWFRQAPGKGREFVAA VSRSGVSTYYADSVKGRFTISRDNSKNTVYLQMNSLR PEDTAVYYCAAAYRGTAINVRRSYSSWGQGTLVTVS SGGGGSGGGSEVQLVESGGGLVQPGNSLRLSCAAS GFTFSSFGMSWVRQAPGKGLEWVSSISGSGSDTLYA DSVKGRFTISRDNAKTTLYLQMNSLRPEDTAVYYCTI GGSLSRSSQGTLVTVSS | 035-35GS-059-9GS-Alb8 | 37 |
| ABII320 | EVQLLESGGGLVQPGGSLRLSCVHSGPTFRTDTMGW FRQAPGKGREFVAAVTWNSGRINYADSVKGRFTISRD NSKNTAYLQMNSLRPEDTAVYYCAAHRFVVGGNRVE DWRYWGQGTLVTVSSGGGGSGGGSEVQLVESGGG LVQPGNSLRLSCAASGFTFSSFGMSWVRQAPGKGLE WVSSISGSGSDTLYADSVKGRFTISRDNAKTTLYLQM NSLRPEDTAVYYCTIGGSLSRSSQGTLVTVSSGGGGS GGGSEVQLLESGGGLVQPGGSLRLSCAASGRTFNNY NMGWFRQAPGKGREFVAAVSRSGVSTYYADSVKGR FTISRDNSKNTVYLQMNSLRPEDTAVYYCAAAYRGTAI NVRRSYSSWGQGTLVTVSS | 035-9GS-Alb8-9GS-059 | 38 |
| ABII321 | VQLLESGGGLVQPGGSLRLSCVHSGPTFRTDTMGWF RQAPGKGREFVAAVTWNSGRINYADSVKGRFTISRD NSKNTAYLQMNSLRPEDTAVYYCAAHRFVVGGNRVE DWRYWGQGTLVTVSSGGGGSGGGSEVQLVESGGG LVQPGNSLRLSCAASGFTFSSFGMSWVRQAPGKGLE WVSSISGSGSDTLYADSVKGRFTISRDNAKTTLYLQM NSLRPEDTAVYYCTIGGSLSRSSQGTLVTVSSGGGGS GGGSEVQLLESGGGLVQPGGSLRLSCAASGRTFNNY NMGWFRQAPGKGREFVAAVSRSGVSTYYADSVKGR FTISRDNSKNTVYLQMNSLRPEDTAVYYCAAAYRGTAI NVRRSYSSWGQGTLVTVSS | 035-9GS-Alb8-9GS-059 (first E deleted) | 39 |
| ABII322 | VQLLESGGGLVQPGGSLRLSCAASGRTFNNYNMGW FRQAPGKGREFVAAVSRSGVSTYYADSVKGRFTISRD NSKNTVYLQMNSLRPEDTAVYYCAAAYRGTAINVRRS YSSWGQGTLVTVSSGGGSGGGGSGGGGC*GGGGS GGGGSGGGEVQLLESGGGLVQPGGSLRLSCVHSGP TFRTDTMGWFRQAPGKGREFVAAVTWNSGRINYADS VKGRFTISRDNSKNTAYLQMNSLRPEDTAVYYCAAHR FVVGGNRVEDWRYWGQGTLVTVSS | 059-27GSC with C at position 14-035 | 40 |
| ABII323 | VQLLESGGGLVQPGGSLRLSCAASGRTFNNYNMGW FRQAPGKGREFVAAVSRSGVSTYYADSVKGRFTISR DNSKNTVYLQMNSLRPEDTAVYYCAAAYRGTAINVR RSYSSWGQGTLVTVSSGGGGSGGGGSGGGGC*GG | 059-35GSC with C at position | 41 |

TABLE XV-continued

Biparatopic VHH constructs ABII314 to ABII323

| Clone | Sequence information | Description | SEQ ID NO: |
|---|---|---|---|
| | GGSGGGGSGGGGSGGGGSEVQLLESGGGLVQPGG SLRLSCVHSGPTFRTDTMGWFRQAPGKGREFVAAVT WNSGRINYADSVKGRFTISRDNSKNTAYLQMNSLRP EDTAVYYCAAHRFVVGGNRVEDWRYWGQGTLVTSS | | 15-035 |

9.2 Production, Purification and PEGylation of Humanized Half-Fife Extended Biparatopic VHH Constructs:

His$_6$-tagged biparatopic VHH constructs ABII314, ABII315, ABII322 and ABII323 are purified via affinity chromatography (IMAC or protein A), cation exchange chromatography (SP Sepharose, Source 30S or POROS 50HS) and size exclusion chromatography (Superdex75 or Sephacryl S100). At protein purity levels of minimally 90% (determined via SDS-PAGE and subsequent Coomassie Brilliant Blue staining), PEGylation is performed.

Intermolecular S—S bonds of VHHs are first reduced by adding DL-Dithiothreitol solution (DTT) to a final concentration of 10 mM followed by 2 to 3 h incubation at room temperature or overnight at 4° C. The reducing agent is subsequently removed via size exclusion chromatography (Superdex 75/200) in D-PBS running buffer, collecting the main peak. Immediately after removing the reducing agent, the biparatopic polypeptide construct is incubated with a 5 fold molar excess of PEG for 1 h at room temperature or overnight at 4° C. The PEGylated polypeptide is separated from free PEG and non-PEGylated polypeptide via cation exchange chromatography (MacroCap SP). A final polishing step and buffer change to D-PBS is performed via preparative size exclusion chromatography on Superdex200 or Sephacryl S200. The quality of the purified PEGylated polypeptide is verified via SDS-PAGE followed by CBB- and PEG-staining as described before by Natarajan et al (1995) in Bioconjugate chemistry 16:113-121.

9.3 Characterization of Half-Life Extended Humanized Biparatopic Anti-A-beta VHH Constructs by TR-FRET:

In order to compare the binding properties of the half-life extended biparatopic VHH constructs described above to those of monoclonal antibodies (IgG) 3D6 and m266, ABII315 to ABII320, ABII322 and ABII323 are tested in ABII002 and ABII050 competition TR-FRET assays (see Examples 8.1 and 3.2). Average IC50s derived from at least two independent experiments are summarized in Table XVI.

TABLE XVI

IC50 values for half life extended anti-A-beta biparatopic VHHs in absence/presence of albumin.

| VHH | IC50 (nM) ABII002 assay | IC50 (nM) ABII050 assay |
|---|---|---|
| Monovalent VHHs and Fabs | | |
| ABII002 | 2.9 | NC |
| ABII035 | 3.5 | NC |
| ABII050 | NC | 6.3 |
| ABII059 | NC | 12.8 |
| Fab3D6 | 3.4 | NC |
| Fab266 | NC | 0.52 |

TABLE XVI-continued

IC50 values for half life extended anti-A-beta biparatopic VHHs in absence/presence of albumin.

| VHH | IC50 (nM) ABII002 assay | IC50 (nM) ABII050 assay |
|---|---|---|
| Multivalent VHHs and IgGs | | |
| ABII315-PEG20 | 0.13 | 0.28 |
| ABII315-PEG40 | Not tested | 0.31 |
| ABII322-PEG40 | 0.14 | 0.17 |
| ABII323-PEG40 | 0.18 | 0.20 |
| ABII316 | 0.19 | 0.31 |
| ABII316 + 10 µM HSA | 0.05 | 0.06 |
| ABII317 | 0.29 | 0.49 |
| ABII318 | 0.13 | 0.28 |
| ABII319 | 0.26 | 0.33 |
| ABII320 | 0.25 | 0.21 |
| ABII059-27GS-ABII035-MSA | 0.19 | 0.18 |
| ABII059-27GS-ABII035-MSA_D3 | 0.10 | 0.12 |
| IgG 3D6 | 1.9 | NA |
| IgG m266 | NA | 0.53 |

NC: no competition detected
MSA: mouse serum albumin
MSA_D3: domain III of mouse serum albumin In the ABII002 TR-FRET competition assay, all half-life extended VHH constructs tested show a highly improved potency between 6.5 fold and 14.6 fold (for ABII315-PEG20) compared to 3D6 IgG (IC50 of 1.9 nM). When compared to IgG m266, all VHH constructs show significantly better IC50 values in the ABII050 TR-FRET competition assay, with VHH ABII320 having the lowest IC50 of 0.21 nM, 2.5 fold improved over IgG266.

Compared to the potency of monovalent VHH ABII035, the tailored VHH construct with the highest potency (ABII315-PEG20) show a 27 fold improved IC50 in the ABII002 TR-FRET competition assay. VHH construct ABII320 show a 61-fold improved potency over monovalent ABII059 in the ABII050 TR-FRET competition assay.

The increased potency of the biparatopic constructs over the monomeric building blocks ABII035 and ABII059 confirms the results obtained with the non-humanized, non-matured constructs (Example 8.1) and supports the hypothesis of intramolecular binding of one biparatopic VHH construct to one A-beta peptide molecule (cf. Example 8.2 above). Furthermore, these experiments demonstrate that the half-life extension techniques applied to the VHH constructs as described above do not interfere with binding of the constructs to the A-beta peptide.

To assess whether the binding of ALB8-containing VHH constructs to the A-beta peptide is affected by HSA (as present in the bloodstream), biparatopic constructs equivalent to ABII316-ABII320 but containing the non-humanized VHH building blocks are tested in both competition TR-FRET assays in presence and absence of µM amounts of albumin. In both assay formats, pre-incubation with 6.5-10 µM human, dog or bovine albumin (the latter two albumin variants showing no detectable interaction with ALB8) do not affect potency in the TR-FRET assays.

To test whether ALB8 can still bind to albumin in the context of the biparatopic VHH constructs, a kinetic analysis of the VHH constructs for binding to a chip coated with HSA is performed (Biacore). Comparable affinities were determined for monovalent ALB8 and the ALB8 fusion construct tested, indicating that HSA-binding of the ALB8 building block is not affected.

9.4 Inhibition of A-Beta Fibril Formation:

In a further experiment, a dilution series of the biparatopic VHH construct ABII320 is evaluated for its capacity to inhibit formation of A-beta fibrils in vitro as described under Example 3.5 and is compared to the activity of its monovalent building blocks ABII035 and ABII059 and control antibodies. The maximum inhibition at the highest concentration of the VHH construct tested (26 µM) is calculated as an average of two independent experiments. While a consistent background inhibition of approximately 17% is detected when using non-related (non-A-beta specific) VHHs as a control, monovalent 3D6 and m266 Fab fragments show a reproducible dose-dependent inhibition with maximal inhibition of 82%. (Intact) IgGs 3D6 and m266 result in 75% and 83% inhibition, respectively. Monovalent VHHs ABII035 and ABII059 show a maximum inhibition of 54% and 80%, respectively, while the half-life extended biparatopic VHH construct ABII320 shows a maximum inhibition capacity of 84% at 26 µM.

9.5 Binding to Soluble APP-Alpha:

Soluble APP-alpha (sAPPalpha) is released from its cell bound precursor protein APP by alpha-secretase activity. The amino acid sequence of sAPPalpha contains the first sixteen amino acid residues of the A-beta peptide, but does not contain the correct 3D6 epitope, as a free N-terminal amino acid residue in the A-beta peptide is essential for full 3D6 interaction. Epitope mapping indicates that N-terminal region-specific VHH ABII001 and its derivatives interact with a distinct epitope compared to monoclonal antibody 3D6. VHH-binding to sAPPalpha in comparison to A-beta is tested using a TR-FRET-based assay setup. Biotinylated sAPPalpha (Sigma) at a final concentration of 0.82 nM is mixed with the same concentration of streptavidin-Europium labeled beads and 4.4 nM of AlexaFluor647-labeled ABII320. The following non-labeled compounds are tested for competition: ABII320, sAPPalpha, IgG m266, IgG 3D6, ABII035 and A-beta(1-40). Two independent experiments are performed applying a dilution series of the competitor compounds. Average 1050 values are 0.72 nM, 25.6 nM, 0.23 nM, and 14 nM for non-labeled ABII320, ABII035, A-beta(1-40) and sAPPalpha, respectively. As expected, no competition is observed for IgG m266 and IgG 3D6. In this assay set-up, ABII320 interacts 63-fold better with A-beta(1-40) than with sAPPalpha. In a parallel set-up using biotinylated A-beta(1-40) instead of biotinylated sAPPalpha, ABII320 interacts at least 20000-fold better with A-beta(1-40) than with sAPPalpha (IC50 estimated based on extrapolated data at higher concentrations), indicating that ABII320 prefers binding to A-beta (1-40) over sAPPalpha.

9.6 Epitope Mapping for Biparatopic VHH Constructs:

A-beta(1-42) derived peptides displayed as peptide microarrays (PepStar™) are used to determine the epitopes of VHHs. PepStar™ peptide microarrays (JPT Peptide Technologies, Germany) are customized peptide microarray sets for rapid screening of antibody/VHH peptide interaction displayed on glass slides. The peptides of the microarray represent a 12/11 scan derived from the primary structure of A-beta (1-42) immobilized via their N-terminus. In addition, truncated peptides of the N-terminus representing the first 16 to the first 7 amino acids of A-beta(1-42) are immobilized via their C-terminus. Upon incubation with the VHH, the binding event can be detected by reading the fluorescence intensity of labeled secondary antibody directed against the VHH.

After blocking the microarray with blocking buffer (PBS, 1% BSA, 0.1% Tween20) over night at 4° C., it is incubated for 2 h at 4° C. with 200 µl of the biparatopic VHH construct ABII320 in wash buffer (PBS, 5 mM DTT, 0.05% Triton X-100, 5% Glycerol, 1% BSA) at a concentration of 5 µg/ml. In order to remove excess VHH, the microarray is incubated three times for two minutes on ice with wash buffer. Thereafter, the microarray is incubated for one hour at 4° C. with an anti-VHH Alexa Fluor 647 (Boehringer Ingelheim Pharma GmbH & Co KG, Germany) in wash buffer at a concentration of 0.5 µg/ml. The anti-VHH is derived from a goat serum after immunization with the VHH dimer G6-G6. Unbound secondary antibody is removed by incubating the microarray three times for two minutes on ice with wash buffer. Finally the slide is dried in a centrifuge at 800×g for three minutes and scanned with the ProScanArray from Perkin Elmer using a 633 nm laser. The data are analyzed with the ScanArray Express® software from Perkin Elmer.

As a result, peptide spots having a diameter of 420 µm are obtained which are analyzed for fluorescence intensity, from which interaction of the VHH with the peptides can be assessed in a semi-quantitative manner. Thus, incubation of the biparatopic VHH construct ABII320 with the peptide microarrays reveals that ABII320 interacts with residues 1-11 and 15-24 of the A-beta peptide. The alanine scan indicated that residues Asp1, Glu3, Phe19, Phe20 and Asp23 of the A-beta peptide are essential for the binding of the biparatopic VHH, which is consistent with the data obtained from crystal structure analyses. The same results are obtained using two other biparatopic VHH constructs which include the ABII035 and ABII059 VHH domains.

9.7 Determination of Binding Constants Using Kinetic Exclusion Assay (KinExA):

Affinities of three biparatopic VHH constructs for the A-beta peptide are determined using KinExA (Kinetic Exclusion Assay). KinExA is a technology with the ability to measure unmodified molecules in solution phase (Darling, R. J. and Brault, P.-A.: Kinetic exclusion assay technology: Characterization of Molecular Interactions; Assay and Drug Development Technologies 2(6):647 (2004)). The KinExA method measures the concentration of uncomplexed VHH molecules in a mixture of VHH, antigen, and VHH-antigen complex. The concentration of uncomplexed VHH is measured by exposing the solution phase mixture to solid phase immobilized antigen for a very brief period of time. The "contact time" between the solution phase mixture and the solid phase immobilized antigen is kept short enough that dissociation of VHH-antigen complex is insignificant. When the possibility of significant dissociation of VHH-antigen complex is kinetically excluded, only uncomplexed ("free") VHH can bind to the solid phase. The amount of free VHH that binds to the solid phase (measured by fluorescence emission from a secondary label) is directly proportional to the concentration of free VHH in the solution phase sample.

A-beta(1-28) peptide (Anaspec, USA) is used as antigen for the incubation with biparatopic VHHs. Fusion protein "His.Xa.Abeta1-28.GS.p38" is used to prepare the solid phase for binding the uncomplexed VHHs. The structure of the fusion protein is as follows: His-tag, factor Xa cleavage site, A-beta(1-28) peptide, GS-linker, murine p38 alpha and has the following sequence:

(SEQ ID NO: 144)
MHHHHHHIEGRDAEFRHDSGYEVHHQKLVFFAEDVGSNKGGSGGSQERPT

FYRQELNKTIWEVPERYQNLSPVGSGAYGSVCAAFDTKTGHRVAVKKLSR

PFQSIIHAKRTYRELRLLKHMKHENVIGLLDVFTPARSLEEFNDVYLVTH

LMGADLNNIVKCQKLTDDHVQFLIYQILRGLKYIHSADIIHRDLKPSNLA

VNEDCELKILDFGLARHTDDEMTGYVATRWYRAPEIMLNWMHYNQTVDIW

SVGCIMAELLTGRTLFPGTDHIDQLKLILRLVGTPGAELLKKISSESARN

YIQSLAQMPKMNFANVFIGANPLAVDLLEKMLVLDSDKRITAAQALAHAY

FAQYHDPDDEPVADPYDQSFESRDLLIDEWKSLTYDEVISFVPPPLDQEE

MES.

The fusion protein is expressed in *E. coli*, purified using Ni-NTA (Qiagen, Germany) and alkylated with Iodoacetamide (Sigma, USA). Polymethylmethacrylate beads (Sapidyne Instruments Inc., USA) are coated with the fusion protein in PBS with 0.02% $NaN_3$, blocked with 1% BSA in the same buffer and used for all experiments as solid phase. The KinExA experiments are conducted with a KinExA 3000 and the KinExA Pro software (Sapidyne Instruments Inc., USA) at room temperature (ca. 21° C.). PBS with 0.02% $NaN_3$ is used as running buffer. For all experiments, antigen is serially diluted into PBS with 0.1% BSA and 0.02% $NaN_3$ having a constant VHH concentration. The mixtures of antigen and VHH are incubated for 24 h at room temperature prior to measurement. The flow rate of the samples and the labeling antibody for all experiments is 0.25 ml/min.

The secondary fluorescence labeled antibody for the measurement of the ABII320 VHH construct (first VHH construct) is the Alexa 647-conjugated goat anti-G6G6 (anti-VHH) described under 9.6 above. This antibody is used at a volume of 500 μl and a concentration of 0.5 μg/ml in PBS with 0.1% BSA and 0.02% $NaN_3$. The ABII320 is additionally measured as described in the presence of recombinant human albumin (Albcult™, novozymes, USA). Binding of the PEGylated ABII322 VHH construct (second VHH construct) to the solid phase is determined using 500 μl of a rabbit anti-PEG (Epitomics Inc., USA) at a concentration of 0.1 μg/ml in PBS with 0.1% BSA and 0.02% $NaN_3$ on line 13 of the instrument in combination with 250 μl of an Alexa 647-conjugated goat anti-rabbit (Molecular Probes Inc., USA) at a concentration of 0.25 μg/ml in the same buffer. Binding of the HSA-biparatopic VHH construct fusion protein shown in Table IV above (SEQ ID NO:32; third VHH construct) to the solid phase is determined using 500 μl of a goat anti-HSA (Bethyl Laboratories Inc., USA) at a concentration of 0.5 μg/ml in PBS with 0.1% BSA and 0.02% $NaN_3$ on line 13 of the instrument in combination with 500 μl of an Alexa 647-conjugated rabbit anti-goat (Molecular Probes Inc., USA) at a concentration of 0.5 μg/ml in the same buffer.

The equilibrium titration data are fit to a 1:1 binding model using KinExA Pro software Version 1.0.3 (Sapidyne Instruments Inc., USA). The first VHH construct (biparatopic VHH ABII320) is measured at concentrations of 3, 5 and 10 μM. The sample volume is 5 ml each. The measured $K_D$ is 1.1±0.3 pM and 0.4±0.1 pM in the presence of 1% recombinant human albumin. The second VHH construct (biparatopic PEGylated VHH ABII322) is measured at concentrations of 3, 4, 5 and 6 pM. The sample volume is 11 ml each. The measured $K_D$ is 0.6±0.2 pM. The third VHH construct (HSA-VHH fusion protein) is measured at concentrations of 2, 3 and 4 pM. The sample volume is 5 ml each. The measured $K_D$ is 0.5±0.3 pM.

9.8 Binding to pyroglutamyl-Abeta:

Pyroglutamyl (pGlu)-A-beta is a major component of neuritic plaques in Alzheimer's disease. It is formed by cyclization of the N-terminal glutamate at position 3 catalyzed by glutaminyl cyclase (QC) resulting in a very amyloidogenic variant of A-beta. The amino acid sequence of pGlu-A-beta contains the amino acid residues 3-42 of the A-beta peptide. The first two N-terminal amino acids which are essential for full interaction with antibody 3D6 are missing. Affinities for the pGlu-A-beta-ABII320/ABII322/m266/3D6 interaction are determined via surface plasmon resonance (Biacore) using C-terminally biotinylated pGlu-A-beta(1-28) captured on a streptavidin sensor chip as described before (Example 2). Purified polypeptides ABII320 or ABII322 or antibodies m266 or 3D6 are injected at 9 different concentrations (between 0.195 and 50 nM for ABII320, 0.39-100 nM for ABII322 and 0.782-200 nM for 3D6 and m266) for 3 min and allowed to dissociate for 10 min. Association and dissociation curves can be fitted using a 1:1 interaction model and an accurate $K_D$ value can be determined. The affinities are found to be 2 nM for ABII320, 1 nM for ABII322, 224 pM for the antibody m266 and no binding could be observed for the antibody 3D6.

Example 10

Binding of Anti-A-beta VHHs to Amyloid Plaques

VHHs are profiled in a tissue amyloid plaque immunoreactivity (TAPIR) assay according to their capability to bind to amyloid plaques in Tg2576 mouse brain slices. The TAPIR assay allows a qualitative (dense core and/or diffuse amyloid plaques) as well as quantitative assessment (minimum effective dosis MED) of the VHHs. For the assay, cryostat-cut coronal sections of plaque-positive mice are prepared, mounted onto 76×26 mm Superfrost slides (Roth) and stored at −20° C. Cryosections are thawed for 20 minutes, fixed in 3% paraformaldehyde (PFA) for 10 minutes on ice. Sections are then incubated in 0.3% hydrogen peroxide for 30 minutes, blocked with PBS containing 2.5% bovine serum albumin (BSA) and 2% mouse serum for 1.5 hours and incubated with a myc-tagged VHH or Fab at different concentrations (3.0 mg/ml to 4.11 ng/ml), dissolved in PBS containing 2.5% BSA. The slices are then incubated for 1.5 hours with 10 mg/ml biotinylated mouse anti c-myc monoclonal antibody (9E10) (Sigma-Aldrich), dissolved in PBS containing 2.5% BSA (except for slices incubated with biotinylated ABII320). The sections are incubated for 1.5 hours with Vectastain ABC ELITE Kit solution (Vector Laboratories) prepared according to manufacturer's instructions, and visualised using Vector VIP SK 4600 solution (Vector Laboratories), again prepared according to manufacturer's instruction. The sections are progressively dehydrated by 5 minute incubations in 60-, 80- and 100% ethanol and 100% isopropanol and cleared for 5 minutes in xylene. The sections are then mounted with Entellan new mounting medium (Merck) and covered with 24×50 mm coverslips (Menzel-Glaeser). The results are summarized in the following table.

In addition to ABII320 and Fab fragments of monoclonal antibody m266 described above, several other (myc-tagged) biparatopic VHH constructs were analysed in the above TAPIR assay. The structure of VHH constructs ABII300 to ABII305 is shown in Table XVII below and, in all cases, includes VHH domains ABII002 (SEQ ID NO:62) and ABII050 (SEQ ID NO:100), in different orders and combined with either an albumin binding VHH domain (ABII300 to ABII304) or a PEG40 moiety (ABII305).

From the results, it can be seen that biparatopic VHHs ABII300, ABII301, ABII302, ABII303 and ABII304 as well as ABII305-PEG40 reveal the same affinity to bona fide tissue amyloid plaques (dense core and diffuse type of plaques) in the TAPIR assay. A particular order of the linkers or conjugation to PEG40 does not appear to have a significant effect on plaque affinity.

TABLE XVII

Structure of biparatopic VHH constructs ABII300 to 305 and results obtained in TAPIR assay

| VHH | Domain Structure | Epitope | MED [ug/ml] |
|---|---|---|---|
| m266 (Fab) | | central | no binding |
| ABII300 | ABII050-GS9-Alb8-GS9-ABII002 | N-term and central | 0.11 > x > 0.04 |
| ABII301 | ABII050-GS35-ABII002-GS9-Alb8 | N-term and central | 0.11 > x > 0.04 |
| ABII302 | ABII050-GS9-ABII002-GS9-Alb8 | N-term and central | 0.11 > x > 0.04 |
| ABII303 | ABII002-GS35-ABII050-GS9-Alb8 | N-term and central | 0.11 > x > 0.04 |
| ABII304 | ABII002-GS9-Alb8-GS9-ABII050 | N-term and central | 0.11 > x > 0.04 |
| ABII320 | ABII035-GS9-Alb8-GS9-ABII059 | N-term and central | 0.11 > x > 0.04 |
| ABII305-PEG40 | ABII050-GSC35(PEG at Cys at position 5)-ABII002 | N-term and central | 0.11 > x > 0.04 |

Example 11

Pharmacodynamic of Half-Life Extended Biparatopic Anti-A-Beta VHH Constructs

To determine the pharmacokinetic and pharmacodynamic properties of VHHs, samples are injected either i.v. or i.p. into APP transgenic mice. Plasma samples are taken by bleeding the V. saphena. A predose sample was taken before the VHHs, IgGs or vehicle application and after 4 and 24 hours.

As the binding of the VHHs and the IgGs interferes with the detection in the ELISA, the A-beta:VHH or A-beta:IgG complexes are denatured prior to the assay in order to detect the total amount of plasma A-beta(1-40). In brief, samples are denatured with 6M GuHCl (Sigma Aldrich) and purified over a solid-phase extraction column. 60 mg Oasis HLB 96-well plates (Waters) are set into extraction plate manifolds (Waters) connected to house vacuum. Columns are activated with 1 mL methanol (MeOH), followed by 1 mL $H_2O$. GuHCl-extracted samples are loaded and washed sequentially with 1 mL volumes of 5 and 30% MeOH and A-beta is then eluted with 2% $NH_4OH$ in 90% MeOH. Eluted samples are collected and vacuum-centrifuged (Eppendorf Vacufuge) at 1400 rpm, 60° C. for 90 min. Once samples are dried completely, they are reconstituted in blocking buffer and stored at −20° C. until analysis. Total plasma levels of A-beta(1-40) are determined by sandwich ELISA (4G8/anti-A-beta(1-40), mesoscale discoveries) according to the manufacturer's instruction.

Predose total A-beta(1-40) levels for APP transgenic mice are approximately 1.25 nM in plasma. In these mice injected with 15 nmol/kg of biparatopic VHHs or IgG (same dose, normalized to binding sites) the level of total A-beta in plasma peaked around 4 hours after i.v. application. Data are expressed as 'fold increase over predose' in which the A-beta (1-40) plasma concentrations determined at 4 and 24 hrs after injection are divided by the predose levels. Results are shown in Table XVIII.

TABLE XVIII

Fold increase and AUD of plasma A-beta(1-40) after i.v. injection of anti-A-beta VHHs, compared to anti-A-beta antibodies 3D6 and m266 plasma A-beta(1-40) fold increase over predose

| | APP transgenic mice | | | |
|---|---|---|---|---|
| | exp. | dose (nmol/kg) | 4 hrs | 24 hrs | AUD |
| ABII300 | 14/16 | 15 i.v. | 37.78 | 21.00 | 632.5 |
| ABII301 | 14/16 | 15 i.v. | 26 | 13.34 | 402.9 |
| ABII305 | 16 | 15 i.v. | 33.86 | 15.81 | 877.5 |
| ABII306 | 21 | 15 i.v. | 45.05 | 32.83 | 862.5 |
| ABII316 | 24-26 | 15 i.v. | 21.88 | 9.26 | 649 |
| ABII317 | 24-26 | 15 i.v. | 35.91 | 18.95 | 1615 |
| ABII318 | 24-26 | 15 i.v. | 13.45 | 5.81 | 807.9 |
| ABII319 | 24-26 | 15 i.v. | 36.53 | 21.53 | 1313 |
| ABII320 | 24-26 | 15 i.v. | 42.36 | 17.57 | 969.9 |
| ABII315-PEG40 | 24-26 | 15 i.v. | 28.78 | 12.14 | 761 |
| m266 IgG1 | 20 | 7.5 i.v.* | 25.79 | 17.9 | 528.9 |
| 3D6 IgG2b | 20 | 7.5 i.v.* | 29.47 | 25.88 | 673.2 |

*15 nmol/kg, when calculated for binding sites (2 per IgG molecule)

Thus, compared to the IgG molecules known in the art, biparatopic VHH constructs have the potential to show up to 50% higher peak levels for total plasma A-beta (4 hrs) and >2 fold increased AUD values, indicating superiority of these VHH constructs over the IgGs in capturing A-beta.

To confirm that the level of free/unbound plasma A-beta decreases subsequent to administration of the VHH construct, a competitive ELISA is developed. Briefly, A-beta(1-40) is captured with an A-beta(1-40)-specific antibody coupled to an ECL-ELISA plate (mesoscale discoveries). The VHH or IgG molecules that are used to treat the animals in passive immunotherapy are tagged using the MSD Sulfo-Tag NHS-Ester (mesoscale discoveries) according to the manufacture's manual and used as detection tool in this sandwich ELISA format. A-beta(1-40) that is bound to the VHH or to IgG can not be detected in these settings whereas free/unbound A-beta (1-40) is detectable. To compare data from different assays, all values are normalized to the data from a vehicle treated group. APP transgenic mice are treated with VHHs or IgGs as indicated and plasma is collected and analyzed for free/unbound A-beta(1-40). As soon as 2 hours after i.p. injection of 132 nmol/kg anti-A-beta VHHs (ABII320 and ABII322, respectively), the levels of free/unbound A-beta(1-40) decreased strongly and highly significant from baseline levels (appr. 2 nM) down to below the detection limit at 2 pM. Equivalent dose of 3D6-IgG (10 mg/kg, 132 nmol/kg binding sites=66 nmol/kg IgG) is able to reduce unbound A-beta(1-40) in plasma only down to a level of 52 pM (FIG. 1). In this comparison the biparatopic VHH constructs ABII320 and ABII322 show, at the same dose, an unexpectedly much stronger decrease in free/unbound A-beta in plasma compared to 3D6 IgG, again indicating superiority in A-beta capture over IgG (3D6). This makes such VHH constructs particularly useful in terms of therapeutic efficacy of VHHs. Specifically, a more efficient depletion of A-beta in plasma is expected to completely prevent the influx of A-beta from plasma into the brain, thereby generating a steeper concentration gradient between the brain and plasma A-beta pools, thereby accelerating efflux of A-beta from the brain into the plasma.

Example 12

BBB Crossing VHHs

In order to further improve the blood brain barrier (BBB) crossing characteristics of the VHH constructs, bispecific VHHs are constructed comprising the biparatopic VHHs and the BBB crossing VHHs FC44 and FC5 (as described in detail in WO2002/057445). These VHHs improve the BBB crossing by binding to a target protein expressed on the BBB, after which the VHHs are transcytosed through the endothelial cells and released in the brain parenchyme. As such, VHHs genetically fused to the FC44 and FC5 VHHs are expected to undergo an active transport into the brain, resulting in higher brain levels and improved therapeutic effect. Constructs ABII400-ABII407, comprising the FC44 or FC5 VHHs, are generated via gene assembly using appropriate sets of overlapping oligonucleotides. SEQ ID NOs and amino acid sequences are listed in Table XIX below. In summary, VHHs are generated that contain the FC5 or FC44 VHH either between the ABII035 and ABII059 VHH building, or between the HSA binding VHH and ABII035 or ABII059 building blocks, or at the amino or carboxy-terminal end of the molecule (see Table XIX). VHHs are expressed in *E. coli* or in *Pichia pastoris* and purified as described in Example 9.2. Purified VHHs are assessed in an in vitro BBB crossing assay as described (WO2002/057445 and further references therein). In addition, radiolabeled or non-radiolabeled VHHs comprising the FC5 and FC44 building blocks are administered in vivo and the brain levels are determined using either liquid scintillation counting or ELISA.

TABLE XIX

Biparatopic anti-A-beta VHH constructs, additionally comprising FC5 and FC44 moieties

| VHH construct ID | | domain structure | SEQ ID NO: |
|---|---|---|---|
| ABII400 | EVQLLESGGGLVQPGGSLRLSCVHSGPTFRTDTMG WFRQAPGKGREFVAAVTWNSGRINY ADSVKGRFTISRDNSKNTAYLQMNSLRPEDTAVYYC AAHRFVVGGNRVEDWRYWGQGTLV TVSSGGGGSGGGSEVQLQASGGGLVQAGGSLRLS CAASGFKITHYTMGWFRQAPGKEREF VSRITWGGDNTFYSNSVKGRFTISRDNAKNTVYLQM NSLKPEDTADYYCAAGSTSTATPL RVDYWGKGTQVTVSSGGGGSGGGSEVQLVESGG GLVQPGNSLRLSCAASGFTFSSFGMSW VRQAPGKGLEWVSSISGSGSDTLYADSVKGRFTISR DNAKTTLYLQMNSLRPEDTAVYYC TIGGSLSRSSQGTLVTVSSGGGGSGGGSEVQLLES GGGLVQPGGSLRLSCAASGRTFNNY NMGWFRQAPGKGREFVAAVSRSGVSTYYADSVKG RFTISRDNSKNTVYLQMNSLRPEDTA VYYCAAAYRGTAINVRRSYSSWGQGTLVTVSS | 035-<br>9GS-<br>FC5-<br>Alb8-<br>9GS-<br>059 | 145 |
| ABII401 | EVQLLESGGGLVQPGGSLRLSCVHSGPTFRTDTMG WFRQAPGKGREFVAAVTWNSGRINY ADSVKGRFTISRDNSKNTAYLQMNSLRPEDTAVYYC AAHRFVVGGNRVEDWRYWGQGTLV TVSSGGGGSGGGSEVQLVESGGGLVQPGNSLRLS CAASGFTFSSFGMSWVRQAPGKGLEW VSSISGSGSDTLYADSVKGRFTISRDNAKTTLYLQMN SLRPEDTAVYYCTIGGSLSRSSQ GTLVTVSSGGGGSGGGSEVQLQASGGGLVQAGGS LRLSCSASVRTFSIYAMGWFRQAPGK EREFVAGINRSGDVTKYADFVKGRFSISRDNAKNMV YLQMNSLKPEDTALYYCAATWAYD TVGALTSGYNFWGQGTQVTVSSGGGGSGGGSEVQ LLESGGGLVQPGGSLRLSCAASGRTF NNYNMGWFRQAPGKGREFVAAVSRSGVSTYYADS VKGRFTISRDNSKNTVYLQMNSLRPE DTAVYYCAAAYRGTAINVRRSYSSWGQGTLVTVSS | 035-<br>9GS-<br>Alb8-<br>9GS-<br>FC44-<br>9GS-<br>059 | 146 |
| ABII402 | EVQLLESGGGLVQPGGSLRLSCVHSGPTFRTDTMG WFRQAPGKGREFVAAVTWNSGRINY ADSVKGRFTISRDNSKNTAYLQMNSLRPEDTAVYYC AAHRFVVGGNRVEDWRYWGQGTLV TVSSGGGGSGGGSEVQLVESGGGLVQPGNSLRLS CAASGFTFSSFGMSWVRQAPGKGLEW VSSISGSGSDTLYADSVKGRFTISRDNAKTTLYLQMN SLRPEDTAVYYCTIGGSLSRSSQ GTLVTVSSGGGGSGGGSEVQLLESGGGLVQPGGS LRLSCAASGRTFNNYNMGWFRQAPGK GREFVAAVSRSGVSTYYADSVKGRFTISRDNSKNTV YLQMNSLRPEDTAVYYCAAAYRGT AINVRRSYSSWGQGTLVTVSSGGGGSGGGSEVQL QASGGGLVQAGGSLRLSCAASGFKIT HYTMGWFRQAPGKEREFVSRITWGGDNTFYSNSVK GRFTISRDNAKNTVYLQMNSLKPED | 035-<br>9GS-<br>Alb8-<br>9GS-<br>059-<br>9GS-<br>FC5 | 147 |

TABLE XIX-continued

Biparatopic anti-A-beta VHH constructs, additionally comprising FC5 and FC44 moieties

| VHH construct ID | | domain structure | SEQ ID NO: |
|---|---|---|---|
| | TADYYCAAGSTSTATPLRVDYWGKGTQVTVSS | | |
| ABII403 | EVQLQASGGGLVQAGGSLRLSCSASVRTFSIYAMG WFRQAPGKEREFVAGINRSGDVTKY ADFVKGRFSISRDNAKNMVYLQMNSLKPEDTALYYC AATWAYDTVGALTSGYNFWGQGTQ VTVSSGGGGSGGGSEVQLLESGGGLVQPGGSLRL SCVHSGPTFRTDTMGWFRQAPGKGRE FVAAVTWNSGRINYADSVKGRFTISRDNSKNTAYLQ MNSLRPEDTAVYYCAAHRFVVGGN RVEDWRYWGQGTLVTVSSGGGGSGGGSEVQLVES GGGLVQPGNSLRLSCAASGFTFSSFG MSWVRQAPGKGLEWVSSISGSGSDTLYADSVKGRF TISRDNAKTTLYLQMNSLRPEDTAV YYCTIGGSLSRSSQGTLVTVSSGGGGSGGGSEVQL LESGGGLVQPGGSLRLSCAASGRTF NNYNMGWFRQAPGKGREFVAAVSRSGVSTYYADS VKGRFTISRDNSKNTVYLQMNSLRPE DTAVYYCAAAYRGTAINVRRSYSSWGQGTLVTVSS | FC44-9GS-035-9GS-Alb8-9GS-059 | 148 |
| ABII404 | EVQLLESGGGLVQPGGSLRLSCVHSGPTFRTDTMG WFRQAPGKGREFVAAVTWNSGRINY ADSVKGRFTISRDNSKNTAYLQMNSLRPEDTAVYYC AAHRFVVGGNRVEDWRYWGQGTLV TVSSGGGGSGGGSGGGGSGGGGSGGGGSGGGG GSGGGGSEVQLLESGGGLVQPGGSLRLS CAASGRTFNNYNMGWFRQAPGKGREFVAAVSRSG VSTYYADSVKGRFTISRDNSKNTVYL QMNSLRPEDTAVYYCAAAYRGTAINVRRSYSSWGQ GTLVTVSSGGGGSGGGSEVQLVESG GGLVQPGNSLRLSCAASGFTFSSFGMSWVRQAPG KGLEWVSSISGSGSDTLYADSVKGRF TISRDNAKTTLYLQMNSLRPEDTAVYYCTIGGSLSRS SQGTLVTVSSGGGGSGGGSEVQL QASGGGLVQAGGSLRLSCSASVRTFSIYAMGWFRQ APGKEREFVAGINRSGDVTKYADFV KGRFSISRDNAKNMVYLQMNSLKPEDTALYYCAAT WAYDTVGALTSGYNFWGQGTQVTVSS | 035-35GS-059-9GS-Alb8-9GS-FC44 | 149 |
| ABII405 | EVQLLESGGGLVQPGGSLRLSCVHSGPTFRTDTMG WFRQAPGKGREFVAAVTWNSGRINY ADSVKGRFTISRDNSKNTAYLQMNSLRPEDTAVYYC AAHRFVVGGNRVEDWRYWGQGTLV TVSSGGGGSGGGSEVQLQASGGGLVQAGGSLRLS CSASVRTFSIYAMGWFRQAPGKEREF VAGINRSGDVTKYADFVKGRFSISRDNAKNMVYLQM NSLKPEDTALYYCAATWAYDTVGA LTSGYNFWGQGTQVTVSSGGGGSGGGSEVQLLES GGGLVQPGGSLRLSCAASGRTFNNYN MGWFRQAPGKGREFVAAVSRSGVSTYYADSVKGR FTISRDNSKNTVYLQMNSLRPEDTAV YYCAAAYRGTAINVRRSYSSWGQGTLVTVSSGGGG SGGGSEVQLVESGGGLVQPGNSLRL SCAASGFTFSSFGMSWVRQAPGKGLEWVSSISGSG SDTLYADSVKGRFTISRDNAKTTLY LQMNSLRPEDTAVYYCTIGGSLSRSSQGTLVTVSS | 035-9GS-FC44-9GS-059-9GS-Alb8 | 150 |
| ABII406 | EVQLQASGGGLVQAGGSLRLSCAASGFKITHYTMG WFRQAPGKEREFVSRITWGGDNTFY SNSVKGRFTISRDNAKNTVYLQMNSLKPEDTADYYC AAGSTSTATPLRVDYWGKGTQVTV SSGGGGSGGGSEVQLLESGGGLVQPGGSLRLSCV HSGPTFRTDTMGWFRQAPGKGREFVA AVTWNSGRINYADSVKGRFTISRDNSKNTAYLQMNS LRPEDTAVYYCAAHRFVVGGNRVE DWRYWGQGTLVTVSSGGGGSGGGSEVQLLESGG GLVQPGGSLRLSCAASGRTFNNYNMGW FRQAPGKGREFVAAVSRSGVSTYYADSVKGRFTISR DNSKNTVYLQMNSLRPEDTAVYYC AAAYRGTAINVRRSYSSWGQGTLVTVSSGGGGSGG GSEVQLVESGGGLVQPGNSLRLSCA | FC5-9GS-035-9GS-059-9GS-Alb8 | 151 |

TABLE XIX-continued

Biparatopic anti-A-beta VHH constructs, additionally comprising FC5 and FC44 moieties

| VHH construct ID | | domain structure | SEQ ID NO: |
|---|---|---|---|
| | ASGFTFSSFGMSWVRQAPGKGLEWVSSISGSGSDT LYADSVKGRFTISRDNAKTTLYLQM NSLRPEDTAVYYCTIGGSLSRSSQGTLVTVSS | | |
| ABII407 | EVQLLESGGGLVQPGGSLRLSCVHSGPTFRTDTMG WFRQAPGKGREFVAAVTWNSGRINY ADSVKGRFTISRDNSKNTAYLQMNSLRPEDTAVYYC AAHRFVVGGNRVEDWRYWGQGTLV TVSSGGGSGGGGSGGGGSGGGGSGGGGSGGG GSGGGGSEVQLLESGGGLVQPGGSLRLS CAASGRTFNNYNMGWFRQAPGKGREFVAAVSRSG VSTYYADSVKGRFTISRDNSKNTVYL QMNSLRPEDTAVYYCAAAYRGTAINVRRSYSSWGQ GTLVTVSSGGGGSGGGSEVQLQASG GGLVQAGGSLRLSCAASGFKITHYTMGWFRQAPGK EREFVSRITWGGDNTFYSNSVKGRF TISRDNAKNTVYLQMNSLKPEDTADYYCAAGSTSTA TPLRVDYWGKGTQVTVSSGGGGSG GGSEVQLVESGGGLVQPGNSLRLSCAASGFTFSSF GMSWVRQAPGKGLEWVSSISGSGSD TLYADSVKGRFTISRDNAKTTLYLQMNSLRPEDTAV YYCTIGGSLSRSSQGTLVTVSS | 035-35GS-059-9GS-FC5-9GS-Alb8 | 152 |

Example 13

Industrial Manufacturing Process for PEGylated Biparatopic Polypeptides of the Invention

13.1 Fermentation:

Any of the polypeptides ABII305, ABII306, ABII314, ABII315, ABII322, and ABII323 can be expressed in the cytoplasm of different *E. coli* strains like W3110, TG1, BL21, BL21(DE3), HMS174, HMS174(DE3), MM294 under control of an inducible promoter. This promoter can be chosen from lacUV5, tac, T7, trp, T5, araB. The cultivation media are preferably fully defined according to Wilms et al., 2001 (Wilms, B., Hauck, A., Reuss, M., Syldatk, C., Mattes, R., Siemann, M., and Altenbuchner, J.: High-Cell-Density Fermentation for Production of L-N-Carbamoylase Using an Expression System Based on the *Escherichia coli* rhaBAD Promoter. Biotechnology and Bioengineering, 73: 95-103 (2001)), DeLisa et al., 1999 (DeLisa, M. P., Li, J. C., Rao, G., Weigand, W. A., and Bentley, W. E.: Monitoring GFP-operon fusion protein expression during high cell density cultivation of *Escherichia coli* using an on-line optical sensor. Biotechnology and Bioengineering, 65: 54-64.(1999)) or equivalent. However, supplementation of the medium with amino acids like isoleucine, leucine, lysine, methionine, phenylalanine, threonine, tryptophan and valin or complex media components such as soy peptone or yeast extract may be beneficial. The process for fermentation is performed in a fed-batch mode. Conditions: Temperature 30-40° C., pH 6-7.5, dissolved oxygen is kept above 20%. After consumption of the initial C-source the culture is fed with the feed media stated above (or equivalent). When a dry cell weight in the fermenter of 40 to 90 g/L is reached the culture is induced with an appropriate inducer corresponding to the used promoter system (e.g. IPTG, lactose, arabinose). The induction can either be performed as a pulsed full induction or as a partial induction by feeding the respective inducer into the fermenter over a prolonged time. The production phase should last 4 hours at least. The cells are recovered by centrifugation in bowl centrifuges, tubular bowl centrifuges or disc stack centrifuges, the culture supernatant is discarded.

13.2 Purification:

The *E. coli* cell mass is resuspended in 6- to 8-fold amount of lysis buffer (phosphate or Tris buffer, pH 7-8.5). Cell lysis is preferably performed by high pressure homogenization followed by removing of the cell debris by centrifugation in bowl, tubular bowl or disc stack centrifuges. Supernatant containing the target protein is optionally filtrated using a 0.22-10 μm filter and separated via cation exchange chromatography (e.g. Toyopearl MegaCap® II SP-550EC, Toyopearl GigaCap S-650M, SP Sepharose BB, SP Sepharose FF or S HyperCel™) at pH 7-8.5. Elution is performed by a linear increasing NaCl gradient at pH 7-8.5. Fractions containing the target protein are pooled and subsequently incubated with 5-10 mM DTT in order to prevent dimerization or aggregation mediated by free cysteine residues. After further addition of 0.8-1 M ammonium sulfate or 2-3 M NaCl, solution is separated via hydrophilic interaction chromatography (e.g. Phenyl Sepharose HP, Phenyl Sepharose FF, Butyl Sepharose HP, Butyl Sephrose FF, Butyl Toyopearl 650 (S,M,C), Phenyl Toyopearl 650 (S,M,C)) at pH 7-8.5. Elution is carried out at pH 7-8.5 by a linear decreasing ammonium sulfate or NaCl gradient in presence of 5 mM DTT. Fractions containing the target protein with a purity level of minimally 90% are pooled and desalted by diafiltration in presence of 5 mM DTT followed by concentration to approximately 5 mg/ml. Subsequent refolding is performed by diluting the protein solution 1:5-1:20 with 50 mM Tris, 150 mM NaCl, 4 mM Cystamin, 10 mM CHAPS at pH 8.5 to a final protein concentration of 0.25-1 mg/ml. Refolding solution is incubated under stirring for 12-36 h at room temperature and then separated by cation exchange chromatography (e.g. SP Sepharose FF, SP Sepharose HP, Toyopearl SP-650 (S, M, C)) at pH 7-8.5. Elution is performed by a linear increasing NaCl gradient at pH 7-8.5. Fractions containing monomeric target protein are pooled and activated for PEGylation by addition of reducing agents such as DTT, DTE or TCEP. The solution is subsequently incubated at room temperature for 2 hours. After diafiltration against Na-phosphate buffer pH 6.5-7.5 or 20 mM HEPES buffer pH 6.5-7.5 or Tris buffer pH 8.0 and concentration to 5-10 mg/ml, 40-kDa maleimide-polyethyleneglycole (PEG) is added (protein to PEG ratio of 1:2-1:10). Solution is incubated under stirring for 3-18 h at room temperature and subsequently filtrated using a 0.22 μm filter. PEGylated target protein is separated from free PEG and non-PEGylated target protein via cation exchange chromatography (SP Sepharose HP, Toyopearl SP 650M, MacroCap™SP, Source™30S or Fractogel®EMD (M)) at pH 5-7. Elution is performed by a linear increasing NaCl gradient. Fractions containing mono-PEGylated target are pooled and formulated in 25 mM Na-phosphate, 220 mM endotoxin free trehalose, pH 7.5 via diafiltration.

Example 14

Pharmaceutical Formulation and Use 14.1 Pharmaceutical Formulation:
Any of the humanized biparatopic polypeptide constructs of the invention, such as ABII314 to AbII323, can be selected for the manufacture of a pharmaceutical formulation for subcutaneous application having a composition as follows:

| | |
|---|---|
| Drug substance: | 100 mg/ml (1 to 3 nmol/ml) |
| Phosphate buffer: | 25 mM |
| Trehalose: | 220 mM |
| Tween-20: | 0.02% |

Drug substance is formulated in a solution having the above composition, sterilized and stored at 2 to 8° C.
14.2 Pharmaceutical Use:
The solution as prepared under 14.1 above is applied to a patient in need thereof, such as a human being suffering from AD, by subcutaneous injection into the belly in a volume of 1 to 2 ml (dosage of 100 to 200 mg) every two to four weeks.

The invention claimed is:

1. A polypeptide comprising a first immunoglobulin single variable domain and a second immunoglobulin single variable domain, wherein the CDR sequences of said first immunoglobulin variable domain (CDR(1) sequences) and the CDR sequences of said second immunoglobulin variable domain (CDR(2) sequences) are defined as follows:
CDR(1)1: SEQ ID NO:14
CDR(1)2: SEQ ID NO:15
CDR(1)3: SEQ ID NO:16
CDR(2)1: SEQ ID NO:17
CDR(2)2: SEQ ID NO:18
CDR(2)3: SEQ ID NO:19.

2. A polypeptide comprising a first immunoglobulin single variable domain and a second immunoglobulin single variable domain, wherein the CDR sequences of said first immunoglobulin variable domain (CDR(1) sequences) and the CDR sequences of said second immunoglobulin variable domain (CDR(2) sequences) are defined as follows:
CDR(1)1: SEQ ID NO:17
CDR(1)2: SEQ ID NO:18
CDR(1)3: SEQ ID NO:19
CDR(2)1: SEQ ID NO:14
CDR(2)2: SEQ ID NO:15
CDR(2)3: SEQ ID NO:16.

3. A polypeptide comprising a first immunoglobulin single variable domain and a second immunoglobulin single variable domain, wherein said first immunoglobulin single variable domain is VHH domain ABII035 (SEQ ID NO:44), and said second immunoglobulin single variable domain is VHH domain ABII059 (SEQ ID NO:45), or wherein said first immunoglobulin single variable domain is VHH domain ABII059 (SEQ ID NO:45), and said second immunoglobulin single variable domain is VHH domain ABI1035 (SEQ ID NO:44).

4. A polypeptide comprising SEQ ID NO: 32, SEQ ID NO: 38, SEQ ID NO: 39, SEQ ID NO: 40, or SEQ ID NO: 41; wherein said SEQ ID NO: 40 is PEGylated at cysteine residue 137, and wherein SEQ ID NO: 41 is PEGylated at cysteine residue 138.

5. A polypeptide consisting of SEQ ID NO: 32, SEQ ID NO: 38, SEQ ID NO: 39, SEQ ID NO: 40, or SEQ ID NO: 41; wherein said SEQ ID NO: 40 is PEGylated at cysteine residue 137, and wherein SEQ ID NO: 41 is PEGylated at cysteine residue 138.

6. A pharmaceutical composition comprising (i) as the active ingredient the polypeptide according to claim 1, and (ii) a pharmaceutically acceptable carrier, and optionally (iii) a diluent, excipient, adjuvant and/or stabilizer.

7. A pharmaceutical composition comprising (i) as the active ingredient the polypeptide according to claim 2, and (ii) a pharmaceutically acceptable carrier, and optionally (iii) a diluent, excipient, adjuvant and/or stabilizer.

8. A pharmaceutical composition comprising (i) as the active ingredient the polypeptide according to claim 3, and (ii) a pharmaceutically acceptable carrier, and optionally (iii) a diluent, excipient, adjuvant and/or stabilizer.

9. A pharmaceutical composition comprising (i) as the active ingredient the polypeptide according to claim 4, and (ii) a pharmaceutically acceptable carrier, and optionally (iii) a diluent, excipient, adjuvant and/or stabilizer.

10. The polypeptide according to claim 1, wherein the polypeptide additionally comprises a half-life extending moiety.

11. The polypeptide according to claim 2, wherein the polypeptide additionally comprises a half-life extending moiety.

12. The polypeptide according to claim 3, wherein the polypeptide additionally comprises a half-life extending moiety.

* * * * *